United States Patent [19]

Hidaka et al.

[11] Patent Number: 5,216,150
[45] Date of Patent: Jun. 1, 1993

[54] DERIVATIVES OF ISOQUINOLINE (AND NAPHTHALENE) SULFONAMIDES

[75] Inventors: Hiroyoshi Hidaka, 1101-1-5-104, Hachimanyama, Tenpaku-ku, Nagoya-shi, Aichi; Tomohiko Ishikawa; Masatoshi Hagiwara, both of Nagoya; Tsutomu Inoue, Funabashi; Kenji Naitoh, Akishima; Osamu Sakuma, Tama; Masayuki Yuasa, Akishima; Tadashi Morita, Kashiwa; Tadashi Toshioka, Urayasu; Isao Umezawa, Tokyo; Takashi Inaba, Higashimurayama, all of Japan

[73] Assignees: Hiroyoshi Hidaka, Nagoya; Tobishi Yakuhin Kogyo Kabushiki Kaisha, Tokyo, both of Japan

[21] Appl. No.: 758,808

[22] Filed: Sep. 12, 1991

Related U.S. Application Data

[62] Division of Ser. No. 453,623, Dec. 20, 1989, Pat. No. 5,081,246.

[30] Foreign Application Priority Data

Dec. 26, 1988 [JP] Japan .................................. 63-325910
Mar. 30, 1989 [JP] Japan ...................................... 1-76419
Apr. 10, 1989 [JP] Japan ...................................... 1-87868

[51] Int. Cl.$^5$ .................. C07D 401/12; C07D 401/14
[52] U.S. Cl. ..................... 540/597; 540/595; 544/127; 544/130; 544/159; 544/295; 544/362; 544/370; 544/389; 544/391; 544/392; 544/394; 546/19; 546/140; 546/149; 546/206; 546/242; 546/338; 548/561; 75/491
[58] Field of Search ............... 544/295, 360, 363, 389, 544/392; 546/19, 149; 540/597

[56] References Cited

PUBLICATIONS

Wagner, et al., "Chemical Abstracts", vol. 91, 1979, col. 91:108231u.
Markwardt, et al., "Chemical Abstracts", vol. 92, 1980, col. 92:176396x.
Wagner, et al., "Chemical Abstracts", vol. 96, 1982, col. 96:104709m.
Claeson, et al., "Chemical Abstracts", vol. 100, 1984, col. 100:156982r.
Strürzebecher, et al., "Die Pharmazie", vol. 42(2), 1987, p. 114.

Primary Examiner—C. Warren Ivy
Assistant Examiner—James H. Turnipseed
Attorney, Agent, or Firm—Ladas & Parry

[57] ABSTRACT

Novel quinoline sulfonamino derivatives having a vessel smooth muscle relaxation activity as well as a platelet agglutination inhibitory activity and inhibitory activity to protein kinase A, myosin light chain kinase, proteinkinase C, and calmodulindependent proteinkinase II, but having little action or cardio function; a process for the production of the derivatives, and a pharmaceutical composition containing the derivative.

1 Claim, No Drawings

DERIVATIVES OF ISOQUINOLINE (AND NAPHTHALENE) SULFONAMIDES

This is a divisional of copending application Ser. No. 07/453,623 filed on Dec. 20, 1989, now U.S. Pat. No. 5,081,246.

BACKGROUND OF THE INVENTION

1. Field of the Invention

The present invention relates to compounds having a vessel smooth muscle relaxation activity, a process for the production thereof, and to the use thereof.

2. Description of the Related Art

Quinoline compounds having a vessel smooth muscle relaxation activity are described in, for example, Japanese Unexamined Patent Publication (KOKAI) Nos. 60-81168, 61-126026, 61-271221, 61-293914, 62-103066, and 63-211267; and U.S. Pat. Nos. 4,456,757, 4,525,589, 4,560,755, 4,634,770, 4,678,783, 4,709,032, and 4,798,897.

Among the compounds described in the above references, some have a satisfactory smooth muscle relaxation activity, but have problems with relation to toxicity, organ-specificity, and safety.

SUMMARY OF THE INVENTION

Accordingly, the objects of the present invention are to provide novel compounds having a satisfactory smooth muscle relaxation activity, and a low toxicity, high organ-specificity, and high safety.

More particularly, the present invention provides a compound represented by the formula (I):

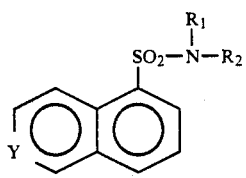

(I)

wherein Y represents N, $H_3C-N$ or CH;

$R_1$ represents a hydrogen atom, an optionally substituted lower alkyl group, a formyl group, a halophenylpropargyl group, an optionally substituted aralkyl group or optionally substituted phenyl; and (1) $R_2$ represents a group represented by the formula (II):

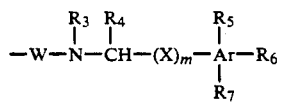

(II)

wherein $R_3$ represents a hydrogen atom, an optionally substituted lower alkyl group, a formyl group, a halophenylpropargyl group, an optionally substituted aralkyl group or optionally substituted phenyl; or $R_1$ and $R_3$ together form a lower alkylene group;

$R_4$ represents a hydrogen atom or a lower alkyl group;

$R_5$ represents a hydrogen atom, a halogen atom, a nitro group, a lower alkyl group, an optionally substitute hydroxyl group, an optionally substituted N-substituted amino group, an optionally substituted carboxy group, a polyfluoro-lower alkyl group, a cyano group, a hydroxymethyl group, a methylthio group, methyl sulfinyl group or methylsulfonyl group;

$R_6$ represents a hydrogen atom, a halogen atom or a lower alkoxy group; or $R_5$ and $R_6$ together form a lower alkylenedioxy group;

$R_7$ represents a hydrogen atom or a lower alkoxy group;

X represents a vinylene group or an ethynylene group;

Ar represents a phenyl group, a naphthyl group or a heterocyclyl group;

m represents an integer of 1 to 3; and

W represents a lower alkylene group, an optionally substituted phenylene group or an optionally substituted phenylene-lower alkylene group; or (2) $R_2$ represents a group represented by the formula (III):

(III)

wherein $R_{10}$ represents a hydrogen atom, a nitro group, an optionally substituted amino group, an optionally substituted hydroxyl group, a lower alkyl group, or a halogen atom; or $R_1$ and $R_{10}$ together form a lower alkylene group;

$R_{11}$ represents a hydrogen atom, a hydroxyl group or a lower alkoxy group;

$R_{12}$ and $R_{13}$ each represent a hydrogen atom, or together represent $=O$;

Ar has the same meaning as defined under the formula (II);

n represents an integer of 1 to 3; and

A represents the group $>CR_{14}R_{15}$ or $>NR_{14}$; wherein $R_{14}$ represents a hydrogen atom, an optionally substituted hydroxy group, an optionally substituted phenyl group, an acyl group, a substituted carbonyl group, an optionally substituted alkoxycarbonyl, a substituted carbamoyl, an optionally substituted amino group, an arylsulfonyl group, an aralkylsulfonyl group, an aralkyl group, or a heterocyclyl group; and $R_{15}$ represents a hydrogen atom or a lower alkoxy group, or $R_{15}$ and $R_{14}$ together represent an alkylenedioxy group or $=O$; and quaternary ammonium salts of the compound of the formula (I), and nontoxic salts of the compound of the formula (I).

The present invention above provides a process for the production of a compound represented by the formula (I) wherein $R_2$ represents a group represented by the formula (II), comprising the steps of (1) reacting a compound represented by the formula (IV):

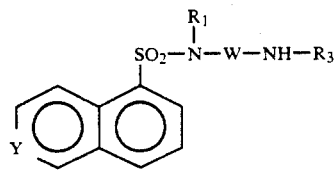

(IV)

wherein Y, W, R$_1$ and R$_3$ have the same meanings as defined above, with a compound represented by the formula (V):

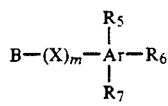

(V)

wherein B represents —CH$_2$Hal or —CO—R$_4$, and other symbols have the same meanings as defined in claim 1; and optionally (2) reducing a compound produced in the spet (1), and/or optionally (3) alkylating or formylating a compound produced in the step (1) or (2).

The present invention moreover provides a process for the production of a compound represented by the formula (I) wherein R$_2$ represents a group represented by the formula (II), comprising the steps of:

(1) reacting a compound represented by the formula (VI):

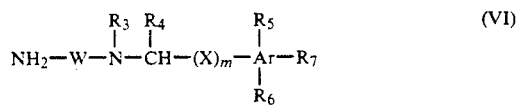

(VI)

with a compound represented by the formula (VII):

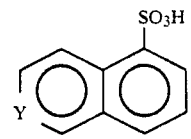

(VII)

or a reactive derivative thereof or a salt thereof, wherein all the symbols in the formula (VI) and (VII) have the same meanings as defined above, and optionally, (2) alkylating a compound produced in the step (1).

The present invention still further provides a process for the production of a compound represented by the formula (I), according to claim 1, wherein R$_2$ represents a group represented by the formula (III), comprising the steps of:

(1) reacting a compound represented by the formula (VIII).

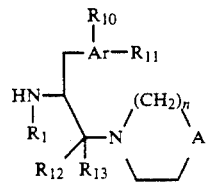

(VIII)

with a compound represented by the formula (VII):

(VII)

or a reactive derivative thereof or a salt thereof, wherein all the symbols in the formulae (VIII) and (VIII) have the some meanings as defined above;

and optionally carrying out one or more than one of the following steps (2) to (8), (2) hydrolysis to form a free hydroxyl group or an amino group;

(3) deprotection of a protecting group for a hydroxyl or amino group;

(4) acylation or substituted-alkoxy-carbonylation of a hydroxyl group or an amino group;

(5) alkylation of a hydroxyl group or an amino group;

(6) amination or hydroxylation of a carbonyl group;

(7) reduction of a nitro group to an amino group; and (8) carbonylation of an acetal.

The present invention also provides a pharmaceutical composition comprising a compound described above.

DESCRIPTION OF THE PREFERRED EMBODIMENTS

In the definition of the present invention, the optionally substituted lower alkyl includes an unsubstituted lower alkyl and a substituted lower alkyl. "Lower alkyl" means an alkyl containing up to seven carbon atoms, preferably up to four carbon atoms. The unsubstituted lower alkyl include straight chain lower alkyl and branched chain lower alkyl and are, for example, methyl, ethyl, n-propyl, isopropyl, n-butyl, isobutyl, tert-butyl, pentyl, hexyl and heptyl.

In the definition of R$_1$ and R$_3$, the substituted lower alkyls include an optionally substituted amino lower alkyl, such as 2-amino ethyl and 3-amino propyl, N,N-dimethyl amino propyl, 4-piperidyl lower alkyl such as 4-piperidyl propyl, a morpholino lower alkyl such as morpholinoethyl, and piperidino lower alkyl such as piperidinoethyl. The halophenylpropargyl includes fluoro- chloro-, brom- and iode-phenylproparyls, and is preferably p-chlorophenylpropargyl. The optionally substituted aralkyls include unsubstituted aralkyl, for example, a phenyl lower alkyl such as benzyl and phenylethyl, and a substituted phenyl-lower alkyl such as p-methoxybenzyl. The optionally substituted phenyl includes a substituted phenyl such as 3,4-dimethoxy phenyl. The alkylene group formed by R$_1$ and R$_3$ is, for example, a methylene, ethylene, or propylene group.

The lower alkyl as R$_4$ is as defined above.

The halogen as R$_5$ is floro, chloro, bromo or iodo; preferably chloro.

The lower alkyl as R$_5$ is as defined above.

The optionally substituted hydroxy as R$_5$ includes a hydroxyl group, and a substituted hydroxyl group, for example, a lower alkoxy such as methoxy, ethoxy or propoxy.

The optionally N-substituted amino as R$_5$ is an amino, or a lower alkyl amino such as dimethylamino.

The optionally substituted carboxy as R$_5$ includes a carboxyl group, per se., and a substituted carboxy, for example, a lower alkoxy carbonyl such as methoxy carbonyl, ethoxycarbonyl, and propoxycarbonyl.

The polyfluoro-lower alkyl as $R_5$ is, for example, trifluoromethyl.

The halogen as $R_6$ is as defined above for $R_5$

The lower alkoxy as $R_6$ is as defined above for $R_5$.

The lower alkylenedioxy formed by $R_5$ and $R_6$ is, for example, methylenedioxy, 1,2-ethylenedioxy, 1,3-dipropylenedioxy, 1,2-dipropylenedioxy, or the like, preferably 1,2-ethylenedioxy.

The lower alkoxy as $R_7$ is as defined above for $R_5$.

The lower alkylene group as W is, for example, a methylene group, ethylene group, 1,3-propylene group, or 1,4-butylene group.

The phenylene group as W is, for example, a 1,2-phenylene group or 1,3-phenylene. The phenylene lower alkylene group as W is, for example, a 1,2-phenylene- or 1,3-phenylene-lower alkylene group such as 1,2-phenylene-ethylene or a 1,3-phenylene-ethylene group. The optional substituent for the phenylene moiety is, for example, a lower alkoxy carbonyl such as methoxy carbonyl.

The heterocyclyl group as Ar is, for example, a pyridyl such as 2-pyridyl, 3-pyridyl or 4-pyridyl, a pyridyl such as 2 pyridyl, 3-pyridyl or 4-pyridyl, a pyrrolyl such as 2-pyrrolyl or 3-pyrrolyl, a thionyl such as 2-thionyl a 3-thionyl, or a furyl such as 2-furyl or 3-furyl.

The optionally substituted amino as $R_{10}$ includes free amino and substituted amino. In the substituted amino, the substituents are exemplified by a lower alkyl such as methyl, ethyl, propyl or other lower alkyl as defined above, and substituted sulfo such as isoquinoline sulfo, naphtharenesulfo, methanesulfo, toluenesulfo. Accordingly, the substituted amino is, for example, isoquinoline sulfonamide, N-lower alkyl isoquinolinesulfonamide such as N-methyl-sulfonamide, naphtharenesulfonamide, N-lower alkyl naphtharenesulfonamide such as N-methylnaphtharenesulfonamide, methansulfonamide, N-lower alkyl methansulfonamide, N-methyl methansulfonamide, toluenesulfonamide, or N-lower alkyl methansulfonamide such as N-methyl methanesulfonamide. The substituted amino further is phtharimide.

The substituted hydroxy group as $R_{10}$ includes ester, ether and protected hydroxy. The ester is, for example, a substituted sulfonyloxy such as isoquinolinesulfonyloxy, toluenesulfonyloxy or naphtharenesulfonyloxy, or a lower alkanoyloxy such as acetoxy, propionyloxy or butanoyloxy. The ether is, for example, a lower alkoxy such as methoxy, ethoxy or propoxy; an aralkyloxy such as benzyloxy; a lower alkanoyloxy-lower alkoxy such as acetoxy methoxy; or a heterocycle-lower alkoxy such as 2-pyridyl methoxy or 4-pyridylmethoxy.

The lower alkyl as $R_{10}$ is as defined above. The halogen as $R_{10}$ is as defined above. The lower alkoxy as $R_{10}$ is as defined above for $R_5$. The halogen as $R_{10}$ is as defined above for $R_5$. The heterocycle group as $Ar_2$ is, for example, an imidazolyl such as 4-imidazolyl.

The substituted hydroxyl group as $R_{14}$ is, for example, an ether group such as a lower alkoxy defined as above, or an optionally substituted aralkyl, for example, phenyl-lower alkyl optionally substituted on the phenyl, such as benzyl, phenylpropyl, 4-methylbenzyl, 3,4-dichlorobenzyl, or an ester group, for example, a lower alkanoyloxy such as acetoxy or propanoyloxy.

The substituted phenyl as $R_{14}$ is, for example, a lower alkylphenyl for example 3-methylpheny, a lower alkoxyphenyl such as 2,3- or a 4-methoxypheny, mono- or di-holophenyl such as 4-chlorophenyl, 3,4-dichlorophenyl.

The acyl as $R_{14}$ is, for example, an acylphenyl such as benzoyl, on an aralkylcarbonyl such as benzylcarbonyl or phenylpropylcarbony.

The substituted alkoxycarbonyl $R_{14}$ is, for example, a phenyl-lower alkoxycarbonyl such as benzyloxycarbonyl, or tert-butoxy carbonyl.

The substituted carbonyl is, for example, an arylcarbonyl such as phenylcarbonyl, or an aralkyl carbonyl such as benzylcarbonyl.

The substituted amino $R_{14}$ is, for example, a lower alkylamino, an optionally substituted aralkylamine or N,N-lower alkyl aralkylamino, for example, methylamino benzylamino, 3,4-dichlorobenzylamino, N,N-methyl benzylamino or N,N-methyl 3,4-dichloroamino.

The aryl sulfonyl $R_{14}$ is, for example, benzylsulfonyl, a isoquinolinesulfonyl.

The aralkylsulfonyl $R_{14}$ is, for example, benzylsulfonyl or phenyl propylsulfonyl.

The aralkyl $R_{14}$ is, for example, benzyl or phenylpropionyl.

The heterocyclyl group $R_{14}$ is, for example, a pyridyl such as 2-pyridyl, or a pyrimidyl such as 2-pyrimidyl.

Since the present compounds have a nitrogen atom they can form quaternary ammonium salts, or salts such as nontoxic salts. To form a quaternary ammonium salt, a compound of the present invention is reacted with, for example, methyl iodide. The salts of the present invention are preferably nontoxicic salts, for example, salts with an inorganic acid such as hydrochloric acid, sulfuric acid, nitric acid, phosphorus acid, hydrogen bromide, hydrogen iodide or the like, as well as salts with an organic acid, such as citric acid, acetic acid, oxalic acid, tartaric acid, sulfonic acids such as methane sulfonic acid, ethanesulfonic acid benzenesulfonic acid, fumaric acid, maleic acid, malic acid or the like.

In an embodiment for the production of the present compounds, a compound represented by the formula (IV) as described above is reacted with a compound represented by the formula (V) as described above.

In a preferable embodiment of this variation, a compound of the formula (IV), wherein $R_1$ and $R_3$ represent a hydrogen atom, is reacted, and after the reaction, the resulting intermediate is derivatized, for example, alkylated or formulated to introduce $R_1$ and/or $R_3$.

In a particular case, an isoquinolinesulfonamide represented by the formula (IV'):

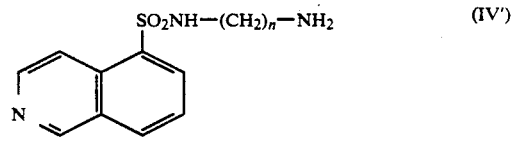

is reacted with a compound of the formula (V), and if necessary, the resulting intermediate is reduce. The reaction is carried out, for example, in a medium such as methanol, dimethylformamide, tetrahydrofuran, dimethyl sulfoxide, diglyme, benzene, at a temperature of 0° C. to 100° C., preferably a room temperature. The reduction is carried out using, for example, sodium borohydride, aluminum lithium hydride or the like, at a temperature of 0° C. to 60° C. preferably at a room temperature. The introduction of $R_1$ and/or $R_3$ can be carried out by using a halide of $R_1$ and/or $R_3$, i.e., Hal-$R_1$ or Hal-$R_2$ while removing hydrogen halide. Where an alkylene halide is used, a compound wherein $R_1$ and $R_3$ are linked is provided. For an introduction of formyl, the intermediate is reacted with formic acid in the presence of acetic anhidride. The above-mentioned reactions are carried out, for example, in chloroform, dimethylacetamide, dimethylformamide or other aprotic solvent, at a temperature of about 0° C. to 100° C., preferably at a room temperature.

In another embodiment for the production of the present compounds, a compound of the formula (VI) is reacted with a compound (VII). In a preferable embodiment, a compound of the formula (VI) wherein $R_3$ is hydrogen atom is reacted with a compound of the formula and after the reaction, the resulting intermediate is alkylated to introduce $R_3$.

In a particular embodiment, a compound of the formula (VI')

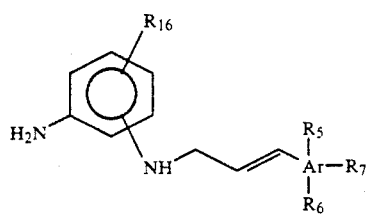

(VI')

wherein $R_{16}$ is an optional substituent on the phenyl moiety W, is reacted with a compound of the formula (VII) to obtain a compound represented by the formula (I-a):

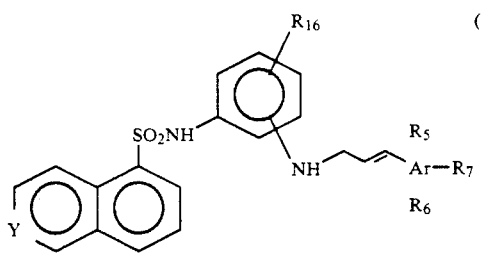

(I-a)

The reaction is carried out in a medium such as pyridine, dimethylformamide, acetonitrile, dioxane, tetrahydrofuran, dichloromethane, chloroform or the like, at a temperature of about 0° C. to 40° C., preferably 20° C. to 30° C.

Note, the product (Ia) is reacted with a compound which introduces the substituent $R_1$ and/or $R_3$. The compound which introduces $R_1$ and/or $R_3$ is, for example, a halogen compound of $R_1$ or $R_3$, i.e., Hal-$R_1$ or Hal-$R_3$ wherein Hal represents a halogen atom.

The reaction is carried out in a medium such as tetrahydrofuran, dimethylformamide, dioxane, deethoxymethane, methanol, ether such as ethyl ether, chloroform, ethyl acetate or the like in the pressure of a base which kinds the resulting hydrogen halide during the reaction, for example a tertiary amine such as pyridine, dimethylaminopyridine, N-methylpiperidine or triethylamine, or an inorganic base such as potassium bicarbonate, potassium hydroxide, sodium carbonate, sodium hydroxide or the like.

The starting material (VI) wherein $R_3$ is a hydrogen atom can be obtained by reacting a compound represented by the formula (VIII):

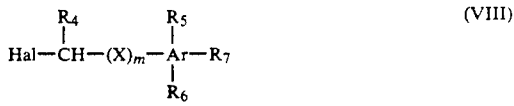

(VIII)

with a compound represented by the formula (IX):

(IX).

For example, to obtain the intermediate (VI'), a compound of the formula (VIII'):

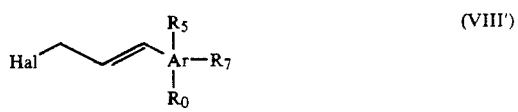

(VIII')

with a compound of the formula (IX'):

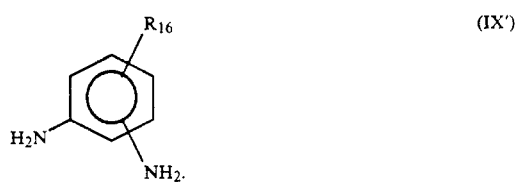

(IX')

These reactions can be carried out under substantially the same condition as for the introduction of $R_1$ and $R_3$.

In another embodiment for the production of the sent compound (I), a compound of the formula (VIII) is reacted with a compound of the formula (VII).

The starting material (VIII) can be obtained by reacting a compound represented by the formula (X):

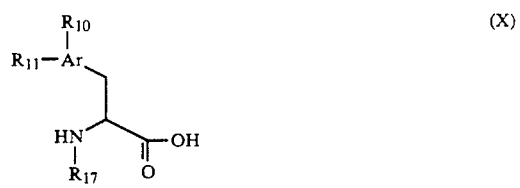

(X)

wherein $R_{17}$ is a hydrogen atom or a lower alkyl, with a compound represented by the formula (XI):

(XI)

By this reaction, the compound (VIII) wherein $R_{12}$ and $R_{13}$ together form =O is obtained. A reduction of this compound provides the compound (VIII) wherein both $R_{12}$ and $R_{13}$ represent a hydrogen atom.

In a particular embodiment, a known compound tyrosine having the amino group protected, and represented by the formula (Xa):

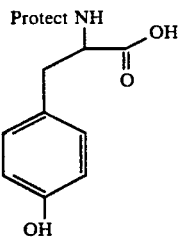

is reacted with pyperazine having the nitrogen atom protected is represented by the formula (XIa):

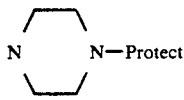

to obtain an intermediate represented by the formula (VIIIa):

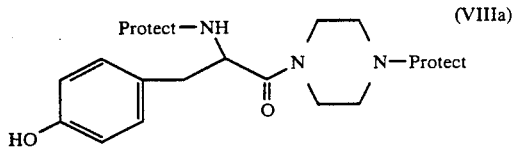

Next, the intermediate (VIIIa) is then condensed with isoquinolinesulfonylchloride to obtain a compound represented by the formula (XII):

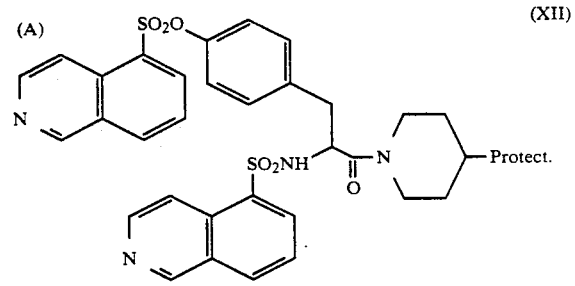

Next, the following modification of the compound (XII) can be carried out to obtain some of the present compounds:

(2a) Hydrolysis to remove the isoquinolinesulfonyl group to free hydroxy on the phenyl ring;
(3a) Deprotection of the piperazine ring;
(4a) Acylation or alkylation of the free hydroxy;
(4a) Acylation of the nitrogen atom of the piperazine moiety;
(5a) Alkylation of the sulfonamide group.

To prepare other compounds of the present invention, bistidine, phenylalanine or the like can be used in place of tyrosine, and/or piperidine or the like can be used in place of piperazine. Moreover, an N-alkylated compound can be used in place of an N-protected compound (IIa), and/or a hydroxy-protected compound of the compound (IIa) can be used. The compound (VIIIa) or (XII) can be reduced to convert the carbonyl structure to the methylene chain. The orth portion of the phenyl ring can be linked with an amino group via an alkylene chain to form a ring structure. Where piperidine is used in place of piperazine, the piperidine moiety can be converted to a corresponding moiety having an acetal structure at the fourth position thereof. After condensation with a sulfonic acid derivative, (8a) the acetal can be carbonylated, (6a) the carbonyl can be converted to hydroxy or an amino group, (4b) the hydroxyl or amino group can be acylated, or (5b) the hydroxyl or amino group can be alkylated, to obtain some of the desired compounds of the present invention.

The reaction of the compound (X) and (XI) is carried out in a medium such as tetrahydrofuran, dioxane, dichloromethane, or other aprotic solvent at a temperature of about 0° C. to 40° C., preferably 20° C. to 30° C.

The reaction of the compound (VII) and the compound (VIII) is carried out in an aprotic solvent such as tetrahydrofuran, methylene chloride, chloroform, dimethylformamide, or the like in the presence of a hose such as triethylamine or the like at a temperature of about 0° C. to 40° C., preferably 20° C. to 30° C.

The hydrolysis of step (2) is carried out in a solvent such as methanol, tetrahydrofuran, a mixture thereof, dimethyl-sulfoxide or the like, in the presence of a base such as sodium hydroxide, potassium hydroxide or the like.

The reprotection of step (3) is carried out in a solvent such as methanol, ethanol, chloroform, ethyl acetate or the like.

The acylation of step (4) is carried out in a solvent such as chloroform, tetrahydrofuran, pyridine or the like, in the presence of a base such as triethylamine.

The alkylation of step (5) is carried out in a solvent such as dimethylformamide, tetrahydrofuran, ethyl acetate, methanol, methylene chloride, or a mixture thereof.

The hydroxylation of step (6) is carried out in a protonic solvent such as methanol or ethanol in the presence of a reducing agent such as sodium borohydride, sodium cyanoborohydride. The amination of step (6) is carried out, after an imine formation, under the same condition as for the hydroxylation. The reduction of nitro in step (7) is carried out in a solvent, for example, an alcohol such as methanol or ethanol, by catalytic hydrogenation using as a catalyst a noble methanol catalyst such as palladium on carbon.

The conversion of acetol to oxo is carried out by acidic hydrolysis in an aqueous solution.

EXAMPLES

The present invention will now be further illustrated by, but is by no means limited to, the following example.

In the examples, melting points were determined by a melting point measurement apparatus Yamato MP-21 (Yamato Kagaku, Japan) using a capillary; nuclear magnetic resonance spectra ($^1$H-NMR) were determined by JEOL.JNM-FX200 (Nippon Denshi, Japan); molecular weights were determined by JMS-D300 type mass spectrometer (Nippon Denshi, Japan); and infrared absorption spectra (IR) were determined by IRA-1 (Nippon Bunko Kogyo, Japan).

REFERENCE EXAMPLE 1

1-N-(Benzyloxycarbonyl) histidyl]-4-phenylpiperazine 7.13 g of N,N'-dibenzyloxycarbonyl histidine, 3.00 g of 4-phenylpiperazine and 16.1 g of N-hydroxybenzotriazole were dissolved in 100 ml of tetrahydrofuran, and to the mixture was added 3.84 g of DCC (dicyclohexylcarbodiimide), and the whole was stirred at a room temperature for three hours. An insoluble matter was filtered off, the filtrate was concentrated under a reduced pressure, and to the concentrate was added 200 ml of ethyl acetate to reform crystals, which were then filtered off. The filtrate was sequentially washed with 20% potassium carbonate aqueous solution and saturated sodium chloride aqueous solution, dried over magnesium sulfate, and concentrated under a reduced pressure. The resulting residue was dissolved in 60 ml of methanol, and after an addition of a 10% ammonium-methanol solution and stirring at a room temperature for 30 minutes, the solution was concentrated under a reduced pressure to obtain a residue, which was then subjected to silica gel chromatography and eluted with chloroform/methanol (50:1 to 10:1) to obtain 6.61 g of the title compound in a colorless amorphous form.

$^1$H-NMR (CDCl$_3$, δ ppm): 2.81–3.20 (6H, m), 3.40–3.82 (4H, m), 4.95 (1H, m), 5.09 (2H, s), 5.78 (1H, d, J=8.3 Hz), 6.80–6.97 (4H, m), 7.20–7.30 (2H, m), 7.34 (5H, s), 7.55 (1H, s).

REFERENCE EXAMPLE 2

1-[N-(tert-Butoxycarbonyl) histidyl]-4-phenylpiperazine 6.61 g of 1-[N-(benzyloxycarbonyl)histidyl]-4-phenylpiperazine was dissolved in 80 ml of methanol, and to the solution was added 4 g of 5% palladium on carbon catalyst with ice cooling, and the mixture was stirred under a hydrogen atmosphere at a room temperature for 20 hours, and filtered to obtain a filtrate, which was then concentrated under a reduced pressure to obtain 4.26 g of a residue. The residue was dissolved in 80 ml of dimethylformamide, and to the solution were sequentially added 6.8 g of tert-butoxycarboxylic acid anhydride and 10 ml of triethylamine, and the mixture was stirred at a room temperature for 90 minutes. 200 ml of ethyl acetate was added to the reaction mixture, which was then washed twice with saturated sodium chloride aqueous solution, dried over magnesium sulfate, and filtered to obtain a filtrate. The filtrate was concentrated under a reduced pressure to obtain a residue, which was then dissolved in 100 ml of methanol, and to the resulting solution was added 20 ml of 10% sodium hydroxide aqueous solution, and the whole was stirred at a room temperature for 30 minutes. The reaction mixture was concentrated under a reduced pressure to one third of the original volume, and after the addition of 150 ml of water, the concentrate was extracted twice with 80 ml each of chloroform, the resulting chloroform phase was dried over magnesium sulfate, filtered, and concentrated under a reduced pressure to obtain a residue. The residue was applied on a silica gel column, and eluted with chloroform/methanol (50:1 to 20:1) to obtain 4.53 g of the title compound in a colorless amorphous form.

$^1$H-NMR (CDCl$_3$, δ ppm): 1.43 (9H, s), 2.80–3.22 (6H, m), 3.40–3.83 (4H, m), 4.87 (1H, m), 5.46 (1H, br), 6.86–6.93 (4H, m), 7.23–7.31 (2H, m), 7.57 (1H, s).

REFERENCE EXAMPLE 3

1-[2-(tert-Butoxycarbonylamino)-3-imidazol-4(5)-yl-propyl]-4-phenylpiperazine

A solution of 1.3 g of lithium aluminum hydride in 38 ml of tetrahydrofuran was added to a solution of 4.56 g of aluminum chloride in 38 ml of ethyl ether with ice cooling, and the mixture was stirred for 20 minutes with ice cooling. To the mixture was dropwise added a solution of 4.53 g of 1-[N-(tert-butoxycarbonyl)histidyl]-4-phenylpiperazine in 51 ml of tetrahydrofuran, and stirring for one hour with ice cooling, to the reaction mixture was added 20 ml of 25% potassium carbonate aqueous solution, followed by 100 ml of chloroform to obtain a suspension. The suspension was filtered using silica as a filter aid to obtain a filtrate. After the silica was washed with 20% methanol in chloroform, the combined filtrate was concentrated under a reduced pressure to obtain a residue. The residue was applied to a silica gel column, and eluted with chloroform/methanol (40:1 to 10:1) to obtain 3.1 g of the title compound in a colorless amorphous.

H-NMR (CDCl$_3$, δ ppm): 1.44 (9H, s), 2.33 (1H, dd, J=7.3, 12.2 Hz), 2.47 (1H, dd, J=7.8, 12.2 Hz), 2.64 (4H, m), 2.93 (2H, m), 3.20 (4H, m), 3.97 (1H, m), 5.10 (1H, br), 6.81–6.97 (4H, m), 7.21–7.30 (2H, m), 7.58 (1H, s).

EXAMPLE 1

N-{1-[1-(5-Isocuinolinesulfonyl)imidazol-4(5)-yl-methyl]-2-(4-phenylpiperazinyl) ethyl}-5-isoquinolinesulfonamide 3.1 g of the amorphous compound obtained in Reference Example 3 was dissolved in 10 ml of ethyl acetate, and to the solution was added 16 ml of 4N hydrochloric acid in ethyl acetate was added, and the mixture was stirred at a room temperature for 30 hours and evaporated to dryness under a reduced pressure. To the residue were added 70 ml of tetrahydrofuran and 30 ml of chloroform to form a suspension, to which were added 6 g of isoquinolinesulfonic acid chloride and 30 ml of triethylamine, and after stirring at a room temperature for 18 hours, 150 ml of water was added and the whole was extracted twice with 70 ml of chloroform. The extract was dried over magnesium sulfate and concentrated under a reduced pressure to obtain a residue, which was then applied to silica gel column, and eluted with chloroform/methanol (80:1 to 60:1) to obtain 1.86 g of the title compound in a colorless amorphous form.

IR (KBr) cm$^{-1}$: 1618, 1600, 1490, 1380, 1325, 1210, 1170, 1132, 1073;

$^1$H-NMR (CDCl$_3$, δ ppm): 2.00–2.34 (6H, m), 2.59–2.81 (6H, m), 3.39 (1H, m), 6.74–6.89 (3H, m), 7.04 (1H, d, J=1.5 Hz), 7.19–7.29 (3H, m), 7.69 (1H, t, J=7.3 Hz), 7.80 (1H, t, J=1.5 Hz), 8.21 (1H, d, J=8.3 Hz), 8.34 (1H, d, J=8.3 Hz), 8.38–8.46 (3H, m), 8.52 (1H, dd, J=1.0, 7.3 Hz), 8.69 (1H, d, J=6.3 Hz), 8.77 (1H, d, J=6.3 Hz), 9.36 (1H, s), 9.39 (1H, s).

EXAMPLE 2

N-[1-(Imidazol-4(5)-yl-methyl)-2-(4-phenylpiperazinyl-)ethyl]-5-isoquinoline sulfonamide 250 mg of the amorphous compound obtained in Example 1 was dissolved in a mixture of 1 ml of tetrahydrofuran and 5 ml of methanol, and to the solution 1 ml of 4N sodium hydroxide was added. After stirring at a room temperature for 10 minutes, 20 ml of water was added to the mixture, which was then extracted twice with a mixture of 10 ml of chloroform and 2 ml of isopropanol. The extract was dried over magnesium sulfate, and concentrated under a reduced pressure to obtain a residue, which was then applied to a silica gel column, and eluted with chloroform/methanol (20:1) and chloroform/methanol/triethylamine (20:1:0.2) to obtain 163 mg of the title compound in a colorless amorphous form.

IR (KBr) cm$^{-1}$: 1615, 1600, 1490, 1448, 1320, 1225, 1153, 1130;

$^1$H-NMR (CDCl$_3$, δ ppm): 2.06–2.44 (6H, m), 2.67–2.90 (5H, m), 3.02 (1H, dd, J=5.4, 10.0 Hz), 3.25 (1H, m), 6.74–6.90 (4H, m), 7.19–7.33 (2H, m), 7.54 (1H, s), 7.74 (1H, t, J=7.8 Hz), 8.24 (1H, d, J=7.8 Hz), 8.47 (1H, d, J=6.4 Hz), 8.52 (1H, dd, J=1.0, 7.32 Hz), 8.70 (1H, d, J=5.9 Hz), 9.38 (1H, s).

EXAMPLE 3

N-{1-[1-(5-Isoquinolinesulfonyl)imidazol-4(5)-yl-methyl]-2-(phenylpiperazinyl ethyl}-N-methyl-5-isoquinoline sulfonamide 1.45 g of the amorphous compound obtained in Example 1 was dissolved in 20 ml of dimethylformamide, and to the solution were sequentially added 120 mg of 60% sodium hydride and 0.2 ml of methyl iodide with ice cooling, and after stirring for 30 minutes with ice cooling, and 30 ml of water was added. After extraction of the reaction mixture with 30 ml of ethyl acetate, the extract was washed with saturated sodium chloride aqueous solution, dried over magnesium sulfate and concentrated under a reduced pressure to obtain a residue, which was then applied to a silica gel column and eluted with chloroform/methanol (80:1) to obtain 616 mg of the title compound in a colorless amorphous form.

IR (KBr) cm$^{-1}$: 1618, 1600, 1490, 1380, 1320, 1210, 1170, 1140, 1080;

$^1$H-NMR (CDCl$_3$, δ ppm): 2.35–2.47 (6H, m), 2.64 (1H, dd, J=7.8, 14.6 Hz), 2.80 (3H, s), 2.85–2.97 (5H, m), 4.36 (1H, m), 6.82–6.89 (3H, m), 7.08 (1H, d, J=1.5 Hz), 7.21–7.29 (2H, m), 7.61 (1H, t, J=7.3 Hz), 7.75 (1H, t, J=7.8 Hz), 7.87 (1H, d, J=1.5 Hz), 8.14 (1H, d, J=7.8 Hz), 8.25–8.29 (2H, m), 8.37–8.45 (3H, m), 8.64 (1H, d, J=5.9 Hz), 8.76 (1H, d, J=6.3 Hz), 9.31 (1H, s), 9.35 (1H, s).

EXAMPLE 4

N-[1-(Imidazol-4(5)-yl-methyl)-2-(4-phenylpiperazinyl)ethyl]-N-methyl-5-isoquinoline sulfonamide 450 mg of the amorphous compound obtained in Example 3 was dissolved in a mixture of 2 ml of tetrahydrofuran and 10 ml of methanol, and to the solution was added 1 ml of 4 N sodium hydroxide. After stirring at a room temperature for 10 minutes, the reaction mixture was worked up according to the same procedure as described in Example 2 to obtain 299 mg of the title compound in a colorless amorphous form.

IR (KBr) cm$^{-1}$: 1595, 1490, 1448, 1320, 1225, 1150, 1128;

$^1$H-NMR (CDCl$_3$, δ ppm): 2.45–2.65 (6H, m), 2.89 (3H, s), 2.90–3.08 (6H, m), 4.37 (1H, m), 6.68 (1H, s), 6.82–6.90 (3H, m), 7.20–7.32 (3H, m), 7.64 (1H, t, J=7.8 Hz), 8.14 (1H, d, J=7.8 Hz), 8.31 (1H, d, J=6.3 Hz), 8.46 (1H, dd, J=1.0, 7.3 Hz), 8.62 (1H, d, J=5.9 Hz), 9.29 (1H, s).

REFERENCE EXAMPLE 4

N-(tert-Butoxycarbonyl)-3,4-dibenzyloxyphenylalanine benzyl ester 21.12 g of N-(tert-butoxycarbonyl) DOPA was dissolved in 200 ml of dimethylformamide, and after 50 g of benzyl bromide and 40 g of potassium carbonate were added, the mixture was stirred at a room temperature for 40 hours. After the addition of 400 ml of sodium chloride aqueous solution, the reaction mixture was extracted with 500 ml of ethyl acetate, and the extract was washed twice with saturated sodium chloride aqueous solution, dried over magnesium sulfate, filtered, and concentrated under a reduced pressure. To the resulting residue was added hexane to crystallize the title compound, which was then washed, filtered and dried to obtain 30.0 g of the colorless crystals.

$^1$H-NMR (CDCl$_3$, δ ppm): 1.42 (9H, s), 2.99 (2H, d, J=14.14 Hz), 4.59 (1H, m), 4.98 (1H, brd), 5.05 (2H, s), 5.07 (2H, s), 5.11 (2H, s), 6.56 (1H, dd, J=2.0, 7.8 Hz), 6.71 (1H, d, J=2.0 Hz), 6.79 (1H, d, J=7.8 Hz), 7.20–7.50.

REFERENCE EXAMPLE 5

N-(tert-Butoxycarbonyl)-3,4-dibenzyloxyphenylalanine 30.0 g of the crystals obtained in Example 4 was dissolved in 600 ml of methanol, and after the addition of 65 ml of 10% sodium hydroxide, the mixture was stirred at a room temperature for 20 hours, and 1000 ml of water was added. The reaction mixture was adjusted to pH 4 with concentrated hydrochloric acid, and extracted twice with 800 ml of chloroform. The extract was dried over magnesium sulfate and concentrated under a reduced pressure to crystallize the title compound, which was then filtered and washed with hexane to obtain 25.2 g of colorless crystals.

$^1$H-NMR (CDCl$_3$, δ ppm): 1.40 (9H, s), 3.02 (2H, m), 4.49 (1H, brs), 4.88 (1H, brs), 5.11 (4H, s), 6.68 (1H, dd, J=2.0, 7.8 Hz), 6.76 (1H, d, J=2.0 Hz), 6.74 (1H, d, J=7.8 Hz), 7.23–7.45 (10H, m).

REFERENCE EXAMPLE 6

1-[N-(tert-Butoxycarbonyl)-3,4-dibenzyloxyphenylalaninyl]-4-phenylpiperazine 5.67 g of the crystals obtained in Reference Example 5, 1.9 g of N-phenylpiperazine and 1.53 g of N-hydroxybenzotriazole were dissolved in 80 ml of methylene chloride, and after the addition of 2.4 g of DCC, the mixture was stirred at a room temperature for 18 hours. Resulting insoluble matter was filtered off, and washed with ethyl acetate.

The combined filtrate was concentrated under a reduced pressure to obtain a residue, which was then applied to a silica gel column, and eluted with hexane/ethyl acetate (2:1) to obtain 6.39 g of the title compound as colorless amorphous.

$^1$H-NMR (CDCl$_3$, δ ppm): 1.44 (9H, s), 2.39 (1H, m), 2.76–3.10 (6H, m), 3.30 (1H, m), 3.61 (2H, m), 4.78 (1H, m), 5.03 (2H, s), 5.14 (2H, s), 5.42 (1H, brd, J=8.3 Hz), 6.69 (1H, dd, J=2.0, 8.3 Hz), 6.79–6.91 (5H, m), 7.20–7.48 (12H, m).

REFERENCE EXAMPLE 7

1-{2-[N-(tert-Butoxycarbonylamino)]-3-(3,4-dibenzyloxyphenyl)propyl}-4-phenylpiperazine 3.66 g of the colorless amorphous obtained in Reference Example 6 was dissolved in 50 ml of tetrahydrofuran, and the addition of 700 mg of lithium aluminum hydride with ice cooling, the mixture was stirred for 90 minutes with ice cooling, and to the mixture was added water until foaming ended. Then 80 ml of chloroform was added to the reaction mixture to form a suspension, which was then filtered using silica gel as a filter acid to remove insoluble matter. The resulting filtrate was concentrated under a reduced pressure to obtain a residue, which was then applied to a silica gel column, and eluted with hexane/ethyl acetate (3:1) to obtain 2.67 g of the title compound in colorless amorphous form.

$^1$H-NMR (CDCl$_3$, δ ppm): 1.43 (9H, s), 2.24 (2H, m), 2.53 (4H, m), 2.79 (2H, m), 3.16 (4H, m), 3.90 (1H, m), 4.58 (1H, brs), 5.13 (2H, s), 5.16 (2H, s), 6.70 (1H, dd, J=2.0, 8.3 Hz), 6.80–6.93 (5H, m), 7.20–7.46 (12H, m).

REFERENCE EXAMPLE 8

1-[2-Amino-3-(3,4-dibenzyloxyphenyl)propyl]-4-phenylpiperazine 4.35 g of the amorphous compound obtained in Reference Example 7 was dissolved in 20 ml of ethyl acetate, and after the addition of 30 ml of 4 N hydrochloric acid in ethyl acetate, the mixture was stirred at a room temperature for one hour. The reaction mixture was concentrated under a reduced pressure, alkalized with sodium bicarbonate aqueous solution, and extracted twice with 80 ml of chloroform, and the extract was dried over magnesium sulfate and concentrated under a reduced pressure. The resulting residue was applied to a silica gel column and eluted with chloroform-methanol (100:1 to 30:1) to obtain 1.64 g of the title compound in a colorless amorphous form.

$^1$H-NMR (CDCl$_3$, δ ppm): 2.27–2.68 (8H, m), 3.10–3.20 (5H, m), 5.10 (2H, brs), 5.14 (2H, s), 5.17 (2H, s), 6.73 (1H, dd, J=2.0, 8.3 Hz), 6.81–6.94 (5H, m), 7.22–7.46 (12H, m).

EXAMPLE 5

N-{1-[3,4-Dibenzyloxyphenyl)methyl]-2-(4-phenylpiperazinyl)ethyl}-5-isoquinoline sulfonamide 640 mg of the amorphous compound obtained in Reference Example 8 was dissolved in 15 ml of methylene chloride, and to the solution were added 1 ml of triethylamine and 350 mg of 5-isoquinolinesulfonyl chloride with ice cooling, and after stirring for one hour with ice cooling, was added 50 ml of water, and the mixture was extracted twice with 50 ml of chloroform. The extract was dried over magnesium sulfate and concentrated under a reduced pressure to obtain a residue, which was then applied to a silica gel column and eluted with hexane/ethyl acetate (1:1) to obtain 470 mg of the title compound in a colorless amorphous form.

$^1$H-NMR (CDCl$_3$, δ ppm): 2.08–2.24 (6H, m), 2.64–2.91 (6H, m), 3.30 (1H, m), 5.08 (2H, s), 5.10 (2H, s), 6.51 (1H, dd, J=2.0, 8.3 Hz), 6.63 (1H, d, J=2.0 Hz), 6.71 (1H, d, J=8.3 Hz), 6.76–6.89 (3H, m), 7.21–7.43 (12H, m), 7.67 (1H, t, J=7.8 Hz), 8.18 (1H, d, J=8.3 Hz), 8.44 (2H, m), 8.67 (1H, d, J=5.9 Hz), 9.34 (1H, s).

EXAMPLE 6

N-{1-[(3,4-Dibenzyloxyphenyl)methyl]-2-(4-phenylpiperazinyl)ethyl}-N-methyl-5-isoquinoline sulfonamide 470 mg of the amorphous compound obtained in Example 5 was dissolved in 8 ml of dimethylformamide, and to the solution were sequentially added 30 mg of 60% sodium hydride and 0.1 ml of methyl iodide with ice cooling, and after stirring for two hours with ice cooling was added saturated sodium chloride, and the mixture was extracted with 50 ml of ethyl acetate. The extract was washed with saturated sodium chloride aqueous solution, dried over magnesium sulfate and concentrated under a reduced pressure to obtain a residue, which was then applied to a silica gel column and eluted with hexane/ethyl acetate (1:1) to obtain 413 mg of the title compound in a colorless amorphous form.

$^1$H-NMR (CDCl$_3$, δ ppm): 2.34 (1H, dd, J=6.35, 13.2 Hz), 2.42–2.60 (5H, m), 2.65 (1H, dd, J=7.3, 14.2 Hz), 2.81 (1H, dd, J=6.4, 14.2 Hz), 2.86 (3H, s), 2.99 (4H, m), 4.22 (1H, m), 5.03 (2H, s), 5.10 (2H, s), 6.54 (1H, dd, J=2.0, 8.3 Hz), 6.61 (1H, d, J=2.0 Hz), 6.63 (1H, d, J=8.3 Hz), 6.82–6.90 (3H, m), 7.19–7.53 (13H, m), 8.05 (1H, d, J=8.3 Hz), 8.24 (1H, dd, J=1.0, 7.3 Hz), 8.30 (1H, d, J=5.9 Hz), 8.60 (1H, d, J=5.9 Hz), 9.24 (1H, d, J=1.0 Hz).

EXAMPLE 7

N-{1-[(3,4-Dihydroxyphenyl)methyl]-2-(1-phenylpiperazinyl ethyl}-N-methyl-isoquinoline sulfonamide 310 mg of the amorphous compound obtained in Example 6 was dissolved in 2 ml of 1,2-ethanedithiol, and to the solution were added 1 ml of boron trifluoride/ethyl ether, and after stirring at a room temperature for 18 hours, was added saturated sodium bicarbonate aqueous solution, and the reaction mixture was extracted twice with a mixture of chloroform and methanol (10:1). The extract was dried over magnesium sulfate, and concentrated under a reduced pressure to obtain a residue, which was applied to a silica gel column and eluted with chloroform/methanol (80:1 to 20:1) to obtain 148 mg of the title compound in a colorless amorphous form.

IR (KBr) cm$^{-1}$: 1600, 1495, 1448, 1328, 1230, 1155, 1130;

$^1$H-NMR (CDCl$_3$, δ ppm): 2.41 (1H, dd, J=10.25, 14.65 Hz), 2.50–2.98 (7H, m), 3.01 (3H, s), 3.17 (4H, m), 4.06 (1H, m), 6.12 (1H, dd, J=20, 8.3 Hz), 6.20 (1H, d, J=8.3 Hz), 6.28 (1H, d, J=2.0 Hz), 6.82–6.95 (3H, m), 7.26 (2H, m), 7.62 (1H, t, J=7.8 Hz), 8.09 (1H, d, J=6.8 Hz), 8.13 (1H, d, J=9.3 Hz), 8.30 (1H, d, J=6.8 Hz), 8.41 (1H, d, J=4.9 Hz), 9.25 (1H, s).

EXAMPLE 8

N-{1-[(3,4-Dihydroxyphenyl)methyl]-2-(4-phenylpiperazinyl)ethyl}-5-isoquinoline sulfonamide The amorphous compound obtained in Example 5 was treated according to the procedure as described in Example 7 to obtain the title compound in colorless amorphous form.

IR (KBr) cm$^{-1}$: 1610, 1600, 1490, 1445, 1320, 1220, 1150, 1128;

$^1$H-NMR (CDCl$_3$, δ ppm): 2.30–2.60 (6H, m), 2.74–3.02 (6H, m), 3.36 (1H, m), 6.15 (1H, d, J=8.3 Hz), 6.33 (1H, d, J=8.3 Hz), 6.36 (1H, s), 6.76–6.90 (3H, m), 7.19–7.29 (2H, m), 7.65 (1H, t, J=7.8 Hz), 8.16 (1H, d, J=8.3 Hz), 8.33 (1H, d, J=6.5 Hz), 8.39 (1H, d, J=7.3 Hz), 8.51 (1H, d, J=5.5 Hz), 9.28 (1H, s).

REFERENCE EXAMPLE 9

6,7-Dibenzyloxy-3-[4-phenylpiperazinyl)methyl]-1,2,3,4-tetrahydroisoquinoline 1.00 g of the amorphous compound obtained in Reference Example 8 was dissolved in 2 ml of tetrahydrofuran, and to the solution was added 0.25 ml of 37% formalin. After stirring at a room temperature for 30 minutes, 600 mg of 12 N hydrochloric acid was added to the mixture, which was then stirred at a room temperature for two hours. After the addition of saturated sodium bicarbonate aqueous solution, the reaction mixture was extracted twice with 20 ml of chloroform. The extract was dried over magnesium sulfate, and concentrated under a reduced pressure to obtain a residue, which was then applied to a silica gel column and eluted with chloroform/methanol (100:1) to obtain 585 mg of the title compound in a colorless amorphous form.

$^1$H-NMR (CDCl$_3$, δ ppm): 2.28-2.38 (8H, m), 3.02 (1H, m), 3.21 (4H, m), 3.95 (2H, s), 5.11 (4H, s), 6.63 (1H, s), 6.68 (1H, s), 6.80-6.95 (3H, m), 7.20-7.46 (12H, m).

EXAMPLE 9

6,7-Dibenzyloxy-2-(5-isoquinolinesulfonyl)-3-[(4-phenylpiperazinyl)methyl]-1,2,3,4-tetrahydroisoquinoline 580 mg of the amorphous compound obtained in Reference Example 9 was dissolved in 10 ml of methylene chloride, and to the solution were added 1 ml of triethylamine and 400 mg of 5-isoquinoline sulfonyl chloride.HCl with ice cooling. The mixture was stirred at a room temperature for two hours, and after the addition of 20 ml of water, extracted twice with 10 ml of chloroform. The extract was dried over magnesium sulfate and concentrated under reduced pressure to obtain a residue, which was then applied to a silica gel column and eluted with hexane/ethyl acetate (1:1) to obtain 610 mg of the title compound in a colorless amorphous form.

$^1$H-NMR (CDCl$_3$, δ ppm): 2.31 (1H, dd, J=7.8, 11.6 Hz), 2.43 (1H, dd, J=6.8, 11.6 Hz), 2.53 (4H, m), 2.70 (1H, dd, J=2.0, 16.2 Hz), 2.87 (1H, dd, J=4.2, 16.2 Hz), 3.05 (4H, m), 4.26 (1H, d, J=15.6 Hz), 4.48 (1H, d, J=15.6 Hz), 4.49 (1H, m), 5.06 (2H, s), 5.07 (2H, s), 6.56 (1H, s), 6.60 (1H, s), 6.80-6.90 (3H, m), 7.20-7.95 (12H, m), 7.64 (1H, t, J=7.8 Hz), 8.15 (1H, d, J=7.81 Hz), 8.37 (1H, d, J=5.9 Hz), 8.48 (1H, dd, J=1.0, 7.3 Hz), 8.64 (1H, d, J=6.4 Hz), 9.30 (1H, d, J=1.0 Hz).

EXAMPLE 10

6,7-Dihydroxy-2-(5-isoquinolinesulfonyl)-3-[(4-phenylpiperazinyl)methyl]-1,2,3,4-tetrahydroisoquinoline To 314 mg of the amorphous compound obtained in Example 9, were added 2 ml of 1,2-ethanedithiol and 1 ml of boron trifluoride/ethyl ether, and the mixture was stirred at a room temperature for 18 hours. After the addition of saturated sodium bicarbonate aqueous solution, the reaction mixture was extracted twice with a mixture of chloroform and methanol (1:1), and the extract was dried over magnesium sulfate and concentrated under a reduced pressure to obtain a residue, which was then applied to a silica gel column and eluted with chloroform/methanol (50:1 to 20:1) to obtain 213 mg of the title compound in a colorless amorphous form.

IR (KBr) cm$^{-1}$: 1610, 1600, 1490, 1445, 1320, 1225, 1150, 1130;

$^1$H-NMR (CDCl$_3$, δ ppm): 2.35-2.80 (8H, m), 3.11 (4H, m), 4.24 (1H, d, J=16.1 Hz), 4.40 (1H, d, J=16.1 Hz), 4.55 (1H, m), 6.45 (2H, s), 6.80-6.90 (3H, m), 7.20-7.28 (2H, m), 7.67 (1H, t, J=7.8 Hz), 8.14 (1H, d, J=8.5 Hz), 8.40 (1H, d, J=6.3 Hz), 8.50 (1H, dd, J=1.0, 7.3 Hz), 8.59 (1H, d, J=6.4 Hz), 9.25 (1H, d, J=1.0 Hz).

REFERENCE EXAMPLE 10

1-[N-(tert-Butoxycarbonyl)-p-nitrophenylalanyl]-4-phenylpiperazine 7.03 g of p-nitrophenylalanine was suspended in 70 ml of 1,4-dioxane, and to the suspension were added 28 ml of 10% sodium hydroxide aqueous solution and 7.5 g of di-tert-butyl-dicarbonate, and the mixture was stirred at a room temperature for 30 minutes. 200 ml of water and 7 ml of 12 N hydrochloric acid were added to the reaction mixture, which was then extracted with 150 ml of ethyl acetate, and the extract was washed with saturated sodium chloride aqueous solution, dried over magnesium sulfate, and concentrated under a reduced pressure. The resulting residue was dissolved in 150 ml of tetrahydrofuran, and to the solution were added 6.0 g of N-phenylpiperazine and 5.5 g of N-hydroxybenzotriazole, and further added 7.6 g of DCC. After stirring at a room temperature for three hours, the reaction mixture was filtered to remove insoluble matter and the filtrate was concentrated under a reduced pressure, and the resulting residue was dissolved in 200 ml of ethyl acetate. The solution was sequentially washed with 10% potassium carbonate aqueous solution and saturated sodium chloride aqueous solution, dried over magnesium sulfate, and concentrated under a reduced pressure to obtain a residue, which was then applied to a silicon gel column and eluted with hexane/ethyl acetate (2:1) to obtain 11.1 g of the title compound as pale yellow crystals.

$^1$H-NMR (CDCl$_3$, δ ppm): 1.40 (9H, s), 2.83-3.20 (6H, m), 3.37 (1H, m), 3.57-3.70 (3H, m), 3.84 (1H, m), 4.92 (1H, m), 5.40 (1H, d, J=8.3 Hz), 6.85-6.95 (3H, m), 7.24-7.32 (2H, m), 7.38 (2H, d, J=8.8 Hz), 8.16 (2H, d, J=8.8 Hz).

EXAMPLE 11

1-[N-(5-Isoquinolinesulfonyl)-p-nitrophenylalanyl]-4-phenylpiperazine 11.0 g of the crystals obtained in Reference Example 10 was dissolved in 100 ml of ethyl acetate, and after the addition of 100 ml of 4 N hydrochloric acid in ethyl acetate, the reaction mixture was stirred at a room temperature for one hour and concentrated to dryness under a reduced pressure. To the residue was added 200 ml of saturated sodium bicarbonate, and the mixture was extracted twice with 100 ml of chloroform. The extract was dried over magnesium sulfate and concentrated under a reduced pressure to obtain a residue, which was then applied to a silica gel column and eluted with chloroform/methanol (80:1 to 10:1) to obtain free amine. The free amine was dissolved in 100 ml of methylene chloride, and to the solution were sequentially added 8.5 g of 5-isoquinoline sulfonyl chloride.HCl and 20 ml of triethylamine. The reaction mixture was stirred at a room temperature for 18 hours, and after the addition of water, extracted twice with 100 ml of chloroform. The extract was dried over magnesium sulfate and concentrated under a reduced pressure to obtain a residue, which was then applied to a silica gel column and eluted with chloroform/methanol (100:1 to 50:1) to obtain 9.66 g of the title compound as colorless crystals.

Melting point: 184°-188° C. (decomposed);

IR (KBr) cm$^{-1}$: 1660, 1600, 1520, 1420, 1345, 1325, 1230, 1150, 1135;

$^1$H-NMR (CDCl$_3$, δ ppm): 2.72-- 3.06 (6H, m), 3.20-3.61 (4H, m), 4.46 (1H, m), 6.06 (1H, br), 6.83 (2H, d, J=7.8 Hz), 6.94 (1H, t, J=7.3 Hz), 7.10 (2H, t, J=8.8 Hz), 7.29 (2H, m), 7.56 (1H, t, J=7.8 Hz), 7.82 (2H, d, J=8.8 Hz), 8.09 (1H, d, J=7.8 Hz), 8.22-8.29 (2H, m), 8.71 (1H, d, J=6.3 Hz), 9.26 (1H, s).

EXAMPLE 12

1-[N-(5-Isoquinolinesulfonyl)-N-methyl-p-nitrophenylalanyl]-4-phenylpiperazine 5.87 g of the crystals obtained in Example 11 was dissolved in 60 ml of dimethylformamide, and to the solution were sequentially added 500 mg of 60% sodium hydride and 1.5 ml of methyl iodide with ice cooling. After stirring for two hours with ice cooling, water was added to the reaction mixture, which was then extracted with 150 ml of ethyl acetate. The extract was washed with saturated sodium chloride aqueous solution, dried over magnesium sulfate and concentrated under a reduced pressure to obtain a residue, which was applied to a silica gel column and eluted with chloroform/methanol (100:1) to obtain 5.93 g of the title compound in a yellow amorphous form.

IR (KBr) cm$^{-1}$: 1640, 1600, 1535, 1445, 1340, 1225, 1150, 1125;

$^1$H-NMR (CDCl$_3$, δ ppm): 2.60 (1H, dd, J=4.9, 12.7 Hz), 2.83 (1H, m), 2.92–3.06 (3H, m), 3.06 (3H, s), 3.40 (1H, dd, J=7.8, 13.2 Hz), 3.46–3.63 (2H, m), 3.70–3.88 (2H, m), 5.23 (1H, dd, J=4.9, 9.8 Hz), 6.82 (2H, d, J=7.8 Hz), 6.91 (1H, t, J=7.3 Hz), 7.22–7.30 (4H, m), 7.73 (1H, t, J=7.8 Hz), 8.07 (2H, d, J=8.8 Hz), 8.25 (1H, d, J'1.0, 7.3 Hz), 8.48 (1H, d, J=6.4 Hz), 8.71 (1H, d, J=6.4 Hz), 9.37 (1H, d, J=1.0 Hz).

EXAMPLE 13

1-[p-Amino-N-(5-isoquinolinesulfonyl)-N-methylalanyl]-4-phenylpiperazine 6.08 g of the amorphous compound obtained in Example 12 was dissolved in 70 ml of methanol, and to the solution were added 5 ml of 12 N hydrochloric acid and 30 ml of water, and then 5 g of 5% palladium on carbon. The mixture was stirred at a room temperature under a hydrogen atmosphere for 30 minutes, and filtered to remove insoluble matter, and the filtrate was concentrated under a reduced pressure, and to the residue was added 150 ml of saturated sodium bicarbonate aqueous solution, and the mixture was extracted twice with 200 ml of chloroform. The extract was dried over magnesium sulfate and concentrated under a reduced pressure to obtain a residue, which was then applied to a silica gel column and eluted with chloroform/methanol (50:1) to obtain 3.32 g of the title compound in a yellow amorphous form.

IR (KBr) cm$^{-1}$: 1635, 1600, 1495, 1445, 1325, 1220, 1150, 1125;

$^1$H-NMR (CDCl$_3$, δ ppm): 2.47–2.56 (2H, m}, 2.87–3.22 (4H, m), 3.14 (3H, s), 3.33–3.75 (4H, m), 5.14 (1H, dd, J=4.9, 9.8 Hz), 6.50 (2H, d, J=8.3 Hz), 6.80–6.92 (5H, m), 7.22–7.34 (2H, m), 7.69 (1H, t, J=7.8 Hz), 8.20 (1H, d, J=8.3 Hz), 8.36 (1H, dd, J=1.5, 7.3 Hz), 8.40 (1H, d, J=5.9 Hz), 8.68 (1H, d, J=6.4 Hz), 9.34 (1H, s).

EXAMPLE 14

3.75 g of the crystal prepared in Example 11 was treated according to the procedure as described in Example 13 to obtain 2.17 g of 1-[p-amino-N-(5-isoquinolinesulfonyl)phenylalanyl]-4-phenylpiperazine as yellow crystals.

IR (KBr) cm$^{-1}$: 1635, 1600, 1495, 1440, 1320, 1225, 1155, 1135;

$^1$H-NMR (CDCl$_3$, δ ppm): 2.41 (1H, m), 2.59–3.07 (6H, m), 3.17 (1H, m), 3.33 (1H, m), 3.51 (1H, m), 4.35 (1H, m), 5.95 (1H, d, J=9.3 Hz), 6.38 (2H, d, J=8.3 Hz), 6.75 (2H, d, J=8.3 Hz), 6.78 (2H, d, J=7.8 Hz), 6.91 (1H, t, J=7.3 Hz), 7.22–7.30 (2H, m), 7.60 (1H, t, J=8.3 Hz), 8.12 (1H, d, J=8.3 Hz), 8.30–8.35 (2H, m), 8.71 (1H, d, J=5.9 Hz), 9.30 (1H, s).

EXAMPLE 15

1-[N-(5-Isoquinolinesulfonyl)-p-(p-toluenesulfonylamino)phenylalanyl]-4-phenylpiperazine 200 mg of the crystals obtained in Example 14 was dissolved in 5 ml of pyridine, and to the solution was added 90 mg of p-toluenesulfonylchloride with ice cooling, and the mixture was stirred for one hour with ice cooling and poured to 30 ml of saturated sodium bicarbonate aqueous solution. The mixture was extracted twice with 15 ml of chloroform, and the extract was dried over magnesium sulfate and concentrated under a reduced pressure to obtain a residue, which was then applied to a silica gel column and eluted with chloroform/methanol (80:1 to 50:1) to obtain 128 mg of the title compound.

IR (KBr) cm$^{-1}$: 1635, 1600, 1335, 1225, 1155, 1090;

$^1$H-NMR (CDCl$_3$, δ ppm): 2.30 (3H, s), 2.65–2.80 (4H, m), 2.83–3.04 (2H, m), 3.17–3.50 (4H, m), 4.33 (1H, m), 6.14 (1H, d, J=9.3 Hz), 6.70–6.83 (6H, m), 6.93 (1H, t, J=7.3 Hz), 6.77 (1H, s), 7.17 (2H, d, J=8.3 Hz), 7.26–7.36 (2H, m}, 7.59 (1H, t, J=7.3 Hz), 7.59 (2H, d, J=8.3 Hz), 8.13 (1H, d, J=7.8 Hz), 8.30 (2H, m), 8.64 (1H, br), 9.31 (1H, br).

EXAMPLE 16

The same procedure as described in Example 15 was repeated, except that 200 mg of 5-isoquinolinesulfonyl chloride.HCl and 300 mg of the crystals obtained in Example 14 were used and elution was carried out with chloroform/methanol (40:1 to 20:1), to obtain 372 mg of 1-[N-(5-isoquinolinesulfonyl)-p-(5-isoquinolinesulfonylamino)phenylalanyl]-4-phenylpiperazine.

IR (KBr) cm$^{-1}$: 1630, 1600, 1340, 1225, 1155, 1135;

$^1$H-NMR (CDCl$_3$, δ ppm): 2.35–3.07 (9H, m), 3.30 (1H, m), 4.26 (1H, m), 6.67–6.84 (6H, m), 6.89–6.96 (2H, m), 7.23 (2H, t, J=8.8 Hz), 7.52 (1H, t, J=7.8 Hz), 7.54 (1H, t, J=7.8 Hz), 7.98 (1H, d, J=7.8 Hz), 8.07 (1H, d, J=8.3 Hz), 8.25 (1H, d, J=6.8 Hz), 8.31–8.36 (2H, m), 8.54 (1H, d, J=6.3 Hz), 8.65 (2H, d, J=6.4 Hz), 9.17 (1H, s), 9.26 (1H, s), 10.06 (1H, s).

EXAMPLE 17

The same procedure as described in Example 15 was repeated, except that 200 mg of 1-naphtharenesulfonyl chloride and 360 mg of the crystals obtained in Example 14 were used as starting materials and elution was carried out using chloroform/methanol (80:1 to 50:1), to obtain 385 mg of 1-[N-(5-isoquinolinesulfonyl)-p-(1naphtharenesulfonylamino)phenylalanyl]-4-phenylpiperazine.

$^1$H-NMR (CDCl$_3$, δ ppm): 2.40–2.74 (6H, m), 2.80–3.04 (3H, m) 3.33 (1H, m), 4.24 (1H, m), 6.68–6.82 (6H, m), 6.92 (1H, t, J=7.3 Hz), 7.12 (1H, d, J=9.3 Hz), 7.26–7.57 (5H, m), 7.65 (1H, m), 7.78 (1H, d, J=8.3 Hz), 7.88 (1H, d, J=7.8 Hz), 7.99 (1H, d, J=8.3 Hz), 8.16 (1H, dd, J=J=1.0, 7.3 Hz), 8.36 (1H, d, J=5.9 Hz), 8.65 (1H, d, J=6.4 Hz), 8.77 (1H, d, J=8.8 Hz), 9.22 (1H, s), 9.88 (1H, s).

EXAMPLE 18

The same procedure as described in Example 15 was repeated, except that 0.07 ml of methanesulfonyl chloride and 360 mg of the crystals obtained in Example 14 were used as starting materials and elution was carried out using chloroform/methanol (50:1 to 30:1), to obtain 356 mg of 1-[N-(5-isoquinolinesulfonyl)-p-(methanesulfonylamino)phenylalanyl]-4-phenylpiperazine.

IR (KBr) cm$^{-1}$: 1635, 1600, 1330, 1225, 1150;

$^1$H-NMR (CDCl$_3$, δ ppm): 2.38 (1H, m), 2.72 (3H, s), 2.70-2.90 (6H, m), 3.04-3.21 (3H, m), 3.42 (1H, m), 4.39 (1H, m), 6.78 (2H, d, J=7.8 Hz), 6.88 (1H, t, J=7.3 Hz), 6.92 (2H, d, J=8.3 Hz), 7.00 (2H, d, J=8.3 Hz), 7.20-7.30 (3H, m), 7.62 (1H, t, J=7.8 Hz), 8.16 (1H, d, J=8.3 Hz), 8.32 (1H, dd, J=1.0, 7.3 Hz), 8.42 (1H, d, J=5.9 Hz), 8.69 (1H, d, J=6.4 Hz), 9.15 (1H, s), 9.31 (1H, s).

EXAMPLE 19

1-[N-(5-Isoquinolinesulfonyl)-p-methanesulfonylamino-N-methylphenylalanyl]-4-phenylpiperazine 700 mg of the amorphous compound obtained in Example 13 was dissolved in 7 ml of pyridine, and to the solution was added 0.13 ml of methanesulfonyl chloride with ice cooling, and the mixture was stirred for one hour with ice cooling and poured to 50 ml of saturated sodium bicarbonate aqueous solution. The mixture was extracted twice with 30 ml of chloroform. The extract was dried over magnesium sulfate and concentrated under a reduced pressure. The resulting residue was applied to a silica gel column and eluted with chloroform/methanol (100:1 to 50:1) to obtain 790 mg of the title compound.

IR (KBr) cm$^{-1}$: 1635, 1595, 1325, 1220, 1145;

$^1$H-NMR (CDCl$_3$, δ ppm): 2.48-2.59 (2H, m), 2.83 (3H, s), 2.85-3.10 (3H, m), 3.12 (3H, s), 3.22 (1H, dd, J=9.8, 13.2 Hz), 3.44-3.80 (4H, m), 5.16 (1H, dd, J=5.4, 9.8 Hz), 6.80-6.93 (4H, m), 7.04 (4H, s), 7.26 (2H, t, J=8.3 Hz), 7.72 (1H, t, J=7.8 Hz), 8.23 (1H, d, J=8.3 Hz), 8.35 (1H, dd, J=1.0, 7.3 Hz) 8.42 (1H, d, J=5.9 Hz), 8.68 (1H, d, J=5.9 Hz), 9.36 (1H, s).

EXAMPLE 20

The same procedure as described in Example 19 was repeated, except that 360 mg of 1-naphtharenesulfonyl chloride and 700 mg of the amorphous compound obtained in Example 13 were used as starting materials, and elution was carried out using chloroform/methanol (100:1) to obtain 770 mg of 1-[N-(5-isoquinolinesulfonyl)-N-methyl-p-(1-naphtharenesulfonylamino)phenylalanyl]-4-phenylpiperazine.

IR (KBr) cm$^{-1}$: 1635, 1595, 1440, 1330, 1220, 1150, 1120;

$^1$H-NMR (CDCl$_3$, δ ppm): 2.42 (1H, dd, J=4.9, 12.7 Hz), 2.63 (1H, m), 2.85-3.17 (4H, m), 3.07 (3H, s), 3.32-3.73 (4H, m), 5.04 (1H, dd, J=5.4, 10.3 Hz), 6.73-6.96 (7H, m), 7.05 (1H, br), 7.30-7.41 (3H, m) 7.54-7.70 (3H, m], 7.88 (1H, d, J=7.8 Hz), 7.95 (1H, d, J=8.3 Hz), 8.12 (1H, dd, J=1.0, 7.3 Hz), 8.16 (1H, d, J=8.3 Hz), 8.27 (1H, dd, J=1.5, 7.3 Hz), 8.37 (1H, d, J=6.3 Hz), 8.62-8.68 (2H, m), 9.32 (1H, s).

EXAMPLE 21

The same procedure as described in Example 19 was repeated except that 320 mg of 5-isoquinolinesulfonyl chloride.HCL as a sulfonating agent, 500 mg of the amorphous compound obtained in Example 13, 5 ml of pyridine and chloroform/methanol (80:1 to 50:1) as an eluent were used, to obtain 498 mg of 1-[N-(5-isoquinolinesulfonyl-p-(5-isoquinolinesulfonylamino)-N-methylphenylalanyl]-4-phenylpiperazine.

IR (KBr) cm$^{-1}$: 1640, 1595, 1330, 1225, 1155, 1135

$^1$H-NMR (CDCl$_3$, δ ppm): 2.44 (1H, dd, J=4.9, 13.2 Hz), 2.61 (1H, m), 2.85-3.26 (5H, m), 3.05 (3H, s), 3.40-3.70 (3H, m), 5.06 (1H, dd, J=4.9, 9.8 Hz), 6.77 (2H, d, J=8.8 Hz), 6.79-6.97 (5H, m), 7.31 (2H, t, J=7.3 Hz), 7.53 (1H, t, J=8.3 Hz), 7.63 (1H, t, J=8.8 Hz), 8.08 (1H, d, J=8.3 Hz), 8.20 (1H, d, J 8.3 Hz), 8.27-8.32 (2H, m), 8.37 (2H, d, J=6.4 Hz), 8.64 (1H, d, J=6.4 Hz), 8.67 (1H, d, J=6.4 Hz), 9.29 (1H, s), 9.34 (1H, s)

EXAMPLE 22

The same procedure as described in Example 19 was repeated except that 300 mg of p-toluenesulfonyl chloride as a sulfonating agent, 700 mg of the amorphous compound obtained in Example 13, 10 ml of pyridine as an eluate and chloroform/methanol (100:1) were used, to obtain 812 mg of 1-[N-(5-isoquinolinesulfonyl)-N-methyl-p-(p-toluenesulfonylamino)phenylalanyl]-4-phenylpiperazine IR (KBr) cm$^{-1}$: 1635, 1595, 1440, 1325, 1220, 1150;

$^1$H-NMR (CDCl$_3$, δ ppm): 2.32 (3H, s), 2.50 (1H, dd, J=4.9, 12.7 Hz), 2.68 (1H, m), 2.90-3.03 (4H, m), 3.10 (3H, s), 3.29 (1H, m), 3.42-3.73 (3H, m), 5.12 (1H, dd, J=5.4, 9.8 Hz), 6.79-6.97 (7H, m), 7.17 (2H, d, J=8.3 Hz), 7.28 (2H, t, J=7.3 Hz), 7.61 (2H, d, J=8.3 Hz), 7.69 (1H, t, J=7.8 Hz), 8.21 (1H, d, J=8.3 Hz), 8.31 (1H, dd, J=1.5, 7.3 Hz), 8.40 (1H, d, J=5.9 Hz), 8.65 (1H, d, J=6.4 Hz), 9.35 (1H, s).

EXAMPLE 23

1-{(N-(5-Isoquinolinesulfonyl)-p-N'-(5-isoquinolinesulfonyl)-N'-methylamino]-N-methylphenylalanyl}-4-phenylpiperazine 306 mg of the product in Example 21 was dissolved in 5 ml of dimethylformamide, and to the solution were added 25 mg of 60% sodium hydride and 0.1 ml of hydrogen iodide with ice cooling, and the mixture was stirred for one hour with ice cooling. After the addition of 30 ml of saturated sodium chloride, the mixture was extracted with 30 ml of ethyl acetate, and the extract was washed with saturated sodium chloride aqueous solution, dried over magnesium sulfate and concentrated under a reduced pressure. The resulting residue was applied to a silica gel column and eluted with chloroform/methanol (80:1) to obtain 266 mg of the title compound.

IR (KBr) cm$^{-1}$: 1640, 1600, 1445, 1340, 1225, 1150, 1130;

$^1$H-NMR (CDCl$_3$, δ ppm): 2.41-2.61 (2H, m), 2.83-3.09 (3H, m), 3.07 (6H, s), 3.27 (1H, dd, J=10.7, 13.2 Hz), 3.43 (1H, m), 3.56-3.71 (3H, m) 5.18 (1H, dd, J=4.4, 10.7 Hz), 6.80-6.91 (3H, m), 6.94 (2H, d, J=8.8 Hz), 7.00 (2H, d, J=8.8 Hz), 7.21-7.30 (2H, m), 7.60 (1H, t, J=7.8 Hz), 7.73 (1H, t, J=7.8 Hz), 7.98 (1H, d, J=5.9 Hz), 8.14-8.23 (3H, m), 8.36 (1H, d, J=8.4 Hz), 8.40 (1H, d, J=5.9 Hz), 8.46 (1H, d, J=6.4 Hz), 8.69 (1H, d, J=6.4 Hz), 9.29 (1H, s), 9.37 (1H, s).

EXAMPLE 24

The same procedure as described in Example 23 was repeated except that 594 mg of the product of Example 19 was dissolved in 6 ml of dimethylformamide and to the solution were added 60 mg of 60% sodium hydride and 0.1 ml of methyl iodide, to obtain 450 mg of 1-[N-(5-isoquinolinesulfonyl)-p-(N'-methanesulfonyl-N'- methylamino) N-methylphenylalanyl]-4-phenylpiperazine.

IR (KBr) cm$^{-1}$: 1635, 1595, 1445, 1335, 1225, 1150, 1140;

$^1$H-NMR (CDCl$_3$, δ ppm): 2.36 (1H, m), 2.50 (1H, dd, J=3.9, 12.2 Hz), 2.64 (3H, s), 2.81 (1H, m), 2.96–3.16 (2H, m), 3.11 (3H, s), 3.16 (3H, s), 3.31 (1H, dd, J=10.7, 12.7 Hz), 3.37–3.62 (3H, m), 3.78 (1H, m), 5.20 (1H, dd, J=4.4, 10.7 Hz), 6.80 (2H, d, J=7.8 Hz], 6.88 (1H, t, J=7.3 Hz), 7.12 (2H, d, J=8.8 Hz), 7.21–7.31 (4H, m), 7.74 (1H, t, J=7.8 Hz), 8.24 (1H, d, J=7.8 Hz), 8.38 (1H, dd, J=1.0, 7.3 Hz), 8.47 (1H, d, J=6.4 Hz), 8.71 (1H, d, J=6.4 Hz), 9.37 (1H, s).

EXAMPLE 25

The same procedure as described in Example 23 was repeated, except that 587 mg of the product of Example 20 was dissolved in 6 ml of dimethylformamide and to the solution were added 50 mg of 60% sodium hydride and 0.1 ml of methyl iodide, and elution was carried out using chloroform/methanol (100:1), to obtain 490 mg of 1-{N-(5-isoquinolinesulfonyl)-N-methyl-p-[N'-methyl-N'-(1-naphtharenesulfonyl)amino]phenylalanyl}-4-phenylpiperazine.

IR (KBr) cm$^{-1}$: 1640, 1600, 1440, 1330, 1220, 1150, 1125;

$^1$H-NMR (CDCl$_3$, δ ppm): 2.47 (1H, dd, J=4.4, 12.7 Hz), 2.53 (1H, m), 2.80–3.07 (3H, m), 3.07 (3H, s), 3.08 (3H, s), 3.27 (1H, dd, J=10.3, 12.7 Hz), 3.38 (1H, m), 3.51–3.65 (3H, m), 5.17 (1H, dd, J=4.4, 10.3 Hz), 6.81 (2H, d, J=8.8 Hz), 6.88 (1H, t, J=7.3 Hz), 6.98 (4H, s), 7.24 (2H, dd, J=7.3, 8.8Hz), 7.38–7.57 (3H, m), 7.72 (1H, d, J=7.3 Hz), 7.88 (1H, d, J=7.8 Hz), 8.01 (1H, d, J=8.3 Hz), 8.04 (1H, d, J=7.3 Hz), 8.23 (1H, d, J=8.3 Hz), 8.32–8.37 (2H, m), 8.46 (1H, d, J=5.9 Hz), 8.68 (1H, d, J=6.3 Hz), 9.36 (1H, s).

EXAMPLE 26

The same procedure as described in Example 23 was repeated, except that 650 mg of the product of Example 22 was dissolved in 10 ml of dimethylformamide, and to the solution were added 60 mg of 60% sodium hydride and 0.1 ml of methyl iodide, and elution was carried out using chloroform/methanol (100:1), to obtain 603 mg of 1-{N-(5-isoquinolinesulfonyl)-N-methyl-p-[N'-methyl-N'-(p-toluenesulfonyl)amino]phenylalanyl}-4-phenylpiperazine.

IR (KBr) cm$^{-1}$: 1640, 1600, 1440, 1335, 1220, 1145;

$^1$H-NMR (CDCl$_3$, δ ppm): 2.37 (3H, s), 2.52 (1H, dd, J=4.9, 12.7 Hz), 2.55 (1H, m), 2.80–3.10 (3H, m), 2.99 (3H, s), 3.11 (3H, s), 3.28 (1H, dd, J=10.3, 12.7 Hz), 3.40 (1H, m), 3.50–3.68 (3H, m), 5.20 (1H, dd, J=4.9, 10.3 Hz), 6.81 (2H, d, J=8.3 Hz), 6.88 (1H, t, J=7.3 Hz), 6.98 (2H, d, J=8.8 Hz) 7.05 (2H, d, J=8.8 Hz), 7.18 (2H, d, J=8.3 Hz), 7.24 (2H, dd, J=7.3, 8.3 Hz), 7.37 (2H, d, J=8.3 Hz), 7.73 (1H, t, J=7.8 Hz), 8.23 (1H, d, J=8.3 Hz), 8.36 (1H, dd, J=1.0, 7.8 Hz), 8.46 (1H, d, J=6.4 Hz), 8.70 (1H, d, J=6.4 Hz) 9.36 (1H, s).

REFERENCE EXAMPLE 11

1-(N-Benzyloxycarbonyltyrosyl)-4-(tert-butoxycarbonyl)piperazine 21.31 g of N-benzyloxycarbonyltyrosine and 11.79 of N-(tert-butoxycarbonyl)piperazine were dissolved in a mixed solvent of 200 ml of methylene chloride and 100 ml of ethyl acetate, and to the solution was added 14 g of DCC. After stirring at a room temperature for 40 hours, precipitated insoluble matter was filtered off, and the filtrate was concentrated under a reduced pressure, and resulting residue was applied to a silica gel column and eluted with hexane/ethyl acetate (1:1) to obtain 23.9 g of the title compound in a colorless amorphous form $^1$H-NMR (CDCl$_3$, δ ppm): 1.45 (9H, s), 2.80–3.02 (4H, m), 3.14–3.39 (4H, m), 3.49 (2H, m), 4.83 (1H, m), 5.08 (1H, d., J=12 Hz), 5.10 (1H, d, J=12 Hz), 5.69 (1H, d, J=8.8 Hz), 6.17 (1H, br), 6.72 (2H, d, J=8.8 Hz), 7.01 (2H, d, J=8.3 Hz), 7.34 (5H, s).

EXAMPLE 27

1-[N,O-bis(5-isoquinolinesulfonyl) tyrosyl]1-4-(tert-butoxycarbonyl)piperazine 1.00 g of the amorphous compound obtained in Reference Example 11 was dissolved in 20 ml of methanol, to the solution was added 500 mg of 5% palladium on carbon, and the mixture was stirred under a hydrogen atmosphere at a room temperature for 5 hours. After removing insoluble matter by filtration, the filtrate was concentrated under a reduced pressure. To the resulting residue were added sequentially 30 ml of tetrahydrofuran, 630 mg of 5-isoquinolinesulfonyl chloride.HCl and 1.4 ml of triethylamine, and the mixture was stirred at a room temperature for 50 hours, and after the addition of 100 ml of water, extracted twice with 50 ml of chloroform. The extract was dried over magnesium sulfate and concentrated under a reduced pressure. The resulting residue was then applied to a silica gel column and eluted with chloroform/methanol (50:1 to 25:1) to obtain 1.38 g of the title compound in a yellow amorphous form.

$^1$H-NMR (CDCl$_3$, δ ppm): 1.45 (9H, s), 2.53–3.18 (10H, m), 4.29 (1H, m), 6.05 (1H, d, J=9.3 Hz), 6.61 (2H, d, J=8.8 Hz), 6.85 (2H, d, J=8.8 Hz), 7.62 (1H, t, J=7.8 Hz), 7.66 (1H, t, J=7.8 Hz), 8.19 (2H, d, J=7.8 Hz), 8.26–8.31 (3H, m), 8.52 (1H, d, J=5.9 Hz), 8.69 (1H, d, J=5.9 Hz), 8.84 (1H, d, J=6.4 Hz), 9.33 (1H, s), 9.43 (1H, s)

EXAMPLE 28

1-[N,O-bis(5-isoquinolinesulfonyl) tyrosyl]piperazine 366 mg of the amorphous compound prepared in Example 27 was dissolved in 3 ml of chloroform, and to the solution was added 5 ml of 3N hydrochloric acid/ethyl acetate. After stirring at a room temperature for one hour, the mixture was concentrated under a reduced pressure, and to resulting residue was added 50 ml of saturated sodium bicarbonate aqueous solution. The mixture was then twice extracted with 30 ml of a mixed solvent of chloroform/methanol (5:1), and the extract was dried over magnesium sulfate and concentrated under a reduced pressure to obtain 301 mg of a crude preparation of the title compound in a colorless amorphous form.

$^1$H-NMR (CDCl$_3$, δ ppm): 2.11 (1H, m), 2.35 (1H, m), 2.43 (2H, m), 2.70–2.83 (4H, m), 2.90 (1H, m), 3.09 (1H, m), 4.30 (1H, t, J=7.4 Hz), 6.65 (2H, d, J=8.3 Hz), 6.88 (2H, d, J=8.3 Hz), 7.62 (1H, dd, J=7.3, 8.3 Hz), 7.64 (1H, t, J=7.8 Hz), 8.17 (1H, d, J=8.3 Hz), 8.24–8.31 (4H, m), 8.52 (1H, d, J=5.9 Hz), 8.68 (1H, d, J=6.3 Hz), 8.83 (1H, d, J=6.4 Hz), 9.32 (1H, s), 9.43 (1H, s).

EXAMPLE 29

1-Benzyloxycarbonyl-4-N-(5-isoquinolinesulfonyl)-tyrosyl]piperazine 620 mg of the crude product obtained in Example 28 was dissolved in 10 ml of methylene chloride, and to the solution were sequentially added 0.29 ml of benzyloxycarbonyl chloride and 3.04 ml of triethylamine with ice cooling. After stirring for two hours with ice cooling, 40 ml of saturated sodium chloride aqueous solution was added to the reaction mixture, which was then extracted twice with 20 ml of chloroform, and the extract was dried over magnesium sulfate and concentrated under a reduced pressure to obtain a residue. The residue was dissolved in 6 ml of methanol, and after the addition of 2 ml of 1N sodium hydroxide aqueous solution, the mixture was refluxed for two hours, dried over magnesium sulfate and concentrated under a reduced pressure. The resulting residue was applied to a silica gel column and eluted with chloroform/methanol (80:1 to 50:1) to obtain 336 mg of the title compound as colorless crystals.

Melting point: 137°–141° C.

IR (KBr) cm$^{-1}$: 1700, 1630, 1510, 1417, 1318, 1218, 1148, 1128;

$^1$H-NMR(CDCl$_3$—CD$_3$OD, δ ppm): 2.60–2.77 (2H, m), 2.80–3.55 (8H, m), 4.25 (1H, t, J=7.8 Hz), 5.10 (1H, s), 5.12 (1H, s), 6.29, 6.74 (Total 2H, each d, each J=8.3 Hz), 6.60, 7.01 (Total 2H, each d, each J=8.3 Hz), 7.35 (5H, s), 7.60 (1H, t, J=7.8 Hz), 8.15 (1H, d, J=8.3 Hz), 8.26 (1H, d, J=7.8 Hz), 8.29 (1H, d, J=5.9 Hz), 8.57 (1H, d, J=5.9 Hz), 9.25 (1H, s).

EXAMPLE 30

The same procedure as described in Example 29 was repeated to obtain 1-[N-(5-isoquinolinesulfonyl)-tyrosyl]-4-phenylacetylpiperazine in a yellow amorphous form.

IR (KBr) cm$^{-1}$: 1620, 1510, 1435, 1320, 1228, 1152, 1130;

$^1$H-NMR (DMSO-d$_6$, δ ppm): 2.20–3.45 (10H, m), 3.67, 370 (Total 2H, each s), 4.32, 4.82 (Total 1H, each m), 6.45, 6.65 (Total 2H, each d, each J=8.3 Hz), 6.82, 7.00 (Total 2H, each d, each J=8.3 Hz), 7.13–7.39 (5H, m), 7.60–7.74 (1H, m), 8.13–8.42 (3H, m), 8.64 (1H, d, J=5.9 Hz), 9.18 (1H, br), 9.39 (1H, br).

EXAMPLE 31

The same procedure as described in Example 29 was repeated to obtain 1-[N-(5-isoquinolinesulfonyl)-tyrosyl]-4-(3-phenylpropionyl)piperazine as colorless crystals.

Melting point: 172°–178° C.;

IR (KBr) cm$^{-1}$: 1630, 1510, 1440, 1320, 1225, 1150, 1128;

$^1$H-NMR (CDCl$_3$—CD$_3$OD, δ ppm): 2.50–3.47 (14H, m), 4.26 (1H, t, J=7.3 Hz), 6.32 (2H, d, J=8.3 Hz), 6.62 (2H, d, J=8.3 Hz), 7.15–7.34 (5H, m), 7.62 (1H, t, J=7.8 Hz), 8.17 (1H, d, J=7.8 Hz), 8.24–8.33 (2H, m), 8.58 (1H, d, J=5.4 Hz), 9.26 (1H, s).

EXAMPLE 32

1-[N,O-bis(5-isoquinolinesulphonyl)tyrosyl]-4-(3-phenylpropyl)piperazine 301 mg of the crude product obtained in Example 28 and 95 mg of 3-phenylpropyl bromide were dissolved in 5 ml of dimethylformamide, and to the solution were added 66 mg of potassium carbonate and 72 mg of sodium iodide. After stirring at 80° C. for 7 hours, 30 ml of saturated sodium chloride was added to the reaction mixture, which was then extracted with 40 ml of ethyl acetate, and the extract was washed with 30 ml of saturated sodium chloride aqueous solution, dried over magnesium sulfate, and concentrated under a reduced pressure. The resulting residue was applied to a silica gel column and eluted with chloroform/methanol (40:1) to obtain 216 mg of the title compound in a yellow amorphous form.

$^1$H-NMR (CDCl$_3$, δ ppm): 1.60–1.95 (6H, m), 2.06–2.29 (2H, m), 2.53–3.20 (8H, m), 4.28 (1H, m), 5.98 (1H, d, J=9.3 Hz), 6.64 (2H, d, J=8.3 Hz), 6.86 (2H, d, J=8.3 Hz], 7.14–7.35 (5H, m), 7.59 (1H, t, J=7.8 Hz), 7.62 (1H, t, J=7.8 Hz), 8.12 (1H, d, J=8.3 Hz), 8.23–8.29 (4H, m), 8.52 (1H, d, J=5.9 Hz), 8.68 (1H, d, J=6.4 Hz), 8.82 (1H, d, J=6.4 Hz), 9.28 (1H, s), 9.42 (1H, s).

EXAMPLE 33

1-[N-(5-Isoquinolinesulfonyl)tyrosyl]-4-(3-phenylpropyl)piperazine 216 mg of the amorphous compound obtained in Example 32 was dissolved in 3 ml of methanol, and to the solution was added 0.6 ml of 2 N potassium hydroxide aqueous solution. The mixture was refluxed for 10 hours, and after the addition of 30 ml of saturated sodium chloride aqueous solution, extracted twice with 20 ml of a mixed solvent of chloroform/isopropanol (5:1). The extract was dried over magnesium sulfate and concentrated under a reduced pressure, and a resulting residue was applied to a silica gel column and eluted with chloroform/methanol (40:1 to 10:1) to obtain 74 mg of the title compound in a colorless amorphous form.

IR (KBr) cm$^{-1}$: 1630, 1510, 1440, 1320, 1230, 1150, 1128;

$^1$H-NMR (CDCl$_3$, δ ppm): 1.65–1.83 (2H, m), 2.00–2.37 (6H, m), 2.57–2.80 (4H, m), 3.02–3.42 (4H, m), 4.31 (1H, m), 6.30 (2H, d, J=8.3.Hz), 6.41 (1H, d, J=9.3 Hz), 6.65 (2H, d, J=8.3 Hz), 7.15–7.37 (5H, m), 7.60 (1H, t, J=7.8 Hz), 8.16 (1H, d, J=8.3 Hz), 8.23–8.33 (2H, m), 8.58 (1H, br), 9.33 (1H, br).

REFERENCE EXAMPLE 12

1-[N-(tert-Butoxycarbonyl) tyrosyl]-4-phenylpiperazine 19.7 g of N-(tert-butoxycarbonyl)tyrosine, 12.5 g of N-phenylpiperazine and 16.1 g of N-hydroxybenzotriazole were dissolved in 100 ml of tetrahydrofuran, and to the solution was added dropwise a solution of 18.7 g of DCC in 50 ml of tetrahydrofuran for 20 minutes with ice cooling, and the mixture was stirred for one hour. The reaction mixture was filtered to remove insoluble matter, which was then washed with 300 ml of ethyl acetate, and the filtrates were combined and concentrated under a reduced pressure. The resulting residue was dissolved in 500 ml of ethyl acetate, and the solution was washed three times with saturated sodium bicarbonate aqueous solution and once with saturated sodium chloride aqueous solution, dried over magnesium sulfate, and concentrated under a reduced pressure. The resulting residue was applied to a silica gel column and eluted with ethyl acetate/hexane (1:2 to 1:1) to collect desired fractions, which were then combined and concentrated under a reduced pressure. Resulting residue was dissolved in 100 ml of ethyl acetate, and the solution was allowed to stand overnight in a refrigerator and then filtered to remove insoluble matter. The filtrate was concentrated under a reduced pressure, subjected to azeotropic distillation with benzene and dried under a reduced pressure to obtain 40.0 g of the title compound in a colorless amorphous form.

IR (KBr) cm$^{-1}$: 1700, 1620, 1220;

$^1$H-NMR (DMSO.d$_6$, δ ppm): 1.33 (9H, s), 2.6-3.1 (6H, m), 3.4-3.7 (4H, m), 4.55 (1H, m), 6.64 (2H, d, J=8.2 Hz), 6.80 (1H, t, J=7.3 Hz), 6.90 (2H, d, J=7.9 Hz), 7.02 (2H, d, J=8.2 Hz), 7.22 (2H, dd, J=7.3, 7.9 Hz), 9.16 (1H, s).

REFERENCE EXAMPLE 13

1-[2-(tert-Butoxycarbonylamino)-3-(p-hydroxyphenyl)-propyl]-4-phenylpiperazine

With ice cooling, to a solution of 8.0 g of lithium aluminum hydride in 230 ml of tetrahydrofuran a solution of 28.0 g of aluminum chloride in 230 ml of ether was added dropwise for 50 minutes, and after 15 minutes to the resulting solution was added dropwise a solution of 40.0 g of the amorphous compound obtained in Reference Example 12 in 230 ml of tetrahydrofuran, for 15 minutes. The reaction mixture was allowed to become a room temperature, and after the addition of 300 ml of tetrahydrofuran, stirred for 25 minutes. The mixture was filtered to remove insoluble matter which was then washed with tetrahydrofuran. The combined filtrate was concentrated under a reduced pressure, and resulting residue was applied to a silica gel column, and eluted with chloroform/methanol (20:1) to collect fractions, which were then concentrated under a reduced pressure. Then 100 ml of ethyl acetate was added to the residue to crystallize a product. The product was filtered to collect, and washed 5 times with a mother liquid and further 3 times with n-hexane and dried under a reduced pressure to obtain 24.1 g of the title compound as colorless crystals.

Melting point: 199°-202° C. (decomposed)

$^1$H-NMR (DMSO-d$_6$, δ ppm): 1.33 (9H, s), 2.2-2.8 (8H, m), 3.09 (4H, brs), 3.72 (1H, m), 6.5-7.0 (7H, m), 7.20 (2H, t, J=8.3 Hz), 9.10 (1H, s);

IR (KBr) cm$^{-1}$: 1690, 1500, 1230.

REFERENCE EXAMPLE 14

1-[2-Amino-3-(p-hydroxyphenyl)propyl]-4-phenylpiperazine

To a suspension of 23.6 g of the crystals obtained in Reference Example 13 in 100 ml of ethyl acetate, was added dropwise 215 ml of 4N hydrochloric acid solution in ethyl acetate for 30 minutes, and after stirring for 90 minutes, excess hydrochloric acid was removed from the reaction mixture under a reduced pressure. After extraction with 200 ml of water, the separated ethyl acetate layer was extracted with 50 ml of 1N hydrochloric acid aqueous solution. The aqueous layers were combined and neutralized to pH 7.4 with solid sodium bicarbonate, and resulting crystals was collected, washed with water and benzene and dried by phosphorus pentaoxide in a desiccator under a reduced pressure to obtain 16.9 g of the title compound as colorless crystals.

Melting point: >270° C.;

IR (KBr) cm$^{-1}$: 1600, 1470, 1230;

$^1$H-NMR (DMSO-d$_6$, δ ppm): 2.2-3.5 (13H, m), 6.7-6.8 (3H, m), 6.90 (2H, d, J=8.3 Hz), 7.07 (2H, d, J=8.3 Hz), 7.19 (2H, t, J=7.6 Hz), 8.00 (2H, brs), 9.41 (1H, brs).

EXAMPLE 34

N-{1-[p-(5-Isoquinolinesulfonyloxy)benzyl-2-(4-phenylpiperazinyl)ethyl}-5-isoquinolinesulfonamide To a suspension of 22.96 g of the crystals obtained in Reference Example 14 in 700 ml of tetrahydrofuran, was added 51.01 g of 5-isoquinolinesulfonyl chloride.HCl with ice cooling for 5 minutes, and then was added dropwise 103 ml of triethylamine for 30 minutes. After allowing to warm to a room temperature, the reaction mixture was poured into 460 ml of ice water, and the whole was extracted with 920 ml and 230 ml of chloroform. The combined extract was washed with saturated sodium chloride aqueous solution, dried over magnesium sulfate and concentrated to dryness under a reduced pressure. The resulting amorphous residue was applied to a silica gel column and eluted with chloroform/methanol (100:1 to 50:1) to obtain 45.5 g of the title compound in a yellow amorphous form.

IR (KBr) cm$^{-1}$: 1600, 1500, 1130;

$^1$H-NMR (CDCl$_3$, δ ppm): 2.0-3.0 (12H, m), 3.30 (1H, m), 5.51 (1H, brs), 6.7-7.8 (11H, m), 8.20 (1H, d, J=8.2 Hz), 8.28 (2H, d, J=7.7 Hz), 8.4-8.5 (2H, m), 8.53 (1H, d, J=6.1 Hz), 8.67 (1H, d, J=6.1 Hz) 8.81 (1H, d, J=6.1 Hz), 9.35 (1H, s), 9.42 (1H, s).

EXAMPLE 35

N-{1-[p-(5-Isoquinolinesulfonyloxy)benzyl]-2-(4-phenylpiperazinyl)ethyl}-N-methyl-5-isoquinolinesulfonamide To a solution of 25.0 g of the amorphous compound obtained in Example 34 in 200 ml of dimethylformamide was added in three portions 1.64 g of 60% sodium hydride, and after 5 minutes, also was added dropwise 3.14 ml of methyl iodide for two minutes, and the reaction mixture was stirred for one hour. The reaction mixture was poured to 400 ml of ice water, and the whole was extracted with 200 ml, 200 ml and 100 ml of ethyl acetate. The combined extract was washed three times with saturated sodium chloride aqueous solution, dried over magnesium sulfate and concentrated under a reduced pressure, and the resulting residue was applied to a silica gel column and eluted with chloroform/methanol (100:1) to obtain 20.0 g of the title compound in a yellow amorphous form.

$^1$H-NMR (CDCl$_3$, δ ppm): 2.30 (1H, dd, J=6.8, 12.2 Hz), 2.39-2.52 (5H, m), 2.68 (1H, dd, J=7.3, 14.2 Hz), 2.86 (3H, s), 2.89-3.01 (5H, m), 4.18 (1H, m), 6.61 (2H, d, J=8.3 Hz), 6.83-6.92 (5H, m), 7.26 (2H, t, J=7.8 Hz), 7.57 (1H, t, J=7.8 Hz), 7.60 (1H, t, J=7.8 Hz), 8.10 (1H, d, J=8.3 Hz), 8.23-8.28 (3H, m), 8.33 (1H, dd, J=1.0, 7.3 Hz), 8.56 (1H, d, J=5.9 Hz), 8.58 (1H, d, J=5.9 Hz), 8.83 (1H, d, J=5.9 Hz), 9.27 (1H, s), 9.41 (1H, d, J=1.0 Hz).

IR (KBr) cm$^{-1}$: 1620, 1500, 1370, 1325, 1130.

EXAMPLE 36

N-[1-(p-Hydroxybenzyl)-2-(4-phenylpiperazinyl)ethyl]-N-methyl-5-isoquinolinesulfonamide To 17.7 g of the amorphous compound obtained in Example 35 were added 240 ml of methanol, 60 ml of tetrahydrofuran and 29 ml of 2N sodium hydroxide aqueous solution, and the mixture was refluxed for 150 minutes, and then poured to saturated sodium chloride aqueous solution. The mixture was extracted three times with 200 ml of chloroform, and the extract was washed with saturated sodium chloride aqueous solution, dried over magnesium sulfate, and concentrated under a reduced pressure. The resulting residue was applied to a silica gel column and eluted with chloroform/methanol (50:1), and 10.9 g of a yellow amorphous product was obtained from the elute. To the product was added 54 ml of ethanol and the mixture was stirred at a room temperature for one hour, and under ice cooling for 30 minutes to form crystals, which was then collected, washed three times with a mother liquid and twice with benzene, and dried under a reduced pressure to obtain 8.2 g of the title compound as light yellow crystals.

Melting point: 201° C.;

$^1$H-NMR (CDCl$_3$, δ ppm): 2.49 (1H, dd, J=6.8, 9.8 Hz), 2.52-2.77 (7H, m), 2.95 (1H, dd, J=4.4, 14.2 Hz), 3.02 (3H, s), 3.14 (4H, t, J=4.9 Hz), 4.03 (1H, m), 6.26 (2H, d, J=8.3 Hz), 6.61 (2H, d, J=8.8 Hz), 6.86 (1H, t, J=6.8 Hz), 6.91 (2H, d, J=7.3 Hz), 7.27 (2H, t, J=7.8 Hz), 7.60 (1H, t, J=7.3 Hz), 8.11 (1H, d, J=5.9 Hz), 8.14 (1H, d, J=6.4 Hz), 8.33 (1H, dd, J=1.0, 7.3 Hz), 8.47 (1H, d, J=6.3 Hz), 9.27 (1H, s);

IR (KBr) cm$^{-1}$: 1600, 1510, 1445, 1320, 1205, 1150, 1125.

EXAMPLE 37

The amorphous compound obtained in Example 34 was subjected to alkaline hydrolysis according to the procedure as described in Example 36, to obtain N-[1-(p-hydroxybenzyl)-2-(4-phenylpiperazinyl)ethyl]-5-isoquinolinesulfonamide in a colorless amorphous.

$^1$H-NMR (CDCl$_3$, δ ppm): 2.25-2.55 (6H, m), 2.65 (1H, dd, J=13.7, 6.85 Hz), 2.79 (1H, dd, J=13.7, 6.85 Hz), 2.82-3.0 (4H, m), 3.37 (1H, quintet, J=6.85 Hz), 6.42 (2H, d, J=8.57 Hz), 6.69 (2H, d, J=8.57 Hz), 6.84 (2H, d, J=8.57 Hz), 6.85 (1H, t, J=8.57 Hz), 7.26 (2H, t, J=8.57 Hz), 7.69 (1H, t, J=7.42 Hz), 8.22 (1H, d, J=7.99 Hz), 8.38 (1H, d, J=6.28 Hz), 8.43 (1H, dd, J=7.42, 1.0 Hz), 8.59 (1H, d, J=6.28 Hz), 9.34 (1H, d, J=1.0 Hz).

EXAMPLE 38

N-[1-(p-Methoxybenzyl)-2-(4-phenylpiperazinyl)ethyl]-N-methyl-5-isoquinolinesulfonamide 1.51 g of the crystals obtained in Example 36 was dissolved in 20 ml of a mixed solvent of dimethylformamide/tetrahydrofuran (1:1), and to the solution was added 140 mg of 60% sodium hydride with stirring under ice cooling, and stirring was continued for about 30 minutes. After foaming was finished, 490 mg of methyl iodide was added and the mixture was further stirred overnight at a room temperature. After the addition of ice, the reaction mixture was three times extracted with 50 ml of ethyl acetate, and the extract was washed with saturated sodium chloride aqueous solution, dried over magnesium sulfate and concentrated under a reduced pressure. The resulting residue was applied to a silicon gel column and eluted with chloroform/methanol (100:1) to obtain 1.55 g of the title compound as a light brown oil.

$^1$H-NMR (CDCl$_3$, δ ppm): 2.45 (1H, dd, J=7.1, 13.8 Hz), 2.6 (5H, m), 2.65 (1H, m), 2.88 (1H, s), 2.95 (3H, s), 3.05 (4H, m), 3.74 (3H, s), 4.2 (1H, m), 6.5 (2H, d, J=8.5 Hz), 6.9 (5H, m), 7.25 (2H, m), 7.55 (1H, t, J=7.5 Hz), 8.07 (1H, d, J=7.5 Hz), 8.22 (1H, d, J=6.4 Hz), 8.56 (1H, d, J=6.4 Hz), 9.22 (1H, s);

IR (KBr) cm$^{-1}$: 1600, 1510, 1320, 1240, 1150, 1130.

EXAMPLE 39

The same procedures as described in Reference Examples 12 to 14 and Example 34 were repeated except that 1-(2-pyrimidyl)piperazine. dihydrochloride was used in place of N-phenylpiperazine, to obtain N-{1-[p-(5-isoquinolinesufonyloxy)benzyl]-2-[4-(2-pyrimidyl)-piperazinyl]ethyl}-5-isoquinolinesulfonamide in a colorless amorphous form.

$^1$H-NMR (CDCl$_3$, δ ppm): 1.8-1.96 (2H, m), 1.96-2.24 (4H, m), 2.8 (1H, dd, J=13.7, 6.85 Hz), 2.92 (1H, dd, J=13.7, 4.57 Hz), 3.0-3.47 (5H, m), 5.49 (1H, br), 6.47 (1H, t, J=4.57 Hz), 6.70 (2H, d, J=8.57 Hz), 6.94 (2H, d, J=8.57 Hz), 7.64 (1H, t, J=7.42 Hz), 7.70 (1H, t, J=7.42 Hz), 8.17-8.35 (5H, m), 8.37-8.48 (2H, m) 8.52 (1H, d, J=5.71 Hz), 8.68 (1H, d, J=6.28 Hz), 8.82 (1H, d, J=6.28 Hz) 9.37 (1H, s), 9.42 (1H, d, J=1.0 Hz).

EXAMPLE 40

The amorphous compound of the Example 39 was treated as described in Example 37, to obtain N-{1-(p-hydroxybenzyl)-2-[4-(2-pyrimidyl)piperazinyl]ethyl}-5-isoquinolinesulfonamide in a colorless amorphous form.

$^1$H-NMR (CDCl$_3$, δ ppm) 2.05-2.55 (6H, m), 2.66 (1H, dd, J=13.13, 6.85 Hz), 2.82 (1H, dd, J=13.13, 6.28 Hz), 3.2-3.7 (5H, m), 6.42 (2H, d, J=7.99 Hz), 6.46 (1H, t, J=4.57 Hz), 6.72 (2H, d, J=7.99 Hz), 7.68 (1H, t, J=7.42 Hz), 8.20 (1H, d, J=8.57 Hz), 8.27 (2H, d, J=4.57 Hz), 8.35-8.50 (2H, m), 8.57 (1H, d, J=5.71 Hz), 9.31 (1H, s).

EXAMPLE 41

The amorphous compound of Example of 39 was treated as described in Example 35, to obtain N-{1-[p-(5-isoquinolinesulfonyloxy)benzyl]-2-[4-(2-pyrimidyl)-piperazinyl]ethyl}-N-methyl-5-isoquinolinesulfonamide in a colorless amorphous form.

$^1$H-NMR (CDCl$_3$, δ ppm) 2.15-2.36 (5H, m), 2.44 (1H, dd, J=13.7, 6.85 Hz), 2.71 (1H, dd, J=13.13, 6.85 Hz), 2.8-2.95 (1H, m), 2.87 (3H, s), 3.56 (4H, m), 4.17 (1H, quintet, J=6.85 Hz), 6.48 (1H, t, J=4.85 Hz), 6.63 (2H, d, J=9.14 Hz), 6.92 (2H, d, J=9.14 Hz), 7.58 (1H, t, J=6.85 Hz), 7.61 (1H, t, J=6.85 Hz), 8.13 (1H, d, J=7.42 Hz), 8.18-8.38 (6H, m), 8.56 (1H, d, J=6.28 Hz), 8.58 (1H, d, J=6.28 Hz), 8.84 (1H, d, J=6.28 Hz), 9.28 (1H, s), 9.42 (1H, d, J=1.0 Hz)

EXAMPLE 42

The amorphous compound of Example 41 was treated as described in Example 36, to obtain N-{1-(p-hydroxybenzyl)-2-[4-(2-pyrimidyl)piperazinyl]ethyl}-N-methyl-5-isoquinolinesulfonamide in a colorless amorphous form.

IR (KBr) cm$^{-1}$: 1585, 1510, 1355, 1325, 1255, 1130;

$^1$H-NMR (CDCl$_3$, δ ppm) 2.4-2.65 (6H, m), 2.70 (1H, dd, J=13.13, 6.28 Hz), 2.97 (1H, dd, J=13.13, 5.71 Hz), 3.03 (3H, s), 3.77 (4H, t, J=4.57 Hz), 4.04 (1H, m), 6.28 (2H, d, J=8.57 Hz), 6.49 (1H, t, J=5.14 Hz), 6.62 (2H, d, J=8.57 Hz), 7.62 (1H, t, J=7.42 Hz), 8.11 (1H, d, J=6.28 Hz), 8.15 (1H, d, J=7.42 Hz), 8.30 (2H, d, J=5.14 Hz), 8.32 (1H, dd, J=7.42, 1.0 Hz), 8.48 (1H, d, J=6.28 Hz), 9.28 (1H, s).

EXAMPLE 43

The same procedures as described in Reference Examples 12 to 14 and Examples 34 and 35 were repeated except that N-(tert-butoxycarbonyl)phenylalanine was used in place of N-(tert-butoxycarbonyl) tyrosine, to obtain N-[1-benzyl-2-(4-phenylpiperazinyl)ethyl]-N-methyl-5-isoquinolinesulfonamide in a light yellow amorphous form.

IR (KBr) cm$^{-1}$: 1595, 1490, 1300, 1220, 1120;

$^1$H-NMR (CDCl$_3$, δ ppm): 2.45 (1H, dd, J=6.6, 13 Hz), 2.7 (1H, dd, J=8, 13 Hz), 2.55 (5H, m), 3.0 (5H, m), 4.3 (1H, m), 6.84, 6.9 (Total 3H, m), 7.0 (5H, brs), 7.25 (2H, m), 7.5 (1H, t, J=7.5 Hz), 8.05 (1H, d, J=8 Hz), 8.2 (1H, d, J=7.5 Hz), 8.3 (1H, d, J=8 Hz), 8.55 (1H, d, J=6.1 Hz), 9.23 (1H, s).

EXAMPLE 44

The same procedures as described in Reference Examples 12 to 14 and Example 34 were repeated except that N-(2-pyridyl) piperazine was used in place of N-phenylpiperazine, to obtain N-{1-[p-(5-isoquinolinesulfonyloxy)benzyl-2-[4-(2-pyridyl)piperazinyl]ethyl}-5-isoquinolinesulfonamide in a yellow amorphous form.

IR (KBr) cm$^{-1}$: 1615, 1590, 1480, 1430, 1370, 1310, 1150, 1130;

$^1$H-NMR (CDCl$_3$, δ ppm): 1.93–2.21 (6H, m), 2.77 (1H, dd, J=7.3, 14.2 Hz), 2.83–3.00 (3H, m), 3.02–3.19 (2H, m), 3.29 (1H, m), 5.46 (1H, br), 6.47 (1H, d, J=8.8 Hz), 6.62 (1H, dd, J=4.9, 7.3 Hz), 6.69 (2H, d, J=8.8 Hz), 6.92 (2H, d, J=8.8 Hz), 7.44 (1H, ddd, J=1.0, 8.8, 7.3 Hz), 7.64 (1H, t, J=7.8 Hz), 7.70 (1H, dd, J=7.3, 8.3 Hz), 8.13 (1H, dd, J=1.0, 4.9 Hz), 8.22 (1H, d, J=8.3 Hz), 8.28 (2H, d, J=7.3 Hz), 8.43 (2H, m), 8.53 (1H, d, J=5.9 Hz), 8.67 (1H, d, J=6.3 Hz), 8.81 (1H, d, J=5.9 Hz), 9.35 (1H, d, J=1.0 Hz), 9.42 (1H, s).

EXAMPLE 45

The product of Example 44 was treated as described in Example 35 to obtain N-{1-[p-(5-isoquinolinesulfonyloxy)benzyl]-2-[4-(2-pyridyl)piperazinyl]ethyl}-N-methyl-5-isoquinolinesulfonamide.

IR (KBr) cm$^{-1}$: 1590, 1480, 1430, 1370, 1310, 1130;

$^1$H-NMR (CDCl$_3$, δ ppm): 2.23–2.50 (6H, m), 2.69 (1H, dd, J=7.3, 14.2 Hz), 2.86 (3H, s), 2.88 (1H, dd, J=14.2, 10.2 Hz), 3.30 (4H, m), 4.18 (1H, m), 6.55–6.65 (4H, m), 6.90 (2H, d, J=8.8 Hz), 7.47 (1H, ddd, J=1.0, 7.3, 8.8 Hz), 7.58 (1H, dd, J=7.3, 8.3 Hz), 7.60 (1H, t, J=7.8 Hz), 8.11 (1H, d, J=8.3 Hz), 8.17 (1H, dd, J=1.0, 4.9 Hz), 8.22–8.27 (3H, m), 8.33 (1H, dd, J=1.0, 7.3 Hz), 8.56 (1H, d, J=5.9 Hz), 8.58 (1H, d, J=5.9 Hz), 8.84 (1H, d, J=6.4 Hz), 9.28 (1H, s), 9.41 (1H, s).

EXAMPLE 46

The product of Example 45 was treated as described in Example 36 to obtain N-{1-(p-hydroxybenzyl)-2-[4-(2-pyridyl)piperazinyl]ethyl}-N-methyl-5-isoquinolinesulfonamide.

IR (KBr) cm$^{-1}$: 1590, 1475, 1445, 1320, 1230, 1150, 1125;

$^1$H-NMR (CDCl$_3$, δ ppm): 2.48 (1H, dd, J=3.4, 9.4 Hz), 2.50–2.75 (6H, m), 2.95 (1H, dd, J=4.9, 14.7 Hz), 3.02 (3H, s), 3.49 (4H, t, J=4.9 Hz), 4.06 (1H, m), 6.27 (2H, d, J=8.3 Hz), 6.62 (2H, d, J=8.3 Hz), 6.61–6.66 (2H, m), 7.43 (1H, ddd, J=1.0, 7.3, 8.8 Hz), 7.61 (1H, dd, J=7.3, 8.3 Hz), 8.10–8.16 (2H, m), 8.19 (1H, dd, J=1.0, 4.3 Hz), 8.32 (1H, dd, J=1.0, 7.3 Hz), 8.48 (1H, d, J=6.4 Hz), 9.28 (1H, s).

EXAMPLE 47

The same procedures as described in Reference Example 12 to 14 and Examples 34 to 36 were repeated except that N-(m-chlorophenyl)piperazine was used in place of N-phenylpiperazine, to obtain N-{2-[4-(m-chlorophenyl)piperazinyl]-1-(p-hydroxybenzyl)ethyl}-N-methyl-5-isoquinolinesulfonamide in a light yellow amorphous form.

IR (KBr) cm$^{-1}$: 1590, 1320, 1230, 1130;

$^1$H-NMR (CDCl$_3$, δ ppm): 2.5 (1H, dd, J=12.0, 10 Hz), 2.5–2.8 (2H, m), 2.6–2.7 (4H, m), 2.95 (1H, dd, J=4.5, 13.8 Hz), 3.0 (3H, s), 3.15 (4H, m), 4.0 (1H, m), 6.22 (2H, d, J=8.0 Hz), 6.55 (2H, d, J=8.0 Hz), 6.77 (1H, dd, J=8.5, 2.2 Hz), 6.8 (1H, d, J=8.0 Hz), 6.85 (1H, d, J=2.2 Hz), 7.16 (1H, t, J=8.0 Hz), 7.6 (1H, t, J=7.8 Hz), 8.1 (1H, d, J=6.1 Hz), 8.15 (1H, d, J=8.1 Hz), 8.3 (1H, d, J=7.3 Hz), 8.45 (1H, d, J=6.4 Hz), 9.28 (1H, s).

EXAMPLE 48

The same procedures as described in Reference Examples 12 to 14 and Example 34 were repeated except that N-(p-fluorophenyl)piperazine was used in place of N-phenylpiperazine, to obtain N-{2-[4-(p-fluorophenyl)piperazinyl]-1-[p-(5-isoquinolinesulfonyloxy)benzyl]ethyl]}-5-isoquinolinesulfonamide in a colorless amorphous form.

IR (KBr) cm$^{-1}$: 1610, 1500, 1370, 1320, 1210, 1130, 860, 820;

$^1$H-NMR (CDCl$_3$, δ ppm): 2.0–2.3 (5H, m), 2.4–2.9 (6H, m), 3.3 (1H, m), 6.6–6.75 (4H, m), 6.85–7.0 (4H, m), 7.65 (1H, t, J=8.1 Hz), 7.7 (1H, t, J=8.4 Hz), 8.2 (1H, d, J=8.3 Hz), 8.3 (1H, d, J=7.8 Hz), 8.4 (1H, d, J=6.3 Hz), 8.4 (1H, d, J=6.1 Hz), 8.5 (1H, d, J=6.1), 8.65 (1H, d, J=6.1 Hz), 8.8 (1H, d, J=6.3 Hz), 9.3 (1H, s), 9.4 (1H, s).

EXAMPLE 49

The amorphous compound obtained in Example 48 was methylated according to the procedure described in Example 35 to obtain N-{2-[4-(p-fluorophenyl)-piperazinyl]-1-[p-(5-isoquinolinesulfonyloxy)benzyl]ethyl]}-N-methyl-5-isoquinolinesulfonamide in a light yellow amorphous form.

IR (KBr) cm$^{-1}$: 1620, 1510, 1370, 1330, 1210, 1140.

$^1$H-NMR (CDCl$_3$, δ ppm): 2.3 (1H, dd, J=12.1, 6.5 Hz), 24.5 (4H, m), 2.4–2.6 (1H, m), 2.67 (1H, dd, J=13.8, 7.8 Hz), 2.75–3.0 (5H, m), 4.17 (1H, m), 6.63 (2H, d, J=8.6 Hz), 6.7–7.0 (6H, m), 7.57 (1H, t, J=8.0 Hz), 7.60 (1H, t, J=7.6 Hz), 8.1 (1H, d, J=8.0 Hz), 8.2–8.35 (4H, m), 8.55 (1H, d, J=5.4 Hz), 8.56 (1H, d, J=8.1 Hz), 8.83 (1H, d, J=6.3 Hz), 9.27 (1H, d, J=0.7 Hz), 9.40 (1H, d, J=1.0 Hz).

EXAMPLE 50

According to the procedure described in Example 36, 160 mg of the amorphous compound obtained in Example 49 was dissolved in 2 ml of methanol, and to the solution was added 0.5 ml of 2N sodium hydroxide, and the reaction mixture was refluxed for two hours, cooled, and extracted three times with chloroform. The extract was purified on a silica gel column using chloroform/methanol (100:2), to obtain 103 mg of N-{1-(p-hydroxybenzyl)-2-[4-(p-fluorophenyl)piperazinyl]ethyl}-N-methyl-5-isoquinolinesulfonamide in a light yellow amorphous form.

IR (KBr) cm$^{-1}$: 1610, 1500, 1320, 1230, 1150, 1130, 820;

$^1$H-NMR (CDCl$_3$, δ ppm): 2.4–2.6 (2H, m), 2.6–2.8 (1H, m), 2.8–3.0 (1H, m), 2.75 (4H, m), 3.05 (1H, m), 3.1 (1H, m), 6.3 (2H, d, J=8.3 Hz), 6.67 (2H, d, J=8.3 Hz), 6.87 (2H, dd, J=8.3, 10.1 Hz), 6.95 (2H, t, J=8.3 Hz), 7.6 (1H, dd, J=7.6, 8.0 Hz), 8.12 (1H, d, J=9.0 Hz), 8.13 (1H, d, J=6.1 Hz), 8.3 (1H, d, J=7.3 Hz), 8.5 (1H, d, J=6.1 Hz), 9.25 (1H, s).

EXAMPLE 51

The same procedures as described in Reference Examples 12 to 14 and Examples 34 to 36 were repeated except that N-(m-methylphenyl)piperazine was used in place of N-phenylpiperazine, to obtain N-{1-(p-hydroxybenzyl)-2-[4-(m-methylphenyl)piperazinyl]ethyl}-N-methyl-5-isoquinolinesulfonamide in a light yellow amorphous form.

IR (KBr) cm$^{-1}$: 1600, 1440, 1320, 1210, 1190, 1150, 1120;

$^1$H-NMR (CDCl$_3$, δ ppm): 2.30 (3H, s), 2.55 (4H, m), 2.96 (1H, dd, J=11.6, 7.1 Hz), 2.5–2.9 (3H, m), 2.9 (3H, s), 3.1 (4H, m), 4.3 (1H, m), 6.8 (2H, d, J=8.3 Hz), 7.0 (2H, d, J=8.3 Hz), 7.0–7.15 (3H, m), 7.3 (1H, m), 7.55 (1H, t, J=7.8 Hz), 8.1 (1H, d, J=7.8 Hz), 8.2–8.3 (2H, complex), 8.58 (1H, d, J=6.1 Hz), 9.25 (1H, s).

EXAMPLE 52

The same procedures as described in reference Examples 12 to 14 and Example 34 were sequentially repeated except that N-(p-methoxyphenyl)piperazine was used in place of N-phenylpiperazine, to obtain N-{1-[p-(5-isoquinolinesulfonyloxy)benzyl-2-[4-(p-methoxyphenyl)piperazinyl]ethyl}-5-isoquinolinesulfonamide in yellow amorphous form.

IR (KBr) cm$^{-1}$: 1615, 1500, 1360, 1130;

$^1$H-NMR (CDCl$_3$, δ ppm): 1.96–2.22 (6H, m), 2.39–2.52 (2H, m), 2.52–2.67 (2H, m), 2.77 (1H, dd, J=7.3, 14.2 Hz), 2.90 (1H, dd, J=4.4, 14.2 Hz), 3.27 (1H, m), 3.76 (3H, s), 5.50 (1H, br), 6.70 (4H, d, J=8.8 Hz), 6.82 (2H, d, J=8.8 Hz), 6.94 (2H, d, J=8.8 Hz), 7.65 (1H, t, J=7.8 Hz), 7.70 (1H, t, J=7.3 Hz), 8.21 (1H, d, J=8.3 Hz), 8.29 (2H, d, J=7.8 Hz), 8.40–8.43 (2H, m), 8.53 (1H, d, J=5.9 Hz), 8.68 (1H, d, J=6.4 Hz), 8.81 (1H, d, J=5.9 Hz), 9.36 (1H, s), 9.42 (1H, s).

EXAMPLE 53

The amorphous compound of Example 52 was treated with methyl iodide according to the procedure described in Example 35 to obtain N-{1-[p-(5-isoquinolinesulfonyloxy)benzyl]-2-[4-(p-methoxyphenyl)piperazinyl]ethyl}-N-methyl-5-isoquinolinesulfonamide in a yellow amorphous form.

IR (KBr) cm$^{-1}$: 1665, 1615, 1505, 1365, 1320, 1130;

$^1$H-NMR (CDCl$_3$, δ ppm): 2.30 (1H, dd, J=6.8, 12.2 Hz), 2.37–2.51 (5H, m), 2.68 (1H, dd, J=7.3, 14.2 Hz), 2.85 (3H, s), 2.78–2.97 (5H, m), 3.77 (3H, s), 4.16 (1H, m), 6.62 (2H, d, J=8.3 Hz), 6.82 (4H, s), 6.90 (2H, d, J=8.3 Hz), 7.57 (1H, t, J=7.8 Hz), 7.60 (1H, t, J=7.8 Hz), 8.11 (1H, d, J=8.3 Hz), 8.23–8.28 (3H, m), 8.33 (1H, dd, J=1.0, 7.3 Hz), 8.56 (1H, d, J=6.4 Hz), 8.58 (1H, d, J=6.4 Hz), 8.83 (1H, d, J=5.9 Hz), 9.27 (1H, d, J=1.0 Hz), 9.41 (1H, d, J=1.0 Hz).

EXAMPLE 54

The amorphous compound obtained in Example 53 was subjected to alkaline hydrolysis according to the procedure described in Example 36 to obtain N-{1-(p-hydroxybenzyl)-2-[4-(p-methoxyphenyl)piperazinyl]ethyl}-N-methyl-5-isoquinolinesulfonamide as yellow crystals, Melting point: 157°–160° C. (decomposed);

IR (KBr) cm$^{-1}$: 1615, 1510, 1445, 1320, 1305, 1240 1125;

$^1$H-NMR (CDCl$_3$, δ ppm): 2.46–2.74 (7H, m), 2.88–3.02 (5H, m), 3.00 (3H, s), 3.77 (3H, s), 4.06 (1H, m), 6.30 (2H, d, J=8.3 Hz), 6.65 (2H, d, J=8.3 Hz), 6.83 (2H, d, J=9.3 Hz), 6.88 (2H, d, J=9.3 Hz), 7.57 (1H, dd, J=7.3, 8.3 Hz), 8.12 (1H, d, J=8.3 Hz), 8.13 (1H, d, J=6.4 Hz), 8.32 (1H, dd, J=1.0, 7.3 Hz), 8.50 (1H, d, J=6.4 Hz), 9.26 (1H, s).

EXAMPLE 55

The amorphous compound obtained in Example 52 was subjected to alkaline hydrolysis according to the procedure described in Example 37, to obtain N-{1-(p-hydroxybenzyl)-2-[4-(p-methoxyphenyl)piperazinyl]ethyl}- 5-isoquinolinesulfonamide as yellow crystals.

Melting point: 200°–208° C. (decomposed);

IR (KBr) cm$^{-1}$: 1615, 1590, 1510, 1450, 1340, 1230, 1150, 1130, 1025;

$^1$H-NMR (CDCl$_3$, δ ppm): 2.20–2.44 (6H, m), 2.58–2.82 (6H, m), 3.33 (1H, m), 3.77 (3H, s), 5.55 (1H, br), 6.47 (2H, d, J=8.3 Hz), 6.76 (2H, d, J=8.3 Hz), 6.78 (2H, d, J=6.8 Hz), 6.83 (2H, d, J=6.8 Hz), 7.70 (1H, t, J=7.8 Hz), 8.21 (1H, d, J=8.3 Hz), 8.40 (1H, d, J=6.4 Hz), 8.44 (1H, dd, J=1.0, 7.3 Hz), 8.64 (1H, d, J=6.4 Hz), 9.34 (1H, s).

EXAMPLE 56

The same procedures as described in Reference Examples 12 to 14 and Examples 34 and 35 were sequentially repeated except that N-(2-methoxyphenyl)piperazine was used in place of N-phenylpiperazine to obtain N-{1-[p-(5-isoquinolinesulfonyloxy)benzyl]-2-[4-(2methoxyphenyl)piperazinyl]ethyl}-N-methyl-5-isoquinolinesulfonamide, and 800 mg of the compound was subjected to alkaline hydrolysis according to the procedure described in Example 36 to obtain 504 mg of N-{1-(p-hydroxybenzyl)-2-[4-(2-methoxyphenyl)-piperazinyl]ethyl}-N-methyl-5-isoquinolinesulfonamide in a light yellow amorphous form.

IR (KBr) cm$^{-1}$: 1610, 1590, 1500, 1320, 1230, 1130;

$^1$H-NMR (CDCl$_3$, δ ppm): 2.5 (1H, dd, J=13.8, 10.0 Hz), 2.55–2.8 (2H, m), 2.9–3.0 (1H, m), 2.7 (4H, m), 3.0 (4H, m), 3.05 (3H, s), 3.86 (3H, s), 4.0 (1H, m), 6.23 (2H, d, J=8.3 Hz), 6.57 (2H, d, J=8.3 Hz), 6.8–7.1 (4H, m), 7.6 (1H, t, J=8.0 Hz), 8.14 (1H, d, J=6.1 Hz), 8.16 (1H, d, J=7.9 Hz), 8.35 (1H, dd, J=7.4, 1.0 Hz), 9.30 (1H, s).

EXAMPLE 57

1-[2-Amino-3-(p-hydroxyphenyl)propyl]-4-phenyl-piperazine in crystals obtained in Reference Example 14 was reacted with 1-naphtharenesulfonyl chloride according to the procedure of Example 34, and the product thus obtained was treated with methyl iodide according to the procedure described in Example 35, to obtain N-methyl-N-{1-[p-(α-naphtharenesulfonyloxy)-benzyl]-2-(4-phenylpiperazinyl)ethyl}-α-naphtharenesulfonamide in colorless amorphous form.

$^1$H-NMR (CDCl$_3$, δ ppm): 2.26 (1H, dd, J=12.56, 6.85 Hz), 2.42 (4H,m), 2.48 (1H, dd, J=12.56, 6.85 Hz), 2.68 (1H, dd, J=14.85, 6.85 Hz), 2.84 (1H, dd, J=14.85, 6.85 Hz), 2.85 (3H, s), 2.92 (4H,m), 4.12 (1H, quintet, J=6.85 Hz), 6.56 (2H, d, J=8.0 Hz), 6.78–6.92 (5H, m), 7.26 (2H, t, J=8.0 Hz), 7.42 (2H, t, J=8.0 Hz), 7.46–7.58

(2H, m), 7.68 (1H, dt, J=8 0, 1.0 Hz), 7.77–7.90 (2H, m), 7.90–8.07 (3H, m), 8.12 (1H, d, J=8.57 Hz), 8.17 (1H, dd, J=8.57, 1.0 Hz), 8.45 (1H, m), 8.84 (1H, d, J=9.14 Hz).

EXAMPLE 58

The amorphous compound obtained in Example 57 was subjected to alkaline hydrolysis according to the procedure described in Example 36, to obtain N-[1-(p-hydroxybenzyl)-2-.4(-phenylpiperazinyl)ethyl]-N-methyl-α-naphtharenesulfonamide in a colorless amorphous form.

IR (KBr) cm$^{-1}$: 1595, 1315, 1310, 1225, 1150, 1120;
$^1$H-NMR (CDCl$_3$, δ ppm): 2.37 (1H, dd, J=13.70, 6.85 Hz), 2.47 (4H, m), 2.55 (1H, dd, J=13.70, 6.85 Hz), 2.72 (1H, dd, J=14.28, 6.85 Hz), 2.85 (1H, dd, J=14.28, 6.85 Hz), 2.89 (3H, s), 2.97 (4H, m), 4.27 (1H, quinted, J=6.85 Hz), 5.10 (1H, br), 6.57 (2H, d, J=7.99 Hz), 6.78–6.89 (3H, m), 6.91 (2H, d, J=7.99 Hz), 7.25 (2H, t, J=7.99 Hz), 7.43 (1H, t, J=7.42 Hz), 7.50–7.63 (2H, m), 7.86 (1H, dd, J=7.99, 1.0 Hz), 7.98 (1H, d, J=7.42 Hz), 8.22 (1H, dd, J=7.42, 1.0 Hz), 8.56 (1H, dd, J=7.99, 1.0 Hz).

REFERENCE EXAMPLE 15

1-{[2-Amino-3-(p-hydroxy)phenyl]propyl)-4-benzyloxycarbonylpiperazine 1.41 g of 1-(N-tert-butoxycarbonyltyrosyl)-4-(benzyloxycarbonyl)piperazine prepared according to the procedure described in Reference Example 11 was dissolved in 5.6 ml of absolute ethyl acetate, and to the solution was added dropwise 11.25 ml of 4N hydrogen chloride in ethyl acetate with stirring under ice cooling for two minutes, and the reaction mixture was stirred for 2 hours at a room temperature. After the reaction was completed, the solvent was evaporated off under a reduced pressure, and to the residue was added 20 ml of 5% sodium bicarbonate aqueous solution. The mixture was extracted with 30 ml and then 20 ml of a mixed solvent of chloroform/methanol (9:1), and the extract was washed with saturated sodium chloride aqueous solution, dried over magnesium sulfate and filtrated.

The filtrate was evaporated under a reduced pressure to obtain a colorless foam. The foam was applied to a silica gel column and eluted with chloroform/methanol (6:1), to obtain about 700 mg of the title compound in a colorless amorphous form.

$^1$H-NMR (CDCl$_3$, δ ppm): 2.2–2.8 (8H, m), 3.19 (1H, m), 3.50 (7H, brs), 5.13 (2H, s), 6.71 (2H, d, J=8.5 Hz), 7.02 (2H, d, J=8.5 Hz), 7.35 (5H, s).

EXAMPLE 59

N-{2-(4-Benzyloxycarbonylpiperazinyl)-1-[p-(5-isoquinolinesulfonyloxy)benzyl]-ethyl}-5-isoquinolinesulfonamide 680 mg of the amorphous compound obtained in Reference Example 15 was dissolved in 18 ml of absolute tetrahydrofuran, and to the solution was added 1.27 g of 5-isoquinolinesulfonyl chloride.HCl, and then was added dropwise 3.20 ml of triethylamine with stirring under ice cooling for one minute, and the mixture was stirred at a room temperature for 150 minutes. The reaction mixture was diluted with 50 ml of chloroform, washed with water, and the washings was extracted with 20 ml of chloroform. The combined organic extract was washed with saturated sodium chloride aqueous solution, dried over magnesium sulfate and filtered, and the filtrate was evaporated under a reduced pressure. The resulting residue was applied to a silica gel column, and eluted with chloroform/methanol (100:1) to obtain 987 mg of the title compound in a light yellow amorphous form.

IR (KBr) cm$^{-1}$: 1700, 1620, 1500, 1370, 1230, 1130;
$^1$H-NMR (CDCl$_3$, δ ppm): 1.8–2.2 (6H, m), 2.7–3.4 (7H, m), 5.05 (2H, s), 5.36 (1H, brs), 6,67 (2H, d, J=8.4 Hz), 6.89 (2H, d, J=8.4 Hz), 7.2–7.4 (5H, m), 7.62 (1H, d, J=7.7 Hz), 7.69 (1H, d, J=7.7 Hz), 8.2–8.5 (5H, brs), 8.52 (1H, d, J=6.2 Hz), 8.68 (1H, d, J=6.2 Hz), 8.81 (1H, d, J=5.9 Hz), 9.34 (1H, s), 9.41 (1H, s).

EXAMPLE 60

N-{2-(4-Benzyloxycarbonylpiperazinyl)-1-[p-(5-isoquinolinesulfonyloxy)benzyl]-ethyl}-N-methyl-5-isoquinolinesulfonamide 852 mg of the amorphous compound obtained in Example 59 was dissolved in 8.5 ml of absolute dimethylformamide, and to the solution was added 59 mg of 60% sodium hydride with stirring under ice cooling, and further was added 113 μl of methyl iodide, and the reaction mixture was stirred for 2 hours with ice cooling. After the addition of 30 ml of ice water, the reaction mixture was extracted with 30 ml, 20 ml and 20 ml of ethyl acetate, the combined extract was washed with saturated sodium chloride aqueous solution, dried over magnesium sulfate, filtered and concentrated under a reduced pressure. The resulting residue was applied to a silica gel column and eluted with chloroform/methanol (100:1) to obtain 679 mg of the title compound in a light yellow amorphous form.

IR (KBr) cm$^{-1}$: 1700, 1620, 1500, 1370, 1240, 1130;
$^1$H-NMR (CDCl$_3$, δ ppm): 2.23 (5H, brs), 2.3–2.9 (3H, m), 2.83 (3H, s), 3.25 (4H, brs), 4.09 (1H, m), 5.11 (2H, s), 6.60 (2H, d, J=8.7 Hz), 6.86 (2H, d, J=8.7 Hz), 7.34 (5H, brs), 7.5–7.7 (2H, m), 8.12 (1H, d, J=8.2 Hz), 8.1–8.3 (4H, m), 8.56 (2H, m), 8.84 (1H, d, J=6.1 Hz), 9.29 (1H, s), 9.41 (1H, s).

EXAMPLE 61

N-{2-(4-Benzenesulfonyl)piperazinyl-1-[p-(5-isoquinolinesulfonyloxy)benzyl]-ethyl}-N-methyl-5-isoquinolinesulfonamide To 480 mg of the amorphous compound obtained in Example 60 was added 3 ml of a solution of 30% hydrogen bromide in acetic acid, and the mixture was stirred at a room temperature for 80 minutes. Then 50 ml of ether was added to the mixture, which was then stirred. The resulting precipitate was collected and washed with ether and dried under a reduced pressure to obtain 567 mg of N-{1-[p-(5-isoquinolinesulfonyloxy)benzyl]-2-piperazinyl-ethyl}-N-methyl-5-isoquinolinesulfonamide.HBr as colorless crystals.

$^1$H-NMR (DMSO-d$_6$+D$_2$O, δ ppm): 3.06 (3H, s), 3.46 (12H, brs), 4.24 (1H, brs), 6.08 (2H, d, J=8.5 Hz), 6.74 (2H, d, J=8.5 Hz), 7.93 (2H, m), 8.25 (1H, d, J=6.7 Hz), 8.35 (1H, d, J=7.3 Hz), 8.5–8.8 (5H, m), 9.05 (1H, d, J=6.4 Hz), 9.86 (2H, brs).

550 mg of the crystals thus obtained was suspended in 10 ml of absolute tetrahydrofuran, and after stirring with ice cooling, to the suspension were added 84 μl of benzenesulfonyl chloride and 767 μl of triethylamine, and the reaction mixture was stirred at a room temperature for 140 minutes. Then 30 ml of chloroform and 20 ml of water were added to the reaction mixture, and after separation of the layers, the aqueous layer was extracted with 20 ml of chloroform. The chloroform layers were combined, washed with saturated sodium chloride aqueous solution, dried over magnesium sulfate, and filtered. The filtrate was evaporated under a reduced pressure, and the resulting residue was applied to a silica gel column and eluted with chloroform/methanol (100:1) to obtain 331 mg of the title compound in a light yellow amorphous form.

IR (KBr) cm$^{-1}$: 1620, 1500, 1440, 1330, 1170;

$^1$H-NMR (CDCl$_3$, δ ppm): 2.1-2.5 (6H, m), 2.5- 2.8 (6H, m), 2.78 (3H, s), 4.05 (1H, m), 6.60 (2H, d, J=8.7 Hz), 6.83 (2H, d, J=8.7 Hz), 7.37 (1H, t, J=7.8 Hz), 7.5-7.8 (6H, m), 7.98 (1H, d, J=7.9 Hz), 8.1-8.3 (4H, m), 8.49 (1H, d, J=6.1 Hz), 8.55 (1H, d, J=6.1 Hz), 8.84 (1H, d, J=6.1 Hz), 9.17 (1H, s), 9.42 (1H, s).

EXAMPLE 62

N-{2-[(4-Benzenesulfonyl)piperazinyl)-1-(p-hydroxybenzyl)-ethyl}-N-methyl-5-isoquinolinesulfonamide 221 mg of the amorphous compound obtained in Example 61 was dissolved in a mixed solution of 2.69 ml of methanol and 0.66 ml of tetrahydrofuran, and to the solution was added 0.33 ml of 2N sodium hydroxide aqueous solution. The reaction mixture was refluxed for 3.5 hours, and to the mixture were added 30 ml of chloroform and 20 ml of 10% ammonium chloride aqueous solution, and the resulting layers were separated. The aqueous layer was extracted with 20 ml of chloroform, and the chloroform layers were combined, washed with saturated sodium chloride aqueous solution, dried over magnesium sulfate and filtered. The filtrate was evaporated under a reduced pressure, and the resulting residue was applied to a silica gel column and eluted with chloroform/methanol (100:1) to obtain 146 mg of the title compound in a colorless amorphous form.

IR (KBr) cm$^{-1}$: 1620, 1510, 1440, 1320, 1160;

$^1$H-NMR (CDCl$_3$, δ ppm): 2.3-2.5 (2H, m), 2.60 (4H, brs), 2.6-2.8 (2H, m), 2.95 (3H, s), 3.01 (4H, brs), 3.92 (1H, brs), 6.21 (2H, d, J=8.2 Hz), 6.51 (2H, d, J=8.2 Hz), 7.4-7.8 (6H, m), 8.03 (1H, d, J=6.1 Hz), 8.09 (1H, d, J=8.2 Hz), 8.24 (1H, dd, J=1.2, 7.3 Hz), 8.40 (1H, d, J=5.8 Hz), 8.68 (1H, brs), 9.23 (1H, brs).

REFERENCE EXAMPLE 16

O-Benzyl-N-benzyloxycarbonyltyrosinol 27.25 g of O-benzyl-N-benzyloxycarbonyltyrosine methyl ester was dissolved in a mixed solvent of 185 ml of ethanol and 122 ml of tetrahydrofuran, and to the solution were added 5.8 g of lithium chloride and 5.2 g of sodium borohydride under ice cooling. The reaction mixture was stirred at a room temperature for 18 hours, and after the addition of 500 ml of saturated sodium chloride aqueous solution, extracted twice with 300 ml of chloroform. The extract was dried over magnesium sulfate and concentrated under a reduced pressure to obtain 25.4 g of the title compound as colorless crystals.

$^1$H-NMR (CDCl$_3$, δ ppm): 2.79 (2H, d, J=7.4 Hz), 3.51-3.79 (2H, m), 3.89 (1H, m), 4.93 (1H, br), 5.04 (2H, s), 5.08 (2H, s), 6.90 (2H, d, J=8.6 Hz), 7.11 (2H, d, J=8.6 Hz), 7.26-7.46 (5H, m).

REFERENCE EXAMPLE 17

1-[2-Benzyloxycarbonylamino-3-(p-benzyloxyphenyl)-propyl]-4-(tert-butoxycarbonyl)piperazine 5.6 g of the crystals obtained in Reference Example 16 was dissolved in 70 ml of carbon tetrachloride, and after the addition of 4.5 g of triphenylphosphine, the mixture was refluxed for 20 hours. The reaction mixture was filtered to remove insoluble matter, and the filtrate was concentrated under a reduced pressure, and the resulting residue was applied to a silica gel column and eluted with hexane/ethyl acetate (6:1) to obtain 4.96 g of 2-benzyloxycarbonylamino-3-(p-benzyloxyphenyl)-propyl chloride as colorless crystals.

$^1$H-NMR (CDCl$_3$, δ ppm): 2.76-2.90 (2H, m), 3.56-3.80 (2H, m), 4.39 (1H, m), 5.03 (2H, s), 5.05, 5.13 (Total 2H, each s), 6.85, 6.89 (Total 2H, each d, each J=8.3 Hz), 7.00, 7.09 (Total 2H, each d, each J=8.3 Hz), 7.23-7.45 (5H, m).

4.1 g of the above-crystals and 2.23 g of N-(tert-butoxycarbonyl)piperazine were dissolved in 40 ml of dimethylformamide, to the solution were added 1.8 g of methyl iodide and 1.66 g of potassium carbonate, and the mixture was stirred at 120° C. for 3 hours. After the addition of 100 ml of saturated sodium chloride aqueous solution, the reaction mixture was extracted twice with 60 ml of chloroform, and the extract was dried over magnesium sulfate and concentrated under a reduced pressure. The resulting residue was applied to a silica gel column and eluted with hexane/ethyl acetate (2:1) to obtain 2.69 g of the title compound in a colorless amorphous form.

$^1$H-NMR (CDCl$_3$, δ ppm): 1.45 (9H, s), 2.22-2.49 (6H, m), 2.82 (2H, m), 3.36 (4H, m), 3.94 (1H, m), 4.83 (1H, br), 8.03 (2H, s), 5.09 (2H, s), 6.88 (2H, d, J=8.3 Hz), 7.06 (2H, d, J=8.3 Hz), 7.30-7.45 (5H, m).

EXAMPLE 63

N-{2-4-(tert-Butoxycarbonyl)piperazinyl]-1-[p-(5-isoquinolinesulfonyloxy)benzyl]-ethyl)-5-isoquinolinesulfonamide 1.6 g of the amorphous compound obtained in Reference Example 17 was dissolved in 25 ml of methanol, and to the solution was added 1.0 g of 5% palladium on carbon. The mixture was stirred in a hydrogen atmosphere for 20 hours, and filtered to remove insoluble matter. The filtrate was concentrated under a reduced pressure, resulting residue was dissolved in 30 ml of tetrahydrofuran, and to the solution were added 2.8 g of 5-isoquinolinesulfonyl chloride.HCl and 4 ml of triethylamine under ice cooling. After stirring at a room temperature for 3 hours, to the reaction mixture was added 100 ml of water, and the mixture was extracted twice with 70 ml of chloroform, and the extract was dried over magnesium sulfate and concentrated under a reduced pressure. The resulting residue was applied to a silica gel column and eluted with chloroform/methanol (100:1 to 50:1) to obtain 1.27 g of the title compound in a yellow amorphous form.

$^1$H-NMR (CDCl$_3$, δ ppm): 1.40 (9H, s), 1.75-2.18 (6H, m), 2.15-3.07 (6H, m), 3.27 (1H, m), 5.35 (1H, br), 6.67 (2H, d, J=8.3 Hz), 6.90 (2H, d, J=8.3 Hz), 7.65 (1H, t, J=7.8 Hz), 7.69 (1H, t, J=7.8 Hz), 8.21 (1H, d, J=8.3 Hz), 8.27-8.32 (2H, m), 8.37-8.41 (2H, m), 8.53 (1H, d, J=6.4 Hz), 8.69 (1H, d, J=6.9 Hz), 8.82 (1H, d, J=6.4 Hz), 9.36 (1H, s), 9.43 (1H, s).

EXAMPLE 64

940 mg of the amorphous compound obtained in Example 63 was dissolved in a mixed solvent of 7.5 ml of tetrahydrofuran and 7.5 ml of dimethylformamide, and to the solution were sequential added 67 mg of 60% sodium hydride and 0.11 ml of methyl iodide under ice cooling, and the mixture was stirred at a room temperature for one hour. After the addition of 30 ml of saturated sodium chloride aqueous solution, the reaction mixture was extracted with 40 ml of ethyl acetate, and the extract was washed with saturated sodium chloride aqueous solution, dried over magnesium sulfate and concentrated under a reduced pressure. Resulting residue was applied to a silica gel column and eluted with chloroform/methanol (60:1) to obtain 723 mg of N-{2-[4-(tert-butoxycarbonyl)piperazinyl]-[p-(5-isoquinolinesulfonyloxy)benzyl]-ethyl}-N-methyl-5-isoquinolinesulfonamide in a yellow amorphous form.

$^1$H-NMR (CDCl$_3$, δ ppm): 1.44 (9H, s), 2.21 (5H, m), 2.40 (1H, dd, J=6.9, 12.6 Hz), 2.15 (1H, dd, J=7.4, 14.3 Hz), 2.83 (1H, dd, J=6.9, 14.3 Hz), 2.84 (3H, s), 3.17 (9H, m), 4.12 (1H, m), 6.60 (2H, d, J=8.8 Hz), 6.86 (2H, d, J=8.8 Hz), 7.58 (1H, t, J=7.8 Hz), 7.63 (1H, t, J=7.8 Hz), 8.13 (1H, d, J=8.3 Hz), 8.21-8.30 (4H, m), 8.56 (1H, d, J=6.9 Hz), 8.57 (1H, d, J=5.9 Hz), 8.84 (1H, d, J=5.9 Hz), 9.29 (1H, s), 9.42 (1H, s).

EXAMPLE 65

To 720 mg of the amorphous compound obtained in Example 64 was added 10 ml of 4N hydrochloric acid in ethyl acetate, and the mixture was stirred at a room temperature for one hour and concentrated under a reduced pressure. To the mixture was added 30 ml of saturated sodium bicarbonate aqueous solution, and the reaction mixture was extracted twice with 20 ml of a mixed solvent of chloroform/isopropanol (5:1). The extract was dried over magnesium sulfate and concentrated to dryness under a reduced pressure to obtain 620 mg of N-{1-[p-(5-isoquinolinesulfonyloxy)benzyl]-ethyl-2-piperazinyl}-N-methyl-5-isoquinolinesulfonamide in a yellow amorphous form.

$^1$H-NMR (CDCl$_3$, δ ppm): 2.18-2.28 (5H, m), 2.37 (1H, dd, J=7.3, 12.7 Hz), 2.63 (4H, m), 2.66 (1H, dd, J=7.3, 14.8 Hz), 2.83 (3H, s), 2.86 (1H, dd, J=5.4, 14.8 Hz), 4.13 (1H, m), 6.61 (2H, d, J=8.8 Hz), 6.89 (2H, d, J=8.8 Hz), 7.59 (1H, t, J=7.8 Hz), 7.63 (1H, t, J 7.8 Hz), 8.12 (1H, d, J=8.3 Hz), 8.23-8.35 (4H, m), 8.56 (1H, d, J=5.9 Hz), 8.58 (1H, d, J=6.4 Hz), 8.83 (1H, d, J=6.9 Hz), 9.29 (1H, s), 9.42 (1H, s).

EXAMPLE 66

620 mg of the amorphous compound obtained in Example 65 was dissolved in 10 ml of methylene chloride, to the solution were added 0.29 ml of benzyl chloroformate and 0.4 ml of triethylamine with ice cooling. The reaction mixture was stirred for two hours with ice cooling, and after the addition of 40 ml of saturated sodium chloride aqueous solution, extracted twice with 20 ml of chloroform. The extract was dried over magnesium sulfate and concentrated under a reduced pressure, and resulting residue was applied to a silica gel column and eluted with chloroform/methanol (60:1) to obtain 660 mg of light yellow amorphous product showing the same $^1$H-NMR spectrum as that of the compound of Example 60.

EXAMPLE 67

650 mg of the amorphous compound obtained in Example 66 was dissolved in 6 ml of methanol, and to the solution was added 2 ml of 1N sodium hydroxide aqueous solution. The mixture was refluxed for 2 hours, and after the addition of 30 ml of saturated sodium chloride aqueous solution, extracted twice with 200 ml of a mixed solvent of chloroform/isopropanol (5:1). The extract was dried over magnesium sulfate and concentrated under a reduced pressure, and resulting residue was applied to a silica gel column and eluted with chloroform/methanol (80:1 to 50:1) to obtain 386 mg of N-[2-(4-benzyloxycarbonyl-piperazinyl)-1-(p-hydroxybenzyl)ethyl]-N-methyl-5-isoquinolinesulfonamide in a yellow amorphous form.

IR (KBr) cm$^{-1}$: 1693, 1510, 1425, 1320, 1235, 1120;

$^1$H-NMR (CDCl$_3$, δ ppm): 2.39-2.55 (6H, m), 2.64 (1H, dd, J=6.4, 12.7 Hz), 2.87 (1H, dd, J=4.4, 14.6 Hz), 2.97 (3H, s), 3.44 (4H, m), 4.03 (1H, m], 5.13 (2H, s), 6.28 (2H, d, J=8.3 Hz), 6.62 (2H, d, J=8.3 Hz), 7.36 (5H, s), 7.39 (1H, dd, J=7.3, 7.8 Hz), 8.09 (1H, d, J=5.9 Hz), 8.13 (1H, d, J=7.8 Hz), 8.26 (1H, d, J=7.3 Hz), 8.48 (1H, d, J=5.9 Hz], 9.27 (1H, s).

EXAMPLE 68

In the amorphous compound obtained in Example 63, protecting group of the piperazine moiety was removed according to the procedure described in Example 65, and the deprotected intermediate was treated according to the procedures described in Examples 66 and 67 to obtain N-[2-(4-benzyloxycarbonylpiperazinyl)-1-(p-hydroxybenzyl)ethyl]-5-isoquinolinesulfonamide.

IR (KBr) cm$^{-1}$: 1670, 1510, 1425, 1320, 1230, 1150, 1125, 993;

1H-NMR (CDCl$_3$, δ ppm): 2.07-2.23 (4H, m), 2.30 (1H, dd, J=6.3, 13.2 Hz), 2.39 (1H, dd, J=7.8, 13.2 Hz), 2.62 (1H, dd, J=6.8, 14.2 Hz), 2.76 (1H, dd, J=6.4, 14.2 Hz), 3.00-3.38 (5H, m), 5.09 (2H, s), 6.41 (2H, d, J=8.3 Hz), 6.69 (2H, d, J=8.8 Hz), 7.33 (5H, s), 7.68 (1H, dd, J=7.3, 8.3 Hz) 8.21 (1H, d, J=8.3 Hz), 8.35 (1H, d, J=5.9 Hz), 8.40 (1H, dd, J=1.0, 7.3 Hz), 8.61 (1H, d, J=5.9 Hz), 9.34 (1H, s).

EXAMPLE 69

The same procedure as described in Example 68 was repeated except that phenylpropionyl chloride was used in place of benzyl chloroformate, to obtain N-{1-(p-hydroxybenzyl)-2-[4-(3-phenylpropyl)piperazinyl]ethyl}-5-isoquinolinesulfonamide.

IR (KBr) cm$^{-1}$: 1610, 1510, 1445, 1320, 1150, 1130, 993;

$^1$H-NMR (CDCl$_3$, δ ppm): 2.00-2.20 (4H, m), 2.26 (1H, dd, J=5.9, 12.7 Hz), 2.36 (1H, dd, J=7.8, 12.7 Hz), 2.46-2.60 (2H, m), 2.62-2.77 (2H, m) 2.83-3.00 (2H, m), 3.00-3.41 (5H, m), 5.24 (1H, br), 6.43 (2H, d, J=8.3 Hz), 6.71 (2H, d, J=8.3 Hz), 7.13-7.34 (5H, m), 7.69 (1H, dd, J=7.3, 8.3 Hz), 8.20 (1H, d, J=7.8 Hz), 8.34 (1H, d, J=5.9 Hz), 8.40 (1H, dd, J=1.0, 7.3 Hz), 8.63 (1H, br), 9.12 (1H, br).

EXAMPLE 70

The same procedure as described in Example 68 was repeated except that phenylisocyanate was used in place of benzyl chloroformate, to obtain N-[1-(p-hydroxybenzyl)-2-(4-phenylaminocarbonylpiperazinyl)ethyl]-5isoquinolinesulfonamide in yellow amorphous form.

1H-NMR (CDCl$_3$+CD$_3$OD, δ ppm): 2.37 (1H, dd, J=8.8, 14.2 Hz), 2.65 (1H, dd, J=5.4, 13.7 Hz), 2.73-3.20 (4H, m), 3.40-3.95 (7H, m), 6.12 (2H, d, J=8.3 Hz), 6.50 (2H, d, J=8.3 Hz), 7.05 (1H, m), 7.25-7.38 (4H, m), 7.67 (1H, dd, J=7.8, 8.3 Hz), 8.21 (1H, d, J=7.8 Hz), 8.31 (1H, d, J=6.8 Hz), 8.53 (1H, br), 9.23 (1H, br).

EXAMPLE 71

The same procedure as described in Example 68 was repeated except that benzylisocyanate was used in place of benzyl chloroformate, to obtain N-[2-(4-benzylaminocarbonylpiperazinyl)-1-(p-hydroxybenzyl)ethyl]-5-isoquinolinesulfonamide in a yellow amorphous form.

$^1$H-NMR (CDCl$_3$—CD$_3$OD, δ ppm): 2.40-2.71 (2H, m), 2.76-3.23 (4H, m), 3.40-3.80 (7H, m), 4.39 (2H, s), 6.08 (2H, d, J=8.3 Hz), 6.46 (2H, d, J=8.3 Hz), 7.20-7.38 (5H, m), 7.63 (1H, t, J=7.8 Hz), 8.17 (1H, d, J=8.3 Hz), 8.29 (2H, d, J=6.9 Hz), 8.52 (1H, br), 9.23 (1H, br).

EXAMPLE 72

200 mg of the amorphous compound obtained in Example 67 was dissolved in 5 ml of chloroform, and to the solution was added 1 ml of methanol, and also a solution of diazomethane in ether with ice cooling. The reaction mixture was stirred for 90 minutes and then concentrated. Resulting residue was applied to silica gel column and eluted with chloroform/methanol (80:1 to 50:1), to obtain 103 mg of N-[2-(4-benzyloxycarbonylpiperazinyl)-1-(p-methoxybenzyl)ethyl]-N-methyl-5-isoquinolinesulfonamide.

IR (KBr) cm$^{-1}$: 1692, 1508, 1420, 1320, 1235, 1120;

$^1$H-NMR (CDCl$_3$, δ ppm): 2.32-2.45 (5H, m), 2.53-2.65 (2H, m), 2.78-2.90 (1H, m) 2.92 (3H, s), 3.37 (4H, m), 3.73 (3H, s), 4.16 (1H, m), 5.11 (2H, s), 6.50 (2H, d, J=8.3 Hz) 6.82 (2H, d, J=8.3 Hz), 7.35 (5H, m), 7.55 (1H, t, J=7.8 Hz), 8.09 (1H, d, J=8.3 Hz), 8.18 (1H, d, J=6.4 Hz), 8.22 (1H, d, J=7.3 Hz), 8.55 (1H, d, J=6.4 Hz), 9.24 (1H, s).

EXAMPLE 73

The product of Example 68 was treated according to the procedure in Example 72, to obtain N-[2-(4-benzyloxycarbonylpiperazinyl)-1-(p-methoxybenzyl)ethyl]-5-isoquinolinesulfonamide.

$^1$H-NMR (CDCl$_3$, δ ppm): 1.97-2.17 (4H, m), 2.19 (1H, dd, J=4.4, 13.7 Hz), 2.28 (1H, dd, J=6.8, 13.7 Hz), 2.70 (1H, dd, J=6.8, 14.2 Hz), 2.82 (1H, dd, J=5.4, 14.2 Hz), 3.03 (2H, m), 3.15 (2H, m), 3.34 (1H, m), 3.74 (3H, s), 5.07 (2H, s), 5.36 (1H, br), 6.59 (2H, d, J=8.8 Hz), 6.85 (2H, d, J=8.3 Hz), 7.27-7.37 (5H, m), 7.68 (1H, dd, J=7.3, 7.8 Hz), 8.18 (1H, d, J=8.3 Hz), 8.39 (1H, d, J=5.9 Hz), 8.42 (1H, dd, J=1.0, 7.8 Hz), 8.67 (1H, d, J=5.9 Hz), 9.33 (1H, s).

EXAMPLE 74

N-{2-(4-Benzoylpiperazinyl)-1-[p-(5-isoquinolinesulfonyloxy)benzyl]ethyl}-N-methyl-5-isoquinolinesulfonamide 764 mg of the intermediate crystals obtained in Example 61 was suspended in 7 ml of tetrahydrofuran, to the suspension were added 135 mg of benzoyl chloride and 5 minutes later 1.1 ml of triethylamine with ice cooling, and the mixture was stirred for one hour. After adding chloroform and water, the reaction mixture was extracted three times with 30 ml of chloroform, and the extract was washed with saturated sodium chloride aqueous solution, dried over magnesium sulfate and concentrated to dryness under a reduced pressure. 0.82 g of the resulting pale yellow residue was applied to a silica gel column and eluted with chloroform/methanol (100:1) to obtain 198 mg of the title compound in a colorless amorphous form.

IR (KBr) cm$^{-1}$: 1620, 1370, 1130;

$^1$H-NMR (CDCl$_3$, δ ppm): 2.2-2.8 (10H, m), 2.84 (3H, s), 3.1-3.7 (4H, m), 4.14 (1H, m), 6.61 (2H, d, J=8.6 Hz), 6.85 (2H, d, J=8.6 Hz), 7.3-8.6 (14H, m), 8.84 (1H, d, J=5.8 Hz), 9.30 (1H, s), 9.43 (1H, s).

EXAMPLE 75

N-2-(4-Benzoylpiperazinyl)-1-(p-hydroxybenzyl)ethyl]-N-methyl-5-isoquinolinesulfonamide To 349 mg of the amorphous compound obtained in Example 74 were added 4 ml of methanol, 1 ml of tetrahydrofuran and 0.5 ml of 2N sodium hydroxide, and after refluxing for 2 hours, to the reaction mixture were added chloroform, water and sodium chloride. The reaction mixture was three times extracted with 30 ml of chloroform, and the extract was washed with saturated sodium chloride aqueous solution, dried over magnesium sulfate and concentrated under a reduced pressure to obtain 0.25 g of yellow oil. The yellow oil was applied to a silica gel column and eluted with chloroform/methanol (50:1) to obtain 145 mg of the title compound in a colorless amorphous form.

IR (KBr) cm$^{-1}$: 1610, 1440, 1120;

$^1$H-NMR (CDCl$_3$, δ ppm): 2.6-2.9 (8H, m), 2.99 (3H, s), 3.2-3.9 (4H, m), 4.00 (1H, m), 6.25 (2H, d, J=8.5 Hz), 6.56 (2H, d, J=8.5 Hz), 7.41 (5H, s), 7.59 (1H, t, J=7.9 Hz), 8.08 (1H, d, J=6.1 Hz), 8.15 (1H, d, J=7.9 Hz), 8.25 (1H, d, J=7.9 Hz), 8.46 (1H, d, J=6.1 Hz), 9.29 (1H, s)

EXAMPLE 76

The same procedures as described in Examples 74 and 75 were sequentially repeated except that 470 mg of the intermediate crystals in Example 61 and 113 mg of benzylsulfonyl chloride in place of benzoyl chloride were used to obtain 116 mg of N-[2-(4-benzylsulfonylpiperazinyl)-1-(p-hydroxybenzyl)ethyl]-N-methyl-5-isoquinolinesulfonamide in a colorless amorphous form.

IR (KBr) cm$^{-1}$: 1610, 1320, 1150;

$^1$H-NMR (CDCl$_3$, δ ppm): 2.3-2.9 (8H, m), 2.94 (3H, s), 3.0-3.2 (4H, m), 4.03 (1H, m), 4.20 (2H, s), 6.26 (2H, d, J=8.2 Hz), 6.56 (2H, d, J=8.2 Hz), 7.40 (5H, s), 7.60 (1H, t, J=7.9 Hz), 8.07 (1H, d, J=6.4 Hz), 8.15 (1H, d, J=7.9 Hz), 8.22 (1H, d, J=7.9 Hz), 8.46 (1H, d, J=6.4 Hz), 9.29 (1H, s).

EXAMPLE 77

The same procedures as described in Examples 74 and 75 were sequentially repeated except that 382 mg of the intermediate crystals in Example 61 and 133 mg of 5-isoquinolinesulfonamide.HCl in place of benzoyl chloride were used, to obtain N-{1-(p-hydroxybenzyl]-2-[4-(5-isoquinolinesulfonyl)piperazinyl]ethyl}-N-methyl-5-isoquinolinesulfonamide in a colorless amorphous form.

IR (KBr) cm$^{-1}$: 1610, 1320, 1150;

$^1$H-NMR (CDCl$_3$, δ ppm): 2.3-2.8 (8H, m), 2.90 (3H, s), 3.0-3.2 (4H, m), 3.95 (1H, m), 6.29 (2H, d, J=8.6 Hz), 6.53 (2H, d, J=8.6 Hz), 7.50 (1H, t, J=7.9 Hz), 7.75 (1H, t, J=7.9 Hz), 8.0-8.1 (2H, m), 8.17 (1H, d, J=7.9 Hz), 8.26 (1H, d, J=7.9 Hz), 8.3-8.5 (2H, m), 8.53 (1H, d, J=6.1 Hz), 8.70 (1H, d, J=6.1 Hz), 9.19 (1H, s), 9.39 (1H, s).

EXAMPLE 78

The same procedures as described in Examples 59 and 60 were sequentially repeated except that α-naphtharenesulfonyl chloride was used in place of 5-isoquinolinesulfonyl chloride.HCl, to obtain N-{2-(4-benzyloxycarbonylpiperazinyl)-1-[p-(α-naphtharenesulfonyloxy)benzyl]ethyl}-N-methyl-α-naphtharenesulfonamide in a colorless amorphous form.

IR (KBr) cm$^{-1}$: 1700, 1365, 1130, 860, 765;

$^1$H-NMR (CDCl$_3$, δ ppm): 2.05–2.25 (5H, m), 2.41 (1H, dd, J=13.13, 6.85 Hz), 2.55–2.8 (2H, m), 2.84 (3H, s), 3.05–3.25 (4H, m), 4.05 (1H, quintet, J=6.85 Hz), 5.11 (2H, s), 6.57 (2H, d, J=8.57 Hz), 6.82 (2H, d, J=8.57 Hz), 7.25–7.60 (9H, m), 7.60–8.20 (8H, m), 8.42 (1H, m), 8.82 (1H, d, J=7.99 Hz).

EXAMPLE 79

The amorphous compound obtained in Example 78 was subjected to alkaline hydrolysis according to the procedure in Example 62 to obtain N-[2-(4-benzyloxycarbonylpiperazinyl)-1-(p-hydroxybenzyl)ethyl]-N-methyl-α-naphtharenesulfonamide in a colorless amorphous form.

IR (KBr) cm$^{-1}$: 1695, 1670, 1310, 1240, 1120;

$^1$H-NMR (CDCl$_3$, δ ppm): 2.15–2.4 (5H, m), 2.48 (1H, dd, J=12.56, 7.42 Hz), 2.6–2.85 (2H, m), 2.87 (3H, s), 3.15–3.35 (4H, m), 4.20 (1H, quintet, J=6.85 Hz), 5.10 (2H, s), 5.13 (1H, br), 6.58 (2H, d, J=7.99 Hz), 6.89 (2H, d, J=7.99 Hz), 7.33 (5H, s), 7.44 (1H, t, J=7.42 Hz), 7.47–7.63 (2H, m), 7.8–7.93 (1H, m), 7.99 (1H, d, J=7.99 Hz), 8.15 (1H, dd, J=6.85, 1.0 Hz), 8.45–8.6 (1H, m).

EXAMPLE 80

N-{1-[p-(5-Isoquinolinesulfonyloxy)benzyl-2-(4-phenylhomopiperazinyl)ethyl}-5-isoquinolinesulfonamide The same procedure as described in Example 34 except that 1-[2-amino-3-(p-hydroxyphenyl)propyl]-4-phenylhomopiperazine was used in place of 1-[2-amino-3-(p-hydroxyphenyl)propyl]-4-phenylpiperazine, to obtain the title compound in a yellow amorphous form.

IR (KBr) cm$^{-1}$: 1620, 1600, 1365, 1135;

$^1$H-NMR (CDCl$_3$, δ ppm): 2.10–2.36 (7H, m), 2.63 (1H, dd, J=6.8, 13.7 Hz), 2.76 (1H, dd, J=4.9, 13.7 Hz), 2.99–3.29 (6H, m), 6.53 (2H, d, J=8.3 Hz), 6.60 (2H, d, J=8.8 Hz), 6.64 (1H, t, J=7.3 Hz), 6.80 (2H, d, J=8.8 Hz), 7.17 (1H, t, J=8.8 Hz), 7.62 (1H, t, J=7.8 Hz), 7.66 (1H, t, J=7.8 Hz), 8.18 (1H, d, J=8.3 Hz), 8.26 (2H, d, J=7.3 Hz), 8.37–8.38 (2H, m), 8.53 (1H, d, J=5.9 Hz), 8.67 (1H, d, J=6.4 Hz), 8.82 (1H d, J=5.9 Hz), 9.33 (1H, s), 9.42 (1H, s).

EXAMPLE 81

The amorphous compound obtained in Example 80 was treated with methyl iodide according to the procedure in Example 35 to obtain N-{1-[p-(5-isoquinolinesulfonyloxy)benzyl]-2-(4-phenylhomopiperazinyl)ethyl}-N-methyl-5-isoquinolinesulfonamide in a yellow amorphous form.

IR (KBr) cm$^{-1}$: 1620, 1600, 1500, 1365, 1135;

$^1$H-NMR (CDCl$_3$, δ ppm): 1.70 (2H, m), 2.37 (1H, dd, J=8.8, 11.7 Hz), 2.40–2.65 (6H, m), 2.76 (1H, dd, J=4.9, 13.7 Hz), 2.84 (3H, s), 3.23–3.42 (4H, m), 3.98 (1H, m), 6.51–6.65 (5H, m), 6.77 (2H, d, J=8.3 Hz), 7.16 (2H, t, J=7.8 Hz), 7.54 (1H, dd, J=7.3, 8.3 Hz), 7.59 (1H, t, J=7.8 Hz), 8.08 (1H, d, J=7.8 Hz), 8.18–8.26 (4H, m), 8.55 (1H, d, J=5.9 Hz), 8.55 (1H, dd, J=1.0, 6.3 Hz), 8.84 (1H, d, J=6.3 Hz), 9.26 (1H, s), 9.41 (1H, d, J=1.0 Hz).

The amorphous compounds obtained in Examples 80 and 81 were subjected to alkaline hydrolysis according to the procedure described in Example 36, to obtain the following two compounds.

EXAMPLE 82

N-[1-(p-Hydroxybenzyl)-2-(4-phenylhomopiperazinyl)ethyl]-5-isoquinolinesulfonamide Yellow crystals;

Melting point: 170°–178° C. (decomposed);

IR (KBr) cm$^{-1}$: 1615, 1600, 1505, 1365, 1320, 1205, 1155, 1130;

$^1$H-NMR (CDCl$_3$, δ ppm): 1.79 (2H, m), 2.44 (1H, dd, J=8.3, 13.7 Hz), 2.50–2.72 (7H, m), 3.23 (1H, m), 3.30–3.45 (4H, m), 6.24 (2H, d, J=8.3 Hz), 6.51 (2H, d, J=8.3 Hz), 6.66 (2H, d, J=8.3 Hz), 6.68 (1H, t, J=7.3 Hz), 7.23 (2H, dd, J=7.3, 8.3 Hz), 7.64 (1H, t, J=7.8 Hz), 8.19 (1H, d, J=7.8 Hz), 8.27 (1H, d, J=6.4 Hz), 8.34 (1H, dd, J=1.0, 7.3 Hz), 8.53 (1H, d, J=6.4 Hz), 9.33 (1H, brs).

EXAMPLE 83

N-[1-(p-Hydroxybenzyl)-2-(4-phenylhomopiperazinyl)ethyl]-N-methyl-5-isoquinolinesulfonamide Yellow amorphous.

IR (KBr) cm$^{-1}$: 1615, 1600, 1500, 1360, 1320, 1210, 1150, 1125;

$^1$H-NMR (CDCl$_3$, δ ppm): 1.93 (2H, m), 2.40 (1H, dd, J=9.8, 14.2 Hz), 2.56 (1H, dd, J=8.8, 12.7 Hz), 2.70 (2H, m), 2.80–2.92 (4H, m), 3.00 (3H, s), 3.46–3.53 (4H, m), 3.85 (1H, m), 6.19 (2H, d, J=8.3 Hz), 6.51 (2H, d, J=8.3 Hz), 6.65 (1H, t, J=7.3 Hz), 6.69 (2H, d, J=8.3 Hz), 7.21 (2H, dd, J=7.3, 8.8 Hz), 7.58 (2H, t, J=7.3 Hz), 8.07 (1H, d, J=6.4 Hz), 8.12 (1H, d, J=8.3 Hz), 8.27 (1H, dd, J=1.0, 7.3 Hz), 8.45 (1H, d, J=5.9 Hz), 9.27 (1H, s)

REFERENCE EXAMPLE 18

N-tert-Butoxycarbonyl-4-hydroxypiperidine 7.14 g of 4-piperidone.monohydrate.hydrochloride was dissolved in 50 ml of dimethylformamide and 10 ml of water, and to the solution were added 25 ml of diisopropylethylamine and 9.5 g of di-tert-butyl dicarbonate at a room temperature with stirring, and the reaction mixture was stirred for 4 hours. After adding water and saturating with sodium chloride, the reaction mixture was extracted twice with 300 ml of chloroform. The extract was dried over magnesium sulfate and evaporated under a reduced pressure to obtain 9.6 g of residue, which was then dissolved in 100 ml of ethanol. To the solution was added 1.83 g of sodium borohydride with stirring under ice cooling, and the mixture was stirred for 90 minutes under the same condition, and then for 30 minutes at a room temperature. After adding saturated sodium chloride aqueous solution, the reaction mixture was alkalized with sodium bicarbonate and extracted twice with 600 ml of chloroform. The extract was dried over magnesium sulfate and evaporated under a reduced pressure, and resulting residue was subjected to a silica gel column and eluted with hexane/ethyl acetate (2:1), to obtain 8.03 g of the title compound in a colorless amorphous form.

$^1$H-NMR (CDCl$_3$, δ ppm): 1.35–1.6 (2H, m), 1.45 (9H, s), 1.75–1.95 (2H, m), 3.03 (2H, ddd, J=13.13, 10.28, 4.00 Hz), 3.75–3.95 (3H, m).

REFERENCE EXAMPLE 19

4-(p-Methylbenzyloxy)piperidine 2.0 g of the amorphous compound obtained in Reference Example 18 was dissolved in 20 ml of dimethylformamide, to the solution was added 0.48 g of 60% sodium hydride in an ice bath. After removing from the ice bath, the reaction mixture was stirred at a room temperature for 30 minutes, and after adding 1.54 g of p-methylbenzyl chloride, further stirred for 18 hours. The reaction mixture was poured on ice, saturated with sodium chloride and extracted twice with 150 ml of chloroform. The extract was dried over magnesium sulfate and evaporated under a reduced pressure, and resulting residue was applied to a silica gel column and eluted with hexane/ethyl acetate (5:1) to obtain 1.27 g of N-tert-butoxycarbonyl-4-p-methylbenzyloxypiperidine. This compound was dissolved in 3 ml of ethyl acetate, and after adding 12 ml of 3N hydrogen chloride in ethyl acetate at a room temperature with further stirring for 17 hours, the solvent was evaporated off under a reduced pressure. Resulting residue was dissolved in water, and the solution was alkalized with sodium bicarbonate, saturated with sodium chloride and extracted twice with 200 ml of chloroform. The extract was dried over magnesium sulfate and the solvent was evaporated off under a reduced pressure to obtain 830 mg of the title compound in colorless amorphous form.

$^1$H-NMR (CDCl$_3$, δ ppm): 1.55–1.8 (2H, m), 1.9–2.15 (2H, m), 2.34 (3H, s), 2.81 (2H, ddd, J=13.13, 10.28, 4.00 Hz), 3.17 (2H, ddd, J=11.42, 7.42, 4.00 Hz), 3.56 (1H, septet, J=3.71 Hz), 4.50 (2H, s), 5.01 (1H, brs), 7.14 (2H, d, J=7.99 Hz), 7.22 (2H, d, J=7.99 Hz).

REFERENCE EXAMPLE 20

N-tert-Butoxycarbonyl-o-(2-methoxyethoxymethyl)-tyrosine methyl ester 13.39 g of N-tert-butoxycarbonyltyrosine methyl ester was dissolved in 65 ml of tetrahydrofuran and 65 ml of dimethylformamide, and to the solution was added 1.9 g of 60% sodium hydride with stirring in an ice bath. After removing from the ice bath, the mixture was stirred at a room temperature for 30 minutes, and after addition of 5.4 g of methoxyethoxymethyl chloride with ice cooling, stirred for 15 hours allowing to warm to a room temperature. The reaction mixture was poured on ice, saturated with sodium chloride and extracted twice with 800 ml of chloroform. The extract was dried over magnesium sulfate and the solvent was evaporated under a reduced pressure, and resulting residue was applied to a silica gel column and eluted with hexane/ethyl acetate (4:1) to obtain 13.85 g of the title compound in a colorless amorphous form.

$^1$H-NMR (CDCl$_3$, δ ppm): 1.46 (9H, s), 3.02 (2H, m), 3.37 (3H, s), 3.5–3.6 (2H, m), 3.71 (3H, s), 3.75–3.85 (2H, m), 4.54 (1H, m), 4.95 (1H, m), 5.24 (2H, s), 6.96 (2H, d, J=9.71 Hz), 7.04 (2H, d, J=9.71 Hz).

REFERENCE EXAMPLE 21

2-(N-tert-Butoxycarbonylamino)-1-chloro-3-[p-(2-methoxyethoxymethoxy)phenyl]propane 13.85 g of the amorphous compound obtained in Reference Example 20 was dissolved in 90 ml of ethanol and 60 ml of tetrahydrofuran, and to the solution were added 3.11 g of lithium chloride and 2.77 g of sodium borohydride with stirring in an ice bath. After removing from the ice bath, the mixture was stirred at a room temperature for 16 hours, and after addition of satulated sodium chloride aqueous solution, the reaction mixture was alkalized with sodium bicarbonate and extracted twice with 800 ml of chloroform. The extract was dried over magnesium sulfate and the solvent was evaporated off under a reduced pressure, to obtain 11.73 g of N-tert-butoxycarbonyl-o-(2-methoxyethoxymethyl)tyrosinol. This compound was dissolved in 120 ml of of carbon tetrachloride, and to the solution was added 10 g of triphenylphosphine. The mixture was refluxed for 3 hours and further heated at 80° C. for 17 hours. The solvent was evaporated off under a reduced pressure, and the resulting residue was applied to a silica gel column and eluted with chloroform/methanol (100:1) followed by with hexane/ethyl acetate (4:1), to obtain 7.22 g of the title compound in colorless amorphous form.

$^1$H-NMR (CDCl$_3$, δ ppm): 1.43 (9H, s), 2.75–2.9 (2H, m), 3.38 (3H, s), 3.4–3.65 (4H, m), 3.75–3.9 (2H, m), 4.08 (1H, m), 4.79 (1H, m), 5.26 (2H, s), 6.99 (2H, d, J=9.71 Hz), 7.16 (2H, d, J=9.71 Hz).

REFERENCE EXAMPLE 22

N-{2-(tert-Butoxycarbonylamino)-3-[p-(2-methoxyethoxymethoxy)phenyl]propyl}-4-(p-methylbenzyloxy)-piperidine 1.56 g of the amorphous compound obtained in Reference Example 21 was dissolved in 25 ml of dimethylformamide, to the solution were added 0.83 g of the amorphous compound obtained in Reference Example 19, 0.67 g of potassium carbonate and 0.67 g of sodium iodide, and the mixture was stirred at 100° C. for 2 hours, and after adding saturated sodium chloride aqueous solution, extracted twice with 150 ml of chloroform. The extract was dried over magnesium sulfate and the solvent was evaporated off under a reduced pressure. Resulting residue was applied to a silica gel column and eluted with chloroform/methanol (100:1) to obtain 490 mg of the title compound in a colorless amorphous form.

$^1$H-NMR (CDCl$_3$, δ ppm): 1.42 (9H, s), 1.5–1.75 (3H, m), 1.75–2.0 (2H, m), 2.0–2.3 (3H, m), 2.33 (3H, s), 2.55–2.95 (4H, m), 3.25–3.5 (1H, m), 3.38 (3H, s), 3.5–3.65 (2H, m), 3.75–3.95 (3H, m), 4.49 (2H, s), 4.64 (1H, m), 5.25 (2H, s), 6.96 (2H, d, J=9.71 Hz), 7.09 (2H, d, J=9.71 Hz), 7.14 (2H, d, J=9.71 Hz), 9.23 (2H, d, J=9.71 Hz).

EXAMPLE 84

N-{1-p-(5-Isoquinolinesulfonyloxy)benzyl]-2-4-(p-methylbenzyloxy)piperidino]ethyl}-5-isocuinolinesulfonamide 490 mg of the amorphous compound obtained in Reference Example 22 was dissolved in 1 ml of ethyl acetate, and to the solution was added 5 ml of 3N hydrogen chloride in ethyl acetate at a room temperature with stirring, and the reaction mixture was stirred for one-hour. After evaporating off the solvent, resulting residue was alkalized with sodium bicarbonate aqueous solution, and the mixture was saturated with sodium chloride, washed with a small amount of methanol, and extracted twice with 100 ml of chloroform. The extract was dried over magnesium sulfate, and the solvent was evaporated off to obtain a residue comprising N-[2-amino-3-(p-hydroxyphenyl)]propyl-4-(p-methylbenzyloxy)piperidine. The residue was dissolved in 7 ml of tetrahydrofuran, and to the solution were added 545 mg of 5-isoquinolinesulfonyl chloride.HCl and 450 mg of triethylamine at a room temperature with stirring. The reaction mixture was stirred for 18 hours, alkalized with a sodium bicarbonate aqueous solution and extracted twice with 100 ml of chloroform. The extract was dried over magnesium sulfate, and the solvent was evaporated off under a reduced pressure, and resulting residue was applied to a silica gel column and eluted with chloroform/methanol (30:1) to obtain 572 mg of the title compound in colorless amorphous form.

$^1$H-NMR (CDCl$_3$, δ ppm): 1.0–1.33 (3H, m), 1.33–1.54 (1H, m), 1.59–1.88 (2H, m), 1.88–2.25 (4H, m), 2.33 (3H, s), 2.71 (1H, dd, J=14.28, 6.85 Hz), 2.91 (1H, dd, J=14.28, 4.57 Hz), 3.18 (2H, m), 4.34 (2H, s), 6.68 (2H, d, J=9.14 Hz), 6.90 (2H, d, J=9.14 Hz), 7.14 (4H, s), 8.13 (1H, t, J=7.42 Hz), 8.18 (1H, t, J=7.42 Hz), 9.19 (1H, d, J=7.42 Hz), 8.27 (2H, d, J=7.42 Hz), 8.40 (1H, dd, J=7.99, 1.0 Hz), 8.44 (1H, d, J=6.85 Hz), 8.52 (1H, d, J=6.28 Hz), 8.68 (1H, d, J=6.28 Hz), 8.81 (1H, d, J=6.28 Hz), 9.34 (1H, s), 9.41 (1H, s).

EXAMPLE 85

N-{1-(p-Hydroxybenzyl)-2-4-(p-methylbenzyloxy)-piperidino]ethyl}-isoquinolinesulfonamide 400 mg of the amorphous compound obtained in Example 84 was dissolved in 2.5 ml of methanol and 2.5 ml of tetrahydrofuran, to the solution was added 4 ml of 1N sodium hydroxide solution, and the mixture was refluxed for 2 hours. After cooling, the reaction mixture was diluted with water, acidified with citric acid and then alkalized with sodium bicarbonate, and extracted twice with 100 ml of chloroform. The extract was dried over magnesium sulfate, and the solvent was evaporated off under a reduced pressure. Resulting residue was applied to a silica gel column and eluted with chloroform/methanol (20:1) to obtain 172 mg of the title compound in a colorless amorphous form.

$^1$H-NMR (CDCl$_3$, δ ppm): 1.2–1.75 (4H, m), 1.85–2.15 (2H, m), 2.2–2.58 (4H, m), 2.32 (3H, s), 2.58–2.85 (2H, m), 3.15–3.4 (2H, m), 4.41 (2H, s), 4.8 (2H, br), 6.42 (2H, d, J=9.14 Hz), 6.68 (2H, d, J=9.14 Hz), 7.14 (2H, d, J=7.42 Hz), 7.19 (2H, d, J=7.42 Hz), 7.67 (1H, t, J=7.42 Hz), 8.19 (1H, d, J=7.42 Hz), 8.33–8.50 (2H, m), 8.58 (1H, d, J=6.28 Hz), 9.33 (1H, s).

EXAMPLE 86

The same procedure as described in Example 84 was repeated except that N-{2-(tert-butoxycarbonylamino)-3-[p-(2-methoxyethoxymethoxy)phenyl]propyl}-4-(3,4-dichlorobenzyloxy)piperidine was used in place of N-{(2-(tertbutoxycarbonylamino)-3-[p-(2-methoxyethoxymethoxy)phenyl]propyl}-4-(p-methylbenzyloxy)-piperidine, to obtain N-{1-[p-5-isoquinolinesulfonyloxy)benzyl]-2-[4-(3,4-dichlorobenzyloxy) piperidino]ethyl}-5-isoquinolinesulfonamide in a colorless amorphous form.

$^1$H-NMR (CDCl$_3$, δ ppm): 0.95–1.17 (1H, m), 1.17–1.34 (2H, m), 1.34–1.91 (2H, m), 1.91–2.30 (4H, m), 2.72 (1H, dd, J=13.13, 7.42 Hz), 2.89 (1H, dd, J=13.13, 4.57 Hz), 3.20 (2H, m), 4.33 (2H, s), 6.68 (2H, d, J=9.14 Hz), 6.92 (2H, d, J=9.14 Hz), 7.10 (1H, dd, J=9.14, 1.71 Hz), 7.36 (1H, d, J=1.71 Hz), 7.38 (1H, d, J=9.14 Hz), 7.64 (1H, t, J=7.42 Hz), 7.68 (1H, t, J=7.42 Hz), 8.20 (1H, d, J=7.42 Hz), 8.28 (2H, d, J=7.42 Hz), 8.39 (1H, dd, J=7.42, 1.0 Hz), 8.43 (1H, d, J=6.28 Hz), 8.53 (1H, d, J=6.28 Hz), 8.69 (1H, d, J=6.28 Hz), 8.80 (1H, d, J=6.28 Hz), 9.35 (1H, s), 9.42 (1H, s);

IR (KBr) cm$^{-1}$: 1615, 1375, 1130, 860.

EXAMPLE 87

The amorphous compound obtained in Example 86 was subjected to alkaline hydrolysis according to the procedure in Example 85, to obtain N-{1-(p-hydroxybenzyl)-2-4-(3,4-dichlorobenzyloxy)piperidino]ethyl}-5-isoquinolinesulfonamide in a colorless amorphous form.

IR (KBr) cm$^{-1}$: 1615, 1375, 1130, 860;

$^1$H-NMR (CDCl$_3$, δ ppm): 1.2–1.8 (4H, m), 1.9–2.2 (2H, m), 2.2–2.6 (4H, m), 2.62 (1H, dd, J=14.28, 6.85 Hz), 2.75 (1H, dd, J=14.28, 6.28 Hz), 3.29 (2H, m), 4.33 (2H, br), 4.39 (2H, s), 6.38 (2H, d, J=8.57 Hz), 6.67 (2H, d, J=8.57 Hz), 7.12 (1H, dd, J=8.57, 1.71 Hz), 7.38 (1H, d, J=8.57 Hz), 7.39 (1H, d, J=1.71 Hz), 7.67 (1H, t, J=7.42 Hz), 8.20 (1H, d, J=7.42 Hz), 8.37 (1H, d, J=6.28 Hz), 8.40 (1H, dd, J=7.42, 1.0 Hz), 8.58 (1H, d, J=6.28 Hz), 9.32 (1H, s).

REFERENCE EXAMPLE 23

The same procedure as described in Reference Example 21 was repeated, except that N-benzyloxycarbonyl-o-benzyltyrosine methyl ester was used in place of N-tert-butoxycarbonyl-o-(2-methoxyethoxymethyl)tyrosine methyl ester, to obtain 2-benzyloxycarbonylamino-3-(p-benzyloxyphenyl)-1-chloropropane in colorless amorphous form.

$^1$H-NMR (CDCl$_3$, δ ppm): 2.7–2.95 (2H, m), 3.49 (1H, dd, J=11.42, 3.43 Hz), 3.63 (1H, dd, J=11.42, 4.00 Hz), 4.13 (1H, m), 5.00 (1H, m), 5.04 (2H, s), 5.10 (2H, s), 6.92 (2H, d, J=7.99 Hz), 7.15 (2H, d, J=7.99 Hz), 7.3–7.5 (5H, m).

To the amorphous compound so obtained was added N-phenylpiperazine, and the same procedure as described in Reference Example 21 was repeated to obtain 1-{2-(benzyloxycarbonylamino)-3-(p-Benzyloxyphenyl)propyl}-4-phenylpiperazine in a colorless amorphous form.

$^1$H-NMR (CDCl$_3$, δ ppm): 2.34 (2H, d, J=6.85 Hz), 2.4–2.7 (4H, m), 2.75–3.0 (2H, m), 3.14 (4H, t, J=5.14 Hz), 3.99 (1H, m), 4.90 (1H, m), 5.04 (2H, s), 5.10 (2H, s), 6.75–7.0 (5H, m), 7.09 (2H, d, J=8.57 Hz), 7.2–7.5 (12H, m).

EXAMPLE 88

N-{1-(p-Benzyloxy)benzyl]-2-(4-phenylpiperazinyl)ethyl)-5-isoquinolinesulfonamide 500 mg of the 1-substituted 4-phenylpiperazine obtained in Reference Example 23 was dissolved in 1 ml of acetic acid, and to the solution was added 2 ml of 30% hydrogen bromide in acetic acid, and the mixture was stirred for 10 minutes and poured on ice. After adding saturated sodium thiosulfate aqueous solution, the reaction mixture was alkalized with saturated sodium bicarbonate aqueous solution, and extracted twice with 150 ml of chloroform. The extract was dried over magnesium sulfate and the solvent was evaporated off under a reduced pressure, and resulting residue was applied to a silica gel column and eluted with chloroform/methanol (30:1), to obtain 235 mg of 1-{2-amino-3-(p-benzyloxyphenyl)propyl}-4-phenylpiperazine. 235 mg of this compound was dissolved in 5 ml of tetrahydrofuran, and to the solution were added 195 mg of 5-isoquinolinesulfonyl chloride.HCl and 178 mg of triethylamine at a room temperature with stirring, and the mixture was stirred for 16 hours. After adding saturated sodium chloride aqueous solution, the reaction mixture was alkalized with sodium bicarbonate aqueous solution, and extracted twice with 150 ml of chloroform. The extract was dried over magnesium sulfate, and the solvent was evaporated off under a reduced pressure, and resulting residue was applied to a silica gel column and eluted with chloroform/methanol (50:1) to obtain 280 mg of N-{1-[(4-benzyloxy)benzyl]-2-(4-phenylpiperazinyl)ethyl}-5-isoquinolinesulfonamide in a calorless amorphous form.

$^1$H-NMR (CDCl$_3$, δ ppm): 2.1–2.5 (6H, m), 2.7–3.0 (6H, m), 3.37 (1H, m), 4.99 (2H, s), 5.5 (1H, br), 6.71 (2H, d, J=8.57 Hz), 6.81 (3H, t, J=8.57 Hz), 6.90 (2H, d, J=8.57 Hz), 7.24 (2H, t, J=8.57 Hz), 7.3–7.5 (5H, m), 7.68 (1H, t, J=7.42 Hz), 8.17 (1H, d, J=7.99 Hz), 8.43 (1H, d, J=6.28 Hz), 8.46 (1H, d,J=6.85 Hz), 8.67 (1H, d, J=6.28 Hz), 9.32 (1H, s).

EXAMPLE 89

N-{2-[4-(3,4-Dichlorobenzyloxy)piperidino]-1-[p-(5-isoquinolinesulfonyloxy)benzyl]ethyl}-N-methyl-5-isoquinolinesulfonamide 1.70 g of the amorphous compound obtained in Example 86 was dissolved in 10 ml of dimethylformamide, and to the solution was added 93 mg of sodium hydride with stirring in an ice bath, and after stirring for 10 minutes the ice bath was removed. The reaction mixture was stirred at a room temperature for 4 hours, and after adding 150 ml of ethyl acetate, washed three times with water and the washing were extracted with 50 ml of ethyl acetate. The extracts were combined and washed with saturated sodium chloride aqueous solution, dried over magnesium sulfate, and the solvent was evaporated off under a reduced pressure. Resulting residue was applied to a silica gel column (silica gel: Fuji Debison Kagaku, BW-820MH), and eluted with 1% methanol in chloroform to obtain 1.30 g of the title compound in a colorless amorphous form.

IR (CHCl$_3$) cm$^{-1}$: 2920, 2810, 1618, 1583, 1563, 1450, 983, 902;

$^1$H-NMR (CDCl$_3$, δ ppm): 1.30–1.52 (2H, m), 1.60–1.78 (2H, m), 1.95–2.12 (2H, m), 2.15–3.00 (6H, m), 2.84 (3H, s), 3.31 (1H, m), 4.10 (1H, m), 4.42 (2H, s), 6.58 (2H, brd, J=8.5 Hz), 6.87 (2H, brd, J=8.5 Hz), 7.14 (1H, dd, J=8.3, 1.9 Hz), 7.39 (1H, d, J=8.3 Hz), 7.41 (1H, d, J=1.9 Hz), 7.53–7.65 (2H, m), 8.11 (1H, d, J=8.3 Hz), 8.28–8.31 (3H, m), 8.32 (1H, dd, J=7.5, 1.2 Hz), 8.54 (1H, brd, J=6.1 Hz), 8.57 (1H, d, J=6.1 Hz), 8.83 (1H, d, J=6.1 Hz), 9.28 (1H, d, J=1.0 Hz), 9.41 (1H, d, J=1.0 Hz).

EXAMPLE 90

N-{2-[4-(3,4-Dichlorobenzyloxy)piperidino]-1-(p-hydroxybenzyl)ethyl)-N-methyl-5-isoquinolinesulfonamide 1.04 g of the amorphous compound obtained in Example 89 was dissolved in 10 ml of dimethylsulfoxide, to the solution was added a solution of 152 mg of sodium hydroxide in 2 ml of water, and the mixture was stirred at 80° C. for 2 hours. After adding 150 ml of ethyl acetate, the reaction mixture was twice washed with 100 ml of water, and the washings were extracted with 50 ml of ethyl acetate. The ethyl acetate layers were combined, washed with saturated sodium chloride aqueous solution, dried over magnesium sulfate and evaporated to remove the solvent under a reduced pressure. Resulting residue was applied to a silica gel column and eluted with 1% methanol in chloroform to obtain 650 mg of the title compound in a colorless amorphous form.

$^1$H-NMR (CDCl$_3$, δ ppm): 1.50–1.67 (2H, m), 1.75–1.94 (2H, m), 2.15–2.30 (2H, m), 2.40–2.96 (6H, m), 3.00 (3H, s), 3.39 (1H, m), 3.96 (1H, m), 4.47 (2H, s), 6.26 (2H, brd, J=8.5 Hz), 6.61 (2H, brd, J=8.5 Hz), 6.90–7.10 (1H, br), 7.16 (1H, dd, J=8.3, 1.9 Hz), 7.41 (1H, d, J=8.3 Hz), 7.44 (1H, d, J=1.9 Hz), 7.60 (1H, dd, J=8.0, 7.5 Hz), 8.09 (1H, brd, J=6.1 Hz), 8.14 (1H, brd, J=8.0 Hz), 8.31 (1H, dd, J=7.5, 1.2 Hz), 8.47 (1H, d, J=6.1 Hz), 9.28 (1H, brs).

EXAMPLE 91

N-{2-[4-(3,4-Dichlorobenzyloxy)piperidine]-1-(p-methoxybenzyl)ethyl)-N-methyl-5-isoquinolincsulfonamide 350 mg of the amorphous compound obtained in Example 90 was dissolved in 10 ml of dimethylformamide, and to the solution 82.8 mg of methyl iodide was added with stirring in an ice bath. The mixture was stirred for 30 minutes, and after removing the ice bath further stirred for 2 hours at a room temperature. To the reaction mixture was added 100 ml of ethyl acetate, and the mixture was washed three times with 50 ml of water. The washing were extracted with 50 ml of ethyl acetate, the ethyl acetate layer was washed with water. The ethyl acetate layers were combined, washed with saturated sodium chloride aqueous solution, dried over magnesium sulfate, and evaporated to remove the solvent under a reduced pressure. Resulting residue was applied to a silica gel column and eluted with 1% methanol in chloroform to obtain 297 mg of the title compound in a colorless amorphous form.

IR (CHCl$_3$) cm$^{-1}$: 2910, 2835, 1615, 1585, 1322, 1125, 986;

$^1$H-NMR (CDCl$_3$, δ ppm): 1.38–1.60 (2H, m), 1.69–1.85 (2H, m), 2.06–2.22 (2H, m), 2.36 (1H, dd, J=13.0, 7.3 Hz), 2.51–2.76 (4H, m), 2.88 (1H, m), 2.93 (3H, s), 3.34 (1H, m), 3.73 (3H, s), 4.13 (1H, m), 4.44 (2H, s), 6.50 (2H, dm, J=8.8 Hz), 6.83 (2H, dm, J=8.8 Hz), 7.14 (1H, dd, J=8.0, 1.9 Hz), 7.40 (1H, d, J=8.0 Hz), 7.43 (1H, d, J=1.9 Hz), 7.56 (1H, dd, J=8.3, 7.3 Hz), 8.08 (1H, brd, J=8.3 Hz), 8.29 (1H, dd, J=7.3, 1.2 Hz), 8.55 (1H, d, J=6.3 Hz), 9.23 (1H, brs).

EXAMPLE 92

The same procedures as described in Examples 34 and 35 were sequentially repeated except that 1-[2-amino-3-(p-hydroxyphenyl)propyl]-4-phenylpiperidine was used in place of 1-[2-amino-3-(p-hydroxyphenyl)-propyl]-4-phenylpiperazine, to obtain N-{1-[p-(5-isoquinolinesulfonyloxy)benzyl]-2-(4-phenylpiperidino)ethyl}-N-methyl-5-isoquinolinesulfonamide in a colorless amorphous form.

$^1$H-NMR (CDCl$_3$, δ ppm): 1.15–1.75 (4H, m), 1.80–2.10 (2H, m), 2.20–2.50 (3H, m), 2.60–2.80 (2H, m), 2.80–3.05 (3H, m), 2.86 (3H, s), 4.13 (1H, d, J=6.85 Hz), 6.62 (2H, d, J=7.99 Hz), 6.91 (2H, d, J=7.99 Hz), 7.12 (2H, dd, J=6.85, 1.0 Hz), 7.16–7.40 (3H, m), 7.58 (1H, t, J=7.42 Hz), 7.61 (1H, t, J=7.42 Hz), 8.11 (1H, d, J=7.42 Hz), 8.26 (3H, dd, J=6.85, 1.0 Hz), 8.36 (1H, dd, J=7.42, 1.0 Hz), 8.56 (1H, d, J=6.28 Hz), 8.59 (1H, d, J=6.28 Hz), 8.83 (1H, d, J=6.28 Hz), 9.28 (1H, s), 9.41 (1H, d, J=1.0 Hz).

EXAMPLE 93

The amorphous compound obtained in Example 92 was subjected to alkaline hydrolysis according to the procedure in Example 36, to obtain N-[1-(p-hydroxybenzyl)-2-(4-phenylpiperidino)ethyl]-N-methyl-5-isoquinolinesulfonamide in a colorless amorphous form.

IR (KBr) cm$^{-1}$: 1615, 1515, 1325, 1125;

$^1$H-NMR (CDCl$_3$, δ ppm): 1.55–1.95 (5H, m), 2.22 (2H, dt, J=6.28, 1.7 Hz), 2.35–2.60 (3H, m), 2.70 (1H, dd, J=12.56, 5.71 Hz), 2.8–3.25 (3H, m), 3.06 (3H, s), 3.98 (1H, m), 6.23 (2H, d, J=8.57 Hz), 6.59 (2H, d, J=8.57 Hz), 7.15–7.40 (5H, m), 7.62 (1H, t, J=7.42 Hz), 8.10 (1H, d, J=6.85 Hz), 8.16 (1H, d, J=7.42 Hz), 8.35 (1H, dd, J=7.42, 1.0 Hz), 8.47 (1H, d, J=6.28 Hz), 8.29 (1H, s).

EXAMPLE 94

The same procedures as described in Examples 34 and 35 were sequentially repeated except that 1-[2-amino-3-(p-hydroxyphenyl)propyl]-4,4-ethylenedioxypiperidine was used in place of 1-[2-amino-3-(p-hydroxyphenyl)propyl]-4-phenylpiperazine, to obtain N-{2-(4,4-ethylenedioxypiperidino)-1-[p-(5-isoquinolinesulfonyloxy)benzyl]ethyl}-N-methyl-5-isoquinolinesulfonamide in a colorless amorphous form.

$^1$H-NMR (CDCl$_3$, δ ppm): 1.4–1.6 (4H, m), 2.22 (1H, dd, J=12.56, 6.85 Hz), 2.25–2.5 (5H, m), 2.6–2.8 (1H, m), 2.8–2.95 (1H, m), 2.84 (3H, s), 3.90 (4H, s), 4.11 (1H, q, J=6.85 Hz), 6.61 (2H, d, J=8.57 Hz), 6.89 (2H, d, J=8.57 Hz), 7.61 (1H, t, J=7.42 Hz), 7.63 (1H, t, J=7.42 Hz), 8.12 (1H, d, J=7.42 Hz), 8.26 (2H, d, J=7.42 Hz), 8.27 (1H, d, J=7.42 Hz), 8.35 (1H, d, J=7.42 Hz), 8.57 (1H, d, J=6.28 Hz), 8.58 (1H, d, J=6.28 Hz), 8.84 (1H, d, J=6.28 Hz), 9.29 (1H, s), 9.42 (1H, s).

EXAMPLE 95

N-{1-[p-(5-Isocuinolinesulfonyloxy)benzyl]-2-(4-oxopiperidino)ethyl}-N-methyl-5-isoquinolinesulfonamide 2.57 g of the product of Example 94 was dissolved in 50 ml of 3N hydrochloric acid, and after refluxing for 6 hours and then cooling, the reaction mixture was alkalized with saturated sodium bicarbonate aqueous solution and extracted twice with 200 ml of chloroform. The extract was dried over magnesium sulfate and evaporated under a reduced pressure to remove the solvent, and resulting residue was applied to a silica gel column and eluted with chloroform/methanol (50:1) to obtain 2.22 g of the title compound in a colorless amorphous form.

$^1$H-NMR (CDCl$_3$, δ ppm): 2.1–2.25 (4H, m), 2.31 (1H, dd, J=13.13, 6.85 Hz), 2.4=2.65 (6H, m), 2.65–2.85 (1H, m), 2.79 (3H, s), 4.10 (1H, q, J=6.85 Hz), 6.52 (2H, d, J=7.71 Hz), 6.78 (2H, d, J=7.71 Hz), 7.49 (1H, t, J=7.42 Hz), 7.55 (1H, t, J=7.42 Hz), 8.05 (1H, d, J=7.99 Hz), 8.10–8.20 (3H, m), 8.20 (1H, d, J=7.42 Hz), 8.46 (1H, d, J=6.28 Hz), 8.48 (1H, d, J=6.28 Hz), 8.76 (1H, d, J=6.28 Hz), 9.20 (1H, s), 9.34 (1H, s).

EXAMPLE 96

N-{2-4-(N'-Benzyl-N'-methylamino)piperidino]-1-[p-(5-isoquinolinesulfonyloxy)benzyl]ethyl}-N-methyl-5-isoquinolinesulfonamide 1.0 g of the product of Example 95 was dissolved in 15 ml of methanol, to the solution were added 270 mg of benzylmethylamine and 120 mg of sodium cyanoborohydride at a room temperature with stirring, and the reaction mixture was stirred for 18 hours. After addition of saturated sodium bicarbonate aqueous solution, the reaction mixture was twice extracted with 150 ml of chloroform. The extract was dried over magnesium sulfate and evaporated under a reduced pressure to remove the solvent, and resulting residue was applied to a silica gel column and eluted with chloroform/methanol (30:1), to obtain 380 mg of the title compound in a colorless amorphous form.

$^1$H-NMR (CDCl$_3$, δ ppm): 1.0–1.45 (2H, m), 1.45–1.65 (1H, m), 1.65–2.0 (3H, m), 2.13 (3H, s), 2.15–2.45 (3H, m), 2.5–2.9 (4H, m), 2.84 (3H, s), 3.49 (3H, s), 4.07 (1H, q, J=6.85 Hz), 6.61 (2H, d, J=7.99 Hz), 6.89 (2H, d, J=7.99 Hz), 7.28 (5H, s), 7.58 (1H, t, J=7.42 Hz), 7.60 (1H, t, J=7.42 Hz), 8.11 (1H, d, J=7.99 Hz), 8.25 (1H, d, J=6.28 Hz), 8.26 (2H, d, J=7.42 Hz), 8.34 (1H, dd, J=7.42, 1.0 Hz), 8.55 (1H, d, J=6.28 Hz), 8.57 (1H, d, J=6.28 Hz), 8.83 (1H, d, J=6.28 Hz), 9.26 (1H, s), 9.41 (1H, s).

EXAMPLE 97

N-{2-4-(N-Benzyl-N-methylamino)piperidino]-1-(p-hydroxybenzyl)ethyl}-N-methyl-5-isocuinolinesulfonamide 380 mg of the amorphous compound obtained in Example 96 was dissolved in 2 ml of tetrahydrofuran and 2 ml of methanol, to the solution was added 4 ml of 1 N sodium hydroxide aqueous solution, and the mixture was refluxed for 3 hours and cooled. The reaction mixture was poured to water, acidified with citric acid and then alkalized with sodium bicarbonate, washed with a small amount of methanol, and extracted twice with 100 ml of chloroform. The extract was dried over magnesium sulfate and evaporated to remove the solvent under a reduced pressure, and resulting residue was applied to a silica gel column and eluted with chloroform/methanol (20:1) to obtain 147 mg of the title compound in a colorless amorphous form.

$^1$H-NMR (CDCl$_3$, δ ppm): 1.35–1.95 (4H, m), 1.95–2.25 (2H, m), 2.19 (3H, s), 2.3–2.7 (4H, m), 2.75–3.15 (3H, m), 3.01 (3H, s), 3.57 (2H, s), 3.95 (1H, m), 6.25 (2H, d, J=8.3 Hz), 6.58 (2H, d, J=8.55 Hz), 7.2–7.4 (5H, m), 7.60 (1H, t, J=7.57 Hz), 8.11 (1H, d, J=5.86 Hz), 8.12 (1H, d, J=8.06 Hz), 8.32 (1H, d, J=7.33 Hz), 8.46 (1H, d, J=6.35 Hz), 9.28 (1H, s).

EXAMPLE 98

The same procedures as described in Examples 96 and 97 were sequentially repeated except that benzylamine was used in place of benzylmethylamine, to obtain N-{2-[4-(N-benzylamino)piperidino]-1-(p-hydroxybenzyl)ethyl}-N-methyl-5-isoquinolinesulfonamide in a colorless amorphous form.

$^1$H-NMR (CDCl$_3$, δ ppm): 1.2–1.6 (2H, m), 1.7–2.0 (2H, m), 2.0–2.3 (2H, m), 2.35–2.7 (4H, m), 2.7–3.5 (3H, m), 3.0 (3H, s), 3.83 (2H, s), 3.95 (1H, m), 6.24 (2H, d, J=7.99 Hz), 6.56 (2H, d, J=7.99 Hz), 7.32 (5H, m), 7.59 (1H, t, J=7.42 Hz), 8.10 (1H, d, J=6.28 Hz), 8.12 (1H, d, J=7.42 Hz), 8.30 (1H, d, J=7.42 Hz), 8.46 (1H, d, J=6.28 Hz), 9.26 (1H, s).

EXAMPLE 99

N-{2-(4-hydroxypiperidino)-1-p-(5-isoquinolinesulfonyloxy)benzyl]ethyl)-N-methyl-5-isoquinolinesulfonamide 200 mg of the amorphous compound obtained in Example 95 was dissolved in 5 ml of methanol, to the solution was added in portions 35.2 mg of sodium borohydride at a room temperature with stirring, and the mixture was stirred for 2 hours and evaporated to remove the solvent. Resulting residue was applied to a silica gel column and eluted with chloroform/methanol (100:4), to obtain 116 mg of the title compound as pale yellow oil.

IR (KBr) cm$^{-1}$: 1620, 1500, 1370, 1320, 1130, 860;

$^1$H-NMR (CDCl$_3$, δ ppm): 1.2–1.4 (2H, m), 1.5–1.8 (4H, m), 1.9–2.1 (2H, m), 2.25 (1H, dd, J=12.6, 7.3 Hz), 2.4 (1H, dd, J=12.7, 7.1 Hz), 2.7 (1H, dd, J=13.8, 7.0 Hz), 2.8–2.95 (1H, m), 2.55 (1H, brs), 2.83 (3H, s), 3.55 (1H, m), 4.1 (1H, m), 6.6 (2H, d, J=8.5 Hz), 6.87 (2H, d, J=8.5 Hz), 7.6 (1H, t, J=8.3 Hz), 7.63 (1H, t, J=7.8 Hz), 8.12 (1H, d, J=8.3 Hz), 8.23 (1H, d, J=5.1 Hz), 8.26 (1H, d, J=5.1 Hz), 8.3 (1H, dd, J=1.2, 3.3 Hz), 8.54 (1H, d, J=4.1 Hz), 8.57 (1H, d, J=4.1 Hz), 8.83 (1H, d, J=6.1 Hz), 9.28 (1H, s), 9.4 (1H, s).

EXAMPLE 100

N-{2-(4-Hydroxypiperidino)-1-[p-(5-isoquinolinesulfonyloxy)benzylethyl)-N-methyl-5-isoquinolinesulfonamide 150 mg of the oil obtained in Example 99 was dissolved in 3 ml of methanol, to the solution was added 1 ml of 10% sodium hydroxide aqueous solution, and the reaction mixture were refluxed for 2 hours and evaporated to remove the solvent under a reduced pressure, the resulting residue was acidified with citric acid and then alkalized with a sodium bicarbonate aqueous solution, and the mixture was extracted three times with 20 ml of chloroform. The extract was dried over magnesium sulfate and evaporated to remove the solvent under a reduced pressure, and the resulting residue was subjected to a silica gel preparative thin layer chromatographic and separated b chloroform/methanol (20:1), to obtain 87 mg of the title compound in a colorless amorphous form.

IR (KBr) cm$^{-1}$: 1610, 1510, 1320, 1150, 1125;

$^1$H-NMR (CDCl$_3$, δ ppm): 1.4–1.7 (2H, m), 1.8–2.0 (2H, m), 2.1–2.4 (4H, m), 2.3–2.6 (1H, m), 2.7 (1H, dd, J=12.7, 4.8 Hz), 2.8 (1H, dd, J=14.6, 4.7 Hz), 2.95 (1H, dd, J=12, 2.5 Hz), 2.99 (3H, s), 3.7 (1H, m), 3.9 (1H, m), 6.15 (2H, d, J=8.3 Hz), 6.5 (2H, d, J=8.3 Hz), 7.6 (1H, t, J=7.6 Hz), 8.0 (1H, d, J=6.1 Hz), 8.15 (1H, d, J=8.3 Hz), 8.33 (1H, dd, J=7.3, 1.0 Hz), 8.4 (1H, d, J=6.1 Hz), 9.24 (1H, s).

EXAMPLE 101

N-[1-(p-Hydroxybenzyl)-2-(4-hydroxypiperidino)ethyl]-N-methyl-5-isoquinolinesulfonamide 100 mg of the amorphous compound obtained by Example 100 was dissolved in 5 ml of a mixture of ethyl acetate/methanol (1:1), to the solution was added an excess amount of diazomethane in ether, and the reaction mixture was allowed to stand overnight at a room temperature. The solvent in the reaction mixture was evaporated off under a reduced pressure, and resulting residue was subjected to a silica gel preparative thin layer chromatography and separated by chloroform/methanol (20:1) to obtain 80.4 mg of the title compound in colorless amorphous form.

IR (KBr) cm$^{-1}$: 1510, 1320, 1240, 1150, 1120, 1030;

$^1$H-NMR (CDCl$_3$, δ ppm): 1.3–1.5 (2H, m), 1.7–2.0 (4H, m), 2.0–2.3 (2H, m), 2.35 (1H, dd, J=13.0, 7.1 Hz), 2.55 (1H, dd, J=10.0, 6.9 Hz), 2.62 (1H, dd, J=10.3, 7.3 Hz), 2.89 (1H, dd, J=14.8, 6.3 Hz), 2.6–2 75 (1H, m), 2.93 (3H, s), 3.6 (1H, m), 4.12 (1H, m), 3.73 (3H, s), 6.5 (2H, d, J=8.7 Hz), 6.84 (1H, d, J=8.7 Hz), 7.56 (1H, t, J=8.0 Hz), 8.1 (1H, d, J=8.3 Hz), 8.2 (1H, d, J=6.1 Hz), 8.3 (1H, d, J=7.3 Hz), 8.55 (1H, d, J=6.1 Hz), 9.24 (1H, s).

EXAMPLE 102

N-1-(p-Acetoxybenzyl)-2-(4-acetoxypiperidino)ethyl-N-methvl-5-isocuinolinesulfonamide 230 mg of the amorphous compound obtained in Example 100 was dissolved in 2 ml of pyridine, to the solution was added 1 ml of acetic anhydride, and the reaction mixture was allowed to stand overnight at a room temperature. To the mixture was added 20 ml of ice water, and the mixture was stirred for one hour and extracted twice with 20 ml of ethyl acetate. The extract was washed with saturated sodium chloride aqueous solution, dried over magnesium sulfate and evaporated to remove the solvent under a reduced pressure. Resulting residue was applied to a silica gel column and eluted with chloroform/methanol (100:1) to obtain 234.3 mg of the title compound in a colorless amorphous form.

IR (KBr) cm$^{-1}$: 1760, 1730, 1360, 1320, 1240, 1215, 1200, 1030;

$^1$H-NMR (CDCl$_3$, δ ppm): 1.58 (3H, s), 2.03 (3H, s), 2.30 (3H, s), 2.91 (3H, s), 1.4–1.8 (4H, m), 2.2–2.9 (4H, m), 4.2 (1H, m), 4.7 (1H, m), 6.77 (2H, d, J=6.6 Hz), 6.8 (2H, d, J=6.6 Hz), 7.5 (1H, t, J=8.0 Hz), 8.1 (1H, d, J=8.1 Hz), 8.2 (1H, d, J=7.4 Hz), 8.29 (1H, d, J=6.1 Hz), 8.57 (1H, d, J=6.1 Hz), 9.27 (1H, s).

EXAMPLE 103

The same procedure as described in Example 84 was repeated except that N-{2-(tert-butoxycarbonylamino)-3-[p-(2-methoxyethoxymethoxy)phenyl]propyl)-4-acetoxypiperidine synthesized in a similar manner was used in place of N-{2-(tert-butoxycarbonylamino)-3-[p-(2-methoxyethoxymethoxy)phenyl]propyl}-4-(p-methylbenzyloxy)piperidine, to obtain N-{2-[4-acetoxypiperidino]-1-[p-(5-isoquinolinesulfonyloxy)benyl]ethyl}-5-isoquinolinesulfonamide in a colorless amorphous form.

$^1$H-NMR (CDCl$_3$, δ ppm): 0.8–1.05 (1H, m), 1.2–1.55 (3H, m), 1.6–2.15 (5H, m), 1.99 (3H, s), 2.15–2.33 (1H, m), 2.73 (1H, dd, J=13.13, 6.85 Hz), 2.89 (1H, dd, J=13.13, 4.57 Hz), 3.22 (1H, m), 4.51 (1H, m), 5.43 (1H, br), 6.70 (2H, d, J=8.57 Hz), 6.91 (1H, d, J=8.57 Hz), 7.66 (1H, t, J=7.42 Hz), 7.68 (1H, d, J=7.42 Hz), 8.20 (1H, d, J=7.42 Hz), 8.30 (2H, d, J=7.42 Hz), 7.39 (1H, dd, J=7.42, 1.0 Hz), 8.42 (1H, d, J=6.28 Hz), 8.53 (1H, d, J=6.29 Hz), 8.70 (1H, d, J=6.28 Hz), 8.81 (1H, d, J=6.28 Hz), 9.34 (1H, s), 9.43 (1H, s).

EXAMPLE 104

N-{2-[4-Hydroxypiperidino-1-p-(5-isoquinolinesulfonyloxy)benzyl]ethyl}-5-isoquinolinesulfonamide 1.5 g of the product obtained in the Example 103 was dissolved in 8 ml of methanol, to the solution was added 8 ml of 1N sodium hydroxide aqueous solution, and the mixture was stirred for two hours, and after adding water, extracted twice with 100 ml of chloroform. The extract was washed with a saturated sodium chloride aqueous solution, dried over magnesium sulfate and evaporated to remove the solvent under a reduced pressure. The Resulting residue was applied to a silica gel column an eluted with chloroform/methanol (30:1), to obtain 800 mg of the title compound in a colorless amorphous form.

$^1$H-NMR (CDCl$_3$, δ ppm): 0.6–0.9 (1H, m), 1.05–1.3 (1H, m), 1.3–1.5 (2H, m), 1.5–1.9 (3H, m), 1.9–2.2 (2H, m), 2.2–2.4 (1H, m), 2.72 (1H, dd, J=13.70, 6.85 Hz), 2.89 (1H, dd, J=1.82, 4.57 Hz), 3.19 (1H, m), 3.46 (1H, m), 6.72 (2H, d, J=8.57 Hz), 6.72 (2H, d, J=8.57 Hz), 7.66 (1H, t, J=7.42 Hz), 7.69 (1H, t, J=7.42 Hz), 8.21 (1H, d, J=7.99 Hz), 8.29 (2H, d, J=7.42 Hz), 8.41 (1H, d, J=7.99 Hz), 8.44 (1H, d, J=6.28 Hz), 8.53 (1H, d, J=6.28 Hz), 8.69 (1H, d, J=6.28 Hz), 8.81 (1H, d, J=6.28 Hz), 9.35 (1H, s), 9.42 (1H, s).

EXAMPLE 105

N-3,4-Dichlorobenzyl-N-[1-(p-hydroxybenzyl)-2-(4-hydroxypiperidino)ethyl]-5-isoquinolinesulfonamide 400 mg of the amorphous compound obtained in Example 104 was dissolved in 5 ml of dimethylformamide, to the solution were added 130 mg of 3,4-dichlorobenzyl chloride and 28 mg of 60% sodium hydride with stirring under ice cooling, and the mixture was al.owed to warm to a room temperature and stirred for 18 hours. After adding saturated sodium chloride aqueous solution, the reaction mixture was extracted twice with 100 ml of chloroform, and the extract was washed with saturated sodium chloride aqueous solution, dried over magnesium sulfate and evaporated to remove the solvent under a reduced pressure. The resulting residue was applied to a silica gel column and eluted with chloroform/methanol (30:1), to obtain 228 mg of N-(3,4-dichlorobenzyl)-N-{2-(4-hydroxypiperidino)-1-[P-(5-isoquinolinesulfonyloxy)benzyl]ethyl}-5-isoquinolinesulfonamide.

228 mg of the above compound was dissolved in 1.5 ml of methanol, to the solution was added 1 ml of 1N sodium hydroxide aqueous solution, and the mixture was refluxed for 3 hours and then cooled, and after dilution with water, acidified with citric acid and then alkalized with sodium bicarbonate, and extracted twice with 100 ml of chloroform. The extract was dried over magnesium sulfate and evaporated to remove the solvent, and resulting residue was applied to a silica gel column and eluted with chloroform/methanol (20:1) to obtain 162 mg of the title compound in a colorless amorphous form.

$^1$H-NMR (CDCl$_3$, δ ppm): 1.2–1.6 (2H, m), 1.6–2.0 (3H, m), 2.0–2.2 (2H, m), 2.4–2.9 (5H, m), 3.5 (1H, m), 4.21 (1H, q, J=6.08 Hz), 4.44 (1H, d, J=16.36 Hz), 4.66 (1H, d, J=16.11 Hz), 6.51 (2H, d, J=8.55 Hz), 6.79 (2H, d, J=8.55 Hz), 7.17 (1H, dd, J=8.30, 1.96 Hz), 7.25 (1H, d, J=8.06 Hz), 7.33 (1H, d, J=1.96 Hz), 7.57 (1H, t, J=7.57 Hz), 8.12 (1H, d, J=8.3 Hz), 8.25 (1H, d, J=6.10 Hz), 8.33 (1H, dd, J=7.32, 0.98 Hz), 8.50 (1H, d, J=5.86 Hz), 9.21 (1H, s).

EXAMPLE 106

N-[1-(p-Hydroxybenzyl)-2-(4-hydroxypiperidino)ethyl]-N-p-methylbenzyl-5-isoquinolinesufonamide The same procedure as described in Example 105 was repeated except that 4-methylbenzyl chloride was used in place of 3,4-dichlorobenzyl chloride was used to obtain the title compound in colorless amorphous form.

$^1$H-NMR (CDCl$_3$+CD$_3$OD, δ ppm): 1.2–1.55 (2H, m), 1.55–2.15 (5H, m), 2.33 (3H, s), 2.33–2.85 (5H, m), 3.5 (1H, m), 3.98 (1H, q, J=6.59 Hz), 4.52 (1H, d, J=15.63 Hz), 4.78 (1H, d, J=15.62 Hz), 6.36 (2H, d, J=8.05 Hz), 6.66 (2H, d, J=8.06 Hz), 7.08 (2H, d, J=7.56 Hz), 7.29 (2H, d, J=7.57 Hz), 7.60 (1H, t, J=7.57 Hz), 8.12 (1H, d, J=8.06 Hz), 8.28 (1H, d, J=6.10 Hz), 8.39 (1H, d, J=7.32 Hz), 8.48 (1H, d, J=6.35 Hz), 9.20 (1H, s).

EXAMPLE 107

N-{2-(4-Hydroxypiperidino)-1-[p-(5-isoquinolinesulfonyloxy)benzyl]ethyl)-N-methyl-5-isoquinolinesulfonamide The amorphous compound obtained in Example 103 was treated with methyl iodide according to the procedure in Example 89 and the intermediate product was subjected to alkaline hydrolysis according to the procedure in Example 104, to obtain the same product as in Example 99.

$^1$H-NMR (CDCl$_3$, δ ppm): 1.20–1.42 (2H, m), 1.68 (2H, m), 2.01 (2H, m), 2.22 (1H, dd, J=7.3, 13.2 Hz), 2.40 (1H, dd, J=7.3, 13.2 Hz), 2.43–2.60 (2H, m), 2,66 (1H, dd, J=6.8, 13.7 Hz), 2.84 (3H, S), 2.85 (1H, dd, J=6.4, 13.7 Hz), 3,58 (1H, m), 4.10 (1H, m), 6.61 (2H, d, J=8.8 Hz), 6.88 (2H, d, J=8.8 Hz), 7.59 (1H, t, J=7.8 Hz), 7.63 (1H, t, J=7.8 Hz), 8.12 (1H, d, J=8.3 Hz), 8.23–8.35 (4H, m), 8.55 (1H, d, J=6.4 Hz), 8.58 (1H, d, J=6.4 Hz), 8.83 (1H, d, J=5.9 Hz), 9.29 (1H, s), 9.42 (1H, s).

REFERENCE EXAMPLE 24

1-(N-Benzyloxycarbonyltyrosyl)-4-phenylpiperazine 12.3 g of N-benzyloxycarbonyltyrosine and 6.6 g of N-phenylpiperazine were dissolved in 150 ml of methylene chloride, and to the solution was added 8.4 g of DCC, and the mixture was stirred at a room temperature for 5 hours. Precipitated insoluble matter was filtered off and the filtrate was concentrated under a reduced pressure, and resulting residue was applied to a silica gel column and eluted with hexane/ethyl acetate (1:1 to 1:2) to obtain 10.5 g of the title compound in a colorless amorphous form.

$^1$H-NMR (CDCl$_3$, δ ppm): 2.63 (1H, m), 2.88–3.24 (6H, m), 3.48 (1H, m), 3.68 (2H, m), 4.88 (1H, m), 5.07 (1H, d, J=12.7 Hz), 5.11 (1H, d, J=12.7 Hz), 5.34 (1H, br), 5.67 (1H, d, J=8.8 Hz), 6.71 (2H, d, J=8.3 Hz), 6.84 (2H, d, J=8.3 Hz), 6.90 (1H, t, J=7.3 Hz), 7.04 (2H, d, J=8.3 Hz), 7.26 (2H, t, J=7.3 Hz), 7.34 (5H, s).

EXAMPLE 108

1-[N,O-Bis(5-isoquinolinesulfonyl)tyrosyl]4-phenylpiperazine 4.59 g of the amorphous compound obtained in Reference Example 24 was dissolved in 50 ml of methanol, to the solution was added 3 g of 5% palladium on carbon, and the mixture was stirred for 17 hours at a room temperature in a hydrogen atmosphere. The resulting insoluble matter was filtered off, and the filtrate was concentrated under a reduced pressure to obtain a residue, which was then suspended in 50 ml of chloroform. To the suspension were sequentially added 5.7 g of 5-isoquinolinesulfonyl chloride.HCl and 10 ml of triethylamine with ice cooling, and then mixture was stirred for 3 hours at a room temperature. After adding 200 ml of water, the mixture was extracted twice with 100 ml of chloroform, the extract was dried over magnesium sulfate and concentrated under a reduced pressure. Resulting residue was applied to a silica gel column and eluted with chloroform/methanol (80:1 to 30:1), to obtain 5.46 g of the title compound in a yellow amorphous form.

$^1$H-NMR (CDCl$_3$, δ ppm): 2.50-2.90 (7H, m), 2.92-3.17 (2H, m), 3.24 (1H, m), 4.32 (1H, m), 5.99 (1H, br), 6.65 (2H, d, J=8.8 Hz), 6.80 (2H, d, J=7.8 Hz), 6.89 (2H, d, J=8.8 Hz), 6.94 (1H, t, J=7.3 Hz), 7.29 (2H, dd, J=7.3, 8.3 Hz), 7.51 (1H, t, J=7.8 Hz), 7.59 (1H, dd, J=7.3, 8.3 Hz), 8.09-8.31 (5H, m), 8.50 (1H, d, J=6.4 Hz), 8.69 (1H, d, J=5.9 Hz), 8.81 (1H, d, J=5.9 Hz), 9.28 (1H, s), 9.39 (1H, s).

EXAMPLE 109

1-[N,O-Bis(5-isoquinolinesulfonyl)N-methyltyrosyl]-4-phenylpiperazine 2.27 g of the amorphous compound obtained in Example 108 was dissolved in 30 ml of dimethylformamide, to the solution were sequentially added 160 mg of 60% sodium hydride and 0.3 ml of methyl iodide with ice cooling, and the mixture was stirred for 90 minutes with ice cooling. After adding 80 ml of water, the reaction mixture was extracted with 100 ml of ethyl acetate, and the extract was washed with 80 ml of saturated sodium chloride aqueous solution, dried over magnesium sulfate and concentrated under a reduced pressure. The resulting residue was applied to a silica gel column and eluted with chloroform/methanol (60:1), to obtain 1.8 g of the title compound in a yellow amorphous form.

IR (KBr) cm$^{-1}$: 1668, 1475, 1360, 1130;

$^1$H-NMR (CDCl$_3$, δ ppm): 2.45 (1H, dd, J=4.6, 13.1 Hz), 2.63 (1H, m), 2.82-3.07 (4H, m), 3.03 (3H, s), 3.13-3.29 (2H, m), 3.43-3.65 (4H, m), 5.11 (1H, dd, J=4.6, 10.3 Hz), 6.76 (2H, d, J=8.6 Hz), 6.85 (2H, d, J=8.0 Hz), 6.88 (1H, t, J=8.6 Hz), 7.29 (2H, dd, J=8.0, 8.6 Hz), 7.49 (1H, dd, J=8.3, 7.3 Hz), 7.70 (1H, dd, J=8.3, 7.3 Hz), 8.16 (1H, dd, J=1.0, 7.3 Hz), 8.21 (2H, d, J=8.3 Hz), 8.30 (1H, dd, J=1.0, 7.3 Hz), 8.41 (1H, d, J=6.4 Hz), 8.51 (1H, d, J=6.4 Hz), 8.68 (1H, d, J=6.4 Hz), 8.80 (1H, d, J=6.4 Hz), 9.36 (1H, s), 9.40 (1H, s).

EXAMPLE 110

1-[N-(5-Isoquinolinesulfonyl)-N-methyltyrosyl]-4-phenylpiperazine 1.15 g of the amorphous compound obtained in Example 109 was suspended in 20 ml of methanol, to the solution was added 2 ml of 2N sodium hydroxide aqueous solution, and the mixture was refluxed for 90 minutes. After adding 100 ml of water, the reaction mixture was extracted twice with 50 ml of chloroform, and the extract was dried over magnesium sulfate and concentrated under a reduced pressure. Resulting residue was applied to a silica gel column and eluted with chloroform/methanol (80:1 to 50:1), to obtain 820 mg of the title compound in a colorless amorphous form.

IR (KBr) cm$^{-1}$: 1638, 1590, 1440, 1326 1150;

$^1$H-NMR (CDCl$_3$, δ ppm): 2.56 (1H, dd, J=5.4, 12.7 Hz), 2.61 (1H, m), 2.90-3.22 (3H, m), 3.15 (3H, s), 3.43 (1H, m), 3.51-3.71 (4H, m), 5.13 (1H, dd, J=5.9, 9.8 Hz), 5.53 (1H, br), 6.62 (2H, d, J=8.8 Hz), 6.84 (2H, d, J=7.8 Hz), 6.89 (1H, t, J=7.3 Hz), 6.90 (2H, d, J=8.3 Hz), 7.26 (2H, t, J=7.8 Hz), 7.70 (1H, dd, J=7.3, 8.3 Hz), 8.21 (1H, d, J=8.3 Hz), 8.32 (1H, dd, J=1.0, 7.3 Hz), 8.38 (1H, d, J=5.9 Hz), 8.66 (1H, d, J=5.9 Hz), 9.33 (1H, br).

EXAMPLE 111

The product of Example 108 was subjected to alkaline hydrolysis according to the procedure described in Example 110 to obtain 1-[N-(5-isoquinolinesulfonyl)-tyrosyl]-4-phenylpiperazine in a yellow amorphous form.

IR (KBr) cm$^{-1}$: 1630, 1590, 1510, 1440, 1325, 1220, 1150, 1128;

$^1$H-NMR (CDCl$_3$—CD$_3$OD, δ ppm): 2.60 (1H, m), 2.72-2.77 (2H, m), 2.88 (4H, m), 3.10-3.43 (3H, m), 4.37 (1H, t, J=7.8 Hz), 6.40 (2H, d, J=8.3 Hz), 6.72 (2H, d, J=8.3 Hz), 6.83 (2H, d, J=7.8 Hz), 6.91 (1H, t, J=7.3 Hz), 7.27 (2H, dd, J=7.8, 8.3 Hz), 7.63 (1H, dd, J=7.3, 8.3 Hz), 8.17 (1H, d, J=8.3 Hz), 8.30 (1H, dd, J=1.0, 7.3 Hz), 8.38 (1H, d, J=6.4 Hz), 8.60 (1H, d, J=6.4 Hz), 9.24 (1H, s).

REFERENCE EXAMPLE 25

N-Benzyloxycarbonylhomopiperazine

To 230 ml of dimethylformamide were added 25 g of homopiperazine and 5.4 g of sodium bicarbonate and then 25 ml of water followed by dropwise addition of 10 g of benzyloxycarbonyl chloride with stirring under ice cooling, and the mixture was stirred at a room temperature overnight. After evaporating off dimethylformamide under a reduced pressure, the reaction mixture was extracted three times with 100 ml of chloroform, and the extract was dried over magnesium sulfate and evaporated to remove the solvent under a reduced pressure. The resulting residue was applied to a silica gel column and eluted with chloroform/methanol (9:1), to obtain 9 g of the title compound as a light yellow liquor liquid.

IR (KBr) cm$^{-1}$: 1695, 1420;

$^1$H-NMR (CDCl$_3$, δ ppm): 1.8 (2H, m), 2.8-3.0 (4H, m), 3.4-3.65 (4H, m), 5.15 (2H, s), 7.4 (5H, s).

REFERENCE EXAMPLE 26

1-N-(tert-Butoxycarbonyl)-N-methyl]tyrosyl-4-benzyloxycarbonylhomopiperazine 1.0 g of N-tert-butoxycarbonyl-N-methyltyrosine was dissolved in 70 ml of methylene chloride, and after adding 793 mg of N-benzyloxycarbonylhomopiperazine and adding at a stroke 837 mg of DCC at a room temperature with stirring, the mixture was stirred at a room temperature overnight. The solvent was evaporated off under a reduced pressure, and to the resulting residue was added benzene. Insoluble matter was filtered off, and the filtrate was applied to a silica gel column and eluted with hexane/ethyl acetate (6:4 to 6:5) to obtain 1.06 g of the title compound as a light yellowish oil.

Acetylated derivative of this compound has the following properties.

IR (KBr) cm$^{-1}$: 1760, 1695, 1215, 1200;

$^1$H-NMR (CDCl$_3$, δ ppm): 1.3, 1.4 (Total 9H, each s), 1.85 (1H, m), 2.3 (3H, s), 2.82 (3H, brs), 2.7-2.9 (2H, m), 3.0-3.8 (8H, m), 5.15 (2H, brs), 7.0 (2H, d, J=8.3 Hz), 7.35 (5H, brs).

REFERENCE EXAMPLE 27

1-{3'-(p-Acetoxyphenyl)-2'[N-(tert-butoxycarbonyl)-N-methylamino]propyl}-4-benzyloxycarbonylhomopiperazine 3.56 g of the product obtained in Reference Example 26 was dissolved in 60 ml of absolute tetrahydrofuran, to the solution was added 20 ml of 1.0M borane in tetrahydrofuran with stirring under ice cooling, and the mixture was stirred overnight at a room temperature. The solvent was evaporated off under a reduced pressure, and resulting residue was dissolved in 10 ml of pyridine. To the solution was added 5 ml of acetic anhydride, and the mixture was allowed to stand overnight at a room temperature. After an addition of ice, the mixture was stirred for 30 minutes and extracted twice with 60 ml of chloroform. The extract was washed with saturated sodium chloride aqueous solution, dried over magnesium sulfate and evaporated to remove the solvent under a reduced pressure. Resulting residue was applied to a silica gel column and eluted with chloroform/methanol (100:1), to obtain 2.0 g of the title compound in a light yellow amorphous form.

IR (KBr) cm$^{-1}$: 1760, 1690, 1215, 1200;

$^1$H-NMR (CDCl$_3$, δ ppm): 1.25, 1.27 (Total 9H, each s), 1.6–1.9 (2H, m), 2.27 (3H, s), 2.4–2.8 (11H, m), 8.6 Hz), 7.1 (2H, d, J=8.6 Hz), 7.25, 7.33 (Total 5H, each s).

EXAMPLE 112

N-[1-(p-Acetoxybenzyl)-2-(4-benzyloxycarbonyl-homopiperazinyl)ethyl]-N-methyl-5-isoquinolinesulfonamide 1 g of the amorphous compound obtained in Reference Example 27 was dissolved in 28 ml of methylene chloride, to the solution were added 2 ml of 2,6-lutidine, and then 2 ml of tert-butyldimethylsilyltrifluoromethane sulfonate with stirring at a room temperature, and the reaction mixture was stirred for 16 hours. After an addition of ice, the reaction mixture was extracted twice with 70 ml of ethyl acetate, and the extract was washed with saturated sodium chloride aqueous solution, dried over magnesium sulfate and evaporated to remove the solvent under a reduced pressure. To resulting residue were added 20 ml of tetrahydrofuran and 4.28 ml of 1.0M tetrabutylammonium fluoride in tetrahydrofuran with stirring, and the reaction mixture was stirred at a room temperature for 40 minutes. After adding ice, the reaction mixture was extracted twice with 70 ml of chloroform, and the extract was washed with saturated sodium chloride aqueous solution, dried over magnesium sulfate and evaporated to remove the solvent under a reduced pressure. Resulting residue was applied to a silica gel column and eluted with chloroform/methanol (95:5 to 90:10), to obtain 723 mg of 1-[3'-(p-acetoxyphenyl)-2'-(N-methylamino)propyl]-4-benzyloxycarbonylhomopiperazine.

$^1$H-NMR (CDCl$_3$, δ ppm): 1.8 (2H, m), 2.3 (3H, s), 2.48 (3H, d, J=2.0 Hz), 2.35–3.8 (9H, m), 3.4–3.6 (4H, m), 5.1 (2H, s), 7.0 (2H, d, J=8.5 Hz), 7.2 (2H, brd, J=8.5 Hz), 7.35 (5H, s). 723 mg of the above compound was dissolved in 25 ml of dimethylformamide, and to the mixture was added 401 mg of triethylamine and then 564 mg of 5-isoquinolinesulfonyl chloride.HCl with stirring under ice cooling, and the mixture was stirred overnight at a room temperature. After adding water, the reaction mixture was extracted twice with 70 ml of ethyl acetate, and the extract was washed with saturated sodium chloride aqueous solution, dried over magnesium sulfate and evaporated to remove the solvent under a reduced pressure. Resulting residue was applied to a silica gel column and eluted with chloroform/methanol (100:1) to obtain 796 mg of the title compound in a light yellow amorphous form.

$^1$H-NMR (CDCl$_3$, δ ppm): 1.7 (2H, m), 2.3 (3H, s), 2.7–2.8 (8H, m), 2.90, 2.91 (Total 3H, each s), 3.3–3.55 (4H, m), 4.1 (1H, m), 5.1 (2H, s), 6.7 (2H, d, J=8.3 Hz), 6.9 (2H, d, J=8.3 Hz), 7.34, 7.36 (Total 5H, each s), 7.53, 7.55 (Total 1H, each t, J=7.6 Hz), 8.1 (1H, d, J=6.1 Hz), 8.18 (2H, d, J=6.5 Hz), 8.55 (1H, d, J=6.1 Hz), 9.25 (1H, s).

EXAMPLE 113

N-[2-(4-Benzyloxycarbonylhomopiperazinyl)-1-(p-hydroxybenzyl)ethyl-N-methyl-5-isoquinolinesulfonamide 400 mg of the amorphous compound obtained in Example 112 was dissolved in 10 ml of methanol, to the solution was added 2 ml of 10% sodium hydroxide and the mixture was stirred for 10 minutes. The reaction mixture was acidified with citric acid aqueous solution and then alkalized with saturated sodium bicarbonate aqueous solution, and extracted twice with 50 ml of chloroform. The extract was dried over magnesium sulfate and evaporated to remove the solvent under a reduced pressure. The resulting residue was applied to a silica gel column and eluted with chloroform/methanol (100:2) to obtain 339 mg of the title compound in a colorless amorphous form.

IR (KBr) cm$^{-1}$: 1700, 1330, 1210, 1150, 1120;

$^1$H-NMR (CDCl$_3$, δ ppm): 1.8 (2H, m), 1.37, 1.38 (Total 1H, each dd, J=10.0, 13.8 Hz), 1.55 (1H, dd, J=13.8, 9.8 Hz), 2.75 (4H, m), 2.7 - 3.0 (2H, m), 3.0 (3H, s), 3.5 (4H, m), 3.8 (1H, m), 5.13 (2H, s), 6.17 (2H, d, J=8.0 Hz), 6.50, 6.51 (Total 2H, each d, J=8.0 Hz), 7.49, 7.50 (total 1H, each t, J=7.7 Hz), 8.03 (1H, d, J=6.1 Hz) 8.13 (1H, d, J=7.8 Hz), 8.23 (1H, d, J=7.1 Hz), 6.43 (1H, d, J=6.1 Hz), 9.24 (1H, s), 7 35 (5H, s).

EXAMPLE 114

220 mg of the amorphous compound obtained in Example 113 was dissolved in 2 ml of acetic acid, to the solution was added 6 ml of 25% hydrogen bromide in acetic acid, and the mixture was stirred at a room temperature for 20 minutes. 40 ml of dry ether was added to the reaction mixture to form a white precipitate, which was then alkalized with saturated sodium bicarbonate aqueous solution and extracted twice with 20. ml of chloroform/isopropanol (5:1). The extract was dried over magnesium sulfate and evaporated to remove the solvent under a reduced pressure, and resulting residue was applied to a silica gel column and eluted with chloroform/methanol (20:80 to 30:70) to obtain 67 mg of N-[1-(p-hydroxy) benzyl-2-homopiperazinylethyl]-N-methyl-5-isoquinolinesulfonamide as a light yellow oil.

$^1$H-NMR (CDCl$_3$, δ ppm): 1.75 (2H, m), 2.3–3.0 (12H, m), 2.93 (3H, s), 3.96 (1H, m), 6.3 (2H, d, J=8.3 Hz), 6.6 (2H, d, J=8.3 Hz), 7.6 (1H, t, J=8.1 Hz), 8.1 (1H, d, J=5.3 Hz), 8.12 (1H, d, J=8.3 Hz), 8.2 (1H, d, J=7.4 Hz), 8.45 (1H, d, J=6.1 Hz), 9.26 (1H, s).

REFERENCE EXAMPLE 28

1-Benzyloxycarbonyl-4-(N-tert-butoxycarbonyl-tyrosyl)homopiperazine 15.29 g of N-tert-butoxycarbonyltyrosine and 12.73 g of N-benzyloxycarbonylhomopiperazine were dissolved in 280 ml of tetrahydrofuran, to the solution were added 8.09 g of 1-hydroxybenzotriazole hydrate and 11.77 g of DCC at a room temperature with stirring, and the reaction mixture was stirred for 16 hours. The reaction mixture was evaporated to remove the solvent under a reduced pressure, to the residue was added benzene, and insoluble matter was filtered by suction and washed with benzene. The benzene layers were combined and evaporated off under a reduced pressure. The resulting residue was applied to a silica gel column and eluted with chloroform/methanol (100:1), to obtain 26.42 g of the title compound in colorless amorphous form.

$^1$H-NMR (CDCl$_3$, δ ppm): 1.41 (9H, s), 1.5.-2.0 (2H, m), 2.75-3.05 (2H, m), 3.05-3.7 (8H, m), 4.67 (1H, m), 5.10, 5.12 (Total 2H, each s), 5.25 (1H, m), 6.0 (1H, br), 6.68, 6.72 (Tot=1 2H, each d, J =8.57 Hz), 7.02, 7.03 (Total 2H, each d, J=8.57 Hz), 7.32, 7.34 (Total 5H, each s).

EXAMPLE 115

N-(2-(4-Benzyloxycarbonyl)homopiperazinyl-1-p-(5-isoquinolinesulfonyloxy)benzyl]ethyl)-5-isoquinolinesulfonamide 3.0 g of the amorphous compound obtained in Reference Example 28 was dissolved in 20 ml of tetrahydrofuran, to the solution was added 24 ml of 1M borane in tetrahydrofuran, and the mixture was stirred under a nitrogen atmosphere at a room temperature for 15 hours. After the reaction was completed, the solvent was evaporated off under a reduced pressure and to the resulting residue was added 3 g of potassium bicarbonate. The mixture was stirred for 30 minutes at a room temperature and extracted twice with 200 ml of chloroform. The extract was dried over magnesium sulfate and concentrated under a reduced pressure, to obtain 1-benzyloxycarbonyl-4-[2-(tert-butoxycarbonyl-amino)-3-(p-hydroxyphenyl)propyl]homopiperazine.

This compound was dissolved in 6 ml of ethyl acetate, to the solution was added 30 ml of 4N hydrogen chloride in ethyl acetate, and the mixture was stirred at a room temperature for 30 minutes. The reaction mixture was evaporated under a reduced pressure and the resulting residue was alkalized with a saturated sodium bicarbonate aqueous solution and extracted twice with 200 ml of chloroform. The extract was dried over magnesium sulfate and evaporated to remove the solvent under a reduced pressure, to obtain 2.43 g of 1-[2-amino-3-(p-hydroxyphenyl)propyl]-4-benzyloxy carbonyl-homopiperazine.

This intermediate was dissolved in 65 ml of tetrahydrofuran, to the solution were added 4.03 g of 5-isoquinolinesulfonyl chloride.HCl and 8.9 ml of triethylamine at a room temperature with stirring, and the mixture was stirred for 16 hours. After an addition of a saturated sodium bicarbonate solution, the mixture was extracted twice with 300 ml of chloroform, and the extract was dried over magnesium sulfate and evaporated to remove the solvent under a reduced pressure. Resulting residue was applied to a silica gel column and eluted with chloroform/methanol (20:1), to obtain 2.26 g of the title compound in a colorless amorphous form.

$^1$H-NMR (CDCl$_3$, δ ppm): 1.43 (2H, m), 2.2 (6H, m), 73 (2H, m), 2.9-3.4 (5H, m), 5.07 (2H, s), 5.34 (1H, br), 6.62 (2H, d, J=8.57 Hz), 6.84, 6.86 (Total 2H, each d, J=8.57 Hz), 7.32, 7.33 (Total 5H, each s), 7.63 (1H, t, J=8.28 Hz), 7.67 (1H, m), 8.16 (1H, t, J=8.28 Hz), 7.67 (1H, m), 8.16 (1H, t, J=7.42 Hz), 8.22 - 8.45 (4H, m), 8.53 (1H, d, J=6.28 Hz), 8.66 (1H, dd, J=6.57, 1.0 Hz), 8.82 (1H, d, J=6.28 Hz), 9.31, 9.34 (Total 1H, each s), 9.42 (1H, s).

EXAMPLE 116

1.0 g of the product obtained in Example 115 was dissolved in 5 ml of methanol and 5 ml of tetrahydrofuran, to the solution was added 10 ml of 1N sodium hydroxide, and the mixture was refluxed for 2 hours and then cooled. The reaction mixture was acidified with citric acid and then alkalized with sodium bicarbonate, the produced insoluble matter, was then dissolved in methanol. The solution was extracted twice with 100 ml of chloroform, and the extract was dried over magnesium sulfate and concentrated under a reduced pressure. Resulting residue was applied to a silica gel column and eluted with chloroform/methanol (20:1), to obtain 458 mg of N-{2-(4-benzyloxycarbonyl-homopiperazinyl)-1-(p-hydroxybenzyl)ethyl}-5-isoquinolinesulfonamide in a colorless amorphous form.

huH-NMR (CDCl$_3$, δ ppm): 1.72 (2H, brs), 2.3-2.9 (8H, m), 3.1-3.7 (5H, m), 5.12 (2H, s), 6.27 (2H, d, J=7.32 Hz), 6.57 (2H, d, J=7.32 Hz), 7.6 (1H, br), 7.33 (6H, s), 7.63 (1H, t, J=7.57 Hz), 8.17 (1H, d, J=8.3 Hz), 8.33 (2H, d, J=7.08 Hz), 8.52 (1H, brs), 9.28 (1H, brs).

EXAMPLE 117

N-{1-[p-(5-Isoquinolinesulfonyloxy)benzyl]-2-homopiperazinylethyl}-5-isoquinolinesulfonamide To 1.0 g of the product obtained in Example 115, was added 6 ml of 30% hydrogen bromide in acetic acid at a room temperature with stirring, and the mixture was further stirred for 24 hours. After an addtion of 100 ml of ether the reaction mixture was stirred for 30 minutes to form a salt, which was then colected by filtration, washed with ether and dried in a desiccator. The salt was dissolved in water, and the solution was alkalized with sodium bicarbonate and extracted twice with 100 ml of chloroform. The extract was dried with magnesium sulfate and evaporated to remove the solvent under a reduced pressure, to obtain 830 mg of the title compound in a colorless amorphous form.

$^1$H-NMR (CDCl$_3$, δ ppm): 1.37 (2H, m), 2.1-2.9 (12H, m), 3.22 (1H, m), 6.62 (2H, d, J=8.79 Hz), 6.87 (2H, d, J=8.54 Hz), 7.64 (1H, t, J=7.82 Hz), 7.66 (1H, t, J=7.82 Hz), 8.18 (1H, d, J=8.31 Hz), 8.23-8.36 (3H, m), 8.40 (1H, d, J=6.35 Hz), 8.53 (1H, d, J=6.1 Hz), 8.67 (1H, d, J=6.11 Hz), 8.81 (1H, d, J=6.35 Hz), 9.33 (1H, s), 9.42 (1H, s).

EXAMPLE 118

N-{1-[p-(5-Isoquinolinesulfonyloxy)benzyl-2-[4-(3-phenylpropionyl)homopiperazinyl]ethyl}-5-isoquinolinesulfonamide 420 mg of the amorphous compound obtained in Example 117 was dissolved in 6 ml of methylene chloride, to the solution were added 125 mg of 3-phenylpropionyl chloride and 100 mg of triethylamine at a room temperature with stirring, and the mixture was stirred for 17 hours. The reaction mixture was alkalized with a saturated sodium bicarbonate aqueous solution and extracted twice with 50 ml of chloroform. The extract was dried over magnesium sulfate and evaporated to remove the solvent. Resulting residue was applied to a silica gel column and eluted with chloroform/methanol (30:1) to obtain 400 mg of the title compound in colorless amorphous form.

$^1$H-NMR (CDCl$_3$, δ ppm): 1.46 (2H, m), 1.9–2.4 (6H, m), 2.4–2.6 (2H, m), 2.6–2.82 (2H, m), 2.82–2.98 (2H, m), 2.98–3.12 (1H, m), 3.12–3.33 (3H, m), 3.4 (1H, t, J=6.28 Hz), 6.61, 6.63 (Total 2H, each d, J=8.57 Hz), 6.82, 6.85 (Total 2H, each d, J =8.57 Hz), 7.1–7.35 (5H, m), 7.64 (1H, t, J=8.28 Hz), 7.66 (1H, t, J=8.28 Hz), 8.1–8.45 (5H, m), 8.52 (1H, d, J=6.28 Hz), 8.67 (1H, dd, J=6.28, 1.0 Hz), 8.82 (1H, d, J=6.28 Hz), 9.33, 9.34 (Total 1H, each s), 9.42 (1H, s).

EXAMPLE 119

N-{1-(p-Hydroxybenzyl)-2-[4-(3-phenylpropionyl)-homopiperazinyl]ethyl}-5-isoquinolinesulfonylamide 400 mg of the amorphous compound obtained in Example 118 was dissolved in 2 ml of methanol and 2 ml of tetrahydrofuran, to the solution was added 4 ml of 1N sodium hydroxide, and the mixture was refluxed for 3 hours and then cooled. The reaction mixture was acidified with citric acid and then alkalized with sodium bicarbonate to form an insoluble matter, which was then dissolved in a small amount of methanol and extracted twice with 50 ml of chloroform. The extract was dried over magnesium sulfate and evaporated to remove the solvent under a reduced pressure. Resulting residue was applied to a silica gel column and eluted with chloroform/methanol (30:1), to obtain 230 mg of the title compound in a colorless amorphous form.

$^1$H-NMR (CDCl$_3$, δ ppm): 1.64 (2H, m), 2.3–2.85 (10H, m), 2.96 (2H, t, J=8.3 Hz), 3.15–3.6 (5H, m), 6.31, 6.35 (Total 2H, each d, J=8.30 Hz), 6.57, 6.61 (Total 2H, each d, J=8.30 Hz), 7.1–7.4 (5H, m), 7.65 (1H, t, J=8.06 Hz), 8.19 (1H, d, J=8.23 Hz), 8.25–8.4 (2H, m), 8.55 (1H, d, J=6.28 Hz), 9.32 (1H, s).

REFERENCE EXAMPLE 29

1-Benzyloxycarbonyl-4-(N-tert-butoxycarbonyl-o-methyl)tyrosylhomopiperazine 5.0 g of the amorphous compound obtained in Reference Example 28 was dissolved in 25 ml of tetrahydrofuran and 25 ml of dimethylformamide, to the solution was added 0.41 g of 60% sodium hydride with stirring under ice cooling, and then the mixture was allowed to warm to a room temperature and stirred for 30 minutes. After adding 1.43 g of methyl iodide, the reaction mixture was stirred for 16 hours, and after an addition of a saturated sodium chloride aqueous solution, extracted twice with 300 ml of chloroform. The extract was dried over magnesium sulfate and evaporated to remove the solvent under a reduced pressure. Resulting residue was applied to a silica gel column and eluted with chloroform/methanol (100:1), to obtain 3.76 g of the title compound in a colorless amorphous form.

$^1$H-NMR (CDCl$_3$, δ ppm): 1.41 (9H, s), 1.65–2.0 (2H, m), 2.8–3.05 (2H, m), 3.05–3.65 (8H, m), 3.77 (3H, s), 5.68 (1H, m), 5.10 (2H, s), 5.23 (1H, m), 6.79 (2H, d, J=8.3 Hz), 7.11 (2H, d, J=8.54 Hz), 7.33 (5H, s).

REFERENCE EXAMPLE 30

1-(N-tert-Butoxycarbonyl-o-methyl)tyrosyl-4-phenyl-acetylhomopiperazine 1.02 g of the amorphous compound obtained in Reference Example 29 was dissolved in 25 ml of methanol, to the solution was added 250 mg of 5% palladium on carbon with ice cooling, and after warming the mixture to a room temperature, the catalytic reduction was carried out for 6 hours. The catalyst was filtered off and washed with methanol, and the methanol solution was evaporated to obtain 800 mg of (N-tert-butoxycarbonyl-o-methyl)tyrosylhomopiperazine.

400 mg of the compound was dissolved in 6 ml of methylene chloride, to the solution were added 195 mg of phenylacety- chloride and 190 mg of triethylamine, and the mixture was stirred at a room temperature for 24 hours. The reaction mixture was alkalized with a saturated sodium bicarbonate aqueous solution and extracted twice with 100 ml of chloroform, and the extract was dried over magnesium sulfate and evaporated to remove the solvent under a reduced pressure. Resulting residue was applied to a silica gel column and eluted with chloroform/methanol (50:1), to obtain 433 mg of the title compound in a colorless amorphous form.

$^1$H-NMR (CDCl$_3$, δ ppm): 1.41 (9H, s), 1.6–2.0 (2H, m), 2.7–3.75 (12H, m), 3.77, 3.78 (Total 3H, each s), 4.65 (1H, m), 5.13, 5.24 (Total 1H, each d, J=9.14 Hz), 6.78, 6.79 (Total 2H, each d, J=9.71 Hz), 7.08, 7.11 (Total 2H, each d, J=9.71 Hz), 7.28 (5H, m).

EXAMPLE 120

1-[N-(5-Isoquinolinesulfonyl)-o-methyltyrosyl-4-phenylacetylhomopiperazine 433 mg of the amorphous compound obtained in Reference Example 30 was dissolved in 1 ml of ethyl acetate, to the solution was added 4 ml of 4N hydrogen chloride in ethyl acetate, and after stirring for 30 minutes at a room temperature, the solvent was evaporated off under a reduced pressure. To resulting residue was added a saturated sodium bicarbonate aqueous solution, and the solution was twice extracted with ml of chloroform. The extract was dried over magnesium sulfate and concentrated under a reduced pressure. To resulting residue were added 6 ml of tetrahydrofuran, as well as 275 mg of 5-isoquinoline-sulfonyl chloride.HCl and 1.2 ml of triethylamine at a room temperature with stirring, and the mixture was further stirred for 18 hours. The reaction mixture was alkalized with a saturated sodium bicarbonate aqueous solution and extracted twice with 50 ml of chloroform, and the extract was dried over magnesium sulfate and evaporated to remove the solvent under a reduced pressure. Resulting residue was applied to a silica gel column and eluted with chloroform/methanol (30:1), to obtain 439 mg of the title compound in a colorless amorphous form.

$^1$H-NMR (CDCl$_3$, δ ppm): 1.5–1.9 (2H, m), 2.4–2.9 (3H, m), 2.9–4.0 (9H, m), 3.67, 3.68, 3.70 (Total 3H, each s), 4.18 (1H, m), 6.18 (1H, m), 6.25 - 6.5 (2H, m), 6.7 (2H, m), 7.28 (5H, m), 7.54, 7.56 (Total 1H, each t, J=7.81 Hz), 8.09 (1H, t, J=7.81 Hz), 8.15–8.3 (2H, m), 8.63 (1H, m), 9.22, 9.26 (Total 1H, each s).

EXAMPLE 121

1[-N,O-Dimethyl-N-(5-isoquinolinesulfonyl)tyrosyl-4-phenylacetylhomopiperazine 439 mg of the amorphous compound obtained in Example 120 was dissolved in 2.5 ml of tetrahydrofuran and 2.5 ml of dimethylformamide, to the solution was added 30 mg of 60% sodium hydride with ice cooling, and then the mixture was warmed to a room temperature and stirred for 30 minutes. After an addition of 110 mg of methyl iodide, the reaction mixture was further stirred for 16 hours. After an addition of a saturated sodium chloride aqueous solution, the reaction mixture was extracted twice with 50 ml of chloroform, and the extract was dried over magnesium sulfate and evaporated to remove the solvent under a reduced pressure. Resulting residue was applied to a silica gel column and eluted with chloroform/methanol (30:1), to obtain 348 mg of the title compound in a colorless amorphous form.

$^1$H-NMR (CDCl$_3$, δ ppm): 1.5-2.0 (2H, m), 2.2-4.0 (12H, m}, 3.03, 3.07, 3.08, 3.19 (Total 3H, each s), 3.71, 3.73, 3.75 (Total 3H, each s), 4.9 (1H, m), 6.5-6.78 (2H, m), 6.78-7.0 (2H, m), 7.26 (5H, m), 7.68 (1H, m), 8.1-8.33 (2H, m), 8.42 (1H, m), 8.66 (1H, m), 9.32 (1H, m).

EXAMPLE 122

1-Benzyloxycarbonyl-4-[N,O-bis(5-isoquinolinesulfonyl)tyrosyl]homopiperazine 6.44 g of the amorphous compound obtained in Reference Example 28 was dissolved in 6 ml of ethyl acetate, to the solution was added 60 ml of 4N hydrogen chloride in ethyl acetate at a room temperature with stirring, and the mixture was stirred for 3 hours. The reaction mixture was concentrated under a reduced pressure and after an addition of benzene, again concentrated under a reduced pressure, to obtain 1-benzyloxycarbonyl-4-tyrosylhomopiperazine/hydrochloride in an amorphous form.

To this intermediate were added 130 ml of tetrahydrofuran as well as 7.88 g of 5-isoquinolinesulfonyl chloride.HCl and 18 ml of triethylamine, and the mixture was stirred for 18 hours at a room temperature. The reaction mixture was alkalized with a saturated sodium bicarbonate aqueous solution and extracted twice with 700 ml of chloroform, and the extract was dried over magnesium sulfate and evaporated to remove the solvent under a reduced pressure. Resulting residue was applied to a silica gel column and eluted with chloroform/methanol (30:1) to obtain 5.50 g of the title compound in a colorless amorphous form.

$^1$H-NMR (CDCl$_3$, δ ppm): 1.65 (2H, m), 2.4-3.8 (10H, m), 4.17 (1H, m), 5.1 (2H, m), 6.02 (1H, d, J=9.52 Hz), 6.47, 6.51 (Total 2H, each d, J=8.55 Hz), 6.75 (2H, d, J=8.55 Hz), 7.29, 7.33 (Total 5H, each s), 7.58, 7.60 (Total 1H, each t, J=8.06 Hz), 8.1 8.3 (5H, m), 8.52 (1H, d, J=6.11 Hz), 8.64 (1H, d, J=6.10 Hz), 8.84 (1H, d, J=5.37 Hz), 9.29 (1H, s), 9.41 (1H, s).

EXAMPLE 123

1-Benzyloxycarbonyl-4-[N-(5-isoquinolinesulfonyl)-tyrosyl]homopiperazine 5.50 g of the amorphous compound obtained in Example 122 was dissolved in 30 ml of methanol and 30 ml of tetrahydrofuran, to the solution was added 60 ml of 1N sodium hydroxide, and the mixture was refluxed for 2 hours and then cooled. The reaction mixture was acidified with citric acid and then alkalized with sodium bicarbonate, resulting insoluble matter was dissolved with a small amount of methanol, and the solution was extracted twice with 400 ml of chloroform. The extract was dried over magnesium sulfate and evaporated to remove the solvent under a reduced pressure, and resulting residue was applied to a silica gel column and eluted with chloroform/methanol (20:1) to obtain 3.1 g of the title compound in a colorless amorphous form.

$^1$H-NMR (CDCl$_3$+CD$_3$OD, δ ppm): 1.82 (2H, m), 2.48 (1H, m), 2.68 (1H, dt, J=6.85, 5.71 Hz), 3.1-3.8 (8H, m), 4.16 (1H, m), 5.12, 5.13 (Total 2H, each s), 6.14, 6.17 (Total 2H, each d, J=8.55 Hz), 6.52, 6.53 (Total 2H, each d, J=8.55 Hz), 7.33, 7.35 (Total 5H, each s), 7.61 (1H, m), 8.16 (1H, d, J=8.06 Hz), 8.2 8.45 (2H, m), 8.53 (1H, d, J=6.11 Hz), 9.21 (1H, s).

REFERENCE EXAMPLE 31

N-Benzyloxycarbonyltyrosine and N-tert-butoxycarbonylhomopiperazine were treated according to the procedure in Reference Example 28 to obtain 1-(Nbenzyloxycarbonyl)tyrosyl-4-tertbutoxycarbonylhomopiperazine in a colorless amorphous form.

$^1$H-NMR (CDCl$_3$, δ ppm): 1.42, 1.44 (Total 9H, each s), 1.6-2.0 (2H, m), 2.7-3.8 (10H, m), 4.75 (1H, m), 5.04 (1H, d, J=11.42 Hz), 5.13 (1H, d, J=11.42 Hz), 5.5 (1H, m), 6.72 (2H, m), 7.02 (2H, m), 7.34 (5H, s).

REFERENCE EXAMPLE 32

1-(O-Acetyl-N-benzyloxycarbonyl)tyrosyl-4-tert-butoxycarbonylhomopiperazine 690 mg of the amorphous compound obtained in Reference Example 31 was dissolved in 7 ml of pyridine, and to the solution was added 3.5 ml of acetic anhydride at a room temperature with stirring, and the mixture was further stirred for 18 hours. After pouring the reaction mixture to saturated sodium hydroxide aqueous solution to alkalize, the mixture was extracted twice with 100 ml of chloroform. The extract was washed with a saturated sodium chloride aqueous solution, dried over magnesium sulfate, and evaporated to remove the solvent under a reduced pressure. Resulting residue was applied to a silica gel column and eluted with chloroform/methanol (100:1) to obtain 670 mg of the title compound in a colorless amorphous form.

$^1$H-NMR (CDCl$_3$, δ ppm): 1.41, 1.43 (Total 9H, each s), 1.5-2.0 (2H, m), 2.28 (3H, s), 2.8-3.7 (10H, m), 4.7 (1H, m), 5.05 (1H, d, J=11.4 Hz), 5.13 (1H, d, J=11.4 Hz), 5.52 (1H, m), 6.99 (2H, d, J=7.42 Hz), 7.21 (2H, d, J=7.42 Hz), 7.34 (5H, s).

REFERENCE EXAMPLE 33

1-(O-Acetyl-N-benzyloxycarbonyl)tyrosyl-4-(3-phenylpropyl)homopiperazine 670 mg of the amorphous compound obtained in reference Example 32 was dissolved in 2 ml of ethyl acetate, and to the solution was added 7 ml of 3N hydrogen chloride in ethyl acetate at a room temperature with stirring, and the mixture was further stirred for 30 minutes, alkalized with sodium bicarbonate aqueous solution, saturated with sodium chloride, and extracted twice with 100 ml of ethyl acetate. The extract was dried over magnesium sulfate and evaporated under a reduced pressure, to obtain 460 mg of 1-(0-acetyl-N-benzyloxycarbonyl)tyrosylhomopiperazine.

This compound was dissolved in 6 ml of dimetylformamide, and to the solution were added 150 mg of potassium carbonate, 160 mg of sodium iodide and 210 mg of 1-bromo-3-phenylpropane at a room temperature with stirring, and the mixture was stirred for 20 hours. After an addition of a saturated sodium chloride aqueous solution, the reaction mixture was extracted twice with 100 ml of chloroform, and the extract was dried over magnesium sulfate and evaporated to remove the solvent under a reduced prssure. Resulting residue was applied to a silica gel column and eluted with chloroform/methanol (100:1) to obtain 430 mg of the title compound in a colorless amorphous form.

$^1$H-NMR (CDCl$_3$, δ ppm): 1.5–2.0 (6H, m), 2.26 (3H, s), 2.3–2.7 (6H, m), 2.9–3.8 (6H, m), 4.84 (1H, m), 5.03 (1H, d, J=11.99 Hz), 5.12 (1H, d, J=11.99 Hz), 5.6 (1H, m), 6.97 (2H, dd, J=8.57, 1.0 Hz), 7.1–7.3 (7H, m), 7.33 (5H, s).

REFERENCE EXAMPLE 34

1-(3-Phenylpropyl)-4-tyrosylhomopiperazine 25 430 mg of the amorphous compound obtained in Reference Example 33 was dissolved in 5 ml of methanol, to the solution was added 120 mg of potassium carbonate at a room temperature with stirring, and the reaction mixture was stirred for 70 hours. After an addition of a saturated sodium chloride aqueous solution, the reaction mixture was acidified with citric acid and extracted twice with 100 ml of chloroform. The extract was dried over magnesium sulfate and evaporated to remove the solvent under a reduced pressure. Resulting residue was applied to a silica gel column and eluted with chloroform/methanol (100:1) to obtain 395 mg of 1-(N-benzyloxycarbonyl)tyrosyl-4-(3-phenylpropyl)-homopiperazine.

This compound was dissolved in 15 ml of methanol, and to the solution were added 0.05 ml of concentrated hydrochloric acid and 150 mg of 5% palladium on carbon with ice cooling. After warming the reaction mixture to a room temperature, the catalytic reduction was carried out in a hydrogen atmosphere for 8 hours. The palladium on carbon catalyst was filtered by suction, and washed with methanol. The filtrates were combined and evaporated to remove the solvent under a reduced pressure, and to resulting residue was added saturated sodium chloride aqueous solution. The mixture was alkalized with a sodium bicarbonate aqueous solution, precipitated insoluble matter was dissolved by adding a small amount of methanol, and the mixture was extracted twice with 80 ml of chloroform. The extract was dried over magnesium sulfate and evaporated to remove the solvent under a reduced pressure, and resulting residue was applied to a silica gel column and eluted with chloroform/methanol (20:1), to obtain 180 mg of the title compound in a colorless amorphous form.

$^1$H-NMR (CDCl$_3$, δ ppm): 1.75 (4H, m), 2.3–2.8 (10H, m), 2.92 (1H, m), 3.1–3.8 (4H, m), 3.86 (1H, q, J=6.28 Hz), 6.65, 6.66 (Total 2H, each d, J=8.57 Hz), 6.99, 7.00 (Total 2H, each d, J=8.57 Hz), 7.1–7.35 (5H, m).

EXAMPLE 124

1-[N-(5-Isoquinolinesulfonyl)tyrosyl]-4-(3-phenylpropyl)homopiperazine 180 mg of the amorphous compound obtained in Reference Example 34 was dissolved in 4 ml of tetrahydrofuran, and to the solution were added 137 mg of 5-isoquinolinesulfonyl chloride.HCl and 0.2 ml of triethylamine at a room temperature with stirring, and the mixture was stirred for 15 hours. After an addition of a saturated sodium chloride aqueous solution, the reaction mixture was alkalized with sodium bicarbonate, and the precipitated insoluble matter was made oily by adding a small amount of methanol, and the mixture was extracted twice with 50 ml of chloroform. The extract was dried over magnesium sulfate and evaporated to remove the solvent under a reduced pressure. Resulting residue was applied to a silica gel column and a preparative thin layer chromatographic plate and eluted with chloroform/methanol (10:1), to obtain 130 mg of the title compound in colorless amorphous form.

$^1$H-NMR (CDCl$_3$+CD$_3$OD, δ ppm): 1.76 (4H, m), 2.3–2.8 (10H, m), 3.1–3.7 (4H, m), 4.22 (1H, m), 6.17, 6.19 (Total 2H, each d, J=8.57 Hz), 6.53, 6.56 (Total 2H, each d, J=8.57 Hz), 7.1–7.4 (5H, m), 7.57, 7.59 (Total 1H, each t, J=8.28 Hz), 8.12 (1H, d, J=8.28 Hz), 8.15–8.35 (2H, m), 8.53 (1H, dd, J=6.28, 1.0 Hz), 9.18 (1H, s).

EXAMPLE 35

1-[N-(tert-Butoxycarbonyl)-p-nitrophenylalanyl]-4-(p-methoxyphenyl)piperazine 9.00 g of N-(tert-butoxycarbonyl)-p-nitrophenylalanine was dissolved in 120 ml of tetrahydrofuran, 100 ml of methylene chloride and 100 ml of chloroform, and to the solution were sequentially added 7.68 g of N-(p-methoxyphenyl) piperazine dihydrochloride and 4.44 g of N-hydroxybenzotriazole monohydrate as well as 20 ml of triethylamine and 6 g of DCC, and the mixture was stirred at a room temperature for 18 hours. The reaction mixture was concentrated to one third of the original volume under a reduced pressure, and after adding 200 ml of 2.5% potassium carbonate aqueous solution, extracted twice with 200 ml of chloroform. The extract was dried over magnesium sulfate and concentrated under a reduced pressure to crystallize a product, which was washed with methanol to obtain 10.75 g of the title compound as colorless crystals.

$^1$H-NMR (CDCl$_3$, δ ppm): 1.40 (9H, s), 2.73 (1H, m), 2.87–3.00 (3H, m), 3.04 (1H, dd, J=6.3, 13.2 Hz), 3.17 (1H, dd, J=7.3, 13.2 Hz), 3.35 (1H, m), 3.55–3.70 (2H, m), 3.77 (3H, s), 3.84 (1H, m), 4.92 (1H, m), 5.4 (1H, d, J=8.8 Hz), 6.83 (4H, s), 7.38 (2H, d, J=8.8 Hz), 8.16 (2H, d, J=8.8 Hz).

REFERENCE EXAMPLE 36

1-N-(tert-Butoxycarbonyl)-p-aminophenylalanyl]-4-(p-methoxyphenyl)piperazine 10.75 g of the crystals obtained in Reference Example 35 was dissolved in a mixed solvent of 100 ml of tetrahydrofuran and 20 ml of methanol, and to the solution was added 5 g of 5% palladium on carbon, and the mixture was stirred for 2 hours at a room temperature in a hydrogen atmosphere. After filtering off insoluble matter, the filtrate was concentrated under a reduced pressure, and resulting residue was applied to a silica gel column and eluted with chloroform/methanol (200:1 to 100:1), to obtain 10.08 g of the title compound in a colorless amorphous form.

$^1$H-NMR (CDCl$_3$, δ ppm): 1.43 (9H, s), 2.42 (1H, m), 2.75–3.00 (4H, m), 3.13 (1H, m), 3.43 (1H, m), 3.57 (1H, m), 3.63 - 3.73 (2H, m), 3.76 (3H, s), 4.78 (1H, m), 5.43

(1H, br), 6.59 (2H, d, J=8.3 Hz), 6.82 (4H, s), 6.98 (2H, d, J=8.3 Hz).

REFERENCE EXAMPLE 37

1-[3-(p-Aminophenyl)-2-(tert-butoxycarbonylamino)-propyl-4-(p-methoxyphenyl)piperazine 2.54 g of lithium aluminum hydride was suspended in 75 ml of tetrahydrofuran, to the suspension was added a solution of 8.91 g of aluminum chloride in 75 ml of ether with ice cooling, and also a solution of 10.08 g of the amorphous compound obtained in Reference Example 36 in 100 ml of tetrahydrofuran was added dropwise for 20 minutes with ice cooling. Under the same condition the mixture was stirred for one hours, and after terminating the reaction by adding a small amount of water, 70 ml of 30% potassium carbonate aqueous solution and 200 ml of chloroform were added to the reaction mixture, which was then filtered to remove insoluble matter using silica gel as a filter aid. The insoluble matter was washed with 20% methanol in chloroform, and the filtrates were combined and concentrated under a reduced pressure. 200 ml of saturated sodium bicarbonate aqueous solution was added to the residue, the mixture was extracted twice with 100 ml of chloroform, and the extract was dried over magnesium sulfate and concentrated under a reduced pressure. Resulting residue was applied to a silica gel column and eluted with chloroform/methanol (100:1) to obtain 7.72 g of the title compound in a colorless amorphous form.

$^1$H-NMR (CDCl$_3$, δ ppm): 1.43 (9H, s), 2.30 (2H, d, J=6.8 Hz), 2.48-2.68 (4H, m), 2.78 (2H, t, J=6.3 Hz), 3.06 (4H, t, J=4.9 Hz), 3.76 (3H, s), 3.86 (1H, m), 4.59 (1H, br), 6.62 (2H, d, J=8.3 Hz), 6.82 (2H, d, J=9.3 Hz), 6.89 (2H, d, J=9.3 Hz), 6.98 (2H, d, J=8.3 Hz).

REFERENCE EXAMPLE 38

1-[2-(tert-Butoxycarbonylamino)-3-(p-phthalimidephenyl)propyl]-4-(p-methoxyphenyl)piperazine 7.0 g of the amorphous compound obtained in Reference Example 37 was dissolved in 70 ml of chloroform, to the solution was added 2.66 g of phthalic anhydride. The mixture was refluxed for one hour, concentrated under a reduced pressure, and after an addition of 100 ml of toluene, further refluxed for 2 hours. The solvent was evaporated off under a reduced pressure, and resulting residue was applied to a silica gel column and eluted with chloroform/methanol (100:1 to 50:1), to obtain 8.91 g of the title compound as colorless crystals.

$^1$H-NMR (CDCl$_3$, δ ppm): 1.45 (9H, s), 2.37 (2H, d, J=6.8 Hz), 2.51-2.71 (4H, m), 2.96 (2H, d, J=5.4 Hz), 3.09 (4H, t, J=4.9 Hz), 3.77 (3H, s), 4.01 (1H, m), 4.66 (1H, br), 6.83 (2H, d, J=9.3 Hz), 6.90 (2H, d, J=9.3 Hz), 7.36 (4H, s), 7.79 (2H, dd, J=3.4, 5.4 Hz), 7.96 (2H, dd, J=3.4, 5.4 Hz).

EXAMPLE 125

N-{(2-4-(p-Methoxyphenyl)piperazinyl]-1-(p-phthalimidebenzyl)ethyl}-5-isoquinolinesulfonamide 8.91 g of the crystals obtained in Reference Example 38 was dissolved in 50 ml of ethyl acetate, to the solution was added 100 ml of 4N hydrogen chloride in ethyl acetate, and the mixture was stirred at a room temperature for 1 hour. The reaction mixture was concentrated under a reduced pressure, and to the residue was added 200 ml of saturated sodium bicarbonate aqueous solution, and the mixture was extracted twice with 100 ml of 20% methanol/chloroform. The extract was dried over magnesium sulfate and concentrated under a reduced pressure to crystallize an amino-free compound. The crystals was suspended in 120 ml of tetrahydrofuran, to the suspension were added 5.0 g of 5-isoquinolinesulfonyl chloride.HCl and 20 ml of triethylamine with ice cooling, and after warming to a room temperature, the mixture was stirred for 2 hours. After adding 200 ml of water, formed crystals was collected. The filtrate was extracted twice with 100 ml of chloroform, and the extract was dried over magnesium sulfate and concentrated to dryness under a reduced pressure to obtain a residue. The residue with the crystals was sequentially washed with methanol, ethyl acetate and hexane to obtain 6.49 g of the title compound as colorless crystals.

Melting point: 20420 -211° C. (decomposed);

IR (KBr) cm$^{-1}$: 1710, 1510, 1370, 1235, 1150, 1130;

$^1$H-NMR (CDCl$_3$, δ ppm): 2.03-2.33 (6H, m), 2.46-2.59 (2H, m), 2.59-2.72 (2H, m), 2.85 (1H, dd, J=7.3, 13.7 Hz), 3.10 (1H, dd, J=4.4, 13.7 Hz), 3.41 (1H, m), 3.77 (3H, s), 5.63 (1H, br), 6.73 (2H, d, J=9.3 Hz), 6.83 (2H, d, J=9.3 Hz), 7.20 (2H, d, J=8.8 Hz), 7.29 (2H, d, J=8.8 Hz), 7.74 (1H, t, J=8.3 Hz), 7.80 (2H, dd, J=3.4, 5.4 Hz), 7.96 (2H, dd, J=3.4, 5.4 Hz), 8.24 (1H, d, J=8.3 Hz), 8.48-8.52 (2H, m), 8.72 (1H, d, J=6.4 Hz), 9.36 (1H, s).

EXAMPLE 126

N-{2-[4-(p-Methoxyphenyl)piperazinyl]-1-(p-phthalimidebenzyl)ethyl}-N-methyl-5-isoquinolinesulfonamide 4.71 g of the crystals obtained in Example 125 was dissolved in 70 ml of dimethylformamide, to the solution were sequentially added 500 mg of 60% sodium hydride and 1 ml of methyl iodide with ice cooling, and the mixture was stirred under the same condition for 3 hours. The reaction was terminated by adding a small amount of water, and after adding 200 ml of saturated ammonium chloride aqueous solution, the mixture was extracted twice with 100 ml of chloroform. The extract was dried over magnesium sulfate and concentrated under a reduced pressure. To resulting residue were added 50 ml of acetic anhydride and 1.2 g of sodium acetate, and the mixture was stirred for one hour at 80° C. and then concentrated to dryness under a reduced pressure, and resulting residue was dissolved in 200 ml of ethyl acetate. The solution was sequentially washed with 100 ml of saturated sodium bicarbonate aqueous solution and 100 ml of saturated sodium chloride aqueous solution, dried over magnesium sulfate, and concentrated under a reduced pressure. Resulting residue was applied to a silica gel column and eluted with chloroform/methanol (100:1) to obtain 4.84 g of the title compound as colorless crystals.

Melting point: 170°-172° C.;

IR (KBr) cm$^{-1}$: 1710, 1610, 1510, 1375, 1300, 1235, 1145, 1125;

$^1$H-NMR (CDCl$_3$, δ ppm): 2.48 (1H, dd, J=7.3, 13.2 Hz), 2.50-2.63 (4H, m), 2.66 (1H, dd, J=7.3, 13.2 Hz), 2.82 (1H, dd, J=6.8, 14.2 Hz), 2.86-2.96 (4H, m), 2.97 (3H, s), 3.02 (1H, dd, J=6.8, 14.2 Hz), 3.77 (3H, s), 4.32 (1H, m), 6.84 (4H, s), 7.15 (2H, d, J=8.8, Hz), 7.22 (2H, d, J=8.8 Hz), 7.61 (1H, t, J=7.3 Hz), 7.81 (2H, dd, J=2.9, 5.4 Hz), 7.97 (2H, dd, J=2.9, 5.4 Hz), 8.13 (1H, d, J=8.3 Hz), 8.31 (2H, d, J=6.4 Hz), 8.60 (1H, d, J=6.3 Hz), 9.23 (1H, s).

EXAMPLE 127

1.5 g of the crystals obtained in Example 125 was suspended in 30 ml of ethanol, to the suspension was added 3 ml of hydrozine hydrate, and the mixture was refluxed for one hour. After adding 10% sodium hydroxide aqueous solution, the reaction mixture was extracted twice with 30 ml of chloroform. The extract was dried over magnesium sulfate and concentrated under reduced pressure to form crystals, which was washed with a mixed solvent of ethyl acetate and methanol, to obtain 1.14 g of N-{1-(p-aminovenzyl)-2-[4-(p-methoxyphenyl)-piperazinyl]ethyl}-5-isoquinolinesulfonamide as light yellow crystals.

Melting point: 210°–211° C.;

IR (KBr) cm$^{-1}$: 1615, 1510, 1330, 1245, 1225, 1150, 1130, 1025;

$^1$H-NMR (CDCl$_3$, δ ppm): 2.12–2.34 (6H, m), 2.53–2.72 (5H, m), 2.85 (1H, dd, J =4.9, 14.2 Hz), 3.31 (1H, m), 3.52 (2H, br], 3.77 (3H, s), 5.48 (1H, br), 6.43 (2H, d, J=8.3 Hz), 6.75 (2H, d, J=9.3 Hz), 6.77 (2H, d, J=8.3 Hz), 6.83 (2H, d, J=9.3 Hz), 7.70 (1H, t, J=7.8 Hz), 8.20 (1H, d, J=8.3 Hz), 8.44 (1H, d, J=6.4 Hz), 8.47 (1H, dd, J=1.0, 7.3 Hz), 8.68 (1H, d, J=6.4 Hz), 9.35 (1H, s).

EXAMPLE 128

4.64 g of the crystals obtained in Example 126 was suspended in 80 ml of ethanol, to the suspension 8 ml of hydrazine hydrate was added, and the mixture was refluxed for 90 minutes. After adding 100 ml of 10% sodium hydroxide, the reaction mixture was extracted twice with 80 ml of chloroform, and the extract was dried over magnesium sulfate and concentrated under a reduced pressure. Resulting residue was applied to a silica gel column and eluted with chloroform/methanol (100 1 to 50:1), to obtain 3.29 g of N-{1-(p-aminobenzyl)-2-[4-(p-methoxyphenyl)piperazinyl]ethyl }-N-methyl-5-isoquinolinesulfonamide in a yellow amorphous form.

IR (KBr) cm$^{-1}$: 1620, 1510, 1315, 1235, 1150, 1125;

$^1$H-NMR (CDCl$_3$, δ ppm): 2.43 (1H, dd, J=6.8, 13.2 Hz), 2.53–2.66 (6H, m), 2.85 (1H, dd, J=6.4, 14.2 Hz), 2.87–2.94 (4H, m), 2.92 (3H, s), 3.50 (2H, br), 3.77 (3H, s), 4.20 (1H, m), 6.34 (2H, d, J=8.3 Hz), 6.75 (2H, d, J=8.3 Hz), 6.84 (4H, s), 6.56 (1H, t, J=7.3 Hz), 8.09 (1H, d, J=8.3 Hz), 8.24 (1H, d, J=6.3 Hz), 8.31 (1H, dd, J=1.0, 7.3 Hz), 8.56 (1H, d, J=5.9 Hz], 9.25 (1H, d, J=1.0 Hz).

EXAMPLE 129

500 mg of the amorphous compound obtained in Example 128 was dissolved in 5 ml of pyridine, to the solution was added 305 mg of 5-isoquinolinesulfonyl chloride.HCl under ice cooling, and the mixture was stirred under the same condition for 20 minutes and then at a room temperature for one hour. After adding 30 ml of saturated sodium bicarbonate aqueous solution, the reaction mixture was extracted twice with 20 ml of chloroform, and the extract was dried over magnesium sulfate and concentrated under a reduced pressure. Resulting residue was applied to a silica gel column and eluted with chloroform/methanol (50:1), to obtain 665 mg of N-{1-[p-(5-isoquinolinesulfonylaminobenzyl)]-2-[4-(p-methoxyphenyl)piperazinyl]ethyl}-N-methyl -5-isoquinolinesulfonamide in a yellow amorphous form.

IR (KBr) cm$^{-1}$: 1615, 1510, 1325, 1225, 1150, 1130;

$^1$H-NMR (CDCl$_3$, δ ppm): 2.34 (1H, dd, J=7.3, 12.7 Hz), 2.45–2.61 (6H, m), 2.79–2.94 (5H, m), 2.90 (3H, s), 3.77 (2H, s), 4.04 (1H, m), 6.55 (2H, d, J=8.3 Hz), 6.70 (2H, d, J=8.3 Hz), 6.83 (4H, s), 7.57 (2H, t, J=7.8 Hz), 8.08–8.15 (3H, m), 8.28–8.35 (2H, m), 8.40 (1H, d, J=6.4 Hz), 8.50 (1H, d, J=5.3 Hz), 8.64 (1H, d, J=6.4 Hz), 9.29 (1H, s), 9.31 (1H, d, J=1.0 Hz).

EXAMPLE 130

200 mg of the crystals obtained in Example 127 was dissolved in 3 ml of pyridine, to the solution was added 130 mg of 5-isoquinolinesulfonyl chloride.½ sulfate with ice cooling, and the mixture was stirred with ice cooling for 20 minutes and then at a room temperature for one hour, and after adding 30 ml of saturated sodium bicarbonate aqueous solution, extracted twice with 20 ml of chloroform. The extract was dried over magnesium sulfate and concentrated under a reduced pressure, and resulting residue was applied to a silica gel column and eluted with chloroform/methanol (50:1 to 25:1), to obtain 270 mg of N-(1-[p-(5-isoquinolinesulfonylaminobenzyl)]-2-[4-(p-methoxyphenyl)-piperazinyl]ethyl}-5-isoquinolinesulfonamide in a yellow amorphous form.

IR (KBr) cm$^{-1}$: 1615, 1505, 1330, 1230, 1150, 1125;

$^1$H-NMR (CDCl$_3$, δ ppm): 2.16–2.33 (6H, m), 2.49–2.81 (6H, m), 3.28 (1H, m), 3.76 (3H, s}, 6.69 (2H, d, J=8.3 Hz), 6.73 (2H, d, J=9.3 Hz), 6.79 (2H, d, J=8.3 Hz), 6.82 (2H, d, J=9.8 Hz), 7.61 (1H, t, J=7.8 Hz), 7.67 (1H, t, J=7.8 Hz), 8.16 (1H, d, J=8.3 Hz), 8.19 (1H, d, J=8.3 Hz), 8.34–8.48 (4H, m), 8.62 (2H, d, J=6.4 Hz), 9.33 (1H, s), 9.35 (1H., s).

EXAMPLE 131

N-[[1-(p-[N-5-Isoquinolinesulfonyl)-N-(methylamino)-benzyl]}-2-[4-(p-methoxyphenylpiperazinyl]ethyl ]]-N-methyl-5-isoquinolinesulfonamide 503 mg of the amorphous compound obtained in Example 129 was dissolved in 8 ml of dimethylformamide, to the solution were added 50 mg of 60% sodium hydride and 0.1 ml of methyl iodide with ice cooling, and the mixture was stirred for one hours with ice cooling. After adding 30 ml of saturated sodium chloride aqueous solution, the reaction mixture was extracted with 30 ml of ethyl acetate, and the extract was washed with a saturated sodium chloride aqueous solution, dried over magnesium sulfate and concentrated under a reduced pressure. Resulting residue was applied to a silica gel column and eluted with chloroform/methanol (100:1), to obtain 488 mg of the title compound in a yellow amorphous form.

IR (KBr) cm$^{-1}$: 1610, 1505, 1340, 1320, 1235, 1145, 1125,;

$^1$H-NMR (CDCl$_3$, δ ppm): 2.32 (1H, dd, J=6.4, 13.2 Hz), 2.41–2.56 (5H, m), 2.73–2.98 (6H, m), 2.88 (3H, s), 3.23 (3H, s), 3.77 (3H, s), 4.31 (1H, m), 6.82 (4H, s), 6.89 (2H, d, J=8.3 Hz), 7.01 (2H, d, J=8.3 Hz), 7.63 (1H, t, J=7.8 Hz), 7.64 (1H, t, J=7.8 Hz), 8.02 (1H, d, J=5.9 Hz), 8.13 (1H, d, J=8.3 Hz), 8.19 (1H, d, J=8.3 Hz), 8.23 (1H, d, J=7.3 Hz), 8.34 (1H, d, J=6.3 Hz), 8.40–8.47 (2H, m), 8.60 (1H, d, J=5.9 Hz), 9.28 (1H, s), 9.29 (1H, s).

EXAMPLE 132

N-{1-[p-(4-Picolyloxy)benzyl]-2-4-(2-pyrimidyl)-piperazinyl]ethyl}-N-methyl-5-isoquinolinesulfonamide 100 mg of the amorphous compound obtained in Example 42 was dissolved in 10 ml of a mixture of dried tetrahydrofuran/dried dimethylformamide (1:1), to the solution were added 34.8 mg of 4-picolyl chloride hydrochloride and then 24 mg of triethylamine, and the mixture was stirred at a room temperature for 30 minutes. After adding 10 mg of 60% sodium hydride, the mixture was stirred overnight at a room temperature, and after adding 20 g of water, extracted twice with 20 ml of chloroform. The extract was washed with a saturated sodium chloride aqueous solution, dried over magnesium sulfate, and evaporated to remove the solvent under a reduced pressure. The resulting residue was applied to a silica gel column and extracted with chloroform/methanol (100:1) to obtain 73 mg of the title compound in colorless amorphous form.

NMR (CDCl$_3$) δ ppm: 2.45 (4H, complex), 2.5-2.75 (2H, complex), 2.95 (3H, s), 3.65 (4H, complex), 4.22 (1H, complex), 5.0 (2H, s), 6.49 (1H, t, J=4.26 Hz), 6.6 (2H, d, J=8.0 Hz), 6.9 (2H, d, J=8.0 Hz), 7.4 (2H, brd), 7.6 (1H, t, J=8.3 Hz), 8.11 (1H, d, J=8.3 Hz), 8.23 (1H, d, J=6.64 Hz), 8.3 (2H, d, J=4.26 Hz), 8.37 (1H, dd, J=1.0, 6.6 Hz), 8.57 (1H, d, J=6.6 Hz), 8.65 (2H, brd), 9.25 (1H, d, J=1.0 Hz).

EXAMPLE 133

N-{1-[p-(2-Picolyloxy)benzyl]-2-4-(2-pyrimidyl)-piperazinyl]ethyl}-N-methyl-5-isoquinolinesulfonamide The same procedure as described in Example 132 was repeated except that the same amount of 2-picolyl chloride hydrochloride was used in place of 4-picolyl chloride hydrochloride, to obtain 74.4 mg of the title compound in colorless amorphous form.

NMR (CDCl$_3$) δ ppm: 2.45 (4H, complex), 2.5-2.9 (2H, complex), 2.98 (3H, s), 3.75 (4H, complex), 4.2 (1H, complex), 5.13 (2H, s), 6.46 (1H, t, J=4.8 Hz], 6.65 (2H, d, J=8.0 Hz), 6.9 (2H, d, J=8.0 Hz), 7.15 (1H, complex), 7.58 (2H, t, J=6.9 Hz), 7.75 (1H, complex), 8.1 (1H, d, J=8.0 Hz), 8.2 - 8.35 (2H, complex), 8.3 (1H, d, J=4.8 Hz), 8.58 (1H, d, J =6.6 Hz), 8.6 (1H, brs), 9.25 (1H, s).

EXAMPLE 134

N-{1-p-(4-Picolyloxy)benzyl]-2-[4-(2-pyridyl)-piperazinyl]ethyl}-N-methyl-5-isoquinolinesulfonamide The same procedure as described in Example 132 was repeated except that the product of Example 46 was used in place of the amorphous compound obtained in Example 42, to obtain the title compound in a colorless amorphous form in a yield of 53.5%.

NMR (CDCl$_3$) δ ppm: 2.5 (4H, complex), 2.5-2.75 (2H, complex), 2.95 (3H, s), 3.38 (4H, complex), 4.22 (1H, complex), 5.0 (2H, s), 6.58 (2H, d, J=8.6 Hz), 6.6 (2H, t, J=5.7 Hz), 6.9 (2H, d, J=8.6 Hz), 7.35-7.5 (4H, complex), 7.58 (1H, t, J=7.8 Hz), 8.07 (1H, d, J=8.1 Hz), 8.17 (1H, brd), 8.23 (1H, d, J=6.1 Hz), 8.35 (1H, dd, J=1.0, 7.4 Hz), 8.57 (1H, d, J=6.1 Hz), 8.63 (1H, brd), 8.63 (1H, d, J=5.8 Hz), 9.2 (1H, d, J=1.0 Hz).

EXAMPLE 135

N-{1-(p-(2-Picolyloxy)benzyl]-2-[4-(2-pyridyl)-piperazinyl]ethyl}-N-methyl-5-isoquinolinesulfonamide The same procedure as described in Example 133 was repeated except that the product of Example 46 was used in place of the amorphous compound obtained in Example 42, to obtain the title compound in a colorless amorphous for in a yield of 59.5%.

NMR (CDCl$_3$) δ ppm: 2.5 (4H, complex), 2.5-2.9 (2H, complex), 2.95 (3H, s), 3.38 (4H, complex), 4.22 (1H, complex), 5.12 (2H, s), 6.55 - 6.65 (2H, complex), 6.54 (2H, d, J=8.6 Hz), 6.9 (2H, d, J=8.6 Hz), 7.2-7.25 (1H, complex), 7.4-7.7 (4H, complex), 7.65-7.8 (1H, complex), 8.1 (1H, d, J=7.7 Hz), 8.2 (1H, brd), 8.27 (1H, d, J=6.6 Hz), 8.3 (1H, d, J=6.6 Hz), 8.57 (1H, d, J=6.3 Hz), 8.6 (1H, brs), 9.73 (1H, s).

EXAMPLE 136

N-(2-Aminoethyl)-N-2-(4-benzyloxycarbonyl-piperazinyl)-1-(p-methoxybenzyl)ethyl]-5-isoquinolinesulfonamide 1.0 g of the product obtained in Example 73 was dissolved in 5 ml of tetrahydrofuran, to the solution were added 685 mg of triphenylphosphine and 340 mg of N-tert-butoxycarbonylethanolamine, and then added dropwise a solution of 530 mg of diisopropyl azodicarboxylate in 3 ml of tetrahydrofuran with stirring in a ice bath. After removing from the ice bath, the mixture was stirred at a room temperature for 3 hours and poured to water, and the mixture was alkalized with sodium bicarbonate and extracted twice with 150 ml of chloroform. The extract was dried over magnesium sulfate and the solvent was evaporated off under a reduced pressure. Resulting oil was dissolved in 2 ml of ethyl acetate, to the solution was added 30 ml of 4N hydrochloric acid in ethyl acetate, and the mixture was stirred at a room temperature for 30 minutes. After adding 100 ml of 1N hydrochloric acid, the reaction mixture was washed twice with ethyl acetate, and the aqueous layer was alkalized with sodium Obicarbonate and extracted twice with 150 ml of chloroform. The extract was dried over magnesium sulfate and evaporated to remove the solvent under a reduced pressure, and resulting oil was applied to a silica gel column and eluted with chloroform/methanol (100:1 to 50:1) to obtain 400 mg of the title compound in colorless amorphous form.

IR (KBr) cm$^{-1}$: 1701, 1514, 1325, 1248, 1135, 763, 601;

NMR (CDCl$_3$) δ ppm: 1.99 (2H, brs), 2.15-2.40 (5H, m), 2.55-2.80 (3H, m), 2.90-3.10 (2H, m), 3.20-3.70 (6H, m), 3.73 (3H, s), 4.98 (1H, m), 5.10 (2H, s), 6.54 (2H, d, J=8.55 Hz), 6.77 (2H, J=8.55 Hz), 7.33 (5H, s), 7.62 (1H, dd, J=8.06, 7.57 Hz), 8.14 (1H, d, J=8.06 Hz), 8.34 (1H, d, J=6.10 Hz), 8.39 (1H, d, J=7.57 Hz), 8.63 (1H, d, J=6.10 Hz), 9.28 (1H, s).

EXAMPLE 137

N-[2-(4-Benzyloxycarbonylpiperazinyl-1-p-methoxybenzyl)ethyl]-N-(2-dimethylaminoethyl)-5-isoquinolinesulfonamide 6.08 g of the product obtained in Example 73 was dissolved in 30 ml of tetrahydrofuran, to the solution were added 5.0 g of triphenylphosphine and 1.42 g of N,N-dimethylethanolamine, and then added dropwise a solution of 3.21 g of diisopropyl azodicarboxylate in 10 ml of tetrahydrofuran with stirring in ice bath. After removing from the ice bath, the reaction mixture was stirred at a room temperature for 3 hours, diluted with ethyl acetate, and extracted with 100 ml of 1N hydrochloric acid. The extract was alkalized with sodium bicarbonate and extracted twice with 100 ml of chloroform, and the extract was dried over magnesium sulfate and evaporated to remove the solvent under a reduced pressure. Resulting oil was applied to a silica gel column and eluted with chloroform/methanol (200:1 to 100:1), to obtain 4.99 g of the title compound in a colorless amorphous form.

IR (KBr) cm$^{-1}$: 1703, 1514, 1327, 1247, 1135, 600;

NMR (CDCl$_3$) δ ppm: 2.10–2.45 (5H, m), 2.26 (6H, s), 2.45–2.85 (5H, m), 3.20–3.65 (6H, m), 3.73 (3H, s), 4.00 (1H, m), 5.10 (2H, s), 6.53 (2H, d, J=8.79 Hz), 6.83 (2H, d, J=8.79 Hz), 7.34 (5H, s), 7.56 (1H, dd, J=8.05, 7.57 Hz), 8.10 (1H, d, J=8.05 Hz), 8.31 (1H, d, J=6.10 Hz), 8.35 (1H, d, J=7.57 Hz), 8.59 (1H, d, J=6.10 Hz), 9.25 (1H, s).

EXAMPLE 138

N-(2-Acetoxyethyl)-N-[2-(4-benzyloxycarbonyl-piperazinyl)-1-(p-methoxybenzyl)ethyl]-5-isoquinolinesulfonamide 1.0 g of the product obtained in Example 73 was dissolved in 5 ml of tetrahydrofuran, to the solution were added 220 mg of ethylene glycol monoacetate and 685 mg of triphenylphosphine in place of N-tert-butoxycarbonylethanolamine, according to the procedure described in Example 136, to obtain 600 mg of the title compound in a colorless amorphous form.

NMR (CDCl$_3$) δ ppm: 2.04 (3H, s), 2.20–2.45 (5H, m), 2.60–2.80 (3H, m), 3.20–3.40 (4H, m), 3.45–3.73 (2H, m), 3.74 (3H, s), 4.04 (1H, m), 4.27 (2H, t, J=6.84 Hz), 5.10 (2H, s), 6.54 (2H, d, J=8.55 Hz), 6.82 (2H, d, J=8.55 Hz), 7.34 (5H, s), 7.59 (1H, dd, J=8.05, 7.57 Hz), 8.13 (1H, d, J=8.05 Hz), 8.30 (1H, d, J=6.10 Hz), 8.36 (1H, d, J=7.57 Hz), 9.27 (1H, s).

EXAMPLE 139

N-[2-(4-Benzyloxycarbonylpiperazinyl)-1-(p-methoxybenzyl)ethyl}-N-(2-hydroxyethyl)-5-isoquinolinesulfonamide 600 mg of the amorphous compound obtained in Example 138 was dissolved in 6 ml of methanol and 3 ml of tetrahydrofuran, to the solution was added 6 ml of 1N sodium hydroxide aqueous solution, and the mixture was stirred at a room temperature for 2 hours. The reaction mixture was diluted with water and extracted twice with 50 ml of chloroform, and the extract was washed with saturated sodium chloride aqueous solution, dried over magnesium sulfate and evaporated to remove the solvent under a reduced pressure. Resulting oil was applied to a silica gel column and eluted with chloroform/methanol (100:1 to 50:1) to obtain 403 mg of the title compound in a colorless amorphous form.

IR (KBr) cm$^{-1}$: 1701, 1514, 1433, 1332, 1249, 1136;

NMR (CDCl$_3$) δ ppm: 2.10–2.25 (3H, m), 2.25–2.50 (4H, m), 2.50–2.70 (1H, m), 3.10–3.45 (5H, m), 3.55–3.75 (2H, m), 3.76 (3H, s), 4.00–4.20 (2H, m), 5.08 (2H, s), about 5.4 (1H, br), 6.70 (2H, d, J=8.79 Hz), 6.79 (2H, d, J=8.79 Hz), 7.32 (5H, s), 7.73 (1H, dd, J - 8.30, 7.32 Hz), 8.22 (1H, d, J=8.3 Hz), 8.50 (1H, d, J=7.32 Hz), 8.63 (1H, d, J=6.10 Hz), 8.72 (1H, d, J=6.10 Hz), 9.34 (1H, s).

EXAMPLE 140

N-{2-[4-(3,4-Dichlorobenzylamino)piperidino]-1-(p-methoxybenzyl)ethyl}-N-methyl-5-isoquinolinesulfonamide The amorphous compound obtained in Example 94 was subjected to alkaline hydrolysis, methylation with methyl iodide and potassium carbonate in dimethylformamide/tetrahydrofuran (1:1), and reflux with 3N hydrochloric acid, to obtain N-{1-(p-methoxybenzyl)2-(4-oxopiperidino)ethyl}-N-methyl-5-isoquinolinesulfonamide in a colorless amorphous form.

NMR (CDCl$_3$) δ ppm: 2.37 (4H, t, J=5.99 Hz), 2.40–2.90 (8H, m), 2.94 (3H, s), 3.74 (3H, s), 4.23 (1H, m), 6.51 (2H, d, J=8.55 Hz), 6.83 (2H, d, J=8.55 Hz), 7.55 (1H, dd, J=8.32, 7.50 Hz), 8.10 (1H, d, J=8.32 Hz), 8.19 (1H, d, J=7.50 Hz), 8.19 (1H, d, J=6.10 Hz), 8.55 (1H, d, J=6.10 Hz), 9.25 (1H, s).

3.34 g of this compound was dissolved in 30 ml of methanol, to the solution were added 1.89 g of 3,4-dichlorobenzylamine and 0.6 ml of acetic acid, and the mixture was stirred at a room temperature for 3 hours. The reaction mixture was cooled in a ice bath, and after adding 450 mg of sodium cyanoborohydride, stirred with ice cooling for 30 minutes and then at a room temperature for one hour. This reaction mixture was alkalized with sodium bicarbonate and extracted twice with 150 ml of chloroform, and the extract was dried over magnesium sulfate and evaporated to remove the solvent under a reduced pressure. Resulting oil was applied to a silica gel column and eluted with chloroform/methanol (100:1 to 50:1), to obtain 2.78 g of the title compound in a colorless amorphous form.

IR (KBr) cm$^{-1}$: 1514, 1327, 1249, 1157, 1130, 826, 600;

NMR (CDCl$_3$) δ ppm: 1.05–1.40 (2H, m), 1.60–2.15 (4H, m), 2.30–2.90 (8H, m), 2.93 (3H, s), 3.73 (5H, s), 4.13 (1H, m), 6.49 (2H, d, J=8.79 Hz), 6.83 (2H, d, J=8.79 Hz), 7.15 (1H, dd, J=8.20, 1.95 Hz), 7.38 (1H, d, J=8.20 Hz), 7.44 (1H, d, J=1.95 Hz), 7.56 (1H, dd, J=8.06, 7.57 Hz), 8.08 (1H, d, J=8.06 Hz), 8.19 (1H, d, J=6.35 Hz), 8.29 (1H, d, J=7.57 Hz), 8.55 (1H, d, J=6.35 Hz), 9.23 (1H, s).

EXAMPLE 141

N-2-{4-[N-(3,4-Dichlorobenzyl)-N-methylamino]-piperidino}-1-p-methoxybenzyl)ethyl]]-N-methyl-5-isoquinolinesulfonamide 1.62 g of the amorphous compound obtained in Example 140 was dissolved in 10 ml of tetrahydrofuran and 10 ml of dimethylformamide, to the solution was added 115 mg of 60% sodium hydride with stirring under ice cooling, and the mixture was allowed to react at the same temperature for 5 minutes and then at a room temperature for 15 minutes and again ice-cooled. After adding 405 mg of methyl iodide, the mixture was allowed to react at the same temperature for 5 minutes and then at a room temperature for 2 hours, and poured to water. The mixture was extracted with 200 ml of ethyl acetate, and the extract was washed with a saturated sodium chloride aqueous solution, dried over magnesium sulfate and evaporated to remove the solvent under a reduced pressure. Resulting oil was applied to a silica gel column and eluted with chloroform/methanol (200:1 to 100:1) to obtain 880 mg of the title compound in a colorless amorphous form.

IR (KBr) cm$^{-1}$: 1514, 1329, 1249, 1157, 1131, 826, 600;

NMR (CDCl$_3$) δ ppm: 1.10–2.10 (6H, m), 2.14 (3H, s), 2.20–3.00 (7H, m), 2.93 (3H, s), 3.46 (2H, s), 3.73 (3H, s), 4.12 (1H, m), 6.51 (2H, d, J=8.55 Hz), 6.85 (2H, d, J=8.55 Hz), 7.15 (1H, dd, J=8.30, 1.71 Hz), 7.37 (1H, d, J=8.30 Hz), 7.42 (1H, d, J=1.71 Hz), 7.56 (1H, t, J=7.82 Hz), 8.08 (1H, d, J=7.82 Hz), 8.20 (1H, d, J=6.11 Hz), 8.30 (1H, d, J=7.82 Hz), 8.56 (1H, d, J=6.11 Hz), 9.23 (1H, s).

REFERENCE EXAMPLE 39

4-Chlorocinnamyl alcohol 25.9 g of p-chlorocinnamic acid was dissolved in 250 ml of methanol, to the solution was added 1.5 ml of concentrated sulfuric acid, and the mixture was refluxed for 2 hours. The reaction mixture was poured on ice, and the mixture was alkalized with sodium bicarbonate and extracted twice with 1000 ml of chloroform. The extract was washed with a saturated sodium chloride aqueous solution, dried over magnesium sulfate and evaporated to remove the solvent under a reduced pressure, and resulting residue was applied to a silica gel column and eluted with hexane/ethyl acetate (10:1), to obtain 26.5 g of the methyl p-chlorocinnamate.

This compound was dissolved in 250 ml of toluene, to the solution was added 200 ml of 1.5M diisobutyl aluminum hydride in toluene with stirring under ice cooling, and the mixture was stirred for 2 hours. The reaction mixture was poured on ice, acidified with concentrated hydrochloric acid, and extracted twice with 700 ml of benzene. The extract was washed with a saturated sodium chloride aqueous solution, dried over magnesium sulfate and evaporated to remove the solvent under a reduced pressure, and resulting residue was applied to a silica gel column and eluted with hexane/ethyl acetate (4:1), to obtain 21.0 g of the title compound as colorless crystals, $^1$H-NMR (CDCl$_3$, δ ppm): 4.33 (2H, brs), 6.33 (1H, dt, J=17.1, 5.7 Hz), 6.59 (1H, dt, J=17.1, 2.0 Hz), 7.29 (4H, s).

REFERENCE EXAMPLE 40

N-4-Chlorocinnamyl-1,2-phenylenediamine 11.9 g of the crystals obtained in Reference Example 39 was dissolved in 120 ml of chloroform, to the solution was added 10.1 g of thionyl chloride with stirring in an ice bath, and after removing from the ice bath, the mixture was stirred for one hour while allowing the reaction temperature to rise up to a room temperature. Chloroform and excess thionyl chloride were evaporated off under a reduced pressure, to the residue was added benzene, and the solvent was evaporated off under a reduced pressure. Resulting residue was applied to a silica gel column and eluted with hexane/ethyl acetate (15:1), to obtain 11.3 g of 4-chlorocinnamyl chloride as colorless crystals.

$^1$H-NMR (CDCl$_3$, δ ppm): 4.23 (2H, dd, J=6.3, 1.0 Hz), 6.29 (1H, dt, J=16.6, 6.9 Hz), 6.62 (1H, dt, J=16.6, 1.0 Hz), 7.30 (4H, s).

19.6 g of 1,2-phenylenediamine was dissolved in 300 ml of dimethylformamide, to the solution were added 11.3 g of the above-prepared 4-chlorocinnamyl chloride crystals and 12.5 g of potassium carbonate at a room temperature with stirring, and the mixture was stirred for 48 hours under the same condition. After adding water and sodium chloride, the reaction mixture was extracted twice with 1000 ml of chloroform, and the extract was dried over magnesium sulfate and evaporated to remove the solvent under a reduced pressure. Resulting residue was applied to a silica gel column and eluted with hexane/ethyl acetate (3:1), to obtain 12.85 g of the title compound as colorless crystals.

$^1$H-NMR (CDCl$_3$, δ ppm): 3.4 (3H, brs), 3.93 (2H, dd, J=5.71, 1.0 Hz), 6.36 (1H, dt, J=16.0, 5.71 Hz), 6.59 (1H, dt, J=16.0, 1.0 Hz), 6.68–6.9 (4H, m), 7.28 (4H, s).

EXAMPLE 142

N-[2-(4-Chlorocinnamylamino)phenyl]-5-isoquinolinesulfonamide 12.85 g of the crystals obtained in Reference Example 40 was dissolved in 200 ml of pyridine, to the solution was added 15.1 g of 5-isoquinolinesulfonyl chloride, hydrochloride with stirring in a ice bath, and after removing from the ice bath, the mixture was allowed to react at a room temperature for 18 hours. The reaction mixture was poured on ice, alkalized with sodium bicarbonate and extracted twice with 1000 ml o chloroform. The extract was dried over magnesium sulfate and the solvent was evaporated off under a reduced pressure to form scarcely soluble crystals. To the crystals was added chloroform, the whole was refluxed and then cooled, and the resulting crystals was collected by suction filtration, washed with chloroform and dried under a reduced pressure, to obtain 17.23 g of the title compound as colorless crystals.

Melting point: 205°–208° C. (decomposed);

IR (KBr) cm$^{-1}$: 1600, 1320, 1150, 1135;

$^1$H-NMR (CDCl$_3$+CD$_3$OD, δ ppm): 3.73 (2H, dd, J=5.62, 1.46 Hz), 6.04 (1H, dt, J=15.8, 5.37 Hz), 6.27–6.35 (2H, m), 6.42 (1H, dt, J=16.11, 1.46 Hz), 6.58 (1H, d, J=7.81 Hz), 7.04 (1H, ddd, J=8.30, 6.10, 2.93 Hz), 7.25 (2H, d, J=9.03 Hz), 7.31 (2H, d, J=9.03 Hz), 7.63 (1H, dd, J=8.06, 7.33 Hz), 8.17 (1H, dd, J=7.32, 0.98 Hz), 8.30 (1H, dd, J=7.57, 1.23 Hz), 8.47 (1H, dd, J=6.35, 1.02 Hz), 8.55 (1H, d, J=6.35 Hz), 9.25 (1H, d, J=0.98 Hz).

EXAMPLE 143

N-[2-(4-Chlorocinnamylamino)phenyl]-N-methyl-5-isoquinolinesulfonamide 380 mg of the crystals obtained in Example 142 was dissolved in 6 ml of methanol, to the solution was added 10 ml of a solution of diazomethane in ether at a room temperature with stirring, and the mixture was stirred for 18 hours. The solvent was evaporated off under a reduced pressure to obtain an oil, which was then applied to a silica gel column and eluted with hexane/ethyl acetate (1:1) to obtain acetate, which was then recrystallized from hexane/ethyl acetate to obtain 270 mg of the title compound as colorless crystals.

Melting point: 149°–151° C.;

IR (KBr) cm$^{-1}$: 1595, 1325, 1125, 830, 745;

$^1$H-NMR (CDCl$_3$, δ ppm): 3.24 (3H, s), 3.87 (2H, m), 4.81 (1H, t, J=5.71 Hz), 6.13 (1H, dt, J=19.14, 5.71 Hz), 6.25–6.40 (2H, m), 6.53 (1H, dt, J=19.14, 1.0 Hz), 6.67 (1H, d, J=8.57 Hz), 7.05–7.18 (1H, m), 7.28 (4H, s), 7.67 (1H, t, J=7.42 Hz), 8.19 (1H, d, J=7.42 Hz), 8.28 (1H, d, J=6.28 Hz), 8.32 (1H, dd, J=7.42, 1.0 Hz), 8.51 (1H, d, J=6.28 Hz), 9.30 (1H, d, ( J=1.0 Hz).

EXAMPLE 144

1-(4-Chlorocinnamyl)-4-(5-isoquinolinesulfonyl)-1,2,3,4-tetrahydroquinoxaline 5.0 g of the crystals obtained in Example 142 was dissolved in 75 ml of dimethylformamide, to the solution was added 4.6 g of potassium carbonate and 2.19 g of 1,2-dibromoethane at a room temperature with stirring, and the mixture was stirred for 60 hours. The reaction mixture was poured in water, saturated with sodium chloride, and extracted twice with 400 ml of chloroform. The extract was dried over magnesium sulfate, evaporated to remove the solvent under a reduced pressure. Resulting residue was applied to a silica gel column and eluted with chloroform/methanol (400:1) and then hexane/ethyl acetate (2:1), to obtain 3.32 g of the title compound in yellow amorphous form.

IR (KBr) cm$^{-1}$: 1600, 1340, 1150, 1130, 660;

$^1$H-NMR (CDCl$_3$, δ ppm): 2.68 (2H, t, J=5.71 Hz), 3.49 (2H, dd, J=6.28, 1.0 Hz), 3.89 (2H, t, J=5.71 Hz), 5.43 (1H, dt, J=15.42, 6.28 Hz), 6.10 (1H, dt, J=15.42, 1.0 Hz), 6.48 (1H, dd, J=7.99, 1.0 Hz), 6.75 (1H, dt, J=7.99, 1.0 Hz), 7.09 (2H, d, J=7.99 Hz), 7.12 (1H, dt, J=7.99, 1.0 Hz), 7.31 (2H, d, J=7.99 Hz), 7.54 (1H, dd, J=7.99, 1.0 Hz), 7.59 (1H, t, J=7.99 Hz), 7.77 (1H, d, J=6.28 Hz), 7.94 (1H, d, J=7.99 Hz), 8.30 (1H, d, J=6.28 Hz), 8.38 (1H, dd, J=7.99, 1.0 Hz), 9.03 (1H, d, J=1.0 Hz).

EXAMPLE 145

The same procedure as described in Example 142 was repeated except that N-[3-(3-pyridyl)allyl]-1,2-phenylenediamine was used in place of N-(4-chlorocinnamyl)-1,2-phenylenediamine, to obtain N-{2-[3-(3-pyridyl)allylamino]phenyl}-5-isoquinolinesulfonamide in a brown amorphous form.

$^1$H-NMR (CDCl$_3$, δppm): 2.2 (1H, br), 3.78 (2H, dd, J=5.14, 1.0 Hz), 4.85 (1H, br), 6.14 (1H, dt, J=15.99, 5.14 Hz), 6.33 (2H, d, J=4.57 Hz), 6.42 (1H, dt, J=15.99, 1.0 Hz), 6.58 (1H, d, J=7.42 Hz), 6.98–7.15 (1H, m), 7.26 (1H, dd, J=7.42, 4.57 Hz), 7.59 (1H, t, J=7.42 Hz), 7.65 (1H, dt, J=7.42, 1.0 Hz), 8.16 (1H, d, J=7.99 Hz), 8.30 (1H, d, J=6.85 Hz), 8.35–8.53 (3H, m), 8.56 (1H, d, J=6.28 Hz), 9.32 (1H, s).

EXAMPLE 146

The amorphous compound obtained in Example 145 was treated according to the procedure in Example 143 to obtain N-{2-[3-(3-pyridyl)allylamino)phenyl}-N-methyl-5-isoquinolinesulfonamide.

$^1$H-NMR (CDCl$_3$, δ ppm): 3.24 (3H, s), 3.92 (2H, t, J=4.57 Hz), 4.90 (1H, t, J=5.71 Hz), 6.26 (1H, dt, J=15.42, 5.14 Hz), 6.32 (2H, d, J=4.57 Hz), 6.58 (1H, dt, J=15.42, 1.0 Hz), 6.62–6.74 (2H, m), 7.05–7.20 (1H, m), 7.26 (1H, dd, J=7.99, 4.57 Hz), 7.6–7.75 (1H, m), 8.21 (1H, d, J=7.99 Hz), 8.28 (1H, d, J=6.85 Hz), 8.32 (1H, d, J=6.28 Hz), 8.47 (1H, dd, J=5.71, 1.0 Hz), 8.51 (1H, d, J=6.28 Hz), 8.58 (1H, d, J=1.7 Hz), 9.31 (1H, s).

REFERENCE EXAMPLE 41

2-Amino-3-(4-chlorocinnamylamino pyridine 7.71 g of p-chlorocinnamyl chloride and 13.5 g of 2,3-diaminopyridine were dissolved in 220 ml of dimethylformamide, and to the solution was added 8.6 g of potassium carbonate, and the mixture was stirred at a room temperature for 50 hours, and after adding 300 ml of water, extracted twice with 200 ml of chloroform. The extract was dried over magnesium sulfate and concentrated under a reduced pressure, and resulting residue was applied to a silica gel column and eluted with chloroform/methanol (100:1 to 50:1), to obtain 4.52 g of the title compound as yellow crystals.

$^1$H-NMR (CDCl$_3$, δ ppm): 3.38 (1H, br), 3.92 (2H, m), 4.20 (2H, br), 6.31 (1H, dt, J=16.1, 5.9 Hz), 6.59 (1H, dt, J=16.1, 1.5 Hz), 6.71 (1H, dd, J=4.9, 7.8 Hz), 6.86 (1H, dd, J=1.5, 7.8 Hz), 7.29 (4H, s), 7.63 (1H, dd, J=1.5, 4.9 Hz).

EXAMPLE 147

3-(4-Chlorocinnamylamino)-2-(5-isoquinolinesulfonylamino)pyridine 4.52 g of the crystals obtained in Reference Example 41 was dissolved in 50 ml of pyridine, to the solution were added 5.8 g of 5-isoquinolinesulfonyl chloride hydrochloride and 3 g of dimethylaminopyridine, and the mixture was stirred for 18 hours at a room temperature, after adding 150 ml of water, extracted twice with 80 ml of chloroform. The extract was dried over magnesium sulfate and concentrated under a reduced pressure, and resulting residue was applied to a silica gel column and eluted with chloroform/methanol (100:1), and resulting crystals was washed with ethyl acetate, to obtain 1.2 g of the title compound as yellow crystals.

Melting point: 211°–217° C. (decomposed);

IR (KBr) cm$^{-1}$: 1595, 1550, 1345, 1285, 1250, 1105;

$^1$H-NMR (CDCl$_3$, δ ppm): 3.89 (2H, m), 5.45 (1H, t, J=5.9 Hz), 6.12 (1H, dt, J=16.1, 5.4 Hz), 6.45 (1H, d, J=16.1 Hz), 6.51–6.62 (2H, m), 6.92 (1H, brs), 7.21 (2H, d, J=8.8 Hz), 7.29 (2H, d, J=8.8 Hz), 7.64 (1H, dd, J=7.3, 8.3 Hz), 8.12 (1H, d, J=8.3 Hz), 8.45 (1H, dd, J=1.0, 7.3 Hz), 8.64 (1H, d, J=5.9 Hz), 8.69 (1H, d, J=5.9 Hz), 9.31 (1H, s).

REFERENCE EXAMPLE 42

Methyl 4-amino-3-(4-chlorocinnamylamino)benzoate 5.0 g of methyl 3,4-diaminobenzoate was dissolved in 40 ml of dimethylformamide, and to the solution were added 2.07 g of potassium carbonate and 1.87 g of p-chlorocinnamyl chloride, and reaction was carried out according to the procedure in Reference Example 40, to obtain 2.0 g of the title compound as a light brown oil.

NMR (CDCl$_3$) δ ppm: 3.85 (3H, s), 3.94 (2H, brd), 6.35 (1H, dt, J=5.86, 15.8 Hz), 6.59 (1H, d, J=5.8 Hz), 6.7 (1H, d, J=8.02 Hz), 7.28 (4H, s), 7.4 (1H, d, J=1.4 Hz), 7.46 (1H, dd, J=1.4, 8.0 Hz).

EXAMPLE 148

Methyl 4-(5-isoquinolinesulfonamino)-3-(4-chlorocinnamylamino)benzoate 1.8 g of the oil obtained in Reference Example 42 was dissolved in 18 ml of pyridine, to the solution was added 1.29 g of 5-isoquinolinesulfonyl chloride hydrochloride with stirring under ice cooling, and the mixture was treated according to the procedure in Example 142 to obtain residue, which was then applied to a silica gel column and eluted with chloroform/methanol (100:1), to obtain 1.28 g of the title compound as light yellow crystals.

Melting point: 143°–145° C. (subliming at a higher temperature than melting point);

NMR (CDCl$_3$) δ ppm: 3.78 (2H, brd), 3.82 (3H, s), 6.0 (1H, dt, J=5.86, 15.87 Hz), 6.4 (1H, d, J=15.8 Hz), 6.45

(1H, d, J=8.3 Hz), 7.05 (1H dd, J=1.8, 8.3 Hz), 7.2–7.3 (5H, brs}, 7.60 (1H, t, J=7.6 Hz), 8.15 (1H, d, J=8.3 Hz), 8.29 (1H, dd, J=1.2, 7.3 Hz), 8.43 (1H, d, J=6.1 Hz), 8.61 (1H, d, J=6.1 Hz), 9.3 (1H, d, J=1.2 Hz).

REFERENCE EXAMPLE 43

N-Cinnamyl-1,2-phenylenediamine 3.24 g of ortho-phenylenediamine was dissolved in 30 ml of dimithylformaide, to the solution were added 2.07 g of potassium carbonate and 1.52 g of cinnamyl chloride, and the mixture was stirred overnight at a room temperature. After adding 100 ml of water, the reaction mixture was extracted twice with 100 ml and 50 ml of chloroform, and the extract was washed with a saturated sodium chloride aqueous solution, dried over magnesium sulfate and evaporated to remove the solvent under a reduced pressure. The resulting residue was applied to a silica gel column and eluted with chloroform, to obtain 2.0 g of the title compound as light brown crystals.

Melting point: 59°–66° C. (decomposed);

NMR (CDCl$_3$) δ ppm: 3.3 (2H, brs), 3.93 (2H, brd), 6.4 (1H, d and t, J=5.6, 16.1 Hz), 6.1–6.45 (4H, complex) 5.2–5.7 (5H, complex).

EXAMPLE 149

N-(2-Cinnamylamino)phenyl-5-isoquinolinesulfonamide 1.8 g of the crystals obtained in Reference Example 43 was dissolved in 18 ml of pyridine, to the solution was added 1.83 g of isoquinolinesulfonyl chloride hydrochloride, and the mixture was stirred for 18 hours at a room temperature. After adding 50 ml of water, the reaction mixture was extracted twice with 80 ml of chloroform, and the extract was washed with a saturated sodium chloride aqueous solution, dried over magnesium sulfate and evaporated to remove the solvent under a reduced pressure. The resulting residue was applied to a silica gel column and eluted with chloroform/methanol (100:1), to obtain 2.40 g of the title compound as pale reddish crystals.

Melting point: 181°–185° C.;

NMR (CDCl$_3$) δ ppm: 3.75 (2H, brd), 4.55 (1H, brs), 6.05 (1H, d and t, J=5.6, 16.1 Hz), 6.35 (2H, brd), 6.45 (1H, d, J=16.1 Hz) 6.63 (1H, d, J=8.3 Hz), 7–7.13 (1H, complex), 7.25–7.4 (5H, complex), 7.6 (1H, t, J=8.2 Hz), 8.15 (1H, d, J=8.3 Hz), 8.31 (1H, dd, J=1.0, 8.2 Hz), 8.4 (1H, d, J=6.6 Hz), 8.65 (1H, d, J=6.6 Hz), 9.3 (1H, d, J=1.0 Hz).

REFERENCE EXAMPLE 44

N-(4-Chlorocinnamyl)-1,3-phenylenediamine 3.24 g of metha-phenylenediamine was dissolved in 40 ml of dimethylformamide, to the solution were added 2.07 g of potassium carbonate and 1.87 g of p-chlorocinnamyl chloride, and the mixture was subjected to react according to the procedure in Reference Example 40. The resulting residue was applied to a silica gel column and eluted with n-hexane/ethyl acetate (3:1 to 2:1), to obtain 1.70 g of the title compound as a light brown oil.

NMR (CDCl$_3$) δ ppm: 3.65 (2H, brs), 3.90 (2H, dd, J=1.4, 5.6 Hz), 6.0–6.2 (3H, complex), 6.3 (1H, dd, J=5.6, 15.9 Hz), 6.56 (1H, dd, J=1.4, 15.9 Hz), 6.97 (1H, t, J=8.1 Hz), 7.3 (4H, s).

EXAMPLE 150

N-3-(4-Chlorocinnamylamino)phenyl]-5-isoquinolinesulfonamide 1.7 g of the oil obtained in Reference Example 44 was dissolved in 18 ml of pyridine, to the solution was added 1.99 g of 5-isoquinolinesulfonyl chloride.HCl with stirring under a ice cooling, and the same procedure as described in Example 142 was repeated to obtain 1.45 g of the title compound as a light brown oil.

NMR (CDCl$_3$)δ ppm: 3.8 (2H, brd), 3.92 (1H, brs), 6.15 (1H, d and t, J=5.6, 15.9 Hz), 6.25 (1H, brs), 6.35 (2H, brd), 6.49 (1H, d, J=15.9 Hz), 6.92 (1H, t, J=8.1 Hz), 7.3 (4H, s), 7.51 (1H, t, J=8.3 Hz), 8.1 (1H, d, J=8.3 Hz), 8.35 (1H, dd, J=1.0, 8.3 Hz), 8.45 (1H, d, J=6 1 Hz), 8.65 (1H, d, J=6.4 Hz), 9.3 (1H, d, J=1.0 Hz).

EXAMPLE 151

N-{2-(p-Chlorocinnamylamino)phenyl}-N-(2-hydroxyethyl)-5-isoquinolinesulfonamide 1.5 g of the crystals obtained in Example 142 was dissolved in 8 ml of tetrahydrofuran, to the solution were added 1.32 g of triphenylphosphine and 420 mg of ethylene glycol monoacetate, and also added dropwise a solution of 1.01 g of diisopropyl azodicarboxylate in 2 ml of tetrahydrofuran with stirring in a ice bath. After being removed from the ice bath, the mixture was warmed to a room temperature, stirred for 3 hours, diluted with ethyl acetate and extracted twice with 70 ml of 2N hydrochloric acid. The aqueous layer was alkalized with sodium bicarbonate and extracted twice with 150 ml of chloroform, and the extract was dried over magnesium sulfate and evaporated under a reduced pressure to remove the solvent. Resulting oily residue was dissolved in 20 ml of methanol and 20 ml of tetrahydrofuran, to the solution was added 20 ml of 1N sodium hydroxide aqueous solution, and the reaction was carried out at a room temperature for 2 hours. The reaction mixture was diluted with water and extracted twice with 100 ml and 50 ml each of chloroform, and the extract was dried over magnesium chloride and evaporated under a reduced pressure to remove the solvent. The resulting oil was applied to a silica gel column and eluted with chloroform/methanol (100:1 to 50:1), to obtain 1.59 g of the title compound in a yellow amorphous form.

IR (KBr) cm$^{-1}$=1603, 1516, 1491, 1342, 1161, 1139, 835, 758, 604, 509;

NMR (CDCl$_3$) δ ppm: 3.09 (1H, m), 3.29 (1H, ddd, J=13.43, 4.64, 3.18 Hz), 3.47 (1H, m), 3.75 (1H, m), 3.85 (2H, m), 4.33 (1H, ddd, J=13.43, 8.30, 4.15 Hz), 5.12 (1H, m), 6.16 (1H, dt, J=15.87, 5.62 Hz), 6.23 (1H, dd, J=8.06, 1.47 Hz), 6.40 (1H, td, J=7.33, 1.47 Hz), 6.55 (1H, d, J=16.11 Hz), 6.76 (1H, d, J=8.54 Hz), 7.15 (1H, t, J=8.30 Hz), 7.29 (4H, s), 7.63 (1H, t, J=8.30 Hz), 8.18 (1H, d, J=8.30 Hz), 8.28 (1H, d, J=8.30 Hz), 8.28 (1H, d, J=6.35 Hz), 8.52 (1H, d, J=6.3 Hz), 9.31 (1H, s).

EXAMPLE 152

N-{2-(p-Chlorocinnamylamino)phenyl}-N-(2-dimethylaminoethyl)-5-isoquinolinesulfonamide 2.0 g of the crystals obtained in Example 142 was dissolved in 10 ml of tetrahydrofuran, to the solution were added 1.75 g of triphenylphosphine and 520 mg of N,N-dimethyl ethanolamine, and thereto added dropwise a solution of 1.3 g of diisopropyl azodicarboxylate in 3 ml of being tetrahydrofuran with stirring in ice bath. After being removed from the ice bath, the mixture was warmed to a room temperature, stirred for 3 hours, and then diluted with ethyl acetate, and extracted twice with 100 ml of 2 N hydrochloric acid. The extract was alkalized with a sodium bicarbonate aqueous solution and extracted twice with 200 ml of chloroform. The extract was dried over magnesium sulfate and evaporated under a reduced pressure to remove the solvent, and a resulting oil was applied to a silica gel column and eluted with chloroform/methanol (100:1), to obtain 1.35 g of the title compound in a yellow amorphous form.

IR (KBr) cm$^{-1}$: 1603, 1521, 1491, 1458, 1329, 1160, 1137, 834, 749, 601, 507;

NMR (CDCl$_3$) δ ppm: 2.19 (6H, s), 2.15-2.55 (2H, m), 3.19 (1H, dt, J=12.69, 4.15 Hz), 3.56 (2H, m), 4.35 (1H, m), 5.78 (1H, m), 5.89 (1H, dt, J=15.87, 5.37 Hz), 6.30-6.55 (3H, m), 6.64 (1H, dd, J=7.81, 1.71 Hz), 7.09 (1H, td, J=7.81, 1.71 Hz), 7.23 (2H, d, J=9.03 Hz), 7.30 (2H, d, J=9.03 Hz), 7.57 (1H, dd, J=8.30, 7.57 Hz), 8.11 (1H, d, J=8.30 Hz), 8.24 (1H, d, J=7.57 Hz), 8.40 (1H, d, J=6.35 Hz), 8.53 (1H, d, J=6.35 Hz), 9.26 (1H, s).

EXAMPLES 153 TO 171

In Example 153 to 171 the following general reaction was used.

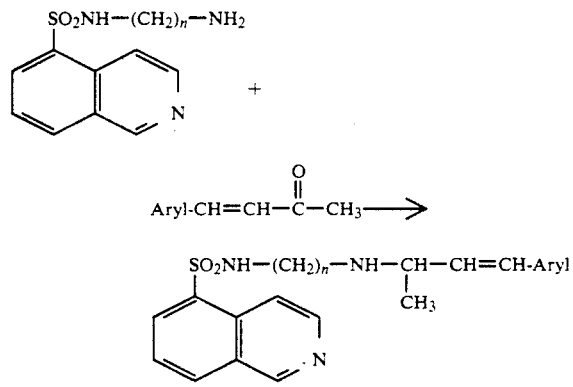

EXAMPLE 153

(n=2, Aryl=4-chlorophenyl)
N-[2-(4-Chloro-α-methylcinnamylamino)ethyl]-5-isoquinolinesulfonamide 7.30 g of N-(2-aminoethyl)-5-isoquinolinesulfonamide was dissolved in 150 ml of methanol, to the solution was added 6.30 g of p-chlorobenzalacetone, and the mixture was stirred at a room temperature for 36 hours. After addition of 1.32 g of sodium tetrahydrideborate with ice-water cooling, the mixture was stirred for 30 minutes. The reaction mixture was concentrated to half of original volume under a reduced pressure, and after adding 300 ml of ethyl acetate, washed three times with water. The aqueous layer was extracted with 100 ml of ethyl acetate, and the extract was washed with water as described above. The ethyl acetate layers were combined, washed twice with a saturated sodium chloride aqueous solution, dried over magnesium sulfate, filtered, and evaporated under a reduced pressure to remove the solvent. The resulting residue was purified using a silica gel column (silica gel: 200 g; eluant: 5% methanol in chloroform), to obtain 6.78 g of the title compound in a colorless amorphous form, while recovering the residual starting material.

$^1$H-NMR (CDCl$_3$, δ ppm): 1.06 (3H, d, J=6.6 Hz), 1.8-2.8 (2H, br), 2.57-2.64 (2H, m), 2.96 (2H, t, J=5.7 Hz), 3.06 (1H, dq, J=7.8, 6.6 Hz), 5.79 (1H, dd, J=15.8, 7.8 Hz), 6.24 (1H, d, J=15.8 Hz), 7.19 (2H, dm, J=8.8 Hz), 7.25 (2H, dm, J=8.8 Hz), 7.67 (1H, dd, J=8.0, 7.6 Hz), 8.28 (1H, dt, J=8.0, 1.0 Hz), 8.42-8.46 (2H, m), 8.69 (1H, d, J=6.1 Hz), 9.35 (1H, d, J=1.0 Hz).

EXAMPLE 154

(n=2, Aryl=phenyl)
N-[2-(α-Methylcinnamylamino)ethyl]-5-isoquinolinesulfonamide

Colorless amorphous form;
$^1$H-NHR (CDCl$_3$, δ ppm): 2.0-3.0 (2H, br), 2.59-2.66 (2H, m), 2.98 (2H, t, J=5.5 Hz), 3.09 (1H, dq, J=8.0, 6.6 Hz), 5.80 (1H, dd, J=15.9, 8.0 Hz), 6.28 (1H, d, J=15.9 Hz), 7.28 (5H, brs), 7.66 (1H, dd, J=8.3, 7.3 Hz), 8.17 (1H, brd, J=8.3 Hz), 8.43 (1H, dd, J=7.3, 1.2 Hz), 8.44 (1H, d, J=6.1 Hz), 8.68 (1H, d, J=6.1 Hz), 9.34 (1H, d, J=1.0 Hz).

EXAMPLE 155

(n=2, Aryl=2,4-difluorophenyl)
N-[2-(2,4-Difluoro-α-methylcinnamylamino)ethyl]-5-isoquinolinesulfonamide Colorless amorphous form;
$^1$H-NMR (CDCl$_3$, δ ppm): 1.06 (3H, d, J=6.4 Hz), 1.3-2.2 (2H, br), 2.57-2.67 (2H, m), 2.96 (2H, t, J=5.6 Hz), 3.04 (1H, dq, J=8.0, 6.4 Hz), 5.81 (1H, dd, J=16.1, 8.0 Hz), 6.35 (1H, d, J=16.1 Hz), 6.79 (1H, d, J=8.3 Hz and 1H, ddd, J=17.6, 8.8, 2.0 Hz), 7.30 (1H, ddd, J=14.9, 8.3, 2.0 Hz), 7.69 (1H, dd, J=8.3, 7.3 Hz), 8.29 (1H, dt, J=8.3, 1.0 Hz), 8.42-8.47 (2H, m), 8.70 (1H, d, J=6.1 Hz), 9.35 (1H, d, J=1.0 Hz).

EXAMPLE 156

(n=2, Aryl=2,4-dichlorophenyl)
N-2-(2,4-Dichloro-α-methylcinnamylamino)ethyl]-5-isoquinolinesulfonamide Colorless amorphous form;
$^1$H-NMR (CDCl$_3$, δ ppm): 1.07 (3H, d, J=6.6 Hz), 1.5-2.5 (2H, br), 2.58-2.65 (2H, m), 2.97 (2H, t, J=5.5 Hz), 3.09 (1H, dq, J=8.0, 6.6 Hz), 5.75 (1H, dd, J=15.8, 8.0 Hz), 6.58 (1H, d, J=15.8 Hz), 7.18 (1H, dd, J=8.5, 2.0 Hz), 7.28 (1H, d, J=8.5 Hz), 7.35 (1H, d, J=2.0 Hz), 7.68 (1H, dd, J=8.0, 7.3 Hz), 8.18 (1H, td, J=8.0, 1.0 Hz), 8.42-8.47 (2H, m), 8.70 (1H, d, J=6.1 Hz), 9.34 (1H, d, J=1.0 Hz).

EXAMPLE 157

(n=2, Aryl=3-chlorophenyl)
N-[2-(3-Chloro-α-methylcinnamylamino)ethyl]-5-isoquinolinesulfonamide Colorless amorphous form;
$^1$H-NMR (CDCl$_3$, δ ppm): 1.06 (3H, d, J=6.6 Hz), 1.3-2.4 (2H, br), 2.56-2.63 (2H, m), 2.97 (2H, t, J, 5.6 Hz), 3.06 (1H, dq, J=7.8, 6.6 Hz), 5.80 (1H, dd, J=15.9, 7.8 Hz), 6.22 (1H, d, J=15.9 Hz), 7.10-7.26 (4H, m), 7.68 (1H, dd, J=8.1, 7.5 Hz), 8.18 (1H, dt, J=8.1, 1.0 Hz), 8.42-8.47 (2H, m), 8.70 (1H, d, J=6.1 Hz), 9.35 (1H, d, J=1.0 Hz).

EXAMPLE 158

(n=2, Aryl=2-nitrophenyl)
N-[2-(α-Methyl-2-nitrocinnamylamino)ethyl]-5-isoquinolinesulfonamide Light yellow amorphous form;
$^1$H-NMR (CDCl$_3$, δ ppm): 1.08 (3H, d, J=6.4 Hz), 1.3–2.6 (2H, br), 2.61–2.67 (2H, m), 2.99 (2H, t, J=5.6 Hz), 3.09 (1H, dq, J=7.8, 6.4 Hz), 5.73 (1H, dd, J=15.6, 7.8 Hz), 6.73 (1H, d, J=15.6 Hz), 7.36–7.56 (3H, m), 7.68 (1H, dd, J=8.3, 7.3 Hz), 7.92 (1H, dd, J=7.9, 1.2 Hz), 8.42–8.47 (2H, m), 8.67 (1H, d, J=6.1 Hz), 9.31 (1H, d, J=1.0 Hz).

EXAMPLE 159

(n=2, Aryl=4-nitrophenyl)
N-[2-(α-Methyl-4-nitrocinnamylamino)ethyl]-5-isoquinolinesulfonylamide Light yellow amorphous form;
$^1$H-NMR (CDCl$_3$, δ ppm): 1.10 (3H, d, J=6.6 Hz), 1.4–2.6 (2H, br), 2.60–2.67 (2H, m), 2.99 (2H, t, J=5.5 Hz), 3.14 (1H, dq, J=7.6, 6.6 Hz), 6.05 (1H, dd, J=15.9, 7.6 Hz), 6.38 (1H, d, J=15.9 Hz), 7.40 (2H, dm, J=8.8 Hz), 7.69 (1H, dd, J=8.3, 7.5 Hz), 8.14 (2H, dm, J=8.8 Hz), 8.23 (1H, brd, J=8.3 Hz), 8.43–8.48 (2H, m), 8.68 (1H, d, J=6.1 Hz), 9.36 (1H, d, J=1.0 Hz).

EXAMPLE 160

(n=2, Aryl=4-methylphenyl)
N-[2-(α,4-Dimethylcinnamylamino)ethyl]-5-isoquinolinesulfonamide Colorless amorphous form;
$^1$H-NMR (CDCl$_3$, δ ppm): 1.05 (3H, d, J=6.6 Hz), 2.0–2.5 (2H, br), 2.33 (3H, s), 2.56–2.64 (2H, m), 2.96 (2H, t, J=5.9 Hz), 3.05 (1H, m), 5.73 (1H, dd, J=15.9, 7.8 Hz), 6.24 (1H, d, J=15.9 Hz), 7.09 (2H, brd, J=8.3 Hz), 7.16 (2H, brd, J=8.3 Hz), 7.67 (1H, t, J=8.0 Hz), 8.17 (1H, brd, J=8.0 Hz), 8.43 (1H, d, J=8.0 Hz), 8.44 (1H, d, J=6.1 Hz), 8.68 (1H, d, J=6.1 Hz), 9.34 (1H, d, J=1.0 Hz).

EXAMPLE 161

(n=2, Aryl=3,4-methylenedioxyphenyl)
N-[2-(α-Methyl-3,4-methylenedioxycinnamylamino)ethyl]-5-isoquinolinesulfonamide Colorless amorphous form;
$^1$H-NMR (CDCl$_3$, δppm): 1.04 (3H, d, J=6.3 Hz), 2.56–2.63 (2H, m), 2.95 (2H, t, J=5.6 Hz), 3.05 (1H, dq, J=8.0, 6.3 Hz), 5.60 (1H, dd, J=15.9, 8.0 Hz), 5.95 (2H, s), 6.18 (1H, d, J=15.9 Hz), 6.70 (1H, dd, J=7.5, 1.5 Hz), 6.73 (1H, d, J=7.5 Hz), 6.79 (1H, d, J=1.5 Hz), 7.68 (1H, dd, J=8.1, 7.5 Hz), 8.19 (1H, brd, J=8.1 Hz), 8.42–8.46 (2H, m), 8.69 (1H, d, J=6.1 Hz), 9.35 (1H, d, J=1.0 Hz).

EXAMPLE 162

(n=2, Aryl=2-pyridyl)
N-{2-[1-Methyl-3-(2-pyridyl)-2-propenylamino]ethyl}-5-isoquinolinesulfonamide $^1$H-NMR (CDCl$_3$, δ ppm): 1.07 (3H, d, J=6.6 Hz), -4.0 (2H, br), 2.62 (2H, dt, J=5.7, 5.7 Hz), 2.97 (2H, t, J=6.4 Hz), 3.06 (1H, dq, J=5.6, 6.6 Hz), 6.35 (1H, d, J=5.6 Hz), 6.37 (1H, s), 7.12 (1H, dddd, J=7.8, 5.0, 2.0, 1.0 Hz), 7.21 (1H, d, J=7.8 Hz), 7.62 (1H, td, J=7.8, 2.0 Hz), 7.68 (1H, dd, J=8.0, 7.3 Hz), 8.18 (1H, brd, J=8.0 Hz), 8.44 (1H, d, J=7.3 Hz), 8.45 (1H, d, J=7.3 Hz), 8.52 (1H, ddd, J=5.0, 2.0, 1.0 Hz), 8.67 (1H, d, J=6.1 Hz), 9.34 (1H, d, J=1.0 Hz).

EXAMPLE 163

(n=2, Aryl=4-pyridyl)
N-{2-[1-Methyl-3-(4-pyridyl)-2-propenylamino]ethyl}-5-isoquinolinesulfonylamide Colorless amorphous form;
$^1$H-NMR (CDCl$_3$, δ ppm): 1.09 (3H, d, J=6.3 Hz), 1.2–1.9 (2H, br), 2.59–2.65 (2H, m), 2.98 (2H, t, J=6.0 Hz), 3.12 (1H, dq, J=7.3, 6.3 Hz), 6.06 (1H, dd, J=15.9, 7.3 Hz), 6.26 (1H, d, J=15.9 Hz), 7.14 (2H, dd, J=6.1, 1.5 Hz), 7.69 (1H, dd, J=8.1, 7.5 Hz), 8.19 (1H, brd, J=8.1 Hz), 8.42–8.47 (2H, m), 8.51 (2H, dd, J=6.1, 1.5 Hz), 8.68 (1H, d, J=6.3 Hz), 9.35 (1H, d, J=1.0 Hz).

EXAMPLE 164

(n=2, Aryl=2-thienyl)
N-{2-[1-Methyl-3-(2-thienyl)-2-propenylamino]ethyl}-5-isoquinolinesulfonamide Colorless amorphous form;
$^1$H-NMR (CDCl$_3$, δ ppm): 1.05 (3H, d, J=6.6 Hz), 1.2–2.5 (2H, br), 2.56–2.64 (2H, m), 2.93–3.05 (3H, m), 5.65 (1H, dd, J=15.6, 8.0 Hz), 6.41 (1H, d, J=15.6 Hz), 6.85 (1H, dd, J=3.7, 2.4 Hz), 6.94 (1H, dd, J=4.9, 3.7 Hz), 7.13 (1H, dd, J=4.9, 2.4 Hz), 7.68 (1H, dd, J=8.3, 7.5 Hz), 8.19 (1H, brd, J=8.3 Hz), 8.42–8.46 (2H, m), 8.69 (1H, d, J=6.1 Hz), 9.35 (1H, d, J=1.0 Hz).

EXAMPLE 165

(n=2, Aryl=2-furyl)
N-{2-[3-(2-Furyl)-1-methyl-2-propenylamino]ethyl}-5-isoquinolinesulfonamide Colorless amorphous form;
$^1$H-NMR (CDCl$_3$, δ ppm): 1.04 (3H, d, J=6.4 Hz), 1.3–1.5 (2H, br), 2.59 (2H, td, J=6.0, 4.9 Hz), 2.95 (2H, t, J=6.0 Hz), 2.98 (1H, dq, J=7.8, 6.4 Hz), 5.75 (1H, dd, J=15.9, 7.8 Hz), 6.10 (1H, d, J=15.9 Hz), 6.16 (1H, d, J=3.2 Hz), 6.35 (1H, dd, J=3.2, 1.9 Hz), 7.32 (1H, d, J=1.9 Hz), 7.68 (1H, dd, J=8.3, 7.5 Hz), 8.19 (1H, brd, J=8.3 Hz), 8.42–8.47 (2H, m), 8.69 (1H, d, J=6.1 Hz), 9.35 (1H, d, J=1.0 Hz).

EXAMPLE 166

(n=2, Aryl=4-fluorophenyl)
N-[2-(4-Fluoro-α-methylcinnamylamino)ethyl]-5-isoquinolinesulfonamide Colorless amorphous form;
$^1$H-NMR (CDCl$_3$, δ ppm): 1.06 (3H, d, J=6.4 Hz), 1.3–2.0 (2H, br), 2.57–2.63 (2H, m), 2.95 (2H, t, J=5.5 Hz), 3.05 (1H, dq, J=8.0, 6.4 Hz), 5.72 (1H, dd, J=15.9, 8.0 Hz), 6.25 (1H, d, J=15.9 Hz), 6.98 (2H, tm, J=8.7 Hz), 7.20–7.27 (2H, m), 7.68 (1H, dd, J=8.1, 7.3 Hz), 8.18 (1H, brd, J=8.1 Hz), 8.42–8.47 (2H, m), 8.69 (1H, d, J=6.1 Hz), 9.35 (1H, d, J=1.0 Hz).

EXAMPLE 167

(n=2, Aryl=4-bromophenyl)
N-[2-(4-Bromo-α-methylcinnamylamino)ethyl]-5-isoquinolinesulfonamide Colorless amorphous form;
$^1$H-NMR (CDCl$_3$, δ ppm): 1.06 (3H, d, J=6.4 Hz), 1.3–2.2 (2H, br), 2.56–2.63 (2H, m), 2.95 (2H, t, J=5.7 Hz), 3.05 (1H, dq, J=8.0, 6.4 Hz), 5.79 (1H, dd, J=15.9, 8.0 Hz), 6.22 (1H, d, J=15.9 Hz), 7.13 (2H, dm, J=8.5 Hz), 7.41 (2H, dm, J=8.5 Hz), 7.68 (1H, dd, J=8.3, 7.4

Hz), 8.19 (1H, brd, J=8.3 Hz), 8.42-8.46 (2H, m), 8.69 (1H, d, J=6.1 Hz), 9.35 (1H, d, J=1.0 Hz).

EXAMPLE 168

(n=2, Aryl=4-isopropylphenyl)
N-[2-(4-isopropyl-α-methylcinnamylamino)ethyl]-5-isoquinolinesulfonamide Colorless amorphous form;
$^1$H-NMR (CDCl$_3$, δ ppm): 1.05 (3H, d, J=6.6 Hz), 1.24 (6H, d, J=6.8 Hz), 1.5-2.5 (2H, br), 2.56-2.63 (2H, m), 2.80-3.05 (3H, m), 5.74 (1H, dd, J=15.9, 8.0 Hz), 6.24 (1H, d, J=15.9 Hz), 7.16 (2H, d, J=8.6 Hz), 7.20 (2H, d, J=8.6 Hz), 7.66 (1H, dd, J=8.3, 7.3 Hz), 8.17 (1H, brd, J=8.3 Hz), 8.43 (1H, dd, J=7.3, 1.0 Hz), 8.44 (1H, d, J=6.1 Hz), 8.69 (1H, d, J=6.1 Hz), 9.34 (1H, d, J=1.0 Hz).

EXAMPLE 169

(n=2, Aryl=4-methoxyphenyl)
N-[2-(4-Methoxy-α-methylcinnamylamino)ethyl]-5-isoquinolinesulfonamide Colorless amorphous form;
$^1$H-NMR (CDCl$_3$, δ ppm): 1.05 (3H, d, J=6.4 Hz), 1.5-2.5 (2H, br), 2.56-2.63 (2H, m), 2.96 (2H, t, J=5.6 Hz), 3.02 (1H, dq, J=8.0, 6.4 Hz), 3.81 (3H, s), 5.64 (1H, dd, J=15.9, 8.0 Hz), 6.21 (1H, d, J=15.9 Hz), 6.83 (2H, dm, J=8.8 Hz), 7.20 (2H, dm, J=8.8 Hz), 7.67 (1H, dd, J=8.3, 7.3 Hz), 8.19 (1H, brd, J=8.3 Hz), 8.44 (1H, dd, J=7.3, 1.2 Hz), 8.44 (1H, d, J=6.1 Hz), 8.69 (1H, d, J=6.1 Hz), 9.34 (1H, d, J=1.0 Hz).

EXAMPLE 170

(n=2, Aryl=4-hydroxyphenyl)
N-[2-(4-hydroxy-α-methylcinnamylamino)ethyl]-5-isoquinolinesulfonamide Colorless crystals;
Melting point: 70°-73° C.;
$^1$H-NMR (CDCl$_3$, δ ppm): 1.06 (3H, d, J=6.4 Hz), 2.61 (2H, brt, J=5.7 Hz), 3.00 (2H, brt, J=5.7 Hz), 3.05 (1H, dq, J=8.0, 6.4 Hz), 3.3-3.5 (3H, br), 5.61 (1H, dd, J=15.9, 8.0 Hz), 6.19 (1H, d, J=15.9 Hz), 6.75 (2H, brd, J=8.5 Hz), 7.10 (2H, brd, J=8.5 Hz), 7.65 (1H, dt, J=8.3, 7.3 Hz), 8.16 (1H, brd, J=8.3 Hz), 8.40-8.46 (2H, m), 8.59 (1H, d, J=6.1 Hz), 9.32 (1H, d, J=1.0 Hz).

EXAMPLE 171

(n=3, Aryl=phenyl)
N-[3-(α-Methylcinnamylamino)propyl]-5-isoquinolinesulfonamide Colorless amorphous form;
$^1$H-NMR (CDCl$_3$, δ ppm): 1.27 (3H, d, J=6.6 Hz), 1.50-1.60 (2H, m), 1.6-2.5 (2H, br), 2.60-2.67 (2H, m), 3.01-3.09 (2H, m), 3.24 (1H, dq, J=7.8, 6.6 Hz), 5.91 (1H, dd, J=15.9, 7.8 H.)z, 6.40 (1H, d, J=15.9 Hz), 7.30 (5H, m), 7.68 (1H, dd, J=8.0, 7.3 Hz), 8.18 (1H, brd, J=8.0 Hz), 8.43 (1H, dd, J=7.3, 1.2 Hz), 8.47 (1H, d, J=6.1 Hz), 8.67 (1H, d, J=6.1 Hz), 9.36 (1H, d, J=1.0 Hz).

EXAMPLES 172 TO 188

In Examples 172 to 188, the following general reaction was used.

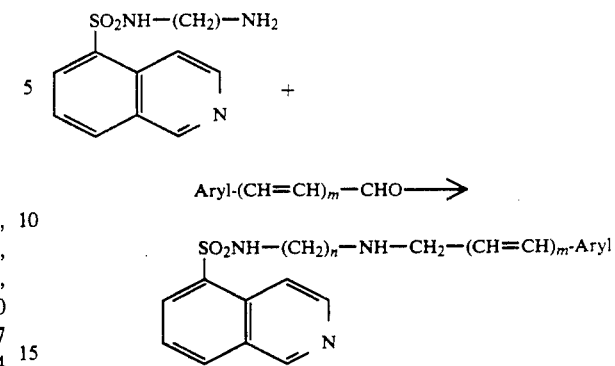

EXAMPLE 172

(n=2, m=1, Aryl=4-chlorophenyl)
N-[2-(4-Chlorocinnamylamino)ethyl]-5-isoquinolinesulfonamide 2.01 g of N-(2-aminoethyl)-5-isoquinolinesulfonamide was dissolved in 30 ml of methanol, to the solution was added 1.60 g of p-chlorocinnamaldehyde, and the mixture was stirred for one hour at a room temperature. After an addition of 350 mg of sodium tetrahydrideborate in portions with ice cooling, the mixture was stirred for 30 minutes. After an addition of ethyl acetate, the reaction mixture was sequentially washed three times with water, and then twice with a saturated sodium chloride aqueous solution, and dried over magnesium sulfate. The mixture was filtered and evaporated to remove the solvent under a reduced pressure. A residue was purified using a silica gel column (silica gel 80 g, eluant: 5% methanol in chloroform), and resulting crystals were washed with benzene/hexane (1:1), to obtain 2.30 g of the title compound as colorless crystals.

Melting point: 120°-123° C.;
$^1$H-NMR (CDCl$_3$, δ ppm): 1.8-3.5 (2H, br), 2.64-2.70 (2H, m), 2.97-3.03 (2H, m), 3.14 (2H, dd, J=6.1, 1.2 Hz), 6.00 (1H, dt, J=15.9, 6.1 Hz), 6.32 (1H, d, J=15.9 Hz), 7.21 (2H, dd, J=8.8, 2.4 Hz), 7.28 (2H, dd, J=8.8, 2.4 Hz), 7.69 (1H, dd, J=8.3, 7.4 Hz), 8.19 (1H, dd, J=8.3, 1.0 Hz), 8.42-8.47 (2H, m), 8.69 (1H, d, J=6.1 Hz), 9.34 (1H, d, J=1.0 Hz).

EXAMPLE 173

(n=2, m=1, Aryl=phenyl)
N-(2-Cinnamylaminoethyl)-5-isoquinolinesulfonamide

Colorless amorphous form;
$^1$H-NMR (CDCl$_3$, δ ppm): 1.8-2.8 (2H, br), 2.64-2.69 (2H, m), 2.97-3.03 (2H, m), 3.14 (1H, dd, J=6.3, 1.2 Hz), 6.02 (1H, dt, J=15.9, 6.3 Hz), 6.46 (1H, dt, J=15.9, 1.2 Hz), 7.30 (5H, s), 7.68 (1H, dd, J=8.1, 7.3 Hz), 8.18 (1H, dt, J=8.1, 1.0 Hz), 8.42-8.48 (2H, m), 8.70 (1H, d, J=6.1 Hz), 9.34 (1H, d, J=1.0 Hz).

EXAMPLE 174

(n=2, m=1, Aryl=4-dimethylaminophenyl)
N-[2-(4-Dimetylaminocinnamylamino)ethyl]-5-isoquinolinesulfonamide Colorless amorphous form;
$^1$H-NMR (CDCl$_3$, δ ppm): 2.65 (2H, brs), 2.70 (2H, dd, J=6.1, 4.9 Hz), 2.96 (6H, s), 3.02 (2H, dd, J=6.1, 4.9 Hz), 3.14 (2H, dd, J=6.6, 1.0 Hz), 5.81 (1H, dt, J=15.9, 6.5 Hz), 6.27 (1H, brd, J=15.9 Hz), 6.66 (2H, brd, J=8.8 Hz), 7.20 (2H, brd, J=8.8 Hz), 7.68 (1H, dd, J=8.0, 7.5 Hz), 8.18 (1H, dt, J=8.0, 1.0 Hz), 8.44 (1H, d, J=6.0 Hz and 1H, d, J=7.5 Hz), 8.71 (1H, d, J=6.1 Hz), 9.34 (1H, d, J=1.0 Hz).

EXAMPLE 175

(n=2, m=1, Aryl=4-fluorophenyl)
N-[2-[4-Fluorocinnamylamino)ethyl]-5-isoquinolinesulfonamide Colorless amorphous form;
$^1$H-NMR (CDCl$_3$, δ ppm): 1.5–2.5 (2H, br), 2.63–2.69 (2H, m), 2.97–3.02 (2H, m), 3.12 (2H, dd, J=6.1, 1.2 Hz), 5.94 (1H, dt, J=15.9, 6.1 Hz), 6.33 (1H, d, J=15.9 Hz), 7.00 (2H, ddd, J=8.6, 8.6, 2.2 Hz), 7.27 (2H, ddd, J=8.6, 5.3, 2.2 Hz), 7.69 (1H, dd, J=8.2, 7.6 Hz), 8.19 (1H, brd, J=8.2 Hz), 8.42–8.48 (2H, m), 8.70 (1H, d, J=6.1 Hz), 9.35 (1H, d, J=1.0 Hz).

EXAMPLE 176

(n=2, m=1, Aryl=4-bromophenyl)
N-[2-(4-Bromophenylcinnamylamino)ethyl]-5-isoquinolinesulfonamide Colorless crystals;
Melting point: 124°–127° C.;
$^1$H-NMR (CDCl$_3$, δ ppm): 2.0–3.5 (2H, br), 2.64–2.69 (2H, m), 2.97–3.03 (2H, m), 3.13 (2H, dd, J=6.1, 1.0 Hz), 6.01 (1H, dt, J=15.9, 6.3 Hz), 6.30 (1H, d, J=15.9 Hz), 7.14 (2H, dm, J=8.6 Hz), 7.41 (2H, dm, J=8.6 Hz), 7.68 (1H, dd, J=8.3, 7.5 Hz), 8.18 (1H, brd, J=8.3 Hz), 8.43–8.47 (2H, m}, 8.68 (1H, d, J=6.1 Hz), 9.34 (1H, d, J=1.0 Hz).

EXAMPLE 177

(n=2, m=1, Aryl=4-isopropylphenyl)
N-[2-(4-Isopropylcinnamylamino)ethyl]-5-isoquinolinesulfonamide $^1$H-NMR (CDCl$_3$, δ ppm): 1.24 (6H, d, J=7.1 Hz), 2.0–2.3 (2H, br), 2.63–2.69 (1H, m), 2.87 (1H, q, J=7.1 Hz), 2.97–3.03 (2H, m), 3.13 (1H, dd, J=6.3, 1.2 Hz), 5.97 (1H, dt, J=15.9, 6.3 Hz), 6.33 (1H, brd, J=15.9 Hz), 7.16 (2H, dm, J=8.3 Hz), 7.23 (2H, dm, J=8.3 Hz), 7.67 (1H, dd, J=8.3, 7.3 Hz), 8.17 (1H, d, J=8.3 Hz), 8.43–8.47 (2H, m), 8.69 (1H, d, J=6.1 Hz), 9.34 (1H, d, J=1.0 Hz).

EXAMPLE 178

(n=2, m=1, Aryl=4-methoxyphenyl)
N-[2-(4-Methoxycinnamylamino)ethyl]-5-isoquinolinesulfonamide Colorless crystals;
Melting point: 92°–95° C.;
$^1$NMR (CDCl$_3$, δ ppm): 2.0–3.0 (2H, br), 2.63–2.69 (2H, m), 2.97–3.06 (2H, m), 3.11 (2H, dd, J=6.3, 1.2 Hz), 3.81 (3H, s), 5.88 (1H, dt, J=15.9, 6.3 Hz), 6.30 (1H, d, J=15.9 Hz), 6.84 (2H, dm, J=8.8 Hz), 7.23 (2H, dm, J=8.8 Hz), 7.68 (1H, dd, J=8.3, 7.5 Hz), 8.19 (1H, brd, J=8.3 Hz), 8.42–8.47 (2H, m), 8.69 (1H, d, J=6.1 Hz), 9.34 (1H, d, J=1.0 Hz).

EXAMPLE 179

(n=2, m=1, Aryl=4-trifluoromethylphenyl).
N-[2-(4-Trifluoromethylcinnamylamino)ethyl]-5isoquinolinesulfonamide Colorless amorphous form;
$^1$H-NMR (CDCl$_3$, δ ppm): 1.5–2.5 (2H, br), 2.66–2.72 (2H, m), 2.98–3.04 (2H, m), 3.19 (2H, dd, J=6.1, 1.2 Hz), 6.14 (1H, dt, J=15.9, 6.1 Hz), 6.41 (1H, d, J=15.9 Hz), 7.39 (2H, brd, J=8.3 Hz), 7.56 (2H, brd, J=8.3 Hz), 7.69 (1H, dd, J=8.3, 7.3 Hz), 8.20 (1H, brd, J=8.3 Hz), 8.42–8.48 (2H, m), 8.70 (1H, d, J=6.1 Hz), 9.35 (1H, d, J=1.0 Hz).

EXAMPLE 180

(n=2, m=2, Aryl=4-trifluoromethylphenyl)
N-{2-[5-(4-Trifluoromethylphenyl)-2,4-pentadienylamino]ethyl}-5-isoquinolinesulfonamide Light yellow amorphous form;
$^1$H-NMR (CDCl$_3$, δ ppm): 1.0–2.5 (2H, br), 2.61–2.67 (2H, m), 2.96–3.05 (2H, m), 3.08 (2H, dd, J=6.3, 1.0 Hz), 5.69 (1H, dt, J=15.0, 6.3 Hz), 6.19 (1H, dd, J=15.0, 10.0 Hz), 6.48 (1H, d, J=15.7 Hz), 6.75 (1H, dd, J=15.7, 10.0 Hz), 7.47 (2H, brd, J=8.3 Hz), 7.57 (2H, brd, J=8.3 Hz), 7.72 (1H, dd, J=8.3, 7.3 Hz), 8.20 (1H, dt, J=8.3, 1.0 Hz), 8.43–8.48 (2H, m), 8.72 (1H, d, J=6.1 Hz), 9.36 (1H, d, J=1.0 Hz).

EXAMPLE 181

(n=2, m=3, Aryl=4-trifluoromethylchenyl)
N-{2-7-(4-Trifluoromethylphenyl)-2,4,6-heptatrienylamino]ethyl}-5-isoquinolinesulfonamide Light yellow amorphous form;
$^1$H-NMR (CDCl$_3$, δ ppm): 2.0–3.5 (2H, br), 2.61–2.67 (2H, m), 2.95–3.01 (2H, m), 3.07 (2H, dd, J=6.3, 1.0 Hz), 5.59 (1H, dt, J=14.6, 6.3 Hz), 6.05–6.22 (1H, m), 6.29–6.34 (2H, m), 6.55 (1H, d, J=15.6 Hz), 6.81–6.93 (1H, m), 7.47 (2H, brd, J=8.3 Hz), 7.55 (2H, brd, J=8.3 Hz), 7.71 (1H, dd, J=8.3, 7.3 Hz), 8.21 (1H, brd, J=8.3 Hz), 8.43–8.48 (2H, m), 8.72 (1H, d, J=6.1 Hz), 9.37 (1H, d, J=1.0 Hz).

EXAMPLE 182

[n=2, m=1,
Aryl=4-(2-methoxyethoxy)methoxyphenyl]
N-{2-[4-(2-methoxyethoxy)methoxycinnamylamino]ethyl}-5-isoquinolinesulfonamide Colorless amorphous form;
$^1$H-NMR (CDCl$_3$, δ ppm): 1.8–2.7 (2H, br), 2.63–2.69 (2H, m), 2.96–3.02 (2H, m), 3.11 (2H, dd, J=6.4, 1.2 Hz), 3.37 (3H, s), 3.53–3.58 (2H, m), 3.80–3.85 (2H, m), 5.27 (2H, s), 5.90 (1H, dt, J=15.9, 4 Hz), 6.30 (1H, d, J=15.9 Hz), 6.99 (2H, dm, J=8.8 Hz), 7.23 (2H, dm, J=8.8 Hz), 7.68 (1H, dd, J=8.3, 7.3 Hz), 8.19 (1H, dt, J=8.3, 1.0 Hz), 8.42–8.47 (2H, m), 8.70 (1H, d, J=6.1 Hz), 9.34 (1H, d, J=1.0 Hz).

EXAMPLE 183

(n=2, m=1, Aryl=4-hydroxyphenyl)
N-[2-(4-Hydroxycinnamylamino)ethyl]-5-isoquinolinesulfonamide Colorless crystals;
Melting point: 156°–159° C.;
$^1$H-NMR (DMSO-d$_6$, δ ppm): 2.44 (2H, brt, J=6.3 Hz), 2.88 (2H, brt, J=6.3 Hz), 3.01 (2H, brd, J=6.1 Hz), 3.39 (3H, br), 5.83 (1H, dt, J=15.9, 6.1 Hz), 6.20 (1H, d, J=15.9 Hz), 6.70 (2H, brd, J=8.3 Hz), 14 (2H, brd, J=8.3 Hz), 7.81 (1H, t, J=7.8 Hz), 8.34–8.46 (3H, m), 8.68 (1H, d, J=6.1 Hz), 9.46 (1H, d, J=1.0 Hz).

EXAMPLE 184

(n=2, m=1, Aryl=1-naphthyl)
N-{2-[3-(1-Naphthyl)-2-propenylamino]ethyl}-5-isoquinolinesulfonamide Colorless crystals;
Melting point: 135°–138° C.;
$^1$H-NMR (CDCl$_3$, δ ppm): 1.5–4.0 (2H, br), 2.68–2.73 (2H, m), 3.01–3.06 (2H, m), 3.26 (1H, dd, J=3, 1.5 Hz), 6.00 (1H, dt, J=15.6, 6.3 Hz), 7.10 (1H, d, J=15.6 Hz), 7.43–7.51 (4H, m), 7.61 (1H, dt, J=8.3, 7.3 Hz), 7.78 (1H, dd, J=7.1, 2.7 Hz), 7.83–7.89 (1H, m), 7.97–8.02 (1H, m), 8.07 (1H, brd, J=8.3 Hz), 8.44 (1H, dd, J=7.3, 1.0 Hz), 8.44 (1H, d, J=6.1 Hz), 8.68 (1H, d, J=6.1 Hz), 9.27 (1H, d, J=1.0 Hz).

EXAMPLE 185

(n=2, m=1, Aryl=3,4,5-trimethoxyphenyl
N-[2-(3,4,5-Trimethoxycinnamylamino)ethyl]-5-isoquinolinesulfonamide Colorless amorphous form;
$^1$H-NMR (CDCl$_3$, δ ppm): 1.5–2.6 (2H, br), 2.65–2.71 (2H, m), 2.97–3.03 (2H, m), 3.15 (2H, dd, J=6.3, 1.2 Hz), 3.85 (3H, s), 3.88 (6H, s), 5.97 (1H, dt, J=15.9, 6.3 Hz), 6.31 (1H, d, J=15.9 Hz), 6.55 (2H, s], 7.69 (1H, dd, J=8.3, 7.5 Hz), 8.20 (1H, brd, J=8.3 Hz), 8.43 (1H, brd, J=6.1 Hz), 8.46 (1H, dd, J=7.5, 1.2 Hz), 8.70 (1H, d, J=6.1 Hz), 9.35 (1H, d, J=1.0 Hz).

EXAMPLE 186

(n=2, m=1, Aryl=4-methoxycarbonylphenyl)
N-[2-(4-Carbomethoxycinnamylamino)ethyl]-5-isoquinolinesulfonamide Colorless crystals;
Melting point 110°–113° C.
$^1$H-NMR (CDCl$_3$, δ ppm): 1.2–2.0 (2H, br), 2.65–2.70 (2H, m), 2.97–3.02 (2H, m), 3.17 (2H, dd, J=5.9, 1.2 Hz), 3.92 (3H, s), 6.15 (1H, dt, J=15.9, 5.9 Hz), 6.41 (1H, d, J=15.9 Hz), 7.36 (2H, dm, J=8.3 Hz), 7.69 (1H, dd, J=8.3, 7.3 Hz), 7.98 (2H, dm, J=8.3 Hz), 8.19 (1H, brd, J=8.3 Hz), 8.43 (1H, brd, J=6.1 Hz), 8.46 (1H, dd, J=7.3, 1.5 Hz), 8.71 (1H, d, J=6.1 Hz), 9.35 (1H, d, J=1.0 Hz).

EXAMPLE 187

(n=2, m=1, Aryl=4-carboxyphenyl)
N-[2-(4-Carboxycinnamylamino)ethyl]-5-isoquinolinesulfonamide Colorless crystals;
Melting points: 239° to 240° C. (decomposed);
$^1$H-NMR (DMSO-d$_6$, δ ppm): 2.49 (2H, brt, J=6.3 Hz), 2.91 (2H, brt, J=6.3 Hz), 3.13 (2H, brd, J=5.7 Hz), 3.0–4.0 (3H, br), 6.24 (1H, dt, J=16.1, 5.7 Hz), 6.44 (1H, d, J=16.1 Hz), 7.44 (2H, brd, J=8.3 Hz), 7.82 (1H, dd, J=8.3, 7.3 Hz), 7.88 (2H, brd, J=8.3 Hz), 8.36 (1H, dd, J=7.3, 1.2 Hz), 8.42 (1H, brd, J=8.3 Hz), 8.44 (1H, brd, J=6.1 Hz), 8.69 (1H, d, J=6.1 Hz), 9.46 (1H, d, J=1.0 Hz)

EXAMPLE 188

(n=3, m=1, Aryl=phenyl)
N-(3-Cinnamylaminopropyl)-5-isoquinolinesulfonamide

Colorless amorphous form;
$^1$H-NMR (CDCl$_3$, δ ppm): 1.5–2.2 (2H, br), 1.59 (2H, tt, J=5.6, 5.6 Hz), 2.66 (2H, t, J=5.6 Hz), 3.06 (2H, t, J=5.6 Hz), 3.30 (2H, dd, J=6.1, 1.5 Hz), 6.21 (1H, dt, J=15.9, 6.1 Hz), 6.52 (1H, d, J=15.9 Hz), 7.21–7.40 (5H, m), 7.67 (1H, dd, J=8.3, 7.5 Hz), 8.18 (1H, d, J=8.3 Hz), 8.43 (1H, dd, J=7.5, 1.2 Hz), 8.44 (1H, d, J=6.1 Hz), 8.63 (1H, d, J=6.1 Hz), 9.35 (1H, d, J=1.0 Hz).

EXAMPLE 189

N-{2-[3-(4-Chlorophenyl)-2-propynylamino]ethyl}-5-isoquinolinesulfonamide (compound 189-I;
N-{2-[Bis-(3-((4-chlorophenyl))-2-propynyl)amino]ethyl}-5-isoquinolinesulfonamide (compound 189-II);
N-[3-(4-Chlorophenyl)-2-propynyl]-N-2-(p-chloropheny)-2-propynylamino]ethyl]-5-isoquinolinesulfonamide (compound 189-III)

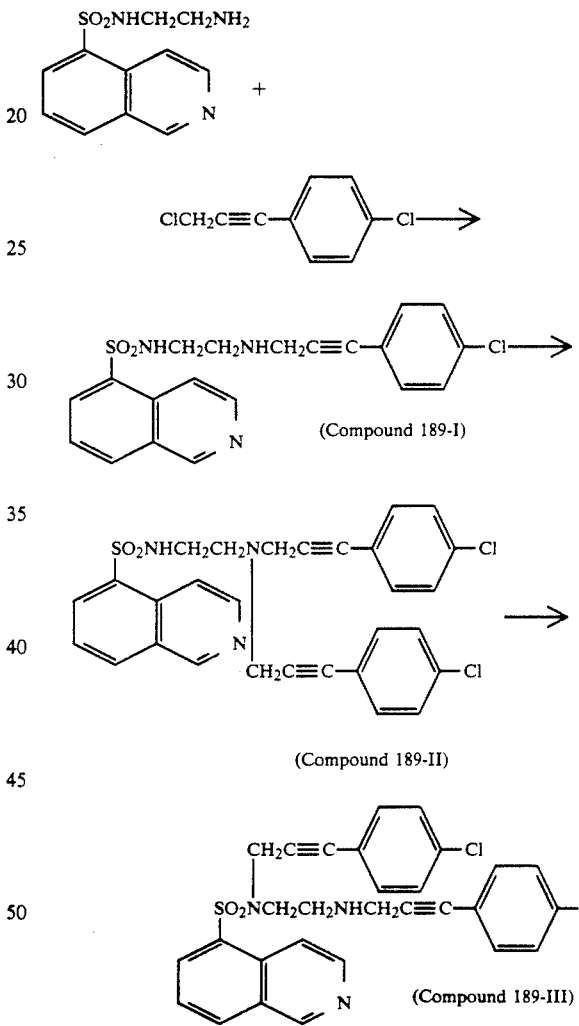

(Compound 189-I)

(Compound 189-II)

(Compound 189-III)

1.90 g of N-(2-aminoethyl)-5-isoquinolinesulfonamide and 1.39 g of 3-p-chlorophenyl-2-propynyl chloride were dissolved in 10 ml of dimethylformamide, to the solution was added 1.38 g of potassium carbonate, and the mixture was stirred for 24 hours at a room temperature. The reaction mixture was poured to 100 ml of ethyl acetate, washed sequentially three times with water and the twice with a saturated sodium chloride aqueous solution, dried over magnesium sulfate, filtered, and evaporated to remove the solvent under a reduced pressure. The resulting residue was separated and purified using a silica gel column (silica gel 100 g; eluant: 5% methanol/chloroform). By crystallizing from a mixture of ether-hexane, 855 mg of compound 189-I as colorless crystals 220 mg of compound 189-II, and 214 mg of compound 189-III in colorless amorphous form were obtained.

Compound 189-I

Colorless crystals;
Melting point; 120°-123° C.;
$^1$H-NMR (CDCl$_3$, δ ppm): 1.30–1.80 (2H, br), 2.75–2.80 (2H, m), 3.00–3.05 (2H, m), 3.39 (1H, s), 7.26 (4H, s), 7.69 (1H, dd, J=8.3, 7.3 Hz), 8.20 (1H, dt, J=8.3, 1.0 Hz), 8.42 (1H, dt, J=6.1, 1.0 Hz), 8.46 (1H, dd, J=7.3, 1.2 Hz), 8.70 (1H, d, J=6.1 Hz), 9.36 (1H, d, J=1.0 Hz).

Compound 189-II

Colorless amorphous form;
$^1$H-NMR (CDCl$_3$, δ ppm): 2.69–2.74 (2H, m), 3.01–3.09 (2H, m), 3.43 (4H, s), 5.48 (1H, t, J=5.0 Hz), 7.27 (4H, dm, J=9.0 Hz), 7.30 (4H, dm, J=9.0 Hz), 7.68 (1H, dd, J=8.3, 7.3 Hz), 8.20 (1H, brd, J=8.3 Hz), 8.42 (1H, brd, J=6.1 Hz), 8.47 (1H, dd, J=7.3, 1.2 Hz), 8.66 (1H, d, J=6.1 Hz), 9.35 (1H, d, J=1.0 Hz).

Compound 189-III

Colorless amorphous form;
$^1$H-NMR (CDCl$_3$, δ ppm): 1.58 (1H, br), 3.02 (2H, t, J=6.0 Hz), 3.55 (2H, t, J=6.0 Hz), 3.64 (2H, s), 4.50 (2H, s), 6.81 (2H, dm, J=8.8 Hz), 7.15 (2H, dm, J=8.8 Hz), 7.27 (2H, dm, J=9.0 Hz), 7.31 (2H, dm, J=9.0 Hz), 7.66 (1H, dd, J=8.3, 7.3 Hz), 8.13,(1H, brd, J=8.3 Hz), 8.48 (1H, dd, J=7.3, 1.2 Hz), 8.57 (1H, brd, J=6.1 Hz), 8.69 (1H, d, J=6.1 Hz), 9.26 (1H, d, J=1.0 Hz).

EXAMPLE 190

N-2-(4-Chloro-N-methylcinnamylamino)ethyl]-5-isoquinolinesulfonamide

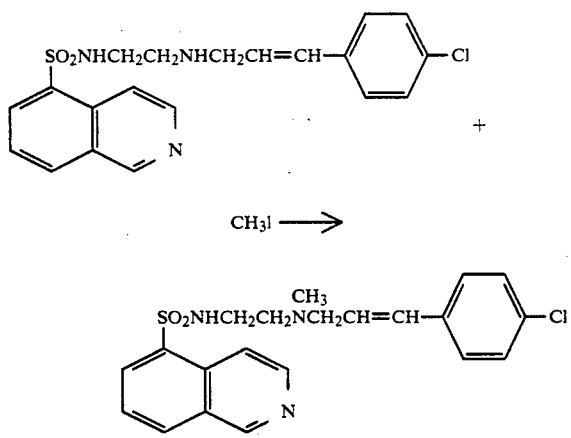

1.50 g of the product of Example 172 was dissolved in 10 ml of chloroform, to the solution was added 3 ml of methyl iodide at a room temperature, and the mixture was stirred for 40 minutes. Excess methyl iodide was immediately evaporated off under a reduced pressure, and resulting residue was purified on a silica gel column (silica gel 50 g, eluant: 5% methanol in chloroform), to obtain 720 mg of the title compound in a colorless amorphous form.

$^1$H-NMR (CDCl$_3$, δ ppm): 1.4–2.1 (1H, br), 1.95 (3H, s), 2.37 (2H, t, J=5.5 Hz), 2.92–3.00 (3H, m), 5.97 (1H, dt, J=15.9, 6.6 Hz), 6.34 (1H, d, J=5.9 Hz), 7.25 (2H, dm, J=8.8 Hz), 7.28 (2H, dm, J=8.8 Hz), 7.68 (1H, dd, J=8.3, 7.8 Hz), 8.19 (1H, brd, J=8.3 Hz), 8.44 (1H, brd, J=6.1 Hz), 8.45 (1H, dd, J=7.8, 1.5 Hz), 8.69 (1H, d, J=6.1 Hz), 9.34 (1H, d, J=1.0 Hz).

EXAMPLE 191

1-(4-Chlorocinnamyl)-4-(5-isoquinolinesulfonyl)piperazine

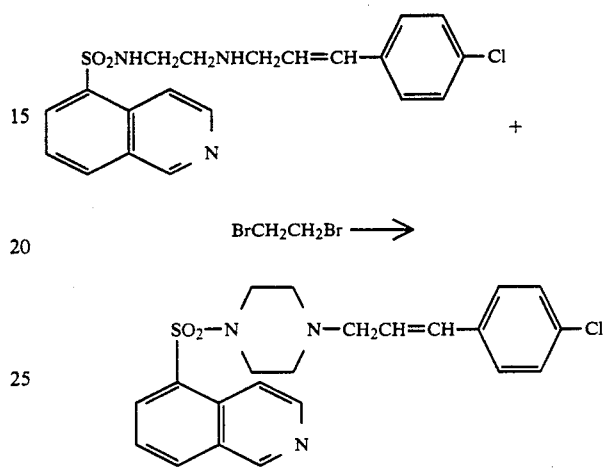

1.31 g of the product of Example 172 was dissolved in 3 ml of dimethylformamide, to the solution were added 644 mg of 1,2-dibromoethane and 1.13 g of anhydrous potassium carbonate at a room temperature, and the mixture was stirred for 24 hours. After adding 100 ml of ethyl acetate, the ethyl acetate layer was sequentially washed with water and a saturated sodium chloride aqueous solution twice in each case, and dried over magnesium sulfate. The solution was filtered and evaporated under a reduced pressure, and resulting residue was purified on a silica gel column (silica gel 50 g, eluant: 5% methanol in chloroform), to obtain 356 mg of the title compound in a colorless amorphous form, while recovering the residual starting material.

$^1$H-NMR (CDCl$_3$, δ ppm): 2.53 (4H, brt, J=4.9 Hz), 3.10 (2H, dd, J=6.6, 1.2 Hz), 3.20 (4H, brt, J=4.9 Hz), 6.07 (1H, dt, J=15.9, 6.6 Hz), 6.43 (1H, d, J=15.9 Hz), 7.24 (4H, s), 7.72 (1H, dd, J=8.1, 7.3 Hz), 8.22 (1H, brd, J=8.1 Hz), 8.37 (1H, dd, J=7.3, 1.2 Hz), 8.55 (1H, brd, J=6.1 Hz), 8.68 (1H, d, J=6.1 Hz), 9.34 (1H, d, J=1.0 Hz).

EXAMPLE 192

N-Ethyl-N-[2-(4-chloro-N-ethylcinnamylamino)ethyl]-5-isoquinolinesulfonamide

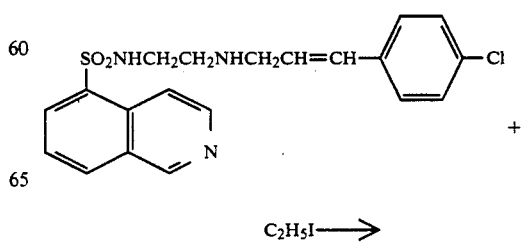

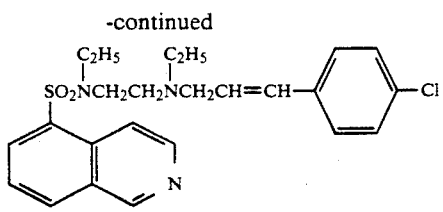

The procedure as described in Example 191 was repeated except that 1.31 g of the product of Example 172 and 2.14 g of ethyl iodide as N-alkylating agent were used, to obtain 720 mg of the title compound in a colorless amorphous form.

$^1$H-NMR (CDCl$_3$, δ ppm): 0.99 (3H, t, J=7.1 Hz), 1.05 (3H, t, J=7.1 Hz), 2.53 (2H, q, J=7.1 Hz), 2.61 (2H, t, J=7.8 Hz), 3.19 (2H, dd, J=6.5, 1.2 Hz), 3.33–3.43 (4H, m), 6.12 (1H, dt, J=15.9, 6.5 Hz), 6.32 (1H, d, J=15.9 Hz), 7.26 (4H, s), 7.62 (1H, dd, J=8.1, 7.3 Hz), 8.14 (1H, dd, J=8.1 Hz), 8.35 (1H, dd, J=7.3, 1.2 Hz), 8.42 (1H, brd, J=6.1 Hz), 8.66 (1H, d, J=6.1 Hz), 9.31 (1H, d, J=1.0 Hz),

EXAMPLE 193

N-[2-(4-Chloro-N-formylcinnamylamino)ethyl]-5-isoquinolinesulfonamide

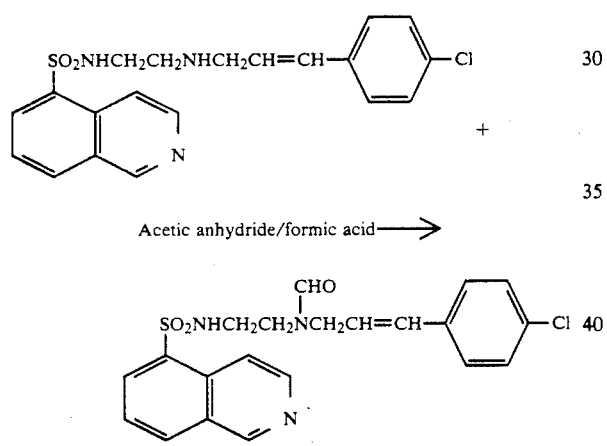

3 ml of formic acid and 3 ml of acetic anhydride were mixed and stirred at a room temperature, and to the mixture was added 1.41 g of the product of Example 172, and the mixture was stirred for one hour. The reaction mixture was added to 50 ml of ethyl acetate and 30 ml of saturated sodium carbonate aqueous solution with ice, and the mixture was stirred, and after foaming was terminated, the ethyl acetate layer was sequentially washed twice with water and once with a saturated sodium chloride aqueous solution, and dried over magnesium sulfate, filtered and evaporated under a reduced pressure. The resulting residue was purified on a silica gel column (silica gel 60 g, eluant: 2% methanol in chloroform), to obtain 1.49 g of the title compound as a mixture of two isomers (3:2) in a colorless amorphous form.

$^1$H-NMR (CDCl$_3$, δ ppm): 3.07–3.16 (2H, m), 3.39–3.47 (2H, m), 3.90 (0.6 x 2H, dd, J=6.3, 1.0 Hz), 4.03 (0.4 x 2H, dd, J=6.3, 1.0 Hz), 5.93 (0.6H, dt, J=15.9, 6.3 Hz), 6.01 (0.4H, dt, J=15.9, 6.3 Hz), 6.40 (0.4H, d, J=15.9 Hz), 6.44 (0.6H, d, J=15.9 Hz), 7.20 (0.6×2H, d, J=8.8 Hz), 7.21 (0.4×2H, d, J=8.8 Hz), 7.26 (0.6×2H, d, J=8.8 Hz), 7.27 (0.4×2H, d, J=8.8 Hz), 7.61 (0.6H, dd, J=8.0, 7.6 Hz), 7.64 (0.4H, dd, J=8.0, 7.6 Hz), 8.05 (0.6H, s), 8.09 (0.4H, s), 8.16 (0.6H, brd, J=8.0 Hz), 8.17 (0.4H, brd, J=8.0 Hz), 8.33–8.42 (2H, m), 8.60 (0.4H, d, J=6.1 Hz), 8.65 (0.6H, d, J=6.1 Hz), 9.33 (1H, d, J=1.0 Hz).

EXAMPLE 194

N-{2-4-Chloro-N-(4-hydroxybenzyl)cinnamylamino)ethyl}-5-isoquinolinesulfonamide 0.2 g of the product of Example 172 and 0.13 g of p-hydroxybenzaldehyde were dissolved in 10 ml of methanol, to the solution were added 60 mg of sodium cyanoborohydride and two drops of acetic acid, and the mixture was stirred for 2 days at a room temperature. The reaction mixture was concentrated under a reduced pressure, and after adding a saturated sodium chloride aqueous solution, extracted three times with 20 ml of ethyl acetate. The extracts were combined, washed with sodium chloride, dried over magnesium sulfate, filtered and concentrated under a reduced pressure. The resulting residue was purified on a silica gel column (silica gel 10 g, eluant: 2% methanol in chloroform), to obtain 150 mg of the title compound in a colorless amorphous form.

$^1$H-NMR (CDCl$_3$, δ ppm): 2.50 (2H, brt), 2.90 (2H, brt), 3.10 (2H, d, J=6.6 Hz), 3.35 (2H, s), 6.06 (1H, dt, J=15.6, 6.6 Hz), 6.35 (1H, d, J=15.9 Hz), 6.75 (2H, d, J=8.5 Hz), 6.97 (2H, d, J=8.5 Hz), 7.30 (4H, s), 7.65 (1H, t, J=8.0 Hz), 8.15 (1H, d, J=8.0 Hz), 8.37–8.41 (2H, m), 8.63 (1H, d, J=6.0 Hz), 9.32 (1H, s).

EXAMPLE 195

2-Methyl-5-{[2-(4-chloro-N,N-dimethylcinnamylammonio)ethyl]aminosulfonyl}isoquinolium diiodide 83 mg of the product of Example 172 was dissolved in 2.0 ml of dimethylformamide, to the solution was added 1.0 ml of methyl iodide, and the mixture was stirred for 4 hours at a room temperature. Excess of methyl iodide and dimethylformamide were evaporated off under a reduced pressure, and the resulting residue was crystallized from 5 ml of a mixture of methanol/chloroform (1:5). Crude crystals thus obtained was recrystallized from 10 ml of a mixture of methanol/chloroform (1:5), to obtain 78 mg of the title compound as light yellow crystals.

Melting point: 199°–200° C.;

$^1$H-NMR (DMSO-d$_6$, δ ppm): 3.09 (6H, s), 3.43 (4H, brs), 4.16 (2H, d, J=7.0 Hz), 4.53 (3H, s), 6.48 (1H, dt, J=15.9, 7.0 Hz), 6.89 (1H, d, J=15.9 Hz), 7.58 (2H, dm, J=9.4 Hz), 7.61 (2H, dm, J=9.4 Hz), 8.21 (1H, t, J=7.9 Hz), 8.72–8.78 (2H, m), 8.90–8.99 (3H, m), 10.22 (1H, brs).

EXAMPLE 196

2-Methyl-5-{N-methyl-N-[2-(4-chloro-N,N-dimethylcinnamylammonio)ethyl]aminosulfonyl}isoquinolium iodide 83 mg of the product of Example 172 was dissolved in 2.0 ml of dimethylformamide, to the solution were added 1.0 ml of methyl iodide and 83 mg of anhydrous sodium carbonate, and the mixture was stirred for 4 hours at a room temperature. Excess methyl iodide and dimethylformamide were evaporated off under a reduced pressure, and after adding 10 ml of a mixture of methanol/chloroform (1:5) the mixture was stirred, and then filtered to remove insoluble matter. The filtrate was concentrated under a reduced pressure, and to the concentrate was added 10 ml of a mixture of methanol/chloroform (1:5) to precipitate an insoluble matter, which was then filtered off. This concentration and filtration procedure was twice repeated, to obtain 145 mg of the title compound in yellow amorphous form.

$^1$H-NMR (DMSO-d$_6$, δ ppm): 2.97 (3H, s), 3.15 (6H, s), 3.60-3.70 (2H, m), 3.70-3.80 (2H, m), 4.21 (2H, d, J=7.3 Hz), 4.54 (3H, s), 6.54 (1H, dt, J=15.6, 7.3 Hz), 6.93 (1H, d, J=15.6 Hz), 7.48 (2H, brd, J=8.5 Hz), 7.63 (2H, brd, J=8.5 Hz), 8.23 (1H, t, J=7.9 Hz), 8.75-8.85 (3H, m), 8.99 (1H, d, J=7.1 Hz), 10.22 (1H, brs).

The isoquinoline compounds other than that of Example 174 can be treated with an excess amount of methyl iodide in dimethylformamide, as described in this Example, to obtain corresponding compounds wherein the nitrogen atom on the isoquinoline ring has been methylated to a quaternary nitrogen atom.

EXAMPLE 197

N-[2-(4-Chlorocinnamylamino)ethyl]-5-isoquinolinesulfonamide dihydrochloride 2.00 g of the product of Example 172 was suspended in 20 ml of methanol, the suspension was made to a clear solution by adding 1 ml of concentrated hydrochloric acid, and stirred for 10 minutes with ice cooling to form crystals. The crystals were collected by filtration, and recrystallized from a mixture of 20 ml of methanol and 3 ml of water to obtain 1.65 g of the corresponding dihydrochloride as colorless crystals.

Melting point: 205°-208° C.;

$^1$H-NMR (DMSO-d$_6$, δ ppm): 2.90-3.05 (2H, m), 3.10-3.20 (2H, m), 3.65-3.75 (2H, m), 4.3-4.9 (br), 6.33 (1H, dt, J=16.1, 7.1 Hz), 6.76 (1H, d, J=16.1 Hz), 7.45 (4H, s), 8.00 (1H, dd, J=8.3, 7.5 Hz), 8.54 (1H, dd, J=7.5, 1.2 Hz), 8.64 (1H, brd, J=8.3 Hz), 8.71 (1H, brd, J=6.4 Hz), 8.80 (1H, br), 8.82 (1H, d, J=6.4 Hz), 9.39 (1H, brs), 9.79 (1H, brs).

EXAMPLE 198

N-[2-(α-Methylcinnamylamino)ethyl]-5-isoquinolinesulfonamide dihydrochloride

The same procedure as described in Example 194 was repeated except that the product of Example 154 was used as a starting material, to obtain the corresponding dihydrochloride as colorless crystals.

Melting point: 80°-85° C.;

$^1$H-NMR (DMSO-d$_6$, δ ppm): 1.40 (3H, d, J=6.5 Hz), 2.89 (2H, m), 3.16 (2H, brt, J=6.5 Hz), 3.91 (1H, m), 5.0-6.0 (br), 6.19 (1H, dd, J=16.1, 7.5 Hz), 6.71 (1H, d, J=16.1 Hz), 7.39 (5H, m), 7.97 (1H, dd, J=8.0, 7.6 Hz), 8.51-8.82 (5H, m), 9.44 (2H, br], 9.76 (1H, d, J=1.0 Hz)

EXAMPLE 199

N-[2-(4-Chloro-α-methylcinnamylamino)ethyl]-5-isoquinolinesulfonamide dihydrochloride The same procedure as described in Example 194 was repeated except that the product of Example 153 was used as a starting material, to obtain the corresponding dihydrochloride as a white hygroscopic powder.

$^1$H-NMR (DMSO-d$_6$, δ ppm): 1.40 (3H, d, J=6.5 Hz), 2.85-3.96 (2H, m), 3.10-3.20 (2H, m), 3.80-4.00 (1H, m), 5.1-6.1 (br), 6.23 (1H, dd, J=15.9, 8.5 Hz), 6.72 (1H, d, J=15.9 Hz), 7.44 (4H, s), 7.99 (1H, dd, J=8.2, 7.4 Hz), 8.54 (1H, dd, J=7.4, 1.2 Hz), 8.64 (1H, brd, J=8.2 Hz), 8.72 (1H, brd, J=6.4 Hz), 8.80 (1H, br), 8.82 (1H, d, J=6.4 Hz), 9.48 (2H, brs), 9.80 (1H, brs).

EXAMPLE 200

N-[2-(4-Bromocinnamylamino)ethyl]-5-isoquinolinesulfonamide dihydrochloride

The same procedure as described in Example 194 was repeated except that the product of Example 176 was used a starting material, to obtain the corresponding dihydrochloride as colorless crystals.

Melting point: 195°-200° C.;

$^1$H-NMR (DMSO-d$_6$, δ ppm): 2.90-3.10 (2H, brs), 3.2-3.3 (2H, m), 3.65-3.75 (2H, brs), 6.35 (1H, dt, J=16.0, 7.1 Hz), 6.76 (1H, d, J=16.0 Hz), 7.38 (2H, d, J=8.5 Hz), 7.57 (2H, d, J=8.5 Hz), 8.10 (1H, t, J=7.6 Hz), 8.67 (1H, d, J=7.6 Hz), 8.78 (1H, d, J=7.6 Hz), 8.90 (1H, brs), 9.05 (1H, brs), 10.0 (1H, s).

EXAMPLE 201

N-(2-Cinnamylaminoethyl)-5-isoquinolinesulfonamide.½ fumarate 303 mg of the product of Example 173 was dissolved in 5 ml of ethyl acetate, to the solution was added a solution of 89 ml of fumaric acid in 2 ml of methanol at a room temperature, and the mixture was stirred for 30 minutes to from crystals, which was then collected by filtration and washed with ethyl acetate to obtain 312 mg of the corresponding 1/2 fumarate as colorless crystals.

Melting point: 153°-156° C.;

$^1$H-NMR (DMSO-d$_6$, δ ppm): 2.69 (2H, brt, J=6.3 Hz), 3.00 (2H, brt, J=6.3 Hz), 3.34 (2H, brd, J=6.1 Hz), 5.0-8.0 (3H, br), 6.16 (1H, dt, J=16.0, 6.1 Hz), 6.51 (1H, d, J=16.0 Hz), 6.54 (1H, s), 7.23-7.3 (2H, m), 7.34-7.40 (3H, m), 7.82 (1H, dd, J=8.1, 7.5 Hz), 8.36 (1H, dd, J=7.5, 1.0 Hz), 8.42 (1H, brd, J=8.1 Hz), 8.44 (1H, brd, J=6.1 Hz), 8.69 (1H, d, J=6.1 Hz), 9.47 (1H, d, J=1.0 Hz).

EXAMPLE 202

N-[2-(α-Methylcinnamylamino)ethyl]-5-isoquinolinesulfonamide ½ fumarate

The same procedure as described in Example 198 was repeated except that the product of Example 154 was used as a starting material to obtain the corresponding ½ fumarate as colorless crystals.

Melting point: 162°-167° C.;

$^1$H-NMR (DMSO-d$_6$, δ ppm): 1.02 (3H, d, J=6.4 Hz), 2.49 (2H, brt, J=6.6 Hz), 2.5-5.7 (3H, br), 2.93 (2H, brt, J=6.6 Hz), 3.17 (1H, dd, J=7.9, 6.4 Hz), 5.91 (1H, dd, J=16.1, 7.9 Hz), 6.35 (1H, d, J=16.1 Hz), 6.55 (1H, s), 7.32 (5H, m), 7.79 (1H, dd, J=8.0, 7.3 Hz), 8.34 (1H, dd, J=7.3, 1.2 Hz), 8.39 (1H, brd, J=8.0 Hz), 8.43 (1H, brd, J=6.1 Hz), 8.69 (1H, d, J=6.1 Hz), 9.45 (1H, d, J=1.0 Hz).

EXAMPLE 203

N-[2-(4-Chloro-α-methylcinnamylamino)ethyl]-5-isoquinolinesulfonamide L-(+)-tartrate 6.60 g of the product of Example 153 was dissolved in 50 ml of ethyl acetate, to the solution was added a solution of 2.38 g of L-(+)-tartaric acid in methanol to form crystals, which was then collected by filtration and washed with ethyl acetate to obtain the corresponding L-(+)-tartrate as colorless crystals.

Melting point: 125°-130° C.;

¹H-NMR (DMSO-d$_6$, δ ppm): 1.14 (3H, d, J=6.3 Hz), 2.64 (2H, brt, J=6.5 Hz), 2.98 (2H, brt, J=6.5 Hz), 3.45 (1H, dd, J=8.0, 6.3 Hz), 3.5-4.7 (6H, br), 4.13 (2H, s), 6.03 (1H, dd, J=15.9, 8.0 Hz), 6.49 (1H, d, J=15.9 Hz), 7.41 (4H, s), 7.81 (1H, dd, J=8.0, 7.3 Hz), 8.36 (1H, brd, J=8.0 Hz), 8.41 (1H, d, J=6.1 Hz), 8.42 (1H, brd, J=7.3 Hz), 8.69 (1H, d, J=6.1 Hz), 9.46 (1H, d, J=1.0 Hz).

EXAMPLE 204

N-(2-Aminoethyl)-N-(2-cinnamylaminoethyl)-5-isoquinolinesulfonamide trihydrochloride To a solution of 1.10 g of the amorphous compound obtained in Example 173, 1.18 g of triphenylphosphine and 0.73 g of 2-(tert-butoxycarbonylamino)ethanol in 15 ml of tetrahydrofuran, was added dropwise a solution of 0.78 g of diethyl azodicarboxylate in 5 ml of tetrahydrofuran for 15 ml with ice cooling, and the mixture was stirred for 4 hours at a room temperature. After again ice-cooling, to the reaction mixture was added 0.39 g of triphenylphosphine, and added dropwise a solution of 0.26 g of diethylazodicarboxylate in 3 ml of tetrahydrofuran, and the reaction mixture was stirred at a room temperature for one hour. The reaction mixture was concentrated under a reduced pressure, and resulting residue was applied to a silica gel column and eluted with chloroform/methanol (19:1), to obtain 0.99 g of a light orange amorphous product. The product was dissolved in 20 ml of methanol, to the solution was added 7.7 ml of 4N hydrochlonic acid in ethyl acetate, and the mixture was stirred at a room temperature for 3 hours. The reaction mixture was evaporated to remove the solvent under a reduced pressure, and thereto was added ethyl acetate to form a solid. The solid was collected by filtration, washed with ethyl acetate and n-hexane, and dried under a reduced pressure to obtain 0.97 g of the title compound as a colorless hygroscopic powder.

NMR (D$_2$O) δ ppm: 3.2-3.5 (4H, m), 3.7-4.0 (6H, m), 6.1-6.3 (1H, m), 6.82 (1H, d, J=15.9 Hz), 7.44 (5H, s), 8.15 (1H, t, J=7.6 Hz), 8.1-8.3 (3H, m), 9.09 (1H, d, J=7.0 Hz), 9.7 (1H, s).

EXAMPLE 205

N-(4-Aminobutyl)-N-[2-(4-chlorocinnamylamino)ethyl]-5-isoquinolinesulfonamide trihydrochlorides To a solution of 0.4 g of the crystals obtained in Example 172. 0.226 g of 4-(tert-butoxycarbonylamino)-butanol and 0.445 g of triphenylphosphine in 5 ml of tetrahydrofuran, was added a solution of 0.295 g of diethyl azodicarboxylate in 2 ml of tetrahydrofuran with stirring under ice cooling. The mixture was allowed to stand at room temperature, and evaporated under a reduced pressure to obtain a residue, which was then applied to a silica gel column and eluted with methanol/chloroform (2:98) to obtain 0.28 g of oil. To a solution of the oil in 1 ml of methanol, as added 4 N hydrochloric acid/ethyl acetate to form a precipitate, which was then collected by filtration, washed with ethyl acetate and dried to obtain 0.2 g of the title compound as a colorless powder.

NMR (D$_2$O) δ ppm: 1.70 (4H, brs), 2.95 (2H, m), 3.30 (2H, m), 3.55 (2H, m), 3.77 (2H, m), 3.89 (2H, dd, J=7.3 Hz), 6.15 (1H, dt, J=15.8, 7.3 Hz), 6.76 (1H, d, J=15.8 Hz), 7.35 (4H, s), 8.11 (1H, t, J=8.0 Hz), 8.6-8.8 (2H, m), 8.98 (1H, d, J=7.0 Hz), 9.75 (1H, s).

EXAMPLE 206

N-[2-(4-Chloro-N-methylcinnamyl amino)ethyl]-N-[2-(4-piperidyl)ethyl]-5-isoquinolinesulfoneamide To a solution of 0.39 g of the amorphous compound obtained in Example 190, 0.145 g of 4-piperidinethanol and 0.265 g of triphenylphosphine in 5 ml of tetrahydrofuran, was added a solution of 0.245 g of diethyl azodicarboxylate in 2 ml of tetrahydrofuran with ice cooling, and the mixture was stirred for one hour at a room temperature and evaporated to remove the solvent under a reduced pressure. After an addition of 30 ml of ethyl acetate, the mixture was extracted three times with 5 ml of 1N hydrochloric acid. The extract was alkalized with sodium bicarbonate and extracted three times with 10 ml of ethyl acetate. The organic layer was dried over magnesium sulfate and evaporated to remove the solvent. The resulting residue was applied to an alumina chromatographic column and eluted with 1% methanol in chloroform to obtain 180 mg of the title compound as colorless oil.

NMR (CDCl$_3$) δ ppm: 0.87-1.05 (2H, m), 1,30-1.45 (5H, m), 1.85 (1H, brs), 2.21 (3H, s), 2.33 (2H, m), 2.51 (2H, t, J=7.6 Hz), 2.89 (2H, m), 3.08 (2H, d, J=6.6 Hz), 3.30 (2H, t, J=7.8 Hz), 3.42 (2H, t, J=7.3 Hz), 6.09 (1H, dt, J=15.8, 6.6 Hz), 6.41 (1H, d, J=15.8 Hz), 7.26 (4H, s), 7.65 (1H, dd, J=8.0, 8.6 Hz), 8.15 (1H, d, J=8.0 Hz), 8.4 (1H, d, J=8.6 Hz), 8.40 (1H, d, J=6.1 Hz), 8.67 (1H, d, J=6.1 Hz), 9.31 (1H, s).

The oil thus obtained was dissolved in 1 ml of methanol, and thereto were added 0.3 ml of 4N hydrochlonic acid in ethyl acetate and then 30 ml of ether, to obtain the corresponding trihydrochloride as colorless powder.

EXAMPLE 207

N-[2-(4-Chloro-N-methylcinnamylamino)ethyl]-N-[2-morpholinoethyl)-5-isoquinolinesulfonamide trihydrochloride To a solution of 1 g of the amorphous compound obtained in Example 190, 0.377 g of 2-N-morpholinoethanol and 1.25 g of triphenylphosphine in 5 ml of tetrahydrofuran, was added dropwise a solution of 0.835 g of diethyl azodicarboxylate in 2 ml of tetrahydrofuran with stirring under ice cooling, and the mixture was stirred for 2 hours. After evaporating off the solvent under a reduced pressure, to the residue was added 20 ml of ethyl acetate, and the mixture was extracted three times with 10 ml of 1N hydrochloric acid. The extract was alkalized with sodium bicarbonate and extracted three times with 10 ml of ethyl acetate. The extract was dried over magnesium sulfate and evaporated under a reduced pressure to remove the solvent. The resulting residue was applied to a silica gel column and eluted with methanol/ethyl acetate (10:90) to obtain an oil.

NMR (CDCl$_3$) δ ppm: 2.18 (3H, s), 2.28-2.33 (4H, m), 2.4 (2.6 (4H, m), 3.07 (2H, d, J=6.6 Hz), 3.4-3.6 (8H, m), 6.07 (1H, dt, J=15.9, 6.6 Hz), 6.40 (1H, d, J=15.9 Hz), 7.26 (4H, s), 7.63 (1H, dd, J=8.0, 7.1 Hz), 8.14 (1H, d, J=8.0 Hz), 8.42 (1H, d, J=7.1 Hz), 8.42 (1H, d, J=7.1 Hz), 8.42 (1H, d, J=6.1 Hz), 8.67 (1H, d, J=6.1 Hz), 9.31 (1H, s).

The oil thus obtained was dissolved 4 ml of methanol, and was added in 2 ml of 4N hydrochloric acid in ethyl acetate, and the solvent was evaporated to remove the solvent under a reduced pressure, the resulting product was recrystallized from ethanol to obtain 0.67 g of the title compound as colorless crystals.

Melting point: 172°–176° C.;

NMR (D$_2$O) δ ppm: 3.04 (3H, s), 3.2–3.6 (8H, m), 3.8–4.1 (10H, m), 6.18 (1H, dt, J=15.9, 7.0 Hz), 6.76 (1H, d, J=15.9 Hz), 7.22 (4H, s), 8.09 (1H, dd, J=7.6, 8.2 Hz), 8.52 (1H, d, J=7.6 Hz), 8.65–8.75 (2H, m), 8.87 (1H, d, J=7.0 Hz), 9.74 (1H, s).

EXAMPLE 208

N-[2-(4-Chloro-N-methylcinnamylamino)ethyl]-N-(2-piperidinoethyl)-5-isoquinolinesulfonamide To a solution of 0.39 g of the amorphous compound obtained in Example 190, 0.145 g of 1-piperidinethanol and 0.369 g of triphenylphosphine in 5 ml of tetrahydrofuran, was added dropwise a solution of 0.245 g of diethyl azodicarboxylate in 2 ml of tetrahydrofuran with stirring under ice cooling. The mixture was stirred for 2 hours and evaporated to remove the solvent under a reduced pressure, and resulting residue dissolved in 30 ml of ethyl acetate and extracted three times with 10 ml of 1N hydrochloric acid. The aqueous layer was alkalized with sodium bicarbonate and extracted three times with 10 ml of ethyl acetate, and the organic extract was dried over magnesium sulfate and evaporated to remove the solvent at a reduced pressure. The resulting residue was applied to a silica gel column and eluted with 2% methanol in chloroform, to obtain 0.37 g of the title compound as a colorless oil.

NMR (CDCl$_3$) δ ppm: 1.3–1.5 (6H, m), 2.20 (3H, s), 2.20–2.30 (4H, m), 2.39 (2H, t, J=7.1 Hz), 2.55 (2H, t, J=7.1 Hz), 3.08 (2H, d, J=6.8 Hz), 3.46 (4H, q, J=7.1 Hz), 6.09 (1H, dt, J=15.9, 6.8 Hz), 6.40 (1H, d, J=15.9 Hz), 7.25 (4H, s), 7.63 (1H, dd, J=7.3, 8.1 Hz), 8.14 (1H, d, J=8.1 Hz), 8.43 (1H, d, J=7.3 Hz), 8.43 (1H, d, J=6.1 Hz), 8.67 (1H, d, J=6.1 Hz), 9.31 (1H, s).

To a solution of above-obtained oil in 3 ml of methanol, was added 0.5 ml of 4N hydrochloric acid in ethyl acetate, and the whole was evaporated to remove the solvent under a reduced pressure. To the concentrate was added ether to form powder, which was then collected by filtration to obtain 0.35 g of the corresponding trihydrochloride as a colorless powder.

NMR (D$_2$O) δ ppm: 1.3–2.0 (6H, m), 2.8–3.0 (2H, m), 3.05 (3H, s), 3.3–3.6 (6H, m), 3.8–4.1 (6H, m), 6.25 (1H, dt, J=15.8, 8.0 Hz), 6.80 (1H, d, J=15.8 Hz), 7.25 (4H, s), 8.13 (1H, t, J=8.0 Hz), 8.60 (1H, d, J=8.0 Hz), 8.68–8.78 (2H, m), 8.95 (1H, d, J=7.0 Hz), 9.70 (1H, s).

EXAMPLE 209

N-[2-(4-Chloro-N-methylcinnamylamino)ethyl]-N-(2-dimethylaminoethyl)-5-isoquinolinesulfonamide To a solution of 1.0 g of the amorphous compound obtained in Example 190, 0.267 g of 2-dimethylamino ethanol and 0.982 g of triphenylphosphine in 5 ml of tetrahydrofuran, was added dropwise a solution of 0.652 g of diethyl azodicarboxylate in 2 ml of tetrahydrofuran with stirring under ice cooling. After 2 hours, the reaction mixture was concentrated under a reduced pressure to remove tetrahydrofuran, and resulting residue was dissolved in 10 ml of ethyl acetate and extracted three times with 10 ml of 1N hydrochloric acid. The aqueous layer was alkalized with sodium bicarbonate and extracted three times with 10 ml of ethyl acetate, and the organic layer was dried over magnesium sulfate and evaporated to removed the solvent under a reduced pressure. The resulting residue was then applied to a silica gel column and eluted with 3% methanol in chloroform, to obtain 0.77 g of the title compound as a colorless oil.

NMR (CDCl$_3$), δ ppm: 2.11 (6H, s), 2.20 (3H, s), 2.38 (2H, t, J=7.3 Hz), 2.54 (2H, t, J=7.3 Hz), 3.08 (2H, d, J=6.6 Hz), 3.38–3.50 (4H, m), 6.08 (1H, dt, J=15.8, 6.6 Hz), 6.40 (1H, d, J=15.8 Hz), 7.26 (4H, s), 7.63 (1H, dd, J=8.1, 7.5 Hz), 8.14 (1H, d, J=8.1 Hz), 8.40–8.45 (2H, m), 8.68 (1H, d, J=6.1 Hz), 9.31 (1H, s).

To a solution of the oil thus obtained in 5 ml of methanol was added 1.4 ml of 4N hydrochloric acid in ethyl acetate, and after evaporating off the solvent under a reduced pressure, to the resulting concentrate was added ether to form powder, which was then collected by filtration and dried to obtain 0.7 g of the corresponding trihydrochloride as a powder.

NMR (D$_2$O) δ ppm: 2.96 (6H, s), 3.03 (3H, s), 3.4–3.6 (4H, m), 3.9–4.1 (6H, m), 6.17 (1H, dt, J=15.9, 7.0 Hz), 6.73 (1H, d, J=15.9 Hz), 7.19 (4H, s), 8.01 (1H, t, J=8.0 Hz), 8.54 (1H, d, J=8.0 Hz), 8.70 (2H, m), 8.91 (1H, d, J=8.0 Hz), 9.78 (1H, s).

EXAMPLE 210

N-(2-Piperidinoethyl)-N-[2-(N-methylcinnamylamino)ethyl-5-isoquinolinesulfonamide The amorphous product obtained in Example 173 was treated according to the procedure described in Example 190, to obtain N-[2-(N-methylcinnamylamino)ethyl]-5-isoquinolinesulfonamide.

NMR (CDCl$_3$) δ ppm: 1.95 (3H, s), 2.37 (2H, t, J=5.7 Hz), 2.93–3.00 (4H, m), 6.00 (1H, dt, J=15.8, 6.6 Hz), 6.38 (1H, d, J=15.8 Hz), 7.31 (5H, s), 7.68 (1H, dd, J=8.3, 7.3 Hz), 8.18 (1H, d, J=8.3 Hz), 8.43–8.47 (2H, m), 8.69 (1H, d, J=6.1 Hz), 9.34 (1H, s).

To a solution of 0.476 g of the above compound, 0.193 g of 1-piperidinethanol and 0.524 g of triphenylphosphine in 5 ml of tetrahydrofuran, was added a solution of 0.348 g of diethyl azodicarboxylate in 2 ml of tetrahydrofuran with stirring under ice cooling, and the mixture was allowed to stand for 3 hours and evaporated to remove the solvent under a reduced pressure. To the concentrate was added 30 ml of ethyl acetate, and the mixture was extracted three times with 10 ml of 1N hydrochloric acid. The extract was alkalized with sodium bicarbonate and extracted three times with 10 ml of ethyl acetate. The ethyl acetate solution was dried over magnesium sulfate and evaporated under a reduced pressure to remove the solvent. The resulting residue was applied to a silica gel column and eluted with 5% methanol in chloroform, to obtain 0.44 g of the title compound as colorless oil.

NMR (CDCl$_3$) δ ppm: 1.3–1.5 (6H, m), 2.20 (3H, s), 2.20–2.30 (4H, m), 2.41 (2H, t, J=6.8 Hz), 2.53 (2H, t, J=6.3 Hz), 3.09 (2H, d, J=6.6 Hz), 3.4–3.55 (4H, m), 6.10 (1H, dt, J=15.8, 6.6 Hz), 6.45 (1H, d, J=15.8 Hz), 7.2–7.4 (5H, m), 7.61 (1H, dd, J=8.0, 7.5 Hz), 8.11 (1H, d, J=8.0 Hz), 8.4–8.5 (2H, m), 8.66 (1H, d, J=6.1 Hz), 9.29 (1H, s).

To the oil thus obtained in 5 ml of methanol was added 0.8 ml of 4N hydrochloric acid in ethyl acetate, and the solution was evaporated to remove the solvent under a reduced pressure. A precipitate obtained by addition of 50 ml of ether was collected by filtration and dried to obtain 0.4 g of the corresponding trihydrochloride as a colorless powder.

NMR (D$_2$O) δ ppm: 1.6–2.0 (6H, m), 2.7–2.9 (2H, m), 3.04 (3H, s), 3.4–3.6 (6H, m), 3.9–4.1 (6H, m), 6.25 (1H,

103 dt, J=15.8, 8.0 Hz), 6.86 (1H, d; J=15.8 Hz), 7.40 (5H, s), 8.14 (1H, t, J=8.0 Hz), 8.6-8.7 (3H, m), 9.0 (1H, d, J=7.0 Hz), 9.72 (1H, s).

EXAMPLE 211

N-Anisyl-N-[2-(4-chlorocinnamylamino)ethyl]-5-isoquinolinesulfonamide 0.4 g of the crystals obtained in Example 172, 0.276 g of anisyl alcohol and 0.524 g of triphenylphosphine were dissolved in 10 ml of tetrahydrofuran, and to the solution was added dropwise a solution of 0.404 g of diisopropyl azodicarboxylate in 2 ml of tetrahydrofuran with stirring under ice cooling. The reaction mixture was warmed to a room temperature and was allowed to stand overnight and then evaporated under a reduced pressure to remove the solvent. The resulting residue was dissolved in 30 ml of ethyl acetate, and the mixture was extracted twice with 30 ml of 1N hydrochloric acid. The extract was alkalized with sodium bicarbonate and extracted twice with 30 ml of ethyl acetate. The ethyl acetate solution was washed with water, dried over magnesium sulfate and evaporated under a reduced pressure to remove the solvent. The resulting residue was applied to a silica gel column and eluted with 1% methanol in chloroform, to obtain 0.22 g of the title compound as a colorless oil.

NMR (CDCl$_3$) δ ppm: 2.61 (2H, t, J=6.6 Hz), 3.14 (2H, d, J=6.1 Hz), 3.34 (2H, t, J=6.6 Hz), 3.74 (3H, s), 4,43 (2H, s), 6.0 (1H, dt, J=15.9, 6.1 Hz), 6.30 (1H, d, J=15.9 Hz), 6.75 (2H, d, J=8.8 Hz), 7.08 (2H, d, J=8.8 Hz), 7.26 (4H, s), 7.66 (1H, dd, J=8.3, 7.3 Hz), 8.17 (1H, brd, J=8.3 Hz), 8.39-8.49 (2H, m), 8.69 (1H, d, J=6.1 Hz), 9.3 (1H, s).

EXAMPLE 212

N-[2-(4-Chlorocinnamylamino)ethyl]N-phenethyl-5-isoquinolinesulfonamide

The procedure described in Example 211 was repeated except that 0.146 g of phenethyl alcohol was used in place of anisyl alcohol, to obtain 0.37 g of the title compound as a colorless oil.

NMR (CDCl$_3$) δ ppm: 1.4 (1H, brs), 2.75-2.90 (4H, m), 3.27 (2H, d, J=6.1 Hz), 3,4-3.6 (4H, m), 6.10 (1H, dt, J=15.9, 6.1 Hz), 6.39 (1H, d, J=15.9 Hz), 6.59-7.05 (2H, m), 7.1-7.2 (3H, m), 7.26 (4H, s), 7.65 (1H, dd, J=8.3, 7.6 Hz), 8.15 (1H, d, J=8.3 Hz), 8.38 (2H, t, J=6.1 Hz), 8.63 (1H, d, J=6.1 Hz), 9.28 (1H, s).

EXAMPLE 213

N-Benzyl-N-[2-(4-chlorocinnamylamino)ethyl]-5-isoquinolinesulfonamide

The procedure described in Example 211 was repeated except that 0.162 g of benzyl alcohol was used in place of anisyl alcohol, to obtain 0.3 g of the title compound as a colorless oil.

NMR (CDCl$_3$) δ ppm: 2.0 (1H, brs), 2.6 (2H, t, J=6.6 Hz), 3.15 (2H, d, J=6.1 Hz), 3.40 (2H, t, J=6.6 Hz), 4.50 (2H, s), 6.0 (1H, dt, J=15.8, 6.1 Hz), 6.30 (1H, d, J=15.8 Hz), 7.15-7.25 (9H, m), 7.66 (1H, dd, J=8.0, 7.6 Hz), 8.16 (1H, d, J=8.0 Hz), 8.4-8.5 (2H, m), 8.70 (1H, d, J=6.1 Hz), 9.31 (1H, s).

EXAMPLE 214

N-[2-(4-Chlorocinnamylamino)ethyl]-N-methyl-5-isoquinolinesulfonamide

The procedure described in Example 211 was repeated except that 48 mg of methanol was used in place of anisyl alcohol, to obtain 0.3 g of the title compound as a colorless oil.

NMR (CDCl$_3$) δ ppm: 1.5 (1H, brs), 2.86 (2H, t, J=6.2 Hz), 2.88 (3H, s), 3.3-3.4 (4H, m), 6.15 (1H, dt, J=15.8, 6.1 Hz), 6.43 (1H, d, J=15.8 Hz), 7.27 (4H, s), 7.69 (1H, dd, J=8.3, 7.3 Hz), 8.18 (1H, d, J=8.3 Hz), 8.38 (1H, d, J=7.3 Hz), 8.50 (1H, d, J=6.3 Hz), 8.67 (1H, d, J=6.3 Hz), 9.31 (1H, s).

REFERENCE EXAMPLE 45

N-(3,4-Dimethoxvphenyl)-5-isoquinolinesulfonamide 3.06 g of 3,4-dimethoxyaniline was dissolved in 30 ml of pyridine, to the solution was added in small portions 5.28 g of 5-isoquinolinesulfonyl chloride.HCl with stirring under ice cooling, and the mixture was stirred for 30 minutes, and further stirred at a room temperature overnight. After evaporating off the pyridine under a reduced pressure and additing 20 ml of water, the mixture was extracted twice with 50 ml of chloroform/isopropanol (10:1). The extract was dried over magnesium sulfate and evaporated under a reduced pressure to remove the solvent. To the resulting residue was added 20 ml of benzene/chloroform (3:1), and the mixture was slightly warmed and collected to obtain 5.64 g of the title compound as colorless crystals.

Melting point: 195°-197° C.;

NMR (CDCl$_3$) δ ppm: 3.67 (3H, s), 3.77 (3H, s), 6.3 (1H, dd, J=8.5, 2.7 Hz), 6.5-6.6 (3H, complex), 7.61 (1H, t, J=8.3 Hz), 8.2 (1H, d, J=8.3 Hz), 8.3 (1H, dd, J=1.3, 7.3 Hz), 8.4 (1H, d, J=6.1 Hz), 8.7 (1H, d, J=6.4 Hz), 9.36 (1H, d, J=1.3 Hz).

REFERENCE EXAMPLE 46

N-(3,4-Dimethoxvphenyl)-N-(2-phthalimidethyl)-5-isoquinolinesulfonamide 500 mg of the crystals obtained in Reference Example 45 was dissolved in 7 ml of dimethylformamide and 4 ml of tetrahydrofuran, to the solution was added 70 mg of 60% sodium hydride with stirring under ice cooling, and the mixture was stirred for 20 minutes, and after adding 406 mg of bromoethylphthalimide, the whole was refluxed for 6 hours with stirring. After adding 10 ml of ice water, the reaction mixture was extracted with 30 ml of ethyl acetate, and the extract was dried over magnesium sulfate and evaporated under a reduced pressure to remove the solvent. The resulting residue was applied to a silica gel column and eluted with chloroform/methanol (100:1) to obtain 320 mg of the title compound as colorless crystals.

Melting point: 197°-201° C.;

NMR (CDCl$_3$) δ ppm: 3.80 (3H, s), 3.88 (3H, s), 3.7-3.78 (2H, complex), 3.75-4.0 (2H, complex), 6.67 (1H, s), 6.68 (1H, s), 6.73 (1H, s), 7.57 (1H, t, J=7.57 Hz), 7.73 (4H, s), 8.0 (1H, dd, J=1.0, 8.3 Hz), 8.05 (1H, d, J=7.3 Hz), 8.24 (1H, dd, J=1.0, 7.57 Hz), 8.44 (1H, brd), 9.1 (1H, brs).

REFERENCE EXAMPLE 47

N-(3,4-Dimethoxyphenyl)-N-(2-aminoethyl)-5-isoquinolinesulfonamide 517 mg of the crystals obtained in Reference Example 46 was dissolved in 5 ml of methanol and 5 ml of chloroform, to the solution was added 60 mg of hydrozine hydrate, and the mixture was refluxed for 3 hours. Crystallized insoluble matter was filtered off, and the filtrate was evaporated under a reduced pressure to remove the solvent. After an addition of 10 ml of ethyl acetate, the whole was filtered to remove the insoluble matter and then evaporated under a reduced pressure to yield 420 mg of the title compound obtained as a slightly yellow oil.

NMR (CDCl$_3$) δ ppm: 2.76 (2H, t, J=6.1 Hz), 3.60 (3H, s), 3.75 (2H, t, J=6.1 Hz), 3.83 (3H, s), 6.48 (1H, s), 6.46 (1H, d, J=9.2 Hz), 6.63 (1H, d, J=9.2 Hz), 7.61 (1H, t, J=7.5 Hz), 8.18 (1H, d, J=8.0 Hz), 8.25 (1H, dd, J=1.3, 8.3 Hz), 8.5 (1H, d, J=6.1 Hz), 9.3 (1H, d, J=1.3 Hz).

EXAMPLE 215

N-(3,4-Dimethoxvphenyl)-N-[2-(4-chlorocinnamylamino)ethyl]-5-isoquinolinesulfonamide 320 mg of the oil obtained in Reference Example 47 was dissolved in 6 ml of dimethylformamide, to the solution were added 200 mg of potassium carbonate and 150 mg of p-chlorocinnamyl chloride, and the mixture was stirred overnight at a room temperature. After adding 20 ml of water the reaction mixture was extracted twice with 30 ml of chloroform. The extract was washed with a saturated sodium chloride aqueous solution, dried over magnesium chloride and evaporated under a reduced pressure to remove the solvent. The resulting residue was applied to a silica gel column and eluted with chloroform/methanol (100:1) to obtain 90 mg of the title compound as colorless crystals.

NMR (CDCl$_3$) δ ppm: 2.75 (2H, t, J=6.1 Hz), 3,36 (1H, d, J=6.1 Hz), 3.6 (3H, s), 3.74 (2H, d, J=6.1 Hz), 3.82 (3H, s), 6.15 (1H, d, and dt, J=15.6, 6.1 Hz), 6.42 (1H, d, J=15.6 Hz), 6.5 (1H, s), 6.61 (1H, d, J=8.1 Hz), 6.48 (1H, d, J=6.1 Hz), 7.3 (4H, brs), 7.63 (1H, t, J=8.1 Hz), 8.16 (1H, d, J=6.1 Hz), 8.17 (1H, d, J=8.1 Hz), 8.3 (1H, dd, J=1.0, 6.1 Hz), 8.5 (1H, d, J=6.1 Hz), 9.3 (1H, d, J=1.0 Hz).

EXAMPLE 216

N-{2-[Bis(4-chlorocinnamyl)amino]ethyl}-5-isoquinolinesulfonamide

In Example 215, prior to elution using chloroform/methanol, elution was carried out using chloroform to obtain 100 mg of the title compound in a colorless amorphous form.

NMR (CDCl$_3$) δ ppm: 2.66 (2H, t, J=6.2 Hz), 3.25 (4H, d, J=6.2 Hz), 3.52 (3H, s), 3.75 (2H, t, J=6.2 Hz), 3.71 (3H, s), 6.1 (2H, d and t, J=15.6, 6.2 Hz), 6.3 (1H, d, J=5.6 Hz), 6.4 (1H, s), 6.4 (2H, d, J=15.6 Hz), 6.45 (1H, d, J=5.6 Hz), 7.3 (8H, s), 7.51 (1H, t, J=8.1 Hz), 8.14 (1H, d, J=6.1 Hz), 8.16 (1H, d, J=8.1 Hz), 8.2 (1H, dd, J=1.0, 6.1 Hz), 8.45 (1H, d, J=6.1 Hz), 9.3 (1H, d, J=1.0 Hz).

As described above, the following compounds were prepared.

EXAMPLE 217

N-[2-4-methoxy-α-methylcinnamylamino)-ethyl]-5-isoquinolinesulfonamide.2HCl

Colorless amorphous form.

IR(KBr)cm$^{-1}$: 3420, 3200-2300, 1720, 1605, 1345, 1280;

UMR(D$_2$O) δ ppm: 1.59 (3H, d, J=6.71 Hz), 3.19 (2H, brt.), 3.38 (2H, brt), 4.01 (3H.s), 4.16 (1H, m), (1H, dd, J=15.9, 8.9 Hz), 6.83 (1H, d, J=15.9 Hz), 7.51 (2H, d, J=8.4 Hz), 7.94 (2H, d, J=8.4 Hz), 8.10 (1H, brt), 8.64 (1H, d, J=8.6 Hz), 8.76 (2H, brt), 8.98 (1H, d, J=7.0 Hz), 9.72 (1H, s).

EXAMPLE 218

N-[2-(4-methoxycarbonyl-N,α-dimethyl-cinnamylamino)ethyl]-5 isoquinolinesulfonamide.2HCl Colorless amorphous form.

IR(KBr)cm$^{-1}$=3420, 3150-2300, 1715, 1605, 1345, 1285;

NMR(D$_2$O) δppm=1.59 (3H, α, J=6.4 Hz), 2.94 (3H, s), 3.44 (4H, brs), 3.99 (3H, s), 4.31 (1H, m), 6.37 (1H, dd, J=16.2, 8.7 Hz), 6.89 (1H, d, J=16.2 Hz), 7.54 (2H, d, J=8.1 Hz), 8.08 (2H, d, J=8.1 Hz), 8.10 (1H, brt), 8.67 (1H, d, J=8.5 Hz), 8,75 (2H, brt), 8.96 (1H, d, J=7.0 Hz), 9.74 (1H, s).

EXAMPLE 219

N-[2-(4-methoxy-N,α-dimethylcinnamyl-amino)ethyl]-5-isoquinolinesulfonamide

Colorless oil.

NMR (CDCl$_3$)δppm: 1.07 (3H, d, J=6.6 Hz), 1.85 (3H, s), 2.3-2.5 (2H, m), 2.91 (2H, t, J=6.0 Hz), 2.95-3.10 (1H, m), 3.80 (3H, s), 5.86 (1H, dd, J=6.0 Hz), 2.95-3.10 (1H, m), 3.80 (3H, s), 5.86 ((1H, dd, J=16.1, 7.3 Hz), 6.24 (1H, d, J=16.1 Hz), 6.84 (2H, d, J=8.8 Hz), 7.24 (2H, d, J=8.8 Hz), 7.68 (1H, dd, J=7.3, 8.0 Hz), 8.20 (1H, α, J=8.0 Hz), 8.4-8.5 (2H, m), 8.66 (1H, d, J=6.1 Hz), 9.34 (1H, s).

EXAMPLE 220

N-(2-methylaminoethyl)-N-[2-(4-chloro N-methylcinnamylamino)ethyl]-5-isoquinolinesulfonamide Colorless oil.

NMR (CDO$_3$)δppm: 1.9-2.2 (1H, br), 2.23 (3H, s), 2.35 (3H, s), 2.59 (2H, t. J=6.6 Hz), 2.80 (2H, t, J=6.1 Hz), 3.12 (2H, α, J=6.6 Hz), 3.4-5.5 (4H, m), 6.10 ((1H, dt, J=15.9, 6.6 Hz), 6.44 ((1H, d, J=15.9 Hz), 7.26 (4H, s), 7.66 (1H, t, J=15.9, 6.6 Hz), 6.44 (1H, d, J=15.9 Hz), 7.26 (4H, s), 7.66 (1H, t, J=7.8 Hz), 8.17 (1H, d, J=7.8 Hz), 8.40 (1H, d, J=7.8 Hz), 8.46 (1H, d, J=6.1 Hz), 8.67 (1H, d, J=6.1 Hz), 9.32 (1H, s).

EXAMPLE 221

N-(2-methylaminoethyl)-N-[2-(4-chloro-N-methylcinnamylamino)ethyl]-5-isoquinolinesulfonamide.3HCl Colorless amorphous form.

NMR(D$_2$O)δppm: 2.80 (3H, s), 3.05 (3H, s), 3.4-3.6 (4H, m), 3.9-4.1 (6H, m), 6.17 (1H, d.t, J=15.9, 7.2 Hz), 6.74 (1H, d, J=15.9 Hz), 7.18 (4H, s), 8.10 (1H, t, J=7.9 Hz), 8.53 (1H, d, J=7.9 Hz), 8.6-8.8 (2H, m), 8.93 (1H, d, J=7.0 Hz), 9.77 (1H, s).

EXAMPLE 222

N-(2-hydroxyethyl)-N-[2-(4-methoxy-N,α-dimethylcinnamylamino)ethyl]-5-isoquinolinesulfonamide Colorless amorphous form.

NMR(CDCl$_3$)δppm: 1.29 (3H, d, J=6.6 Hz), 2.30 (3H, s), 2.7-3.0 (2H, m), 3.2-3.4(5H, m), 3.80 (3H, s), 3.8-3.9 (2H, m), 6.04 (1H, dd, J=16.1, 7.8 Hz), 6.40 (1H, d, J=16.1 Hz), 6.86 (2H, d, J=16.1, 7.8 Hz), 6.40 (1H, d, J=16.1 Hz), 6.86 (2H, d, J=8.7 Hz), 7.32 (2H, d, J=8.7 Hz), 7.32 (2H, d, J=8.7 Hz), 7.68 (1H, dd, J=8.0, 7.3 Hz), 8.19 (1H, d, J=8.0 Hz), 8.26 (1h, d, J=7.3 Hz), 8.58 (1H, d, J=6.1 Hz), 8.68 (1H, d, J=6.1 Hz), 8.68 (1H, d, J=6.1 Hz), 9.33 (1H, s).

EXAMPLE 223

N-[2-(methoxy)ethyl]-N-[2-(N-methyl-4-methoxy-α-methylcinnamylamino)ethyl]-5-isoquinolinesulfonamide Colorless oil NMR(CDCl$_3$)δppm: 1.12 (3H, d. J=6.6 Hz), 2.18 (3H, s), 2.4-2.65 (2H, m), 3.1 (3H, s), 3.10-3.20 (1H, m), 3.35-3.60 (6H, m), 3.81 (3H, s), 5.93 (1H, d,d, J=16.1, 7.3 Hz), 6.31 (1H, d, J=16.1 Hz), 6.85 (2H, d, J=8.7 Hz), 7.62 (1H, dd, J=7.6, 8.1 Hz), 8.13 (1H, d, J=8.1 Hz), 8.35-8.45 (2H, m) 8.67 (1H, d, J=6.1 Hz), 9.30 (1H, s).

EXAMPLE 224

N-[2-(4-chlorocinnamylamino)ethyl]-N-(2-dimethylaminoethyl-5-isoquinolinesulfornamide.3HCl Colorless amorphous form.

IR(KBr)cm$^{-1}$: 3420, 2700, 1340, 1150, 840, 590.
NMR(D$_2$O)δppm: 2.99 (6H, s), 3.33 (2H, t, J=6.8 Hz), 3.55 (2H, t, J=6.8 Hz), 3.8-4.0 (6H, m), 6.18 (1H, dt, J=16.2, 6.7 Hz), 6.76 (1H, d, J=16.2 Hz), 7.32 (4H, s), 8.12 (1H, t, J=8.0 Hz), 8.6-8.8(3H, m), 8.97 (1H, d, J=7.0 Hz), 9.74 (1H, s).

EXAMPLE 225

N-[2-(4-chlorocinnamylamino)ethyl]-N-(2-methylaminoethyl)-5-isoquinolinesulfonamide Colorless amorphous form.

NMR(D$_2$O)δppm: 3.26 (2H, brt), 3.92 (4H, brt), 5.04 (2H, s), 6.1-6.3 (1H, m), 6.77 (1H, d, J=15.6 Hz), 7.38 (4H, s), 7.68 (1H, t, J=6.7 Hz), 8.0-8.3 (2H, m), 8.57 (1H, d, J=5.8 Hz), 8.7-8.9 (3H, m), 9.02 (1H, d, J=7.3 Hz), 9.80 (1H, s).

EXAMPLE 226

N-2-(4-chlorocinnamylamino)ethyl]-N-(2-pyridiylmethyl)-5-isoquinolinesulfonamide.3HCl Pale yellow amorphous form.

IR(KBr)cm$^{-1}$: 3420, 2800, 1350, 1150, 590;
NMR(D$_2$O)δppm: 3.12 (2H, brt), 3.8-4.0 (4H, m), 4.96 (2H, s), 6.0-6.2 (1H, m); 6.70 (1H, d, J=15.7 Hz), 7.37 (4H, brq), 7.93 (1H, t, J=6.3 Hz), 8.16 (2H, brt), 8.54 (1H, d, J=5.8 Hz), 8.61 (1H, d, J=8.5 Hz), 8.7-8.8 (2H, m), 8.83 (1H, s), 9.01 (1H, d, J=6.7 Hz), 9.76 (1H, s).

EXAMPLE 227

N-[2-(4-chlorocinnamylamino)ethyl]-N-(3-pyridylmethyl)-5-isoquinolinesulfonamide.3HCl Pale yellow amorphous form.

IR(KBr)cm$^{-1}$: 3420, 2800, 1350, 1150, 590;
NMR(D$_2$O)δppm: 3.12 (2H, brt), 3.8-4.0 (4H, m), 4.96 (2H, s), 6.0-6.2 (1H, m), 6.70 (1H, d, J=15.7 Hz), 7.37 (4H, brq), 7.93 (1H, t, J=6.3 Hz), 8.16 (2H, brt), 8.54 (1H, d, J=5.8 Hz), 8.61 (1H, d, J=6.7 Hz), 9.76 (1H, s).

EXAMPLE 228

N-[2-(3,4-dimethoxy-α-methylcinnamylamino)ethyl]-5-isoquinolinesulfonamide.2HCl

Yellow amorphous form.

HMR(D$_2$O)δppm: 1.56 (3H, d, J=6.7 Hz), 3.1-3.2 (2H, m), 3.35-3.45 (2H, m), 3.84 (3H, s), 3.91 (3H, s), 4.0-4.5 (1H, m), 6.0 (1H, dd, J=15.6, 9.0 Hz), 6.64 (1H, d, J=15.6 Hz), 6.92 (3H, s), 8.07 (1H, t, J=8.0 Hz), 8.60 (1H, d, J=8.0 Hz), 8.73 (1H, d, J=8.0 Hz), 8.73 (1H, d, J=6.7 Hz), 8.95 (1H, d, J=6.7 Hz), 9.68 (1H, s).

EXAMPLE 229

N-[2-(α-methyl-3,4,5,trimethoxycinnamylamino)ethyl]-5-isoquinolinesulfonamide.2HCl NMR (D$_2$O) δppm: 1.65 (3H, d, J=6.4 Hz), 3.2-3.5 (4H, m), 3.84 (3H, s), 3.91 (6H, s), 4.1-4.3 (1H, m), 6.13 (1H, dd, J=14.1, 8.8 Hz), 6.70 (1H, d, J=14.1 Hz), 6.67 (2H, s), 8.16 (1H, t, J=8.0 Hz), 8.17 (1H, d, J=8.0 Hz), 8.75-8.85 (2H, m), 9.02 (1H, t, J=8.0 Hz), 8.17 (1H, d, J=8.0 Hz), 8.75-8.85 (2H, m), 9.02 (1H, d, J=7.0 Hz), 9.80 (1H, s).

EXAMPLE 230

N-[2-dimethylaminoethyl)-N-[2-(N-methyl-3,4,5-trimethoxycinnamylamino)ethyl]-5-isonolinesulfonamide Colorless oil.

NMR(CDCL$_3$)δppm: 2.12 (6H, s), 2.22 (3H, s), 2.39 (2H, t, J=6.8 Hz), 3.10 (2H, d, J=6.6 Hz), 3.4-3.5 (4H, m), 3.84 (3H, s), 3.87 (6H, s), 6.06 (1H, dt, J=16, 6.6 Hz), 6.40 (1H, d, J=16 Hz), 6.61 (2H, s), 7.64 (1H, t, J=7.4 Hz), 8.15 (1H, d, J=7.4 Hz), 8.44 (2H, m), 8.68 (1H, d, J=6.1 Hz), 9.32 (1H, s).

EXAMPLE 231

N-(2-dimethylaminoethyl)-N-[2-(N-methyl-3,4,5-trimethoxycinnamylamino)ethyl]-5-isoquinolinesulfonamide.3HCl Yellow amorphous form.

NMR (D$_2$O)δppm: 3.00 (6H, s), 3.08 (3H, s), 3.80 (3H, s), 3.82 (6H, s), 3.5-4.1 (10H, m), 6.1 (1H, m), 651 (2H, s), 6.68 (1H, d, J=16 Hz), 8.0 (1H, t, J=16 Hz), 8.5 (2H, m), 8.7 (2H, m), 9.55 (1H, s).

EXAMPLE 232

N-[2-(4-chlorocinnamylamino)ethyl]-N-(3,4,5-trimethoxybenzyl)-5-isoquinolinesulfonamide.2HCl Colorless amorphous form.

IR (KBr)cm$^{-1}$=3420, 2920, 1330, 1130, 590;
NMR (DMSO-d$_6$)δppm: 2.99 (2H, brs), 3.55 (6H, s), 3.56 (3H, s), 3.68 (4H, brs), 4.47 (2H, s), 6.2-6.4 (1H, m), 6.76 (1H, d, J=15.9 Hz), 7.45 (4H, s), 7.95 (1H, t, J=7.9 Hz), 8.54 (1H, d, J=7.6 Hz), 8.6-8.7 (2H, m), 8.78 (1H, d, J=6.3 Hz), 9.48 (2H, brs), 9.73 (1H, s).

EXAMPLE 233

N-cyanomethyl-N-[2-(4-methyoxycorbonyl-N-α-dimethylcinnamylaminolethyl]-5-isoquinoline sulfonamide Colorless oil.

IR (KBr)cm$^{-1}$: =2250, 1718, 1280;
NMR (CDCl$_3$)δppm =1.16 (3H, d, J=6.6 Hz), 2.23 (3H, s), 2.65-2.8 (2H, m), 3.35 (1H, m), 3.43 (2H, t, J=5.6 Hz), 3.91 (3H, s), 4.63 (2H, s), 6.23 (1H, dd, J=15.9, 7.1 Hz), 6.46 (1H, d, J=15.9 Hz), 7.39 (2H, d, J=8.3 Hz), 7.73 (1H, t, J=8.3 Hz), 7.98 (2H, d, J- 8.3 Hz), 8.25 (1H, d, J - 8.3 Hz), 8.4-8.5 (2H, m), 8.70 (1H, d, J=6.1 Hz), 9.36 (1H, s).

EXAMPLE 234

N-cyanomethyl-N-[2-(4-methoxycarbonyl-N,α-dimethylcinnamylamino)ethyl]-5-isoquinolinesulfonamide.2HCl Colorless amorphous form
IRC (KBr)cm$^{-1}$: =1718, 1280;
NMR (CDCl$_3$)δppm: 1.14 (3H, d, J=6.6 Hz), 2.10 (6H, s), 2,21 (3H, s), 2.37 (2H, t, J=7.3 Hz), 2.45–2.65 (2H, m), 3.22 (1H, m), 3.35–3.50 (4H, m), 3.91 (3H, s), 6.21 (1H, dd, J=1.59, 6.8 Hz), 6.42 (1H, d, J=15.9 Hz), 8.15 (1H, t, J=7.7 Hz), 8.7–8.85 (3H, m), 8.99 (1H, d, J=7.0 Hz), 9.76 (1H, s).

EXAMPLE 235

N-(2-dimethylaminoethyl)-N-[2-(4-methoxycarbonyl-N,α-dimethylcinnamylamino)ethyl]-5-isoquinolinesulfonamide Colorless oil.
IRC (KBr)cm$^{-1}$: 1718, 1280;
NMR (CDCl$_3$)δppm: 1.14 (3H, d, J=6.6 Hz), 2.10 (6H, s), 2.21 (3H, s), 2.37 (2H, t, J=7.3 Hz), 2.45–2.65 (2h, m), 3.22 (1H, m), 3.35–3.50 (4H, m), 3.91 (3H, s), 6.21 (1H, dd, J=15.9, 6.8 Hz), 6.42 (1H, d, J=15.9 Hz), 7.38 (2H, d, J=8.3 Hz), 7.63 (1H, t, J=7.9 Hz), 7.98 (2H, d, J=8.3 Hz), 8.14 (1H, d, J=7.9 Hz), 8.4–8.5 (2H, m), 8.67 (1H, d, J=6.4 Hz), 9.31 (1H, s).

EXAMPLE 236

N-(2-dimethylaminoethyl)-N-[2-(4-methoxycarbonyl-N, α-dimethylcinnamylamino)-ethyl]-5-isoquinolinesulfonamide.3HCl Colorless amorphous.
NMR (D$_2$O) δppm: 1.53 (3H, d, J=6.7 Hz), 2.95 (9H, s), 3.3–3.6 (4H, m], 3.9–4.0 (4H, m), 4.0 (3H, 4.25 (1H, m), 6.30 (1H, m), 6.75 (1H, d, J=16.0 Hz), 7.37 (2H, brs), 7.81 (2H, brs), 8.04 (1H, t, J=8.1 Hz), 8.55 (2H, m), 8.65 (1H, d, J=7.0 Hz), 9.60 (1H, s).

EXAMPLE 237

N-(2-morpholinoethyl)-N-[2-(4-methoxycorbonyl-N, α-dimethylcinnamylamino)ethyl]-5-isoquinolinesulfonamide Colorless oil.
IR (KBr)cm$^{-1}$: 1720, 1280;
NMR (CDCl$_3$)δppm: 1.15 (3H, d, J=6.4 Hz), 2.21 (3H, s), 2.25–2.7 (2H, m), 3.1–3.3 (1H, m), 3.4–3.6 (8H, m), 3.91 (3H, s), 6.20 (1H, dd, J=16.1, 7.3 Hz), 6.42 (1H, d, J=16.1 Hz), 7.38 (2H, d, J=8.3 Hz), 7.63 (1H, t, J=7.8 Hz), 8.42 (1H, d, J=7.8 Hz), 8.42 (1H, d, J=7.1 Hz), 8.67 (1H, d, J=7.1 Hz), 9.32 (1H, s).

EXAMPLE 238

N-(2-morpholinoethyl)-N-[2-(4-methoxy-carbonyl-N,α-dimethylcinnamylamino)ethyl-5-isoquino-linesulfonamide.3HCl Colorless amorphous form
NMR (D$_2$O)δppm: 1.55 (3H, d, J=6.8 Hz), 3.00 (3H, s), 3.2–3.7 (8H, m), 3.8–4.1 (8H, m), 4.0 (3H, s), 4.24 (1H, m), 6.35 (1H, m), 6.76 (1H, d, J=16 Hz), 7.40 (2H, brs), 7.82 (2H, brs), 8.06 (1H, t, J=7.5 Hz), 8.5–8.75 (3H, m), 8.80 (1H, d, J=7.0 Hz), 9.63 (1H, s).

EXAMPLE 239

N-(2-aminoethyl)-N-[2-(4-methoxy-carbonyl-N, α-dimethylcinnamylamino)ethyl]-5-isoquinolinesulfonamide Colorless oil.
IR (KBr)cm$^{-1}$: 1718, 1280;
NMR (CDCl$_3$)δppm: 1.13 (3H, d, J=6.6 Hz), 2.19 (3H, s), 2.6 (2H, m), 2.86 (2H, brs), 3.22 (1H, m), 3.37 (4H, t, J=6.9 Hz), 3.91 (3H, s), 6.20 (1H, dd, J=16.0, 6.9 Hz), 6.42 (1H, d, J=16.0 Hz), 7.39 (2H, d, J=8.3 Hz), 8.14 (1H, d, J=8.1 Hz), 8.38 (1H, d, J=8.1 Hz), 8.45 (1H, d, J=6.1 Hz), 8.68 (1H, d, J=6.1 Hz), 9.31 (1H, s).

EXAMPLE 240

N-(2-aminoethyl)-N-[2-(4-methoxycarbonyl-N,α-dimethylcinnamylamino)ethyl]-5-isoquinolinesulfonamide.3HCl Colorless amorphous form.
NMR(D$_2$O)δppm: 1.53 (3H, d, J=6.4 Hz), 2.96 (3H, s), 3.3–3.5 (4H, m), 3.8–4.0 (4H, m), 4.0 (3H, s), 4.2 (1H, m), 6.3 (1H, m), 6.76 (1H, d, J=15.9 Hz), 7.35 (2H, d, J=8.0 Hz), 7.78 (2H, brs), 803 (1H, t, J=7.9 Hz), 8.6 (2H, m), 8.66 (1H, d, J=6.7 Hz), 8.85 (1H, d, J=6.7 Hz), 9.58 (1H, s).

EXAMPLE 241

N-[2-(4-chloro-N-methylcinnamylamino)ethyl]-N-methoxycarbonylmethyl-5-isoquinoline-sulfonamide.2HCl Yellow amorphous form.
IR (KBr)cm$^{-1}$: 3420, 2650, 1750, 1350, 1150, 840, 590;
NMR (D$_2$O)δppm: 3.05 (3H, s), 3.51 (2H, brs), 3.61 (3H, s), 3.89 (2H, brs), 4.06 (2H, d, J=7.3 Hz), 4.45 s), 6.2–6.4 (1H, m), 6.85 (1H, d, J=15.6 Hz), 7.34 (4H, brq), 8.12 (1H, t, J=8.0 Hz), 8.6–8.8 (3H, m), 8.95 (1H, d, J=7.0 Hz), 9.79 (1H, s).

EXAMPLE 242

N-carboxymethyl-N-(2-(4-chloro-N-methylcinamylamino)ethyl]-5-isoquinolinesulfornamide Pale brown amorphous form.
IR (KBr)cm$^{-1}$: 3420, 1620, 1330, 1140, 590:
NMR(DMSO-d$_6$)δppm: 2.43(3H, s), 2.89 (2H, brt), 3.3–3.6 (4H, m), 3.91 (2H, s), 6.2–6.4(1H, m), 6.67 (1H, d, J=15.8 Hz), 7.45 (4H, brq), 7.85 (1H, t, J=8.0), 8.3–8.5 (3H, m), 8.71 (1H, d, J=6.2 Hz), 9.49 (1H, s).

EXAMPLE 243

N-[2-(N-carboxymethyl-4-chloracinnamylamino)ethyl]-N-methyl-5-isoquinoliesulfonamide Pale yellow amorphous form.
IR (KBr)cm$^{-1}$: 3400, 1630, 1320, 1140, 590;
NMR (DMSO-d$_6$)δppm: 2.75 (2H, brt), 2.79 (3H, s), 3.2–3.4(6H, m), 6.1–6.3 (1H, m), 6.50(1H, d, J=16.2 Hz), 7.39 (4H, brq), 7.83 (1H, t, J=7.8 Hz), 8.3–8.5 (3H, m), 8.68 (1H, d, J=6.1 Hz), 9.48 (1H, s).

EXAMPLE 244

N-[2-(4-chloro-N-methylcinnamylamino)ethyl]-N-methyl-5-isoquinolinesulfonamide.2HCl Pale brown amorphous form.
IR (KBr)cm$^{-1}$: 3420, 2670, 1350, 1140, 830, 590;

NMR(D₂O)δppm: 3.00 (3H, s), 3.04 (3H, s), 3.51 (2H, brs), 3.66 (2H, brs), 4.10 (2H, brd), 6.2-6.4 (1H, m), 6.90 (1H, d, J=15.9 Hz), 7.39 (4H, brq), 8.15 (1H, t, J=8.0 Hz), 8.6-8.8 (3H, m), 9.08 (1H, d, J=6.3 Hz), 9.80 (1H, s).

EXAMPLE 245

N-carbamoyl-N-[2-(4-chloro-N-methylcinnamylamino)ethyl]-5-isoquinolinesulfonamide.2HCl Colorless amorphous.

IR (KBr)cm⁻¹: 3420, 2670, 1680, 1350, 1150, 840, 590;

NMR (D₂O)δppm: 3.04 (3H, s), 3.4-3.7 (2H, m), 3.89 (2H, brt), 4.06 (2H, brt), 4.29 (2H, s), 6.2-6.4 (1H, m), 6.86 (1H, d, J=7.0 Hz), 9.80 (1H, s).

EXAMPLE 246

N-[2-(4-chlorocinnamylamino)ethyl]-N-[(5-methyl-4-imidazolyl)methyl]-5-isoquinoline sulfonamide.HCl Pale yellow amorphous form.

IR (KBr) cm⁻¹: 3420, 3020, 1350, 1150, 830, 590;

NMR(D₂O) δppm: 2.49 (3H, s), 3.52 (4H, brs), 4.10 (2H, brd), 4.70 (2H, s), 6.1-6.3 (1H, m), 6.83 (1H, d, J=15.8 Hz), 7.34 (4H, s), 8.10 (1H, d, J=8.0 Hz), 8.6-8.8 (3H, m), 8.83 (1H, s), 8.95 (1H, d, J=7.0 Hz), 9.81 (1H, s).

EXAMPLE 247

N-[2-(4-chloro-N-methoxycarbonylmethylcinnamylamino)ethyl]-N-methyl-5-isoqunilinesulfonamide.2HCl Yellow amorphous form.

IR (KBr)cm⁻¹: 3420, 2620, 1750, 1350, 1140, 840, 590;

NMR(D₂O)δppm: 3.07 (3H, s), 3.73 (4H, brt), 3.89 (3H, s), 4.2 (2H, brd), 4.37 (2H, s), 6.2-6.4 (1H, m), 6.89 (1H, d, J=16.0 Hz), 7.32 (4H, brq), 8.14 (1H, t, J=7.9 Hz), 8.6-8.8 (3H, m), 9.04 (1H, d, J=7.0 Hz), 9.83 (1H, s).

EXAMPLE 248

N-[2-(N-carbamoylmethyl-4-chlorocinnamylamino)-ethyl]-N-methyl-5-isoquinoline-sulfonamide.2HCl Pale yellow amorphous form.

IR (KBr) cm⁻¹: 3400, 1690, 1350, 1140, 830, 590;

NMR (D₂O) δppm: 3.05 (3H, s), 3.5-3.8 (4H, m), 4.1-4.2 (2H, m), 4.23 (2H, s), 6.2-6.4 (1H, m), 6.91 (1H, d, J=15.9 Hz), 734 (4H, brq), 8.11 (1H, t, J=7.0 Hz), 8.6-8.8 (3H, m), 9.00 (1H, d, J=7.0 Hz), 9.80 (1H, s).

EXAMPLE 249

N-[2-(4-chloro-N-cyanomethylcinnamylamino)ethyl]-N-methyl-5-isoquinolinesulfonamide.2HCl Pale brown amorphous form.

IR (KBr)cm⁻¹: 3420, 2570, 1350, 1140, 830, 590;

NMR (DMSO-d₆)δppm: 2.80 (2H, brt) 2.89 (3H, s), 3.3-3.5 (4H, m), 3.89 (2H, s), 6.1- 6.3 (1H, m), 6.64 (1H, d, J=15.8 Hz), 7.43 (4H, brq), 8.09 (1H, t, J=8.0 Hz), 8.63 (1H, d, J=7.6 Hz), 8.7-8.9 (3H, m), 9.98 (1H, s).

EXAMPLE 250

N-[2-(4-chloro-N-methylcinnamylamino)ethyl]-N-morpholinocarbonylmethyl-5-isoquinolinesulfonamide Colorless oil.

IR (KBr)cm⁻¹: 1660, 1330, 1130;

NMR (D₂O)δppm: 2.17 (3H, s), 2.57 (2H, t, J=6.3 Hz), 3.06 (2H, d, J=6.3 Hz), 3.39 (4H, brs), 3.5-3.7 (6H, m), 4.41 (2H, s), 6.06 (1H, dt, J=15.9, 6.3 Hz), 6.40 (1H, d, J=15.9 Hz), 7.27 (4H, s), 7.66 (1H, t, J=8.0 Hz), 8.15 (1H, d. J=8.3 Hz), 8.43 (1H, d, J=6.4 Hz), 8.54 (1H, d, J=8.0 Hz), 8.66 (1H, d, J=6.4 Hz), 9.30 (1H, s).

EXAMPLE 251

N-{2-[N-(2-aminoethyl)-4-chlorocinnamylamino]ethyl}-N-methyl-5-isoquinolinesulfonamide.3HCl Colorless amorphous form.

IR (KBr)cm⁻¹: 3420, 2950, 1490, 1350, 1140, 590;

NMR (D₂O)δppm: 3.05 (3H, s) 3.5-3.8 (8H, m), 4.20 (2H, brd), 6.2-6.4 (1H, m), 6.05 (1H, d, J=15.9 Hz), 7.37 (4H, brq), 8.16 (1H, t, J=7.9 Hz), 8.6-8.8 (3H, m), 9.07 (1H, d, J=7.0 Hz), 9.84 (1H, s).

EXAMPLE 252

N-[2-(4-chloro-N-methylcinnamylamino)ethyl]-N-[2-(1-pyperazinyl)ethyl]-5-isoquinolinesul-fonamide.4HCl Colorless amorphous form.

IR (KBr)cm 3420, 2660, 1460, 1350, 1150, 590;

NMR (D₂O)δppm: 3.04 (3H, s), 3.3-3.7 (12H, m), 3.8-4.1 (6H, m), 6.0-6.2 (1H, m), 6.73 (1H, d, J=15.9 Hz), 7.18 (4H, s), 8.11 (1H, t, J=7.9 Hz), 8.53 (1H, d, J=7.3 Hz), 8.6-8.8 (2H, m), 8.89 (1H, d, J=6.9 Hz), 9.78 (1H, s).

EXAMPLE 253

N-[2-(4-chloro-N-methylcinnamylamino)ethyl]-N-[2-(4-methyl-1-pyperazinyl)ethyl-5-isoquinolinesulfonamide.4HCl Colorless amorphous form IR (KBr)cm⁻¹: 3420, 2660, 1460, 1140, 590;

NMR (D₂O)δppm: 3.02 (3H, s), 3.3-3.7 (12H, m), 3.8-4.1(6H, m), 6.1-6.3 (1H, m), 6.74 (1H, d, J=16.0 Hz), 7.19 (4H, s), 8.11 (1H, t, J=7.9 Hz), 8.55 (1H, d, J=7.0 Hz), 8.6-8.8 (2H, m), 8.90 (1H, d, J=7.0 Hz), 9.79 (1H, s).

EXAMPLE 254

N-[2-(3-methyoxy-α-methylcinnamylamino)ethyl]-5-isoquinolinesulfonamide.2HCl

Pale yellow crystals.

Melting point 115°-118° C.;

IR (KBr)cm⁻¹: 3420, 3200-2600, 1605, 1350, 1162, 1150;

NMR (DMSO-d₆)δppm: 1.40 (3H, d, J=6.4 Hz), 2.90-3.0 (2H, m), 3.15-3.25 (2H, m), 3.78 (3H, s), 3.80-4.0 (1H, m), 6.22 (1H, dd, J=15.9, 8.8 Hz), 6.70 (1H, d, J=15.9 Hz), 6.85-7.05 (3H, m), 7.30 (1H, t, J=7.9 Hz), 7.30 (1H, br, disappears in D₂O), 8.0 (1H, d, J=7.9 Hz), 8.04 (1H, d, J=7.3 Hz), 8.59 (1H, d, J=7.3 Hz), 8.68 (1H, d, J=7.9 Hz), 8.82 (2H, s), 8.91 (1H, m, disappears in D₂O), 9.60 (2H, br, disappears in D₂O), 9.88 (1H, s).

EXAMPLE 255

N-[2-(4-hydroxymethyl-α-methylcinnamyl amino)ethyl]-5-isoquinolinesulfonamide

IR (KBr)cm⁻¹: 1620, 1326, 1160, 1139, 831, 761, 598;

NMR(CDCl₃)δppm: 1.07 (3H, d, J=6.35 Hz), near 1.95 (3H, br), 2.60 (2H, t. J=6.0 Hz), 2.96 (2H, m), 3.05 (1H, m), 4.68 (2H, s), 5.78 (1H, dd, J=15.87, 7.82 Hz), 6.27 (1H, d, J=8.30 Hz), 7.67 (1H, dd, J=8.30, 7.32 Hz), 8.18 (1H, d, J=8.30 Hz), 8.40 (1H, d, J=6.11 Hz), 8.44

(1H, d, J=7.32 Hz), 8.61 (1H, d, J=6.11 Hz), 9.32 (1H, s).

EXAMPLE 256

N-[2-(α-methyl-4-methylthiocinnamylamino)ethyl]-5-isoquinolinesulfonamide

Colorless amorphous form.

IR (KBr)cm$^{-1}$: 1618, 1493, 1324, 1160, 1138, 1094, 830, 807, 760, 598;

NMR (CDCl$_3$)δppm: 105 (3H, d, J=6.35 Hz), 2.48 (3H, s), 2.60 (2H, m), 2.96 (2H, t, J=6.10 Hz), 3.03 (1H, m), 5.75 (1H, dd, J=15.87, 7.81 Hz), 6.22 (1H, d, J - 15.87 Hz), 7.18 (4H, s), 7.67 (1H, dd, J=8.30, 7.32 Hz), 8.17 (1H, d, J=8.30 Hz), 8.43 (1H, d, J=6.10 Hz), 8.44 (1H, d, J=7.32 Hz), 8.68 (1H, d, J=6.10 Hz), 9.34 (1H, s).

EXAMPLE 257

N-[2-(α-methyl-4-methylsulfinylcinnamylamino)ethyl-5-isoquinolinesulfonamide

Colorless amorphous form.

IR (KBr)cm$^{-1}$; 1618, 1326, 1160, 1138, 1089, 1041, 831, 762, 599;

NMR(CDCl$_3$)δppm: 1.11 (3H, d, J=6.59 Hz), 2.0-4.0 (2H, br), 2.65 (2H, m), 2.73 (3H, s), 3.00 (2H, t, J=5.62 Hz), 3.15 (1H, m), 5.96 (1H, dd, J=16.11, 7.81 Hz), 6.36 (1H, d, J=16.11 Hz), 7.42 (2H, d, J=8.30 Hz), 7.58 (2H, d, J=8.30 HZ), 7.68 (1H, dd, J=8.31, 7.32 Hz), 8.10 (1H, d, J=8.30 Hz), 7.68 (1H, dd, J=8.31, 7.32 Hz), 8.19 (1H, d, J=8.31 Hz), 8.44 (1H, d, J=6.1 Hz), 8.44 (1H, d, J=7.32 Hz), 8.67 (1H, d, J=6.10 Hz), 9.35 (1H, s).

EXAMPLE 258

N-[2-(α-methyl-4-methylsulfonyalcvnnamylamino)ethyl]-5-isoquinolinesulfonamide

Colorless amorphous.

IR (KBr)cm$^{-1}$; 1310, 1149, 1090, 960, 832, 765, 599, 542;

NMR (CDCl$_3$)δppm: 1.09 (3H, d, J=6.35 Hz), 2.62 (2H, m), 2.98 (2H, t, J=5.62 Hz), 3.05 (3H, s), 3.10 (1H, m), 6.02 (1H, dd, J=15.87, 7.57 Hz), 6.37 (1H, d, J=15.87 Hz), 3.05 (3H, s), 3.10 (1H, m), 6.02 (1H, dd, J=15,87, 7,57 Hz), 6.37 (1H, d, J=15.87 Hz), 7.44 (2H, d, J=8.30 Hz), 7.69 (1H, dd, J=8.06, 7.57 Hz), 7.85 (2H, d, J=8.30 Hz), 8.20 (1H, d, J=8.06.Hz), 8.44 (1H, d, J=6.35 Hz), 8.45 (1H, d, J=7.57 Hz), 8.67 (1H, d, J=6.35 Hz), 9.36 (1H, s).

EXAMPLE 259

N-[2-(4-cyano-α-methylcinnamylamino)ethyl]-5-isoquinolinesulfonamide

Colorless needles.

Melting point: 62°-65° C.;

IR (KBr)cm$^{-1}$;; 2230, 1620, 1322, 1140, 600;

NMR (CDCl$_3$)δppm: 1.08 (3H, d, J=6.3 Hz), 2.57-2.65 (2H, m), 2.9-3.0 (2H, m), 3.0-3.2 (1H, m), 5.98 (1H, dd, J=15.9, 7.8 Hz), 6,33 (1H, d, J=15.9 Hz), 7.36 (2H, d, J=8.3 Hz), 7.58 (2H, d, J=8.3 Hz), 7.69 (1H, t, J=8.0 Hz), 8.20 (1H, d, J=8.0 Hz), 8.40-8.50 (2H, m), 8.69 (1H, d, J=6.1 Hz), 9.36 (1H, s).

EXAMPLE 260

N-[2-(4-carbamoyl-α-methylcinnamylamino)ethyl]-5-isoquinolinesulfonamide

Color-less needles

Melting point: 66°-70° C.;

IR (KBr)cm$^{-1}$;; 3450, 1662, 1610, 1320, 1160, 1140;

NMR (CDCl$_3$)δppm; 1.08 (3H, d, J=6.4 HZ), 2.61 (2H, M), 2.90-3.20 (3H, m), 5.93 (1H, dd, J=16.1, 7.8 Hz), 6.32 (1H, d, J=16.1 Hz), 7.32 (2H, d, J=8.3 Hz), 7.66 (1H, t, J=8.3 Hz), 7.74 (2H, d, J=8.3 Hz), 8.18 (1H, d, J=8.3 Hz), 7.74 (2H, d, J=8.3 Hz), 8.18 (1H, d, J=8.3 Hz), 8.40-8.50 (2H, m), 8.67 (1H, d, J=6.1 Hz), 9.34 (1H, s).

EXAMPLE 261

N-2-(4-acetamide-α-methylcinnamylamino)ethyl]-5-isoquinolinesulfonamide

Colorless amorphous form.

IR (KBr)cm$^{-1}$; 3300-2800, 1670, 1600, 1538, 1320, 1160, 1140;

NMR (CDCl$_3$)δppm; 1.03 (3H, d, J=6.6 Hz), 2.16 (3H, s), 2.55-2.65 (2H, m), 2.90-3.10 (3H, m), 5.68 (1H, dd, J=15.9, 8.1 Hz), 6.20 (1H, d, J=15.9 Hz), 7.17 (2H, d, J=8.5 Hz), 7.44 (2H, d, J=8.5 Hz), 7.66 (1H, dd, J=8.3, 7.3 Hz), 8.44 (1H, d, J=7.3 Hz), 7.66 (1H, s, disappears in D$_2$O), 8.16 (1H, d, J=8.3 Hz), 8.44 (1H, d, J=7.3 Hz), 8.44 (1H, d, J=6.1 Hz), 8.61 (1H, d, J=6.1 Hz), 9.31 (1H, s).

EXAMPLE 262

N-[2-(3-nitro-3-methoxy-α-methylcinnamylamino)ethyl]-5-isoquinolinesulfonamide.HCl Colorless crystals.

Melting point: 159°-163° C.;

IR (KBr) cm$^{-1}$;; 3450, 3150-2600, 1530, 1330, 116-1140;

NMR (DMSO-d$_6$)δppm: 1.34 (3H, d, J=6.6 Hz), 2.75-3.0 (2H, m), 3.02-3.20 (2H, m}, 3.90 (3H, s), 3.90-4.10 (1H, m), 6.30 (1H, dd, J=15.6, 8.6 Hz), 6.57 (1H, d, J=15.6 Hz), 7.26 (1H, d, J=7.8 Hz), 7.32 (1H, d, J=7.8 Hz), 7.83 (1H, t, J=7.8 Hz), 8.35-8.45 (3H, m), 8.52 (1H, brs, disappears in D$_2$O), 8.7 (1H, d, J=6.1 Hz), 9.25 (2H, brs, disappears in D$_2$O), 9.47 (1H, s).

EXAMPLE 263

N-[2-(2-methoxy-α-methylcinnamylamino)-ethyl]-5-isoquinolinesulfonamide

Colorless amorphous form.

IR (KBr) cm$^{-1}$: 1490, 1463, 1326, 1244, 1160, 1138, 755, 599;

NMR (CDCl$_3$) δppm: 1.05 (3H, d, J=6.35 Hz), 2.6 (2H, m), 2.96 (2H, t, J=5.62 Hz), 3.04 (1H, m), 3.82 (3H, s), 5.79 (1H, dd, J=16.12, 7.94 Hz), 6.85 (1H, brd, J=8.06 Hz), 6.90 (1H, brt, J=7.57 HZ), 7.21 (1H, m), 7.31 (1H, dd, J=16.12, 7.94 Hz), 6.85 (1H, brd, J=8.06 Hz), 6.90 (1H, brt, J=7.57 Hz), 7.21 (1H, m) 7.31 (1H, dd, J=7.57, (1.71 Hz), 7.66 (1H, dd, J=8.06, 7.57 Hz), 8.16 (1H, t, J=8.06 Hz), 8.44 (2H, m), 8.67 (1H, d, J=6.35 Hz), 9.33 (1H, s).

EXAMPLE 264

To confirm the usefulness of the above-mentioned compound of the present invention, the following experiments were carried out.

Vessel Smooth Muscle Relaxation Action (V.R. ED$_{50}$).

A rabbit was killed by bleeding and the superior mesenteric artery was removed and cut to a spiral form to prepare a band-shaped specimen according to a conventional method. The specimen was suspended by loading a strain in Krebs-Henseleit solution through which an oxygen gas containing 5% carbon dioxide was bubbled. The specimen was contracted by adding potassium chloride to maintain a predetermined strain. Thereafter, a test compound was cumulatively administrated. The relaxation activity of the test compound was expressed by $ED_{50}$ (μM), i.e., a concentration of the compound which relaxes the strain to 50% of the strain only in the presence of potassium chloride (as 100%)

Platelet Agglutination Inhibition (P.A.; $IC_{50}$)

(1) Preparation of washed platelets

The blood was obtained from a healthy person and mixed with one tenth volume of 0.38% sodium citrate, and the mixture was centrifuged at 700×G for 10 minutes to obtain a platelet-rich plasma (PRP). To the PRP was added one sixth volume of ACD solution (2.2% sodium citrate, 0.8% citric acid and 2.2% glucose; freshly prepared before use) and the mixture was centrifuged at 1500×G for 10 minutes to obtain a platelet pellet. Next, the platelet pellet was suspended in a modified HEPES-Tyrode solution (135 mM NaCl, 2.7 mM KCl, 1 mM $MgCl_2$, 0.1 mg/ml glucose, 20 mM HEPES; pH 7.4). To this suspension was added one sixth volume of ACD solution, and the whole was further centrifuged at 1500×G for 5 minutes to prepare a platelet pellet. The platelet pellet was then suspended in a modified HEPES Tyrode solution to obtain about $3 \times 10^5/\mu l$ in washed platelet suspension.

(2) Measurement of platelet agglutination

To 270 μl of the washed platelet suspension was added 3 μl of a solution of a test compound dissolved in an appropriate medium in different concentration, and the mixture was pre-incubated at 37° C. for 2 minutes. After an addition of 30 μl of 20 μg/ml collagen solution, the absorbance was measured with 4-channel agglutination analyzer (HEMA Tracer 601; Niko Bioscience).

(3) Determination of effect of test compounds

As a control, the above-mentioned procedure was carried out except that the test medium without a test compound was used, and the absorbance before addition of collagen and the maximum absorbance after addition of collagen were measured, and the difference between both absorbances was taken as 100% agglutination.

For test compound, the absorbance before an addition of collagen and the maximum absorbance after an addition of collagen were measured, and a percent of the inhibition was determined, compared with the control. A concentration of test compound which provides 50% of the inhibition expressed as $IC_{50}$.

Calmodulin-Dependent Phosphodiesterase Inhibition (1) Preparation of Calmodulin-Dependent Phosphodiesterase $(Ca^{2+}PDE)Ca^{2+}PDE$ was partially purified from the brain of rat by DEAE-Sepharose column chromatography.

(2) Preparation of calmodulin

Calmodulin was purified from the calf brain using a calmodulin inhibitor W-7 affinity column.

(3) Measurement of $Ca^{2+}PDE$ activity

A reaction mixture contained 20 μl of 500 mM Tris-HCl (pH 8.0), 20 μl of 50 mM $MgCl_2$, 20 μl of 2 mM $CaCl_2$ (or 10 mM EGTA), 20 μl of 1 mg/ml bovine serum albumin, PDE, 200 mg of calmodulin, test sample and distilled water to make total volume 200 μl. To the mixture was added 20 μl of 4 μM [$^3$H]-cGMP (2.5 μCi/ml), the mixture was incubated at 30° C. for 15 minutes, and then heated in boiling water for 3 to 5 minutes to terminate the reaction, and cooled in ice-water bath. 20 μg of 5'-nucleotidase (Snake venum) was added to the mixture, and the mixture was again incubated at 30° C. for 10 minutes. After addition of about 2 ml of water, the sample was applied to a cation exchange resin column (Biorad AG.AG50W-X4 to adsorbe the [$^3$H]-guanosine and additionally about 2 ml of washing water for the sample was added to the column. The column was washed with about 20 ml of water, and the adsorbed [$^3$H]-guanosine was eluted with 3 ml of 3N $NH_4OH$, and the elute was directly received by a vial. After an addition of 10 ml of an emulsified scintillation solution (ACS-II, AMERSHAM) the radio activity was measured by a scintillation counter LS7500 (Beckmann). The enzyme activity in the presence of calmodulin was taken as 0%, and a concentration of a test compound in μM which provides a 50% inhibition was expressed as $IC_{50}$.

The results are set forth in the following Table.

| Example No. | V.R. ($ED_{50}$) | P.A. ($IC_{50}$) (μM) | $Ca^{2+}PDE(IC_{50})$ (μM) |
|---|---|---|---|
| 1 | | | |
| 2 | 47 | | |
| 3 | | | |
| 4 | 12 | | 53 |
| 5 | | | |
| 6 | | | |
| 7 | 1.6 | | 13 |
| 8 | 1.8 | | 51 |
| 9 | | | |
| 10 | 6.4 | | 37 |
| 11 | | | 59 |
| 12 | | | |
| 13 | 1.2 | | 15 |
| 14 | | | |
| 15 | | | 43 |
| 16 | | | |
| 17 | | | |
| 18 | | | |
| 19 | 22 | | 20 |
| 20 | 1 | | 23 |
| 21 | | | |
| 22 | 1.8 | | |
| 23 | 0.25 | | 66 |
| 24 | 8.3 | | 63 |
| 25 | 0.55 | | 70 |
| 26 | | 10 | |
| 27 | | | |
| 28 | | | |
| 29 | 7.6 | 73 | |
| 30 | | | |
| 31 | 24 ± 7.0 | | |
| 32 | | | |
| 33 | 21 | | |
| 34 | 1.8 | | |
| 35 | 6.9 | | |
| 36 | 0.81 | | 10.5 |
| 37 | 4.4 | | 29 |
| 38 | 8.1 | | |
| 39 | | | |
| 40 | | 4.7 | |
| 41 | 1.8 | 10 | |
| 42 | 6.2 | | |
| 43 | 0.36 | | 3.8 |
| 44 | | | |
| 45 | 7.5 | | |
| 46 | 4 | | 36 |
| 47 | 0.39 | | 18 |
| 48 | 3.9 | | 6.5 |
| 49 | 0.92 | | |
| 50 | 0.67 | 70 | 11 |
| 51 | 0.17 | | 38 |
| 52 | 9.9 | | |
| 53 | 1.3 | | |

-continued

| Example No. | V.R. (ED$_{50}$) | P.A. (IC$_{50}$) ($\mu$M) | Ca$^{2+}$PDE(IC$_{50}$) ($\mu$M) |
|---|---|---|---|
| 54 | 1.7 | | |
| 55 | 8.6 | | |
| 56 | 1.2 | | 39 |
| 57 | 0.75 | | 50 |
| 58 | 0.25 | | 63 |
| 59 | | | |
| 60 | | 10 | |
| 61 | | 10 | |
| 62 | 23 | | |
| 63 | | | |
| 64 | | | |
| 65 | | | |
| 66 | | | |
| 67 | 2.2 | | 3.6 |
| 68 | 3.3 ± 1.4 | 6 | |
| 69 | 14 | | |
| 70 | | | |
| 71 | 14 | 93 | |
| 72 | 4 | | 6.2 |
| 73 | 14 | | 21 |
| 74 | | 2.8 | |
| 75 | 9.7 | | |
| 76 | 2.9 | | |
| 77 | 1.4 | | |
| 78 | 1.8 | | |
| 79 | 5.5 | | |
| 80 | 2.4 | | 13 |
| 81 | 1.7 | | 32 |
| 82 | 0.86 | | 33 |
| 83 | 0.39 | | 24 |
| 84 | 43 | | |
| 85 | | | 75 |
| 86 | 13 | | 24 |
| 87 | 1.7 | | 1.9 |
| 88 | 4.3 | | 14 |
| 89 | | | |
| 90 | 0.33 | | 3.4 |
| 91 | 1.1 | | 10 |
| 92 | | | 63 |
| 93 | 0.31 | | 3.4 |
| 94 | | | |
| 95 | | | |
| 96 | | | |
| 97 | | 39 | |
| 98 | 22 | | |
| 99 | 2.8 | | 61 |
| 100 | 95 | | |
| 101 | 29 | | |
| 102 | 24 | | |
| 103 | | | |
| 104 | | | |
| 105 | 5.4 | | 12 |
| 106 | 8.9 | | 28 |
| 107 | | | |
| 108 | 1.2 | | 10 |
| 109 | 0.59 | | 1.3 |
| 110 | 3.8 | | 9.3 |
| 111 | 7.0 | | 77 |
| 112 | | | |
| 113 | 0.88 | 20 | 1.2 |
| 114 | 54 | 100 | |
| 115 | | | |
| 116 | 1.5 | | |
| 117 | | | |
| 118 | | | |
| 119 | 11 | | 51 |
| 120 | 19 ± 3.0 | | |
| 121 | | | |
| 122 | | | |
| 123 | 4.8 | 22 | |
| 124 | 11 | | |
| 125 | 9.2 | | |
| 126 | | 10 | |
| 127 | | 39 | |
| 128 | 1.8 | | |
| 129 | 0.82 | | |
| 130 | 13 | | |
| 131 | 1.5 | | |
| 132 | | | |
| 133 | | | |
| 134 | | | |
| 135 | | | |
| 136 | | | |
| 137 | | | |
| 138 | | | |
| 139 | | | |
| 140 | | | |
| 141 | | | |
| 142 | 6.8 | | 1.1 |
| 143 | 0.82 | | 1.5 |
| 144 | 1.8 | | 1.0 |
| 145 | | 12 | |
| 146 | 2.8 | | |
| 147 | 1.2 | | 42 |
| 148 | | | |
| 149 | | | |
| 150 | | | |
| 151 | | | |
| 152 | | | |
| 153 | 1.5 | 25 | |
| 154 | | 60 | |
| 155 | 41 | 55 | |
| 156 | 4.4 | 19 | 19 |
| 157 | 3.2 | 36 | 8.6 |
| 158 | 17 | | 21 |
| 159 | 5.1 | 24 | 92 |
| 160 | 1.8 | 56 | |
| 161 | 4.7 | | |
| 162 | 35 | | |
| 163 | 31 | | |
| 164 | 4.1 | | |
| 165 | 11 | | |
| 166 | 1.4 | 90 | |
| 167 | 1.2 | 52 | |
| 168 | 3.6 | 26 | |
| 169 | 4.6 | | |
| 170 | 5.2 | | |
| 171 | 5.4 | | |
| 172 | 1.0 | 51 | 9.4 |
| 173 | | | |
| 174 | 11 | | |
| 175 | 2.0 | | 13 |
| 176 | 1.2 | 55 | 8.5 |
| 177 | 2.7 | 56 | 24 |
| 178 | 2.4 | | 50 |
| 179 | 2.8 | 51 | 7.8 |
| 180 | 1.8 | | 4.8 |
| 181 | 8.4 | 38 | 4.7 |
| 182 | 17 | | |
| 183 | 2.8 | | |
| 184 | 2.8 | | 12 |
| 185 | 0.21 | | |
| 186 | | | |
| 187 | | | |
| 188 | 4 | | |
| 189-I | 0.22 | | 2.7 |
| 189-II | 0.20 | | |
| 189-III | 0.29 | | 1.0 |
| 190 | 0.19 | | |
| 191 | 1.9 | | 26 |
| 192 | 0.12 | | 84 |
| 193 | 3.2 | | 12 |
| 194 | | | 80 |
| 195 | | | |
| 196 | | | |
| 197 | | | |
| 198 | | | |
| 199 | | | |
| 200 | | | |
| 201 | 3.2 | | |
| 202 | 1.3 | | |
| 203 | | | |
| 204 | | | |
| 205 | | | |
| 206 | | | |
| 207 | | | |
| 208 | | | |
| 209 | | | |
| 210 | | | |
| 211 | | | |

| Example No. | V.R. (ED$_{50}$) | P.A. (IC$_{50}$) ($\mu$M) | Ca$^{2+}$+PDE(IC$_{50}$) ($\mu$M) |
| --- | --- | --- | --- |
| 212 | | | |
| 213 | | | |
| 214 | | | |
| 215 | | | |
| 216 | | | |

It was shown that other compounds of the present inventions described above have a platelet agglutination-inhibitory action as well as an inhibitory action against protein kinase A, myosin light chain kinase, protein kinase C, calmodulin-dependent protein kinase II, cyclic AMP dependent phosphodiesterase and the like, but have little effect on cardiac functions.

As seen from the above-mentioned results, the present compound a as described above have a smooth muscle relaxation action, and therefore, are useful as vasodilator or brain circulation-improving agents; and since the present compound have a platelet agglutination-inhibitory action, they are useful as prophylactic or therapeutic agents for thrombosis Moreover, since the present compounds have an inhibitory activity against various kinases, they are useful as anti-tumer agents. The above-mentioned compounds have a low toxicity, and therefore, are applicable as pharmaceutical preparations.

We claim:

1. A compound represented by the formula (I$_a$):

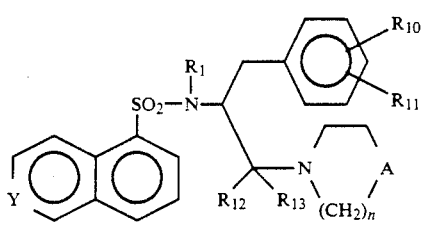

wherein when Y is a nitrogen atom, $R_1$ represents a hydrogen atom, methyl, tolylmethyl or 3,4-dichlorobenzyl;

$R_{10}$ is selected from the group consisting of a hydrogen atom, hydroxy, methoxy, acetoxy, isoquinolylsulfonyloxy, benzyloxy and pyridylmethoxy;

$R_{11}$ is a hydrogen atom or benzyloxy; and when n represents an integer of 2, A is a group represented by the formula:

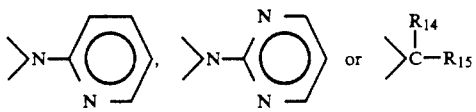

wherein $R_{14}$ is selected from the group consisting of hydroxy, acetoxy, phenyl, tolylmethoxy, 3,4-dichlorobenzyloxy, benzylamino, an amino disubstituted with methyl and 3,4-dichlorobenzyl, 3,4-dichlorobenzylamino and an amino disubstituted with methyl and benzyl;

$R_{15}$ is a hydrogen atom, or together with $R_{14}$ form an ethylenedioxy group or an oxo group; and $R_{12}$ and $R_{13}$ are hydrogen atom; or when n represents an integer of 3

A is a group represented by the formula: $>$N—$R_{16}$ wherein $R_{16}$ is selected from the group consisting of a hydrogen atom, phenyl, benzyloxycarbonyl, benzylcarbonyl, phenthycarbonyl and phenylpropyl; and $R_{12}$ and $R_{13}$ are hydrogen atom, or together form a oxo group; or when Y is a carbon atom, $R_1$ is methyl;

$R_{10}$ is hydroxy or naphthylsulfonyloxy;

$R_{11}$ is a hydrogen atom;

$R_{12}$ and $R_{13}$ are hydrogen atom;

n is an integer of 2; and

A is $>$N-phenyl or $>$N—COOCH$_2$-phenyl;

and quarternary ammonium salts, or salts of the compound of the formula (Ia).

* * * * *